US009132190B2

(12) United States Patent
Benatuil et al.

(10) Patent No.: US 9,132,190 B2
(45) Date of Patent: Sep. 15, 2015

(54) THERAPEUTIC DLL4 BINDING PROTEINS

(71) Applicant: AbbVie Inc., North Chicago, IL (US)

(72) Inventors: Lorenzo Benatuil, Northborough, MA (US); Erwin R. Boghaert, Pleasant Prairie, WI (US); Jijie Gu, Shrewsbury, MA (US); Maria Harris, Shrewsbury, MA (US); Jonathan A. Hickson, Lake Villa, IL (US); Chung-Ming Hsieh, Newton, MA (US); Yuliya Kutskova, Northborough, MA (US); Yingchun Li, Buffalo Grove, IL (US); Zhihong Liu, Gurnee, IL (US); Susan Morgan-Lappe, Chicago, IL (US)

(73) Assignee: AbbVie Inc., North Chicago, IL (US)

( * ) Notice: Subject to any disclaimer, the term of this patent is extended or adjusted under 35 U.S.C. 154(b) by 4 days.

(21) Appl. No.: 14/090,778

(22) Filed: Nov. 26, 2013

(65) Prior Publication Data

US 2014/0093521 A1 Apr. 3, 2014

Related U.S. Application Data

(62) Division of application No. 12/870,276, filed on Aug. 27, 2010, now Pat. No. 8,623,358.

(60) Provisional application No. 61/238,152, filed on Aug. 29, 2009, provisional application No. 61/261,728, filed on Nov. 16, 2009.

(51) Int. Cl.
*A61K 39/395* (2006.01)
*C07K 14/47* (2006.01)
*C07K 16/18* (2006.01)
*C07K 16/22* (2006.01)
*A61K 45/06* (2006.01)
*C07K 7/06* (2006.01)
*C07K 7/08* (2006.01)

(52) U.S. Cl.
CPC .............. *A61K 39/3955* (2013.01); *A61K 45/06* (2013.01); *C07K 7/06* (2013.01); *C07K 7/08* (2013.01); *C07K 14/47* (2013.01); *C07K 16/18* (2013.01); *C07K 16/22* (2013.01); *C07K 2317/21* (2013.01); *C07K 2317/33* (2013.01); *C07K 2317/565* (2013.01); *C07K 2317/567* (2013.01); *C07K 2317/73* (2013.01); *C07K 2317/76* (2013.01); *C07K 2317/92* (2013.01); *C07K 2317/94* (2013.01)

(58) Field of Classification Search
None
See application file for complete search history.

(56) References Cited

U.S. PATENT DOCUMENTS

| 4,526,938 A | 7/1985 | Churchill et al. |
|---|---|---|
| 4,554,101 A | 11/1985 | Hopp |
| 4,816,397 A | 3/1989 | Boss et al. |
| 4,816,567 A | 3/1989 | Cabilly et al. |
| 4,880,780 A | 11/1989 | Trainor et al. |
| 4,946,778 A | 8/1990 | Ladner et al. |
| 4,980,286 A | 12/1990 | Morgan et al. |
| 5,006,309 A | 4/1991 | Khalil et al. |
| 5,063,081 A | 11/1991 | Cozzette et al. |
| 5,089,424 A | 2/1992 | Khalil et al. |
| 5,128,326 A | 7/1992 | Balazs et al. |
| 5,223,409 A | 6/1993 | Ladner et al. |
| 5,225,539 A | 7/1993 | Winter |
| 5,258,498 A | 11/1993 | Huston et al. |
| 5,290,540 A | 3/1994 | Prince et al. |
| 5,294,404 A | 3/1994 | Grandone et al. |
| 5,403,484 A | 4/1995 | Ladner et al. |
| 5,427,908 A | 6/1995 | Dower et al. |
| 5,516,637 A | 5/1996 | Huang et al. |
| 5,530,101 A | 6/1996 | Queen et al. |
| 5,565,332 A | 10/1996 | Hoogenboom et al. |
| 5,571,698 A | 11/1996 | Ladner et al. |
| 5,580,717 A | 12/1996 | Dower et al. |
| 5,585,089 A | 12/1996 | Queen et al. |
| 5,624,821 A | 4/1997 | Winter et al. |
| 5,627,052 A | 5/1997 | Schrader |
| 5,641,870 A | 6/1997 | Rinderknecht et al. |
| 5,648,260 A | 7/1997 | Winter et al. |
| 5,658,727 A | 8/1997 | Barbas et al. |
| 5,679,377 A | 10/1997 | Bernstein et al. |
| 5,693,762 A | 12/1997 | Queen et al. |

(Continued)

FOREIGN PATENT DOCUMENTS

| CN | 101210049 A | 7/2008 |
|---|---|---|
| EP | 0 592 106 A1 | 4/1994 |

(Continued)

OTHER PUBLICATIONS

White et al. (2001, Ann. Rev. Med., 2001, 52:125-145).*

(Continued)

*Primary Examiner* — Laura B Goddard
*Assistant Examiner* — Meera Natarajan
(74) *Attorney, Agent, or Firm* — Finnegan, Henderson, Farabow, Garrett & Dunner, LLP

(57) ABSTRACT

Improved DLL4 binding proteins are described, including antibodies, CDR-grafted antibodies, human antibodies, and DLL4 binding fragments thereof, proteins that bind DLL4 with high affinity, and DLL4 binding proteins that neutralize DLL4 activity. The DLL4 binding proteins are useful for treating or preventing cancers and tumors and especially for treating or preventing tumor angiogenesis, and/or other angiogenesis-dependent diseases such as ocular neovascularization, or angiogenesis-independent diseases characterized by aberrant DLL4 expression or activity such as autoimmune disorders including multiple sclerosis.

46 Claims, No Drawings

(56) References Cited

U.S. PATENT DOCUMENTS

| | | |
|---|---|---|
| 5,698,426 A | 12/1997 | Huse |
| 5,714,352 A | 2/1998 | Jakobovits |
| 5,723,323 A | 3/1998 | Kauffman et al. |
| 5,733,743 A | 3/1998 | Johnson et al. |
| 5,750,753 A | 5/1998 | Kimae et al. |
| 5,763,192 A | 6/1998 | Kauffman et al. |
| 5,766,886 A | 6/1998 | Studnicka et al. |
| 5,780,225 A | 7/1998 | Wigler et al. |
| 5,807,715 A | 9/1998 | Morrison et al. |
| 5,814,476 A | 9/1998 | Kauffman et al. |
| 5,817,483 A | 10/1998 | Kauffman et al. |
| 5,821,047 A | 10/1998 | Garrard et al. |
| 5,824,514 A | 10/1998 | Kauffman et al. |
| 5,855,913 A | 1/1999 | Hanes et al. |
| 5,874,064 A | 2/1999 | Edwards et al. |
| 5,912,015 A | 6/1999 | Bernstein et al. |
| 5,916,597 A | 6/1999 | Lee et al. |
| 5,916,771 A | 6/1999 | Hori et al. |
| 5,934,272 A | 8/1999 | Lloyd et al. |
| 5,939,598 A | 8/1999 | Kucherlapati et al. |
| 5,969,108 A | 10/1999 | McCafferty et al. |
| 5,976,862 A | 11/1999 | Kauffman et al. |
| 5,985,309 A | 11/1999 | Edwards et al. |
| 5,985,320 A | 11/1999 | Edwards et al. |
| 5,985,615 A | 11/1999 | Jakobovits et al. |
| 5,989,463 A | 11/1999 | Tracy et al. |
| 5,998,209 A | 12/1999 | Jokobovits et al. |
| 6,019,968 A | 2/2000 | Platz et al. |
| 6,075,181 A | 6/2000 | Kucherlapati et al. |
| 6,091,001 A | 7/2000 | Jakobovits et al. |
| 6,114,598 A | 9/2000 | Kucherlapati et al. |
| 6,130,364 A | 10/2000 | Jakobovits et al. |
| 6,180,370 B1 | 1/2001 | Queen et al. |
| 6,204,023 B1 | 3/2001 | Robinson et al. |
| 6,660,843 B1 | 12/2003 | Feige et al. |
| 6,699,658 B1 | 3/2004 | Wittrup et al. |
| 6,914,128 B1 | 7/2005 | Salfeld et al. |
| 7,262,028 B2 | 8/2007 | Van Berkel et al. |
| 7,419,821 B2 | 9/2008 | Davis et al. |
| 7,429,486 B2 | 9/2008 | Van Berkel et al. |
| 7,612,181 B2 | 11/2009 | Wu et al. |
| 7,682,833 B2 | 3/2010 | Miller et al. |
| 8,586,714 B2 | 11/2013 | Ghayur et al. |
| 8,623,358 B2 | 1/2014 | Benatuil et al. |
| 8,624,002 B2 | 1/2014 | Gu et al. |
| 8,716,450 B2 | 5/2014 | Ghayur et al. |
| 8,722,855 B2 | 5/2014 | Ghayur et al. |
| 8,735,546 B2 | 5/2014 | Ghayur et al. |
| 8,822,645 B2 | 9/2014 | Ghayur et al. |
| 2002/0137134 A1 | 9/2002 | Gerngross |
| 2002/0142390 A1 | 10/2002 | Allen et al. |
| 2003/0176672 A1 | 9/2003 | Salceda et al. |
| 2003/0186374 A1 | 10/2003 | Hufton et al. |
| 2004/0018577 A1 | 1/2004 | Emerson Campbell et al. |
| 2004/0018590 A1 | 1/2004 | Gerngross et al. |
| 2004/0029129 A1 | 2/2004 | Wang et al. |
| 2004/0031072 A1 | 2/2004 | La Rosa et al. |
| 2004/0141964 A1 | 7/2004 | Abdel-Meguid et al. |
| 2005/0042664 A1 | 2/2005 | Wu et al. |
| 2005/0154192 A1 | 7/2005 | Shirakawa et al. |
| 2005/0187167 A1 | 8/2005 | Bachmann et al. |
| 2006/0078901 A1 | 4/2006 | Buchrieser et al. |
| 2006/0134121 A1 | 6/2006 | Thurston et al. |
| 2006/0160164 A1 | 7/2006 | Miller et al. |
| 2007/0148749 A1 | 6/2007 | Yasuda et al. |
| 2007/0248584 A1 | 10/2007 | Kent |
| 2008/0175847 A1 | 7/2008 | Yan et al. |
| 2008/0187532 A1 | 8/2008 | Gurney et al. |
| 2008/0233140 A1 | 9/2008 | Banchereau et al. |
| 2009/0035308 A1 | 2/2009 | Gill et al. |
| 2009/0041783 A1 | 2/2009 | Takayama et al. |
| 2009/0130114 A1 | 5/2009 | Qian et al. |
| 2009/0175880 A1 | 7/2009 | Keler et al. |
| 2009/0175881 A1 | 7/2009 | Presta et al. |
| 2009/0239259 A1 | 9/2009 | Hsieh |
| 2009/0246199 A1 | 10/2009 | Noguera-Troise et al. |
| 2009/0304693 A1 | 12/2009 | Ghayur et al. |
| 2009/0311253 A1 | 12/2009 | Ghayur et al. |
| 2010/0021953 A1 | 1/2010 | Belfield et al. |
| 2010/0074900 A1 | 3/2010 | Ghayur et al. |
| 2010/0076178 A1 | 3/2010 | Ghayur et al. |
| 2010/0099103 A1 | 4/2010 | Hsieh et al. |
| 2010/0233079 A1 | 9/2010 | Jakob et al. |
| 2010/0260668 A1 | 10/2010 | Ghayur et al. |
| 2011/0008766 A1 | 1/2011 | Ghayur et al. |
| 2011/0044980 A1 | 2/2011 | Ghayur et al. |
| 2011/0117079 A1 | 5/2011 | Benatuil et al. |
| 2011/0189176 A1 | 8/2011 | Skokos |
| 2011/0217237 A1 | 9/2011 | Chen et al. |
| 2011/0263827 A1 | 10/2011 | Ghayur et al. |
| 2011/0318349 A1 | 12/2011 | Ghayur et al. |
| 2012/0014957 A1 | 1/2012 | Ghayur et al. |
| 2012/0087858 A1 | 4/2012 | Ghayur et al. |
| 2012/0258108 A1 | 10/2012 | Ghayur et al. |
| 2012/0263722 A1 | 10/2012 | Ghayur et al. |
| 2013/0171059 A1 | 7/2013 | Ghayur et al. |
| 2013/0195871 A1 | 8/2013 | Ghayur et al. |
| 2013/0236458 A1 | 9/2013 | Hsieh et al. |
| 2014/0134171 A1 | 5/2014 | Ghayur et al. |
| 2014/0134172 A1 | 5/2014 | Gu et al. |
| 2014/0186377 A1 | 7/2014 | Gu at al. |
| 2014/0219912 A1 | 8/2014 | Ghayur at al. |
| 2014/0234208 A1 | 8/2014 | Ghayur et al. |
| 2014/0271458 A1 | 9/2014 | Ghayur at al. |
| 2014/0308286 A1 | 10/2014 | Ghayur et al. |
| 2014/0348835 A1 | 11/2014 | Gu et al. |
| 2014/0356281 A1 | 12/2014 | Ghayur et al. |

FOREIGN PATENT DOCUMENTS

| | | |
|---|---|---|
| EP | 0 239 400 B1 | 8/1994 |
| EP | 0 592 106 B1 | 11/2004 |
| EP | 0 519 596 B1 | 2/2005 |
| GB | 2449354 A | 11/2008 |
| WO | WO 90/02809 A1 | 3/1990 |
| WO | WO 90/05144 A1 | 5/1990 |
| WO | WO 90/14424 A1 | 11/1990 |
| WO | WO 90/14430 A1 | 11/1990 |
| WO | WO 90/14443 A1 | 11/1990 |
| WO | WO 91/05548 A1 | 5/1991 |
| WO | WO 91/09967 A1 | 7/1991 |
| WO | WO 91/10737 A1 | 7/1991 |
| WO | WO 91/10741 A1 | 7/1991 |
| WO | WO 91/17271 A1 | 11/1991 |
| WO | WO 92/01047 A1 | 1/1992 |
| WO | WO 92/02551 A1 | 2/1992 |
| WO | WO 92/03461 A1 | 3/1992 |
| WO | WO 92/09690 A2 | 6/1992 |
| WO | WO 92/11272 A1 | 7/1992 |
| WO | WO 92/15679 A1 | 9/1992 |
| WO | WO 92/18619 A1 | 10/1992 |
| WO | WO 92/19244 A2 | 11/1992 |
| WO | WO 92/20791 A1 | 11/1992 |
| WO | WO 92/22324 A1 | 12/1992 |
| WO | WO 93/01288 A1 | 1/1993 |
| WO | WO 93/06213 A1 | 4/1993 |
| WO | WO 93/11236 A1 | 6/1993 |
| WO | WO 94/02602 A1 | 2/1994 |
| WO | WO 94/18219 A1 | 8/1994 |
| WO | WO 95/15982 A2 | 6/1995 |
| WO | WO 95/20401 A1 | 8/1995 |
| WO | WO 96/20698 A2 | 7/1996 |
| WO | WO 96/33735 A1 | 10/1996 |
| WO | WO 96/34096 A1 | 10/1996 |
| WO | WO 96/36358 A1 | 11/1996 |
| WO | WO 97/20032 A1 | 6/1997 |
| WO | WO 97/29131 A1 | 8/1997 |
| WO | WO 97/32572 A2 | 9/1997 |
| WO | WO 97/44013 A1 | 11/1997 |
| WO | WO 98/16654 A1 | 4/1998 |
| WO | WO 98/24893 A2 | 6/1998 |
| WO | WO 98/31346 A1 | 7/1998 |
| WO | WO 98/31700 A1 | 7/1998 |
| WO | WO 98/50433 A2 | 11/1998 |

(56) References Cited

FOREIGN PATENT DOCUMENTS

| | | |
|---|---|---|
| WO | WO 99/06834 A2 | 2/1999 |
| WO | WO 99/15154 A1 | 4/1999 |
| WO | WO 99/20253 A1 | 4/1999 |
| WO | WO 99/45031 A2 | 9/1999 |
| WO | WO 99/53049 A1 | 10/1999 |
| WO | WO 99/66903 A2 | 12/1999 |
| WO | WO 00/09560 A2 | 2/2000 |
| WO | WO 00/24782 A2 | 5/2000 |
| WO | WO 00/37504 A2 | 6/2000 |
| WO | WO 00/56772 A1 | 9/2000 |
| WO | WO 01/77342 A1 | 10/2001 |
| WO | WO 01/83525 A2 | 11/2001 |
| WO | WO 02/02773 A2 | 1/2002 |
| WO | WO 02/072636 A2 | 9/2002 |
| WO | WO 2006/070290 A2 | 7/2006 |
| WO | WO 2007/024715 A9 | 3/2007 |
| WO | WO 2007/070671 A2 | 6/2007 |
| WO | WO 2007/143689 A2 | 12/2007 |
| WO | WO 2008/019144 A2 | 2/2008 |
| WO | WO 2008/042236 A2 | 4/2008 |
| WO | WO 2008/060705 A2 | 5/2008 |
| WO | WO 2008/076379 A2 | 6/2008 |
| WO | WO 2008/091222 A1 | 7/2008 |
| WO | WO 2008/139202 A1 | 11/2008 |
| WO | WO 2009/026660 A1 | 3/2009 |
| WO | WO 2009/124931 A2 | 10/2009 |
| WO | WO 2009/134776 A2 | 11/2009 |
| WO | WO 2010/032060 A1 | 3/2010 |

OTHER PUBLICATIONS

Ames et al., "Conversion of murine Fabs isolated from a combinatorial phage display library to full length immunoglobulins," *J. Immunol. Methods*, 184: 177-186 (1995).

Anthony et al., "Recapitulation of IVIG Anti-Inflammatory Activity with a Recombinant IgG Fc," *Science*, 320(5874): 373-376 (2008).

Azzazy et al., "Phage display technology: clinical applications and recent innovations," *Clin. Biochem.*, 35: 425-445 (2002).

Babcook et al., "A novel strategy for generating monoclonal antibodies from single, isolated lymphocytes producing antibodies of defined specificities," *Proc. Natl. Acad, Sci. USA*, 93: 7843-7848 (1996).

Barbas et al., "Assembly of combinatorial antibody libraries on phage surfaces: The gene III site," *Proc. Natl. Acad. Sci. USA*, 88: 7978-7982 (1991).

Barbas et al., "In vitro evolution of a neutralizing human antibody to human immunodeficiency virus type 1 to enhance affinity and broaden strain cross-reactivity," *Proc. Natl. Acad. Sci. USA*, 91: 3809-3813 (1994).

Better et al., "*Escherichia coli* Secretion of an Active Chimeric Antibody Fragment," *Science*, 240: 1041-1043 (1988).

Biewenga et al., "IgA1 half molecules in human multiple myeloma and the in vitro production of similar fragments from intact IgA1 molecules," *Clin. Exp. Immunol.*, 51: 395-400 (1983).

Billiard et al., "Dll4—Notch signaling in Flt3-independent dendritic cell development and autoimmunity in mice," *J. Exp. Med.*, 209(5): 1011-1028 (2012).

Bird et al., "Single-Chain Antigen-Binding Proteins," *Science*, 242: 423-426 (1988).

Brinkmann et al., "Phage display of disulfide-stabilized Fv fragments," *J. Immunol. Methods*, 182: 41-50 (1995).

Buchwald et al., "Long-term, continuous intravenous heparin administration by an implantable infusion pump in ambulatory patients with recurrent venous thrombosis," *Surgery*, 88: 507-516 (1980).

Burke et al., "Zotarolimus (ABT-578) eluting stents," *Adv. Drug Del. Rev.*, 58: 437-446 (2006).

Burton et al., "Human Antibodies from Combinatorial Libraries," *Adv. Immunol.*, 57: 191-280 (1994).

Carter et al., "Humanization of an anti-p185$^{HER2}$ antibody for human cancer therapy," *Proc. Natl. Acad. Sci. USA*, 89: 4285-4289 (1992).

Casset et al., "A peptide mimetic of an anti-CD4 monoclonal antibody by rational design," *Biochem. Biophys. Res. Commun.*, 307: 198-205 (2003).

Chen et al., "Selection and analysis of an optimized anti-VEGF antibody: Crystal structure of an affinity matured Fab in complex with antigen," *J. Mol. Biol.*, 293: 865-881 (1999).

Chothia et al., "Canonical Structures for the Hypervariable Regions of Immunoglobulins," *J. Mol. Biol.*, 196: 901-917 (1987).

Chothia et al., "Conformations of immunoglobulin hypervariable regions," *Nature*, 342: 877-883 (1989).

Chothia et al., "Structural Repertoire of the Human $V_H$ Segments," *J. Mol. Biol.*, 227(3): 799-817 (1989).

Clackson et al., "Making antibody fragments using phage display libraries," *Nature*, 352: 624-628 (1991).

Cleek et al., "Biodegradable Polymeric Carriers for a bFGF Antibody for Cardiovascular Application," *Proceed. Intl. Symp. Control. Rel. Bioact. Mater.*, 24:853-854 (1997).

Dall'Acqua et al., "Contribution of Domain Interface Residues to the Stability of Antibody $C_H3$ Domain Homodimers," *Biochemistry*, 37: 9266-9273 (1998).

Duarte et al., "Dosage-Sensitive Requirement for Mouse Dll4 in Artery Development," *Genes & Development*,18(20): 2474-2478 (2004).

During et al., "Controlled Release of Dopamine from a Polymeric Brain Implant: In Vivo Characterization," *Ann. Neurol.*, 25(4): 351-356 (1989).

Durocher et al., "High-level and high-throughput recombinant protein production by transient transfection of suspension-growing human 293-EBNA1 cells," *Nucl. Acids Res.*, 30(2): e9, (9 pages) (2002).

European Application No. 10752666.7: Communication Pursuant to Article 94(3) EPC, dated Mar. 15, 2013, 5 pages.

Foote et al., "Antibody Framework Residues Affecting the Conformation of the Hypervariable Loops," *J. Mol. Biol.*, 224(2): 487-499 (1992).

Fuchs et al., "Targeting Recombinant Antibodies to the Surface of *Escherichia coli*: Fusion to a Peptidoglycan Associated Lipoprotein," *Bio/Technology*, 9: 1369-1372 (1991).

Fukuda et al., "Notch ligand Delta-like 4 blockade attenuates atherosclerosis and metabolic disorders," *Proc. Natl. Acad. Sci. USA*, 109(27): E1868-1877 (2012).

Gale et al., "Haploinsufficiency of Delta-Like 4 Ligand Results in Embryonic Lethality Due to Major Defects in Arterial and Vascular Development," *Proc. Natl. Acad. Sci. USA*, 101(45): 15949-15954 (2004).

Garrard et al., "$F_{AB}$ Assembly and Enrichment in a Monovalent Phage Display System," *Bio/Technology*, 9: 1373-1377 (1991).

Gavilondo et al., "Antibody Engineering at the Millennium," *Biotechniques*, 29: 128-145 (2000).

Gennaro, A.R. (ed.) *Remington: The Science and Practice of Pharmacy*. 19th Edition, Mack Publishing, 1995; Table of Contents.

Giegé et al., Chapter 1, In *Crystallization of Nucleic Aids and Proteins, a Practical Approach*, 2nd ed., (Ducruix and Giegé, eds.) (Oxford University Press, New York, 1999) pp. 1-16.

Gillies et al., "High-Level Expression of Chimeric Antibodies Using Adapted cDNA Variable Region Cassettes." *J. Immunol. Meth.*, 125(1-2): 191-202.

Goldspiel et al., "Human Gene Therapy," *Clin. Pharm.*, 12: 488-505 (1993).

Goodson, J.M., "Dental Applications," Chapter 6, In Medical Applications of Controlled Release, vol. II, Applications and Evaluation, (Langer and Wise: eds.) (CRC Press, Inc., Boca Raton, 1984), pp. 115-138.

Gram et al., "In vitro selection and affinity maturation of antibodies from a naive combinatorial immunoglobulin library," *Proc. Natl. Acad. Sci. USA*. 89: 3576-3580 (1992).

Green et al., "Antigen-specific human monoclonal antibodies from mice engineered with human Ig heavy and light chain YACs," *Nature Genetics*, 7: 13-21 (1994).

Green et al., "Regulation of B Cell Development by Variable Gene Complexity in Mice Reconstituted with Human Immunoglobulin Yeast Artificial Chromosomes," *J. Exp. Med.*, 188(3): 483-495 (1998).

(56) References Cited

OTHER PUBLICATIONS

Griffiths et al., "Human anti-self antibodies with high specificity from phage display libraries," *EMBO J.*, 12(2): 725-734 (1993).
Hammerling et al., eds., "Appendix: Production of Antibody-Producing Hybridomas in the Rodent Systems," In *Monoclonal Antibodies and T-Cell Hybridomas. Research Monographs in Immunology*, vol. 3. (J.L. Turk, General Editor) (Elsevier, New York, 1981), pp. 563-587.
Harding et al., "The immunogenicity of humanized and fully human antibodies," *MAbs*, 2(3): 256-265 (2010).
Harlow et al., *Antibodies: A Laboratory Manual*. Cold Spring Harbor Laboratory, 1988: Table of Contents.
Harrington et al., "Regulation of Multiple Angiogenic Pathways by Dll4 and Notch in Human Umbilical Vein Endothelial Cells," *Microvasc. Res.*, 75(2): 144-154 (2008).
Hawkins et al., "Selection of Phage Antibodies by Binding Affinity Mimicking Affinity Maturation," *J. Mol. Biol.*, 226: 889/896 (1992).
Hay et al., "Bacteriophage cloning and *Escherichia coli* expression of a human IgM Fab," *Hum. Antibod. Hybridomas*, 3: 81-85 (1992).
Hildebrand et al., "Surface coatings for biological activation and functionalization of medical devices," *Surface & Coatings Technology*, 200; 6318-6324 (2006).
Hoey, "DLL4 Blockade Inhibits Tumor Growth and Reduces Tumor-Initiating Cell Frequency," *Cell Stem Cell*, 5: 168-177 (2009).
Holliger et al., "'Diabodies': Small bivalent and bispecific antibody fragments," *Proc. Natl. Acad. Sci. USA*, 90; 6444-6448 (1993).
Holm et al., "Functional mapping and single chain construction of the anti-cytokeratin 8 monoclonal antibody TS1," *Mol. Immunol.*, 44: 1075-1084 (2007).
Hoogenboom et al., "Multi-subunit proteins on the surface of filamentous phage: Methodologies for displaying antibody (Fab) heavy and light chains," *Nucl. Acids Res.*, 19(15): 4133-4137 (1991).
Hoogenboom et al., "Natural and designer binding sites made by phage display technology," *Immunol. Today*, 21(8): 371-378 (2000).
Hoogenboom, H.R., "Designing and optimizing library selection strategies for generating high-affinity antibodies," *Trends Biotechnol.*, 15: 62-70 (1997).
Howard et al., "Intracerebral drug delivery in rats with lesion-induced memory deficits," *J. Neurosurg.*, 71: 105-112 (1989).
Huber et al., "Crystallographic structure studies of an IgG molecule and an Fc fragment," *Nature*, 264: 415-420 (1976).
Huse et al., "Generation of a Large Combinatorial Library of the Immunoglobulin Repertoire in Phage Lambda," *Science*, 246: 1275-1281 (1989).
Huston et al., "Protein engineering of antibody binding sites: Recovery of specific activity in an anti-digoxin single-chain Fv analogue produced in *Escherichia coli*," *Proc. Natl. Acad. Sci. USA*, 85: 5879-5883 (1988).
Huston et al., "Protein Engineering of Single-Chain Fv Analogs and Fusion Proteins," *Methods Enzymol.*, 203: 46-88 (1991).
Inoue et al., "Vascular Endothelial Growth Factor (VEGF) Expression in Human Coronary Atherosclerotic Lesions; Possible Pathophysiological Significance of VEGF in Progression of Atherosclerosis" *Circulation*, 98: 2108-2116 (1998).
International Search Report for Application No. PCT/US2010/047006, mailed on Mar. 10, 2011, 23 pages.
Jackson et al., "In Vitro Antibody Maturation, Improvement of a High Affinity, Neutralizing Antibody Against IL-1β," *J. Immunol.*, 154(7): 3310-3319 (1995).
Johnsson et al., "Comparison of Methods for Immobilization to Carboxymethyl Dextran Sensor Surfaces by Analysis of the Specific Activity of Monoclonal Antibodies," *J. Mol. Recognit.*, 8: 125-131 (1995).
Johnsson et al., "Immobilization of Proteins to a Carboxymethyldextran-Modified Gold Surface for Biospecific Interaction Analysis in Surface Plasmon Resonance Sensors," *Anal. Biochem.*, 198: 268-277 (1991).
Joliot et al., "Antennapedia homeobox peptide regulates neural morphogenesis," *Proc. Natl. Acad. Sci. USA*, 88: 1864-1868 (1991).

Jones et al., "Replacing the complementarity-determining regions in a human antibody with those from a mouse," *Nature*, 321: 522-525 (1986).
Jonsson et al., "Introducing a biosensor based technology for real-time biospecific interaction analysis," *Ann. Biol. Clin.*, 51: 19-26 (1993).
Jonsson, et al., "Real-Time Biospecific Interaction Analysis Using Surface Plasmon Resonance and a Sensor Chip Technology," *BioTechniques*, 11(5): 620-627 (1991).
Kabat et al., "Attempts to Locate Complementarity-Determining Residues in the Variable Positions of Light and Heavy Chains," *Ann. NY Acad. Sci.*, 190: 382-391 (1971).
Kabat et al., *Sequences of Proteins of Immunological Interest*. 5th Edition, 1991; Table of Contents.
Kabat et al., *Sequences of Proteins of Immunological Interest*. 4th Edition, 1987; Table of Contents.
Kabat et al., *Sequences of Proteins of Immunological Interest*. 3rd Edition, 1983; Table of Contents.
Kaufman and Sharp, "Amplification and expression of sequences cotransfected with a modular dihydrofolate reductase complementary DNA gene," *J. Mol. Biol.*, 159(4): 601-621 (1982).
Kellerman et al., "Antibody discovery: The use of transgenic mice to generate human monoclonal antibodies for therapeutics," *Curr. Opin. Biotechnol.*, 13: 593-597 (2002).
Kettleborough et al., "Isolation of tumor cell-specific single-chain Fv from immunized mice using phage-antibody libraries and the reconstruction of whole antibodies from these antibody fragments," *Eur. J. Immunol.*, 24: 952-958 (1994).
Khamaisi et al., "The emerging role of VEGF in diabetic kidney disease," *Neprol. Dial. Transplant.*, 18(8):1427-1430 (2003).
Kim et al., "Identifying amino acid residues that influence plasma clearance of murine IgG1 fragments by site-directed mutagenesis," *Eur. J. Immunol.*, 24: 542-548 (1994).
Kipriyanov et al., "Recombinant Sinale-Chain Fv Fragments Carrying C-Terminal Cysteine Residues: Production of Bivlent and Biotinylated Miniantibodies," *Mol. Immunol.*, 31(14): 1047-1058 (1994).
Kipriyanov et al., "Single-Chain Antibody Streptavidin Fusions: Tetrameric Bifunctional scFv-Complexes with Biotin Binding Activity and Enhanced Affinity to Antigen," *Human Antibodies and Hybridomas*, 6(3): 93-101 (1995).
Kontermann et al. (Eds.), *Antibody Engineering*. Springer-Verlag, Berlin Heidelberg, 2001; Table of Contents.
Krebs et al., "Haploinsufficient Lethality and Formation of Arteriovenous Malformations in Notch Pathway Mutants," *Genes & Development*, 18(20): 2469-2473 (2004).
Krebs et al., "Notch Signaling is Essential for Vascular Morphogenesis in Mice," *Genes & Development*, 14(11): 1343-1352 (2000).
Kriegler, *Gene Transfer and Expression: A Laboratory Manual*. Stockton Press, 1990; Table of Contents.
Kyte et al., "A Simple Method for Displaying the Hydropathic Character of a Protein," *J. Mol. Biol.*, 157(1): 105-132 (1982).
Lam et al., "Microencapsulation of Recombinant Humanized Monoclonal Antibody for Local Delivery," *Proceed. Intl. Symp. Control Rel. Bioact. Mater.*, 24: 759-760 (1997).
Langer and Peppas, "Chemical and Physical Structure of Polymers as Carriers for Controlled Release of Bioactive Agents: A Review," *J. Macromol. Sci. RMC*, C23(1): 61-126 (1983).
Langer. R., "New Methods of Drug Delivery," *Science*, 249: 1527-1533 (1990).
Levy et al., "Inhibition of Calcification of Bioprosthetic Heart Valves by Local Controlled-Release Diphosphonate," *Science*, 228: 190-192 (1985).
Little et al., "Of mice and men: hybridoma and recombinant antibodies," *Immunol. Today*, 21(8): 364-370 (2000).
Liu et al., "Regulation of Notch1 and Dll4 by Vascular Endothelial Growth Factor in Arterial Endothelial Cells: Implications for Modulating Arteriogenesis and Angiogenesis," *Mol. Cell. Biol.*, 23(1): 14-25 (2003).
Lobov et al., "Delta-Like Ligand 4 (Dll4) Is induced by VEGF As a Negative Regulator of Angiogenic Sprouting," *Proc. Natl. Acad. Sci. USA*, 104(9): 3219-3224 (2007).

(56) References Cited

OTHER PUBLICATIONS

Lund et al., "Human Fc gamma RI and Fc gamma RII interact with distinct but overlapping sites on human IgG," *J. Immunol.*, 147: 2657-2662 (1991).
MacCallum et al., "Antibody-antigen Interactions: Contact Analysis and Binding Site Topography," *J. Mol. Biol.*, 262: 732-745 (1996).
Mailhos et al., "Delta4, an Endothelial Specific Notch Ligand Expressed at Sites of Physiological and Tumor Angiogenesis," *Differentiation*, 69(2-3): 134-144 (2001).
Marchalonis et al., "Evolutionary Factors in the Emergence of the Combinatorial Germline Antibody Repertoire," *Adv. Exp. Med. Biol.*, 484: 13-30 (2001).
Marks et al., "By-Passing Immunization: Building High Affinity Human Antibodies by Chain Shuffling," *Bio Technology*, 10: 779-783 (1992).
Marques et al., "Mediation of the Cytokine Network in the Implantation of Orthopedic Devices," Chapter 21, In *Biodegradable Systems in Tissue Engineering and Regenerative Medicine*, (Reis et al., eds.) (CRC Press LLC, Boca Raton, 2005) pp. 377-397.
Martin, A.C.R., "Protein Sequence and Structure Analysis of Antibody Variable Domains," Chapter 31, In *Antibody Engineering.* (Kontermann and Dübel, eds. ), (Springer-Verlag, Berlin, 2001), pp. 422-439.
McCafferty et al., "Phage antibodies: Filamentous phage displaying antibody variable domains," *Nature*, 348: 552-554 (1990).
Mendez et al., "Functional transplant of megabase human immunoglobulin loci recapitulates human antibody response in mice," *Nature Genet.*, 15: 146-156 (1997).
Miller et al., "Design, Construction, and In Vitro Analyses of Multivalent Antibodies," *J. Immunol.*, 170: 4854-4861 (2003).
Milstein et al., "Hybrid hybridomas and their use in immunohistochemistry," *Nature*, 305: 537-540 (1983).
Mizushima et al., "pEF-Bos, a powerful mammalian expression vector," *Nucl. Acids Res.*, 18(17): 5322 (1990).
Morgan and Anderson, "Human Gene Therapy," *Ann. Rev. Biochem.*, 62: 191-217 (1993).
Morrison et al., "Chimeric Human Antibody Molecules: Mouse Antigen-Binding Domains with Human Constant Region Domains," *Proc. Natl. Acad. Sci. USA*, 81(21): 6851-6855 (1984).
Morrison, "Transfectomas Provide Novel Chimeric Antibodies," *Science*, 229(4719): 1202-1207 (1985).
Mulligan, R.C., "The Basic Science of Gene Therapy," *Science*, 260: 926-932 (1993).
Mullinax et al., "Expression of a Heterodimeric Fab Antibody Protein in One Cloning Step," *BioTechniques*, 12(6): 864-869 (1992).
Nakatsu et al., "Angiogenic Sprouting and Capillary Lumen Formation Modeled by Human Umbilical Vein Endothelial Cells (HUVEC) in Fibrin Gels: The Role of Fibroblasts and Angiopoietin-1," *Microvasc. Res.*, 66(2): 102-112 (2003).
Neuberger et al., "Recombinant Antibodies Possessing Novel Effector Functions," *Nature*, 312(5995): 604-608 (1984).
Ning et al., "Intratumoral radioimmunotherapy of a human colon cancer xenograft using a sustained-release gel," *Radiotherapy Oncol.*, 39: 179-189 (1996).
Noguera-Troise et al., "Blockade of Dll4 Inhibits Tumour Growth by Promoting Non-Productive Angiogenesis," *Nature*, 444(7122): 1032-1037 (2006).
Ol et al., "Chimeric Antibodies," *Bio Techniques*, 4(3): 214-221 (1986).
Padlan et al., "Identification of specificity-determining residues in antibodies," *FASEB J.*, 9: 133-139 (1995).
Padlan, E.A., "A Possible Procedure for Reducing the Immunogenicity of Antibody Variable Domains While Preserving Their Ligand-Binding Properties," *Mol. Immunol.*, 28(4/5): 489-498 (1991).
Partial International Search Report for Application No. PCT/US2010/047006, mailed Nov. 22, 2010, 5 pages.
Pascalis et al., *J. Immunol.*, 169: 3076-3084 (2002).
Patel et al., "Up-Regulation of Delta-Like 4 Ligand in Human Tumor Vasculature and the Role of Basal Expression in Endothelial Cell Function," *Cancer Research*, 65(19): 8690-8697 (2005).
Patel et al., "Up-Regulation of Endothelial Delta-Like 4 Expression Correlates with Vessel Maturation in Bladder Cancer," *Clin. Cancer Res.*, 12(16): 4836-4844 (2006).
Persic et al., "An integrated vector system for the eukaryotic expression of antibodies or their fragments after seletion from phage display libraries," *Gene*, 187: 9-18 (1997).
Poljak, R.J., "Production and structure of diabodies," *Structure*, 2: 1121-1123 (1994).
Presta et al., "Humanization of an Antibody Directed Against IgE," *J. Immunol.*, (5): 2623-2632 (1993).
Remmele et al., "Differential Scanning Calorimetry: A Practical Tool for Elucidating Stability of liquid Biophormaceuticals," *Biopharm*, 13: 36-46 (2000).
Remmele et al., "Interleukin-1 Receptor (IL-1R) Liquid Formulation Development using Differential Scanning Calorimetry," *Pharmaceutical Research*, 15(2): 200-208 (1998).
Ridgway et al., "Inhibition of Dll4 Signalling Inhibits Tumour Growth by Deregulating Angiogenesis," *Nature*, 444(7122): 1083-1087 (2006).
Rechmann et al., "Reshaping human antibodies for therapy," *Nature*, 332: 323-327 (1988).
Roberts et al., "RNA-peptide fusions for the in vitro selection of peptides and proteins," *Proc. Natl. Acad. Sci. USA*, 94: 12297-12302 (1997).
Robinson, "Gene therapy—proceeding from laboratory to clinic," *Trends Biotechnol.*, 11(5): 155 (1993) (1 page).
Robinson, *Sustained and Controlled Release Drug Delivery Systems*. Marcel Dekker, Inc., 1978; Table of Contents.
Roguska et al., "Humanization of murine monoclonal antibodies through variable domain resurfacing," *Proc. Natl. Acad. Sci. USA*, 91: 969-973 (1994).
Rudikoff et al., "Single amino acid substitution altering antigen binding specificity," *Proc. Natl. Acad. Sci. USA*, 79: 1979-1983 (1982).
Sainson, "Anti-Dll4 Therapy: Can We Block Tumour Growth by Increasing Angiogenesis?" *Trends Mol. Med.*, 13(9): 389-395 (2007).
Sambrook and Russell (eds.), "Expression of Cloned Genes in *Escherichia coli*," in *Molecular Cloning: A Laboratory Manual.* 2nd Ed., Cold Spring Harbor Laboratory Press, Cold Spring Harbor, NY, 1989.
Saudek et al., "A Preliminary Trial of the Programmable Implantable Medication System for Insulin Delivery," *N. Engl. J. Med.*, 321: 574-579 (1989).
Sawai et al., "Direct Production of the Fab Fragment Derived From the Sperm Immobilizing Antibody Using Polymerase Chain Reaction and cDNA Expression Vectors," *Am. J. Reprod. Immunol.*, 34: 26-34 (1995).
Scehnet et al., "Inhibition of Dll4-Mediated Signaling Induces Proliferation of Immature Vessels and Results in Poor Tissue Perfusion," *Blood*, 109(11): 4753-4760 (2007).
Schier et al., "Identification of functional and structural amino-acid residues by parsimonious mutagenesis," *Gene*, 169: 147-155 (1995).
Sefton, M.V., "Implantable Pumps," *CRC Crit. Rev. Biomed. Eng.*, 14(3): 201-240 (1987).
Seligmann et al., "Immunochemical Study of a Human Myeloma IgG1 Half Molecule," *Ann. Immunol.*, 129 C: 855-870 (1978).
Shapiro et al., "DNA Target Motifs of Somatic Mutagenesis in Antibody Genes," *Crit. Rev. Immunol.*, 22(3): 183-200 (2002).
Shu et al., "Secretion of a single-gene-encoded immunoglobulin from myeloma celis," *Proc. Natl. Acad. Sci. USA*, 90: 7995-7999 (1993).
Shutter et al., "Dll4, a Novel Notch Ligand Expressed in Arterial Endothelium," *Genes & Development*, 14 (11): 1313-1318 (2000).
Sims et al., "A Humanized CD18 Antibody Can Block Function without Cell Destruction," *J. Immunol.*, 151(4): 2296-2308 (1993).
Skerra et al., "Assembly of a Functional Immunoglobulin $F_v$, Fragment in *Escherichia coli*," *Science*, 240: 1038-1041 (1988).
Smolen et al. (Eds.), *Controlled Drug Bioavailability: Drug Product Design and Performance.* vol. 1, John Wiley & Sons, 1984; Table of Contents.
Song et al., "Antibody Mediated Lung Targeting of Long-Circulating Emulsions," *PDA J. Pharm. Sci. Technol.*, 50: 372-377 (1996).

(56) References Cited

OTHER PUBLICATIONS

Staerz et al., "Hybrid antibodies can target sites for attack by T cells," *Nature*, 314: 628-631 (1985).

Studnicka et al., "Human-engineered monoclonal antibodies retain full specific binding activity by preserving non-CDR complementarity-modulating residues," *Protein Eng.*, 7(6): 805-814 (1994).

Suchting et al., "The Notch Ligand Delta-Like 4 Negatively Regulates Endothelial Tip Cell Formation and Vessel Branching," *Proc. Natl. Acad. Sci. USA*, 104(9): 3225-3230 (2007).

Takeda et al., "Construction of Chimaeric Processed Immunoglobulin Genes Containing Mouse Variable and Human Constant Region Sequences," *Nature*, 314(6010): 452-454 (1985).

Taylor et al., "A transgenic mouse that expresses a diversity of human sequence heavy and light chain immunoglobulins," *Nucl. Acids Res.*, 20: 6287-6295 (1992).

Thies et al., "Folding and Association of the Antibody Domain $C_H3$: Prolyl Isomerization Preceeds Dimerization," *J. Mol. Biol.*, 293: 67-79 (1999).

Tolstoshev, "Gene Therapy, Concepts, Current Trials and Future Directions," *Ann. Rev. Pharmacol. Toxicol.*, 32: 573-596 (1993).

Urlaub et al., "Isolation of Chinese hamster cell mutants deficient in dihydrofolate reductase activity," *Proc. Natl. Acad. Sci. USA*, 77: 4216-4220 (1980).

Vajdos et al., "Comprehensive functional maps of the antigen-binding site of an anti-ErbB2 antibody obtained with shotgun scanning mutagenesis," *J. Mol. Biol.*, 320: 415-428 (2002).

Verhoeyen et al., "Reshaping Human Antibodies: Grafting an Antilysozyme Activity," *Science*, 239: 1534-1536 (1988).

Von Mehren et al., "Monoclonal Antibody Therapy for Cancer," *Ann. Rev. Med.*, 54: 343-369 (2003).

Ward at al., "Binding activities of a repertoire of single immunoglobulin variable domains secreted from *Escheria coli*," *Nature*. 341: 544-546 (1989).

West Jr. et al., "Crystal Structure and Immunoglobulin G Binding Properties of the Human Major Histocompatibility Complex-Related Fc Receptor," *Biochemistry*, 39: 9698-9708 (2000).

Winnacker, "Introduction of Gene Technology" in: *From Genes to Clones*. Weller M.G. (Ed.), VCH Publisher, 1987; Table of Contents.

Wu and Grainger, "Drug/device combinations for local drug therapies and infection prophylaxis," *Biomaterials*, 27: 2450-2467 (2006).

Wu and Wu, "Delivery systems for gene therapy," *Biotherapy*, 3: 87-95 (1991).

Wu and Wu, "Receptor-mediated in Vitro Gene Tranformation by a Soluble DNA Carrier System," *J. Biol. Chem.*, 262(10): 4429-4432 (1987).

Wu et al., "Humanization of a murine monoclonal antibody by simultaneous optimization of framework and CDR residues," *J. Mol. Biol.*, 294: 151-162 (1999).

Wu et al., "Simultaneous targeting of multiple disease mediators by a dual-variable-domain immunoglobulin," *Nature Biotechnol.*, 25(11): 1290-1297 (2007).

Yan et al., "Delta-Like 4/Notch Signaling and its Therapeutic Implications," *Clinical Cancer Research*, 13(24): 7243-7246 (2007).

Yelton et al., "Affinity Maturation of the BR96 Anti-Carcinoma Antibody by Codon-Based Mutagenesis," *J. Immunol.*, 155: 1994-2004 (1995).

Zapata et al., "Engineering linear F(ab')$_2$ fragments for efficient production in *Escherichia coli* and enhanced antiproliferative activity," *Protein Eng.*, 8(10): 1057-1062 (1995).

U.S. Appl. No. 14/301,305, filed Jun. 10, 2014 by Ghayur et al.
U.S. Appl. No. 14/219,511, filed Mar. 19, 2014 by Ghayur et al.
U.S. Appl. No. 14/135,107, filed Dec. 19, 2013 by Ghayur at al.
U.S. Appl. No. 14/135,126, filed Dec. 19, 2013 by Ghayur et al.
U.S. Appl. No. 14/301,546, filed Jun. 11, 2014 by Gu et al.
U.S. Appl. No. 14/211,596, filed Mar. 14, 2014 by Ghayur et al.
U.S. Appl. No. 14/211,604, filed Mar. 14, 2014 by Ghayur et al.
"Infliximab," in *The Merck Index*. 14th Ed., John Wiley & Sons, 2006; p. 863.

European Application No. 11751147.7: Extended European Search Report, dated Nov. 7, 2013, 13 pages.

Furukawa et al., "A Role of the Third Complementarity-determining Region in the Affinity Maturation of an Antibody," *J. Biol. Chem.*, 276:27622-27628 (2001).

Harlow et al., *Antibodies: A Laboratory Manual*. Cold Spring Harbor Laboratory, 1988; pp. 555-561, 578-582, and 591-592.

International Search Report and Written Opinion for Application No. PCT/US11/26489, mailed Aug. 22, 2011, 15 pages.

Köhler et al., "Continuous Cultures of Fused Cells Secreting Antibody of Predefined Specificity," *Nature*, 256(5517): 495-497 (1975).

Lamminmäki et al., "Crystal Structure of a Recombinant Anti-estradiol Fab Fragment in Complex with 17β-Estradiol," *J. Biol. Chem.*, 276(39): 36687-36694 (2001).

Padlan et al., "Structure of an antibody-antigen complex: Crystal structure of the HyHEL-10 Fab-lysozyme complex," *Proc. Natl. Acad. Sci., USA*, 86: 5938-5942 (1989).

Presta et al., "Engineering of Therapeutic Antibodies to Minimize Immunogenicity and Optimize Function," *Adv. Drug Del. Rev.*, 58(5-6): 640-656 (2006).

Remington, *The Science and Practice of Pharmacy*; Table of Contents, 1995.

U.S. Appl. No. 14/327,306, filed Jul. 9, 2014 by Ghayur et al.
U.S. Appl. No. 14/332,087, filed Jul. 15, 2014 by Ghayur et al.

* cited by examiner

THERAPEUTIC DLL4 BINDING PROTEINS

REFERENCE TO RELATED APPLICATIONS

This application is a division of U.S. application Ser. No. 12/870,276 filed Aug. 27, 2010, which claims priority to U.S. provisional application No. 61/238,152, filed Aug. 29, 2009, and to U.S. provisional application No. 61/261,728, filed Nov. 16, 2009. All of the aforementioned applications are incorporated by reference in their entireties.

FIELD OF THE INVENTION

The present invention relates to the development and use of improved DLL4 binding proteins and uses thereof in the inhibition, prevention, and/or treatment of cancers, tumors, and/or other angiogenesis-dependent diseases such as ocular neovascularization, or angiogenesis-independent diseases characterized by aberrant DLL4 expression or activity such as autoimmune disorders.

BACKGROUND OF THE INVENTION

Cell-to-cell communication is required for many biological processes such as differentiation, proliferation, and homeostasis. One system utilized by a wide range of eukaryotes is the Notch-signaling pathway. This pathway, especially the Notch receptor, is also critical for functional tumor angiogenesis. Thus, inhibition of Notch receptor function, blockage of the Notch receptor, and/or blockage of the Notch-signaling pathway are potential strategies for anti-cancer compositions and therapies. Small molecule inhibitors of the Notch receptor have proven to be toxic because they suppress wild type (normal) tissue expression of Notch receptors throughout the body. Thus, different members of the Notch-signaling pathway should be considered as potential targets for therapeutics.

A vasculature ligand for the Notch receptor is Delta 4 or Delta-like 4 (DLL4). Largely expressed in the vasculature, DLL4 is critical for vascular development (Yan et al., *Clin. Cancer Res.*, 13(24): 7243-7246 (2007); Shutter et al., *Genes Dev.*, 14(11): 1313-1318 (2000); Gale et al., *Proc. Natl. Acad. Sci. USA*, 101(45): 15949-15954 (2004); Krebs et al., *Genes Dev.*, 14(11): 1343-1352 (2000)). Mice heterozygous for DLL4 are embryonically lethal due to major defects in vascular development (Gale et al., *Proc. Natl. Acad. Sci. USA*, 101(45): 15949-15954 (2004); Duarte et al., *Genes Dev.*, 18(20): 2474-2478 (2004); Krebs et al., *Genes Dev.*, 18(20): 2469-2473 (2004)). The expression of DLL4 can be induced by VEGF (Liu et al., *Mol. Cell Biol.*, 23(1): 14-25 (2003); Lobov et al., *Proc. Natl. Acad. Sci. USA*, 104(9): 3219-3224 (2007)). In turn, DLL4 can negatively regulate VEGF signaling, in part through repressing VEGFR2 and inducing VEGR1 (Harrington et al., *Microvasc. Res.*, 75(2): 144-154 (2008); Suchting et al., *Proc. Natl. Acad. Sci. USA*, 104(9): 3225-3230 (2007)). Exquisite coordination between DLL4 and VEGF is essential for functional angiogenesis.

In addition to its physiological role, DLL4 is up-regulated in tumor blood vessels (Gale et al., *Proc. Natl. Acad. Sci. USA*, 101(45): 15949-15954 (2004); Mailhos et al., *Differentiation*, 69(2-3): 135-144 (2001); Patel et al., *Cancer Res.*, 65(19): 8690-8697 (2005); Patel et al., *Clin. Cancer Res.*, 12(16): 4836-4844 (2006); Noguera-Troise et al., *Nature*, 444(7122): 1032-1037 (2006)). Blockade of DLL4 potently inhibited primary tumor growth in multiple models (Noguera-Troise et al., *Nature*, 444(7122): 1032-1037 (2006); Ridgway et al., *Nature*, 444(7122): 1083-1087 (2006); Scehnet et al., *Blood*, 109(11): 4753-4760 (2007)). The inhibition of DLL4 was even effective against tumors that are resistant to anti-VEGF therapy. The combinatorial inhibition of both DLL4 and VEGF provided an enhanced anti-tumor activity. Interestingly, unlike VEGF inhibition that reduces tumor vessel formation, DLL4 blockade leads to an increase in tumor vasculature density wherein the vessels are abnormal, cannot support efficient blood transport, and are effectively nonfunctional. Thus, DLL4 provides a potential target for cancer treatment.

There is a need in the art for therapeutic agents capable of targeting the DLL4-Notch pathway and thereby inhibiting, or even preventing, tumor angiogenesis and growth.

SUMMARY OF THE INVENTION

The invention provides proteins that bind DLL4, including antibodies, CDR-grafted antibodies, and binding fragments thereof, that are capable of binding DLL4. Preferably, a binding protein described herein binds DLL4 with high affinity. More preferably, a binding protein according to the invention is capable of neutralizing DLL4. The invention also provides methods of making and using DLL4 binding proteins, including human DLL4 binding proteins. Advantageously, the invention eliminates the need to prepare humanized DLL4 binding proteins; thereby, eliminating the complications associated with humanized DLL4 binding proteins.

One aspect of this invention pertains to a binding protein comprising an antigen binding domain capable of binding human DLL4, said antigen binding domain comprising at least one or more CDRs selected from the group consisting of:

CDR-H1:  $X_1-X_2-X_3-X_4-X_5-X_6-X_7$, (SEQ ID NO: 99)

wherein;
$X_1$ is S or N;
$X_2$ is S, G, or N;
$X_3$ is S, N, T, G, or R;
$X_4$ is Y;
$X_5$ is Y or H;
$X_6$ is W; and
$X_7$ is G;

CDR H2: $X_1-X_2-X_3-X_4-X_5-X_6-X_7-X_8-X_9-X_{10}-X_{11}-X_{12}-X_{13}-X_{14}-X_{15}-X_{16}$, (SEQ ID NO: 100)

wherein;
$X_1$ is D;
$X_2$ is I;
$X_3$ is Y, N, or S;
$X_4$ is Y;
$X_5$ is T, N, A, I, S, or R;
$X_6$ is G;
$X_7$ is S, N, T, or G;
$X_8$ is T;
$X_9$ is Y;
$X_{10}$ is Y;
$X_{11}$ is N;
$X_{12}$ is P;
$X_{13}$ is S;
$X_{14}$ is L;
$X_{15}$ is K; and
$X_{16}$ is S, N, D, or G;

CDR-H3:  X₁-X₂-X₃-X₄-X₅-X₆-X₇-X₈-X₉-X₁₀-X₁₁,  (SEQ ID NO: 101)

wherein;
X₁ is E, Y, F, Q, W, L, or A;
X₂ is D, A, S, G, V, E, or N;
X₃ is V, M, L, P, or A;
X₄ is I, A, P, R, S, K, Q, V, G, M, or E;
X₅ is L, Y, F, or M;
X₆ is R, G, S, Q, or A;
X₇ is G;
X₈ is G, A, or S;
X₉ is S, A, L, V, R, or G;
X₁₀ is D; and
X₁₁ is Y, D, S, N, H, E, R, L, P, C, I, M, T, Q, or K;

CDR-L1:  X₁-X₂-X₃-X₄-X₅-X₆-X₇-X₈-X₉-X₁₀-X₁₁,  (SEQ ID NO: 102)

wherein;
X₁ is S;
X₂ is G;
X₃ is Q, E, or D;
X₄ is R, S, G, M, K, L, or T;
X₅ is L;
X₆ is G;
X₇ is D or E;
X₈ is K;
X₉ is Y;
X₁₀ is A or V; and
X₁₁ is S;

CDR-L2:  X₁-X₂-X₃-X₄-X₅-X₆-X₇,  (SEQ ID NO: 103)

wherein;
X₁ is E or Q;
X₂ is D;
X₃ is S, L, T, A, E, or F;
X₄ is K, T, E, N, Q, S, or M;
X₅ is R;
X₆ is P; and
X₇ is S;
and

CDR-L3:  X₁-X₂-X₃-X₄-X₅-X₆-X₇-X₈-X₉,  (SEQ ID NO: 104)

wherein;
X₁ is Q;
X₂ is A;
X₃ is W;
X₄ is D;
X₅ is R, S, M, E, N, G, or K;
X₆ is D or E;
X₇ is T, V, A, S, or M;
X₈ is G, A, or C; and
X₉ is V.

Preferably, the antigen binding domain of a DLL4 binding protein of the invention comprises at least one CDR comprising an amino acid sequence selected from the group consisting of:
residues 31-37 of SEQ ID NO:1 (CDR-H1); residues 52-67 of SEQ ID NO:1 (CDR-H2); residues 100-110 of SEQ ID NO:1 (CDR-H3);
residues 23-33 of SEQ ID NO:111 (CDR-L1); residues 49-55 of SEQ ID NO:111 (CDR-L2); residues 88-96 of SEQ ID NO:111 (CDR-L3);
SEQ ID NO:117 (CDR-H1); SEQ ID NO:118 (CDR-H2); SEQ ID NO:119 (CDR-H3); SEQ ID NO:121 (CDR-H1); SEQ ID NO:122 (CDR-H2); SEQ ID NO:123 (CDR-H3); SEQ ID NO:125 (CDR-H1); SEQ ID NO:126 (CDR-H2); SEQ ID NO:127 (CDR-H3); SEQ ID NO:129 (CDR-H1); SEQ ID NO:130 (CDR-H2); SEQ ID NO:131 (CDR-H3); SEQ ID NO:133 (CDR-H1); SEQ ID NO:134 (CDR-H2); SEQ ID NO:135 (CDR-H3); SEQ ID NO:137 (CDR-H1); SEQ ID NO:138 (CDR-H2); SEQ ID NO:139 (CDR-H3); SEQ ID NO:141 (CDR-H1); SEQ ID NO:142 (CDR-H2); SEQ ID NO:143 (CDR-H3); SEQ ID NO:145 (CDR-H1); SEQ ID NO:146 (CDR-H2); SEQ ID NO:147 (CDR-H3); SEQ ID NO:149 (CDR-H1); SEQ ID NO:150 (CDR-H2); SEQ ID NO:151 (CDR-H3); SEQ ID NO:153 (CDR-H1); SEQ ID NO:154 (CDR-H2); SEQ ID NO:155 (CDR-H3); SEQ ID NO:157 (CDR-H1); SEQ ID NO:158 (CDR-H2); SEQ ID NO:159 (CDR-H3); SEQ ID NO:161 (CDR-H1); SEQ ID NO:162 (CDR-H2); SEQ ID NO:163 (CDR-H3); SEQ ID NO:165 (CDR-H1); SEQ ID NO:166 (CDR-H2); SEQ ID NO:167 (CDR-H3); SEQ ID NO:169 (CDR-H1); SEQ ID NO:170 (CDR-H2); SEQ ID NO:171 (CDR-H3); SEQ ID NO:173 (CDR-H1); SEQ ID NO:174 (CDR-H2); SEQ ID NO:175 (CDR-H3); SEQ ID NO:177 (CDR-H1); SEQ ID NO:178 (CDR-H2); SEQ ID NO:179 (CDR-H3); SEQ ID NO:181 (CDR-H1); SEQ ID NO:182 (CDR-H2); SEQ ID NO:183 (CDR-H3); SEQ ID NO:185 (CDR-H1); SEQ ID NO:186 (CDR-H2); SEQ ID NO:187 (CDR-H3); SEQ ID NO:189 (CDR-H1); SEQ ID NO:190 (CDR-H2); SEQ ID NO:191 (CDR-H3); SEQ ID NO:193 (CDR-H1); SEQ ID NO:194 (CDR-H2); SEQ ID NO:195 (CDR-H3); SEQ ID NO:197 (CDR-H1); SEQ ID NO:198 (CDR-H2); SEQ ID NO:199 (CDR-H3); SEQ ID NO:201 (CDR-H1); SEQ ID NO:202 (CDR-H2); SEQ ID NO:203 (CDR-H3); SEQ ID NO:205 (CDR-H1); SEQ ID NO:206 (CDR-H2); SEQ ID NO:207 (CDR-H1); SEQ ID NO:209 (CDR-H1); SEQ ID NO:210 (CDR-H2); SEQ ID NO:211 (CDR-H3); SEQ ID NO:213 (CDR-H1); SEQ ID NO:214 (CDR-H2); SEQ ID NO:215 (CDR-H3); SEQ ID NO:217 (CDR-L1); SEQ ID NO:218 (CDR-L2); SEQ ID NO:219 (CDR-L3); SEQ ID NO:221 (CDR-L1); SEQ ID NO:222 (CDR-L2); SEQ ID NO:223 (CDR-L3); SEQ ID NO:225 (CDR-L1); SEQ ID NO:226 (CDR-L2); SEQ ID NO:227 (CDR-L3); SEQ ID NO:229 (CDR-L1); SEQ ID NO:230 (CDR-L2); SEQ ID NO:231 (CDR-L3); SEQ ID NO:233 (CDR-L1); SEQ ID NO:234 (CDR-L2); SEQ ID NO:235 (CDR-L3); SEQ ID NO:237 (CDR-L1); SEQ ID NO:238 (CDR-L2); SEQ ID NO:239 (CDR-L3); SEQ ID NO:241 (CDR-L1); SEQ ID NO:242 (CDR-L2); SEQ ID NO:243 (CDR-L3); SEQ ID NO:245 (CDR-L1); SEQ ID NO:246 (CDR-L2); SEQ ID NO:247 (CDR-L3); SEQ ID NO:249 (CDR-L1); SEQ ID NO:250 (CDR-L2); SEQ ID NO:251 (CDR-L3); SEQ ID NO:253 (CDR-L1); SEQ ID NO:254 (CDR-L2); SEQ ID NO:255 (CDR-L3); SEQ ID NO:257 (CDR-L1); SEQ ID NO:258 (CDR-L2); SEQ ID NO:259 (CDR-L3); SEQ ID NO:261 (CDR-L1); SEQ ID NO:262 (CDR-L2); SEQ ID NO:263 (CDR-L3); SEQ ID NO:265 (CDR-L1); SEQ ID NO:266 (CDR-L2); SEQ ID NO:267 (CDR-L3); SEQ ID NO:269 (CDR-L1); SEQ ID NO:270 (CDR-L2); SEQ ID NO:271 (CDR-L3); SEQ ID NO:273 (CDR-L1); SEQ ID NO:274 (CDR-L2); SEQ ID NO:275 (CDR-L3); SEQ ID NO:277 (CDR-L1); SEQ ID NO:278 (CDR-L2); SEQ ID NO:279 (CDR-L3); SEQ ID NO:281 (CDR-L1); SEQ ID NO:282 (CDR-L2); SEQ ID NO:283 (CDR-L3); SEQ ID NO:285 (CDR-L1); SEQ ID NO:286 (CDR-L2); SEQ ID NO:287 (CDR-L3); SEQ ID NO:289 (CDR-L1); SEQ ID NO:290 (CDR-L2); SEQ ID NO:291 (CDR-L3); SEQ ID NO:293 (CDR-L1); SEQ ID NO:294 (CDR-L2); SEQ ID NO:295 (CDR-L3); SEQ ID NO:297 (CDR-L1); SEQ ID NO:298 (CDR-L2); SEQ ID NO:299 (CDR-L3); SEQ ID NO:301 (CDR-L1); SEQ ID NO:302 (CDR-L2); SEQ ID NO:303 (CDR-L3); SEQ ID NO:305 (CDR-L1); SEQ ID NO:306 (CDR-L2); SEQ ID NO:307 (CDR-L3); SEQ ID NO:309 (CDR-L1); SEQ ID NO:310 (CDR-L2); SEQ ID NO:311 (CDR-L3); SEQ ID NO:313 (CDR-L1); SEQ ID NO:314 (CDR-L2); SEQ ID NO:315 (CDR-L3);

residues 31-37 of SEQ ID NO:334 (CDR-H1); residues 52-67 of SEQ ID NO:334 (CDR-H2); residues 100-110 of SEQ ID NO:334 (CDR-H3);

residues 23-33 of SEQ ID NO:335 (CDR-L1); residues 49-55 of SEQ ID NO:335 (CDR-L2); residues 88-96 of SEQ ID NO:335 (CDR-L3);

residues 31-37 of SEQ ID NO:336 (CDR-H1); residues 52-67 of SEQ ID NO:336 (CDR-H2); residues 100-110 of SEQ ID NO:336 (CDR-H3);

residues 23-33 of SEQ ID NO:337 (CDR-L1); residues 49-55 of SEQ ID NO:337 (CDR-L2); residues 88-96 of SEQ ID NO:337 (CDR-L3);

residues 31-37 of SEQ ID NO:338 (CDR-H1); residues 52-67 of SEQ ID NO:338 (CDR-H2); residues 100-110 of SEQ ID NO:338 (CDR-H3);

residues 23-33 of SEQ ID NO:339 (CDR-L1); residues 49-55 of SEQ ID NO:339 (CDR-L2); residues 88-96 of SEQ ID NO:339 (CDR-L3);

residues 31-37 of SEQ ID NO:340 (CDR-H1); residues 52-67 of SEQ ID NO:340 (CDR-H2); residues 100-110 of SEQ ID NO:340 (CDR-H3);

residues 23-33 of SEQ ID NO:341 (CDR-L1); residues 49-55 of SEQ ID NO:341 (CDR-L2); residues 88-96 of SEQ ID NO:341 (CDR-L3);

residues 31-37 of SEQ ID NO:342 (CDR-H1); residues 52-67 of SEQ ID NO:342 (CDR-H2); residues 100-110 of SEQ ID NO:342 (CDR-H3);

residues 23-33 of SEQ ID NO:343 (CDR-L1); residues 49-55 of SEQ ID NO:343 (CDR-L2); residues 88-96 of SEQ ID NO:343 (CDR-L3);

residues 31-37 of SEQ ID NO:344 (CDR-H1); residues 52-67 of SEQ ID NO:344 (CDR-H2); residues 100-110 of SEQ ID NO:344 (CDR-H3);

residues 24-34 of SEQ ID NO:345 (CDR-L1); residues 50-56 of SEQ ID NO:345 (CDR-L2); residues 89-97 of SEQ ID NO:345 (CDR-L3);

residues 31-37 of SEQ ID NO:346 (CDR-H1); residues 52-67 of SEQ ID NO:346 (CDR-H2); residues 100-110 of SEQ ID NO:346 (CDR-H3);

residues 23-33 of SEQ ID NO:347 (CDR-L1); residues 49-55 of SEQ ID NO:347 (CDR-L2); residues 88-96 of SEQ ID NO:347 (CDR-L3);

residues 31-37 of SEQ ID NO:348 (CDR-H1); residues 52-67 of SEQ ID NO:348 (CDR-H2); residues 100-110 of SEQ ID NO:348 (CDR-H3);

residues 24-34 of SEQ ID NO:349 (CDR-L1); residues 50-56 of SEQ ID NO:349 (CDR-L2); residues 89-97 of SEQ ID NO:349 (CDR-L3);

residues 31-37 of SEQ ID NO:350 (CDR-H1); residues 52-67 of SEQ ID NO:350 (CDR-H2); residues 100-110 of SEQ ID NO:350 (CDR-H3);

residues 24-34 of SEQ ID NO:351 (CDR-L1); residues 50-56 of SEQ ID NO:351 (CDR-L2); residues 89-97 of SEQ ID NO:351 (CDR-L3);

residues 31-37 of SEQ ID NO:352 (CDR-H1); residues 52-67 of SEQ ID NO:352 (CDR-H2); residues 100-110 of SEQ ID NO:352 (CDR-H3);

residues 24-34 of SEQ ID NO:353 (CDR-L1); residues 50-56 of SEQ ID NO:353 (CDR-L2); residues 89-97 of SEQ ID NO:353 (CDR-L3);

residues 31-37 of SEQ ID NO:354 (CDR-H1); residues 52-67 of SEQ ID NO:354 (CDR-H2); residues 100-110 of SEQ ID NO:354 (CDR-H3);

residues 24-34 of SEQ ID NO:355 (CDR-L1); residues 50-56 of SEQ ID NO:355 (CDR-L2); residues 89-97 of SEQ ID NO:355 (CDR-L3);

residues 31-37 of SEQ ID NO:356 (CDR-H1); residues 52-67 of SEQ ID NO:356 (CDR-H2); residues 100-110 of SEQ ID NO:356 (CDR-H3);

residues 23-33 of SEQ ID NO:357 (CDR-L1); residues 49-55 of SEQ ID NO:357 (CDR-L2); residues 88-96 of SEQ ID NO:357 (CDR-L3);

residues 31-37 of SEQ ID NO:358 (CDR-H1); residues 52-67 of SEQ ID NO:358 (CDR-H2); residues 100-110 of SEQ ID NO:358 (CDR-H3);

residues 23-33 of SEQ ID NO:359 (CDR-L1); residues 49-55 of SEQ ID NO:359 (CDR-L2); residues 88-96 of SEQ ID NO:359 (CDR-L3);

residues 31-37 of SEQ ID NO:360 (CDR-H1); residues 52-67 of SEQ ID NO:360 (CDR-H2); residues 100-110 of SEQ ID NO:360 (CDR-H3);

residues 23-33 of SEQ ID NO:361 (CDR-L1); residues 49-55 of SEQ ID NO:361 (CDR-L2); residues 88-96 of SEQ ID NO:361 (CDR-L3).

In another embodiment, the binding protein comprises at least 3 CDRs disclosed above.

Preferably, a DLL4 binding protein according to the invention comprises one or more CDRs disclosed above. More preferably, the binding protein comprises three or more CDRs disclosed above. Most preferably, a DLL4 binding protein according to the invention comprises six CDRs described above, i.e., a CDR-H1, a CDR-H2, a CDR-H3, a CDR-L1, a CDR-L2, and a CDR-L3 described above.

In a preferred embodiment, the binding protein comprises at least 3 CDRs selected from the group consisting of the sequences disclosed above.

More preferably, the binding protein comprises 3 CDRs selected from a set of variable domain CDRs selected from the group below.

VH E9 CDR Set
CDR-H1: residues 31-37 of SEQ ID NO:1
CDR-H2: residues 52-67 of SEQ ID NO:1
CDR-H3 residues 100-110 of SEQ ID NO:1
VL E9 CDR Set
CDR-L1: residues 23-33 of SEQ ID NO:111
CDR-L2: residues 49-55 of SEQ ID NO:111
CDR-L3: residues 88-96 of SEQ ID NO:111
VH E9.4 CDR Set
CDR-H1: SEQ ID NO:117
CDR-H2: SEQ ID NO:118
CDR-H3: SEQ ID NO:119

VL E9.4 CDR Set
CDR-L1: SEQ ID NO:229
CDR-L2: SEQ ID NO:230
CDR-L3: SEQ ID NO:231
VH E9.11 CDR Set
CDR-H1: SEQ ID NO:121
CDR-H2: SEQ ID NO:122
CDR-H3: SEQ ID NO:123
VL E9.11 CDR Set
CDR-L1: SEQ ID NO:233
CDR-L2: SEQ ID NO:234
CDR-L3: SEQ ID NO:235
VH E9.14 CDR Set
CDR-H1: SEQ ID NO:125
CDR-H2: SEQ ID NO:126
CDR-H3: SEQ ID NO:127
VL E9.14 CDR Set
CDR-L1: SEQ ID NO:237
CDR-L2: SEQ ID NO:238
CDR-L3: SEQ ID NO:239
VH E9.17 CDR Set
CDR-H1: SEQ ID NO:129
CDR-H2: SEQ ID NO:130
CDR-H3: SEQ ID NO:131
VL E9.17 CDR Set
CDR-L1: SEQ ID NO:241
CDR-L2: SEQ ID NO:242
CDR-L3: SEQ ID NO:243
VH E9.18 CDR Set
CDR-H1: SEQ ID NO:133
CDR-H2: SEQ ID NO:134
CDR-H3: SEQ ID NO:135
VL E9.18 CDR Set
CDR-L1: SEQ ID NO:245
CDR-L2: SEQ ID NO:246
CDR-L3: SEQ ID NO:247
VH E9.19 CDR Set
CDR-H1: SEQ ID NO:137
CDR-H2: SEQ ID NO:138
CDR-H3: SEQ ID NO:139
VL E9.19 CDR Set
CDR-L1: SEQ ID NO:249
CDR-L2: SEQ ID NO:250
CDR-L3: SEQ ID NO:251
VH E9.22 CDR Set
CDR-H1: SEQ ID NO:141
CDR-H2: SEQ ID NO:142
CDR-H3: SEQ ID NO:143
VL E9.22 CDR Set
CDR-L1: SEQ ID NO:253
CDR-L2: SEQ ID NO:254
CDR-L3: SEQ ID NO:255
VH E9.48 CDR Set
CDR-H1: SEQ ID NO:145
CDR-H2: SEQ ID NO:146
CDR-H3: SEQ ID NO:147
VL E9.48 CDR Set
CDR-L1: SEQ ID NO:257
CDR-L2: SEQ ID NO:258
CDR-L3: SEQ ID NO:259
VH E9.65 CDR Set
CDR-H1: SEQ ID NO:149
CDR-H2: SEQ ID NO:150
CDR-H3: SEQ ID NO:151
VL E9.65 CDR Set
CDR-L1: SEQ ID NO:261
CDR-L2: SEQ ID NO:262
CDR-L3: SEQ ID NO:263
VH E9.66 CDR Set
CDR-H1: SEQ ID NO:153
CDR-H2: SEQ ID NO:154
CDR-H3: SEQ ID NO:155
VL E9.66 CDR Set
CDR-L1: SEQ ID NO:265
CDR-L2: SEQ ID NO:266
CDR-L3: SEQ ID NO:267
VH E9.71 CDR Set
CDR-H1: SEQ ID NO:157
CDR-H2: SEQ ID NO:158
CDR-H3: SEQ ID NO:159
VL E9.71 CDR Set
CDR-L1: SEQ ID NO:269
CDR-L2: SEQ ID NO:270
CDR-L3: SEQ ID NO:271
VH E9.13 CDR Set
CDR-H1: SEQ ID NO:161
CDR-H2: SEQ ID NO:162
CDR-H3: SEQ ID NO:163
VL E9.13 CDR Set
CDR-L1: SEQ ID NO:217
CDR-L2: SEQ ID NO:218
CDR-L3: SEQ ID NO:219
VH E9.16 CDR Set
CDR-H1: SEQ ID NO:165
CDR-H2: SEQ ID NO:166
CDR-H3: SEQ ID NO:167
VL E9.16 CDR Set
CDR-L1: SEQ ID NO:221
CDR-L2: SEQ ID NO:222
CDR-L3: SEQ ID NO:223
VH E9.38 CDR Set
CDR-H1: SEQ ID NO:169
CDR-H2: SEQ ID NO:170
CDR-H3: SEQ ID NO:171
VL E9.38 CDR Set
CDR-L1: SEQ ID NO:225
CDR-L2: SEQ ID NO:226
CDR-L3: SEQ ID NO:227
VH E9.2B CDR Set
CDR-H1: SEQ ID NO:173
CDR-H2: SEQ ID NO:174
CDR-H3: SEQ ID NO:175
VL E9.2B CDR Set
CDR-L1: SEQ ID NO:273
CDR-L2: SEQ ID NO:274
CDR-L3: SEQ ID NO:275
VH E9.1F CDR Set
CDR-H1: SEQ ID NO:177
CDR-H2: SEQ ID NO:178
CDR-H3: SEQ ID NO:179
VL E9.1F CDR Set
CDR-L1: SEQ ID NO:277
CDR-L2: SEQ ID NO:278
CDR-L3: SEQ ID NO:279
VH E9.10H CDR Set
CDR-H1: SEQ ID NO:181
CDR-H2: SEQ ID NO:182
CDR-H3: SEQ ID NO:183

VL E9.10H CDR Set
CDR-L1: SEQ ID NO:301
CDR-L2: SEQ ID NO:302
CDR-L3: SEQ ID NO:303
VH E9.5E CDR Set
CDR-H1: SEQ ID NO:185
CDR-H2: SEQ ID NO:186
CDR-H3: SEQ ID NO:187
VL E9.5E CDR Set
CDR-L1: SEQ ID NO:293
CDR-L2: SEQ ID NO:294
CDR-L3: SEQ ID NO:295
VH E9.10C CDR Set
CDR-H1: SEQ ID NO:189
CDR-H2: SEQ ID NO:190
CDR-H3: SEQ ID NO:191
VL E9.10C CDR Set
CDR-L1: SEQ ID NO:281
CDR-L2: SEQ ID NO:282
CDR-L3: SEQ ID NO:283
VH E9.7E CDR Set
CDR-H1: SEQ ID NO:193
CDR-H2: SEQ ID NO:194
CDR-H3: SEQ ID NO:195
VL E9.7E CDR Set
CDR-L1: SEQ ID NO:289
CDR-L2: SEQ ID NO:290
CDR-L3: SEQ ID NO:291
VH E9.12B CDR Set
CDR-H1: SEQ ID NO:197
CDR-H2: SEQ ID NO:198
CDR-H3: SEQ ID NO:199
VL E9.12B CDR Set
CDR-L1: SEQ ID NO:297
CDR-L2: SEQ ID NO:298
CDR-L3: SEQ ID NO:299
VH E9.10E CDR Set
CDR-H1: SEQ ID NO:201
CDR-H2: SEQ ID NO:202
CDR-H3: SEQ ID NO:203
VL E9.10E CDR Set
CDR-L1: SEQ ID NO:285
CDR-L2: SEQ ID NO:286
CDR-L3: SEQ ID NO:287
VH E9.6A CDR Set
CDR-H1: SEQ ID NO:205
CDR-H2: SEQ ID NO:206
CDR-H3: SEQ ID NO:207
VL E9.6A CDR Set
CDR-L1: SEQ ID NO:305
CDR-L2: SEQ ID NO:306
CDR-L3: SEQ ID NO:307
VH E9.7A CDR Set
CDR-H1: SEQ ID NO:209
CDR-H2: SEQ ID NO:210
CDR-H3: SEQ ID NO:211
VL E9.7A CDR Set
CDR-L1: SEQ ID NO:309
CDR-L2: SEQ ID NO:310
CDR-L3: SEQ ID NO:311
VH E9.8H CDR Set
CDR-H1: SEQ ID NO:213
CDR-H2: SEQ ID NO:214
CDR-H3: SEQ ID NO:215
VL E9.8H CDR Set
CDR-L1: SEQ ID NO:313
CDR-L2: SEQ ID NO:314
CDR-L3: SEQ ID NO:315
VH E9.1 CDR Set
CDR-H1: residues 31-37 of SEQ ID NO:334
CDR-H2: residues 52-67 of SEQ ID NO:334
CDR-H3: residues 100-110 of SEQ ID NO:334
VL E9.1 CDR Set
CDR-L1: residues 23-33 of SEQ ID NO:335
CDR-L2: residues 49-55 of SEQ ID NO:335
CDR-L3: residues 88-96 of SEQ ID NO:335
VH E9-SE1 CDR Set
CDR-H1: residues 31-37 of SEQ ID NO:336
CDR-H2: residues 52-67 of SEQ ID NO:336
CDR-H3: residues 100-110 of SEQ ID NO:336
VL E9-SE1 CDR Set
CDR-L1: residues 23-33 of SEQ ID NO:337
CDR-L2: residues 49-55 of SEQ ID NO:337
CDR-L3: residues 88-96 of SEQ ID NO:337
VH E9-SE2 CDR Set
CDR-H1: residues 31-37 of SEQ ID NO:338
CDR-H2: residues 52-67 of SEQ ID NO:338
CDR-H3: residues 100-110 of SEQ ID NO:338
VL E9-SE2 CDR Set
CDR-L1: residues 23-33 of SEQ ID NO:339
CDR-L2: residues 49-55 of SEQ ID NO:339
CDR-L3: residues 88-96 of SEQ ID NO:339
VH E9-SE3 CDR Set
CDR-H1: residues 31-37 of SEQ ID NO:340
CDR-H2: residues 52-67 of SEQ ID NO:340
CDR-H3: residues 100-110 of SEQ ID NO:340
VL E9-SE3 CDR Set
CDR-L1: residues 23-33 of SEQ ID NO:341
CDR-L2: residues 49-55 of SEQ ID NO:341
CDR-L3: residues 88-96 of SEQ ID NO:341
VH E9-SE4 CDR Set
CDR-H1: residues 31-37 of SEQ ID NO:342
CDR-H2: residues 52-67 of SEQ ID NO:342
CDR-H3: residues 100-110 of SEQ ID NO:342
VL E9-SE4 CDR Set
CDR-L1: residues 23-33 of SEQ ID NO:343
CDR-L2: residues 49-55 of SEQ ID NO:343
CDR-L3: residues 88-96 of SEQ ID NO:343
VH E9-SE5 CDR Set
CDR-H1: residues 31-37 of SEQ ID NO:344
CDR-H2: residues 52-67 of SEQ ID NO:344
CDR-H3: residues 100-110 of SEQ ID NO:344
VL E9-SE5 CDR Set
CDR-L1: residues 24-34 of SEQ ID NO:345
CDR-L2: residues 50-56 of SEQ ID NO:345
CDR-L3: residues 89-97 of SEQ ID NO:345
VH E9-SE6 CDR Set
CDR-H1: residues 31-37 of SEQ ID NO:346
CDR-H2: residues 52-67 of SEQ ID NO:346
CDR-H3: residues 100-110 of SEQ ID NO:346
VL E9-SE6 CDR Set
CDR-L1: residues 23-33 of SEQ ID NO:347
CDR-L2: residues 49-55 of SEQ ID NO:347
CDR-L3: residues 88-96 of SEQ ID NO:347
VH E9-SE7 CDR Set
CDR-H1: residues 31-37 of SEQ ID NO:348
CDR-H2: residues 52-67 of SEQ ID NO:348
CDR-H3: residues 100-110 of SEQ ID NO:348

VL E9-SE7 CDR Set
CDR-L1: residues 24-34 of SEQ ID NO:349
CDR-L2: residues 50-56 of SEQ ID NO:349
CDR-L3: residues 89-97 of SEQ ID NO:349
VH E9-SE8 CDR Set
CDR-H1: residues 31-37 of SEQ ID NO:350
CDR-H2: residues 52-67 of SEQ ID NO:350
CDR-H3: residues 100-110 of SEQ ID NO:350
VL E9-SE8 CDR Set
CDR-L1: residues 24-34 of SEQ ID NO:351
CDR-L2: residues 50-56 of SEQ ID NO:351
CDR-L3: residues 89-97 of SEQ ID NO:351
VH E9-FR1 CDR Set
CDR-H1: residues 31-37 of SEQ ID NO:352
CDR-H2: residues 52-67 of SEQ ID NO:352
CDR-H3: residues 100-110 of SEQ ID NO:352
VL E9-FR1 CDR Set
CDR-L1: residues 24-34 of SEQ ID NO:353
CDR-L2: residues 50-56 of SEQ ID NO:353
CDR-L3: residues 89-97 of SEQ ID NO:353
VH E9-FR2 CDR Set
CDR-H1: residues 31-37 of SEQ ID NO:354
CDR-H2: residues 52-67 of SEQ ID NO:354
CDR-H3: residues 100-110 of SEQ ID NO:354
VL E9-FR2 CDR Set
CDR-L1: residues 24-34 of SEQ ID NO:355
CDR-L2: residues 50-56 of SEQ ID NO:355
CDR-L3: residues 89-97 of SEQ ID NO:355
VH E9.71 CDR Set
CDR-H1: residues 31-37 of SEQ ID NO:356
CDR-H2: residues 52-67 of SEQ ID NO:356
CDR-H3: residues 100-110 of SEQ ID NO:356
VL E9.71 CDR Set
CDR-L1: residues 23-33 of SEQ ID NO:357
CDR-L2: residues 49-55 of SEQ ID NO:357
CDR-L3: residues 88-96 of SEQ ID NO:357
VH E9.71(M) CDR Set
CDR-H1: residues 31-37 of SEQ ID NO:358
CDR-H2: residues 52-67 of SEQ ID NO:358
CDR-H3: residues 100-110 of SEQ ID NO:358
VL E9.71(M) CDR Set
CDR-L1: residues 23-33 of SEQ ID NO:359
CDR-L2: residues 49-55 of SEQ ID NO:359
CDR-L3: residues 88-96 of SEQ ID NO:359
VH E9.71(L) CDR Set
CDR-H1: residues 31-37 of SEQ ID NO:360
CDR-H2: residues 52-67 of SEQ ID NO:360
CDR-H3: residues 100-110 of SEQ ID NO:360
VL E9.71(L) CDR Set
CDR-L1: residues 23-33 of SEQ ID NO:361
CDR-L2: residues 49-55 of SEQ ID NO:361
CDR-L3: residues 88-96 of SEQ ID NO:361

In another embodiment, a binding protein comprises a variable heavy chain (VH) set of 3 CDRs selected from any VH set of 3 CDRs in the group above and a variable light chain (VL) set of 3 CDRS selected from any VL set of 3 CDRs in the group above.

In still another embodiment a binding protein comprises a named VH set of 3 CDRs and a correspondingly named VL set of 3 CDRs from the group below. Preferably, a binding protein according to the invention comprises at least two variable domain CDR sets selected from the group of variable domain CDR sets consisting of:
VH E9 CDR Set and VL E9 CDR Set,
VH E9.4 CDR Set and VL E9.4 CDR Set,
VH E9.11 CDR Set and VL E9.11 CDR Set,
VH E9.14 CDR Set and VL E9.14 CDR Set,
VH E9.17 CDR Set and VL E9.17 CDR Set,
VH E9.18 CDR Set and VL E9.18 CDR Set,
VH E9.19 CDR Set and VL E9.19 CDR Set,
VH E9.22 CDR Set and VL E9.22 CDR Set,
VH E9.48 CDR Set and VL E9.48 CDR Set,
VH E9.65 CDR Set and VL E9.65 CDR Set,
VH E9.66 CDR Set and VL E9.66 CDR Set,
VH E9.71 CDR Set and VL E9.71 CDR Set,
VH E9.13 CDR Set and VL E9.13 CDR Set,
VH E9.16 CDR Set and VL E9.16 CDR Set,
VH E9.38 CDR Set and VL E9.38 CDR Set,
VH E9.2B CDR Set and VL E9.2B CDR Set,
VH E9.1F CDR Set and VL E9.1F CDR Set,
VH E9.10H CDR Set and VL E9.10H CDR Set,
VH E9.5E CDR Set and VL E9.5E CDR Set,
VH E9.10C CDR Set and VL E9.10C CDR Set,
VH E9.7E CDR Set and VL E9.7E CDR Set,
VH E9.12B CDR Set and VL E9.12B CDR Set,
VH E9.10E CDR Set and VL E9.10E CDR Set,
VH E9.6A CDR Set and VL E9.6A CDR Set,
VH E9.7A CDR Set and VL E9.7A CDR Set,
VH E9.8H CDR Set and VL E9.8H CDR Set,
VH E9-SE1 CDR Set and VL E9-SE1 CDR Set,
VH E9-SE2 CDR Set and VL E9-SE2 CDR Set,
VH E9-SE3 CDR Set and VL E9-SE3 CDR Set,
VH E9-SE4 CDR Set and VL E9-SE4 CDR Set,
VH E9-SE5 CDR Set and VL E9-SE5 CDR Set,
VH E9-SE6 CDR Set and VL E9-SE6 CDR Set,
VH E9-SE7 CDR Set and VL E9-SE7 CDR Set,
VH E9-SE8 CDR Set and VL E9-SE8 CDR Set,
VH E9-FR1 CDR Set and VL E9-FR1 CDR Set,
VH E9-FR2 CDR Set and VL E9-FR2 CDR Set,
VH E9.71 CDR Set and VL E9.71 CDR Set,
VH E9.71(M) CDR Set and VL E9.71(M) CDR Set, and
VH E9.71(L) CDR Set and VL E9.71(L) CDR Set.

In yet another embodiment, a binding protein described above further comprises a human acceptor framework. Preferably, the human acceptor framework comprises an amino acid sequence selected from the group consisting of:
heavy chain acceptor framework sequences SEQ ID NOS: 6-22,
heavy chain acceptor sequences SEQ ID NOS:35-62,
light chain acceptor sequences SEQ ID NOS:23-34, and
light chain acceptor sequences SEQ ID NOS:63-98.

In another embodiment a binding protein described above comprises a human acceptor framework, which comprises at least one framework region amino acid substitution, wherein the amino acid sequence of the framework is at least 65% identical to the sequence of said human acceptor framework and comprising at least 70 amino acid residues identical to said human acceptor framework.

In another embodiment a binding protein described herein comprises a human acceptor framework that comprises at least one framework region amino acid substitution at a key residue, said key residue selected from the group consisting of:
a residue adjacent to a CDR;
a glycosylation site residue;
a rare residue;
a residue capable of interacting with human DLL4
a canonical residue;
a contact residue between heavy chain variable region and light chain variable region;
a residue within a Vernier zone; and
a residue in a region that overlaps between a Chothia-defined variable heavy chain CDR1 and a Kabat-defined first heavy chain framework.

Preferably, the key residue is selected from the group consisting of: 2H, 4H, 24H, 26H, 27H, 29H, 34H, 35H, 37H, 39H, 44H, 45H, 47H, 48H, 49H, 50H, 51H, 58H, 59H, 60H, 63H, 67H, 69H, 71H, 73H, 76H, 78H, 91H, 93H, 94H, 2L, 4L, 25L, 29L, 27bL, 33L, 34L, 36L, 38L, 43L, 44L, 46L, 47L, 48L, 49L, 55L, 58L, 62L, 64L, 71L, 87L, 89L, 90L, 91L, 94L, 95L.

In another embodiment, a binding protein described herein comprises a consensus human variable domain.

In a preferred embodiment, a binding protein described above comprises at least one variable domain having amino acid sequence selected from the group consisting of:
SEQ ID NOS:1, 111, 116, 228, 120, 232, 124, 236, 128, 240, 132, 244, 136, 248, 140, 252, 144, 256, 148, 260, 152, 264, 156, 268, 160, 216, 164, 220, 168, 224, 172, 272, 176, 276, 180, 300, 184, 292, 188, 280, 192, 288, 196, 296, 200, 284, 204, 304, 208, 308, 212, 312, 334, 335, 336, 337, 338, 339, 340, 341, 342, 343, 344, 345, 346, 347, 348, 349, 350, 351, 352, 353, 354, 355, 356, 357, 358, 359, 360, and 361.

In another embodiment, a binding protein according to the invention comprises two variable domains, wherein said two variable domains have amino acid sequences selected from the group consisting of: SEQ ID NOS:1 and 111, SEQ ID NOS:116 and 228, SEQ ID NOS:120 and 232, SEQ ID NOS: 124 and 236, SEQ ID NOS:128 and 240, SEQ ID NOS:132 and 244, SEQ ID NOS:136 and 248, SEQ ID NOS:140 and 252, SEQ ID NOS:144 and 256, SEQ ID NOS:148 and 260, SEQ ID NOS:152 and 264, SEQ ID NOS:156 and 268, SEQ ID NOS: 160 and 216, SEQ ID NOS: 164 and 220, SEQ ID NOS:168 and 224, SEQ ID NOS:172 and 272, SEQ ID NOS: 176 and 276, SEQ ID NOS:180 and 300, SEQ ID NOS:184 and 292, SEQ ID NOS:188 and 280, SEQ ID NOS:192 and 288, SEQ ID NOS:196 and 296, SEQ ID NOS:200 and 284, SEQ ID NOS:204 and 304, SEQ ID NOS:208 and 308, SEQ ID NOS:212 and 312, SEQ ID NOS:334 and 335, SEQ ID NOS:336 and 337, SEQ ID NOS:338 and 339, SEQ ID NOS: 340 and 341, SEQ ID NOS:342 and 343, SEQ ID NOS:344 and 345, SEQ ID NOS:346 and 347, SEQ ID NOS:348 and 349, SEQ ID NOS:350 and 351, SEQ ID NOS:352 and 353, SEQ ID NOS:354 and 355, SEQ ID NOS:356 and 357, SEQ ID NOS:358 and 359, SEQ ID NOS:360 and 361.

In an embodiment, a binding protein according to the invention comprises heavy chain variable domain ($V_H$), preferably wherein the $V_H$ comprises an amino acid sequence selected from the group consisting of:
SEQ ID NOS:1, 116, 120, 124, 128, 132, 136, 140, 144, 148, 152, 156, 160, 164, 168, 172, 176, 180, 184, 188, 192, 196, 200, 204, 208, 212, 334, 336, 338, 340, 342, 344, 346, 348, 350, 352, 354, 356, 358, and 360.

In yet another embodiment, a binding protein according to the invention comprises a light chain variable domain (a $V_L$), preferably wherein the $V_L$ comprises an amino acid sequence selected from the group consisting of:
SEQ ID NOS:111, 228, 232, 236, 240, 244, 248, 252, 256, 260, 264, 268, 216, 220, 224, 272, 276, 300, 292, 280, 288, 296, 284, 304, 308, 312, 335, 337, 339, 341, 343, 345, 347, 349, 351, 353, 355, 357, 359, and 361.

In a preferred embodiment, a binding protein according to the invention comprises a $V_H$ and a $V_L$, preferably wherein $V_H$ and a $V_L$ are any of those sequences disclosed above.

In another embodiment, the invention provides a binding protein capable of binding human DLL-4, said binding protein comprising:
an Ig constant heavy region having an amino acid sequence selected from the group consisting of SEQ ID NO:2 and SEQ ID NO:3;
an Ig constant light region having an amino acid sequence selected from the group consisting of SEQ ID NO:4 and SEQ ID NO:5;
an Ig variable heavy region having an amino acid sequence selected from the group consisting:
SEQ ID NOS:1, 116, 120, 124, 128, 132, 136, 140, 144, 148, 152, 156, 160, 164, 168, 172, 176, 180, 184, 188, 192, 196, 200, 204, 208, 212, 334, 336, 338, 340, 342, 344, 346, 348, 350, 352, 354, 356, 358, and 360; and
an Ig variable light region having an amino acid sequence selected from the group consisting:
SEQ ID NOS:111, 228, 232, 236, 240, 244, 248, 252, 256, 260, 264, 268, 216, 220, 224, 272, 276, 300, 292, 280, 288, 296, 284, 304, 308, 312, 335, 337, 339, 341, 343, 345, 347, 349, 351, 353, 355, 357, 359, and 361.

Another aspect of the invention pertains to a binding protein comprising an antigen binding domain capable of binding human DLL4, said antigen binding domain comprising at least one or more CDRs selected from the group consisting of:

CDR-H1: $X_1$-$X_2$-$X_3$-$X_4$-$X_5$, (SEQ ID NO: 105)

wherein;
$X_1$ is S, N, or D;
$X_2$ is H or Y;
$X_3$ is W;
$X_4$ is M;
$X_5$ is S or H;

CDR-H2: (SEQ ID NO: 106)
$X_1$-$X_2$-$X_3$-$X_4$-$X_5$-$X_6$-$X_7$-$X_8$-$X_9$-$X_{10}$-$X_{11}$-$X_{12}$-$X_{13}$-$X_{14}$-$X_{15}$-$X_{16}$-$X_{17}$, wherein;
$X_1$ is I, D, M, or T;
$X_2$ is I;
$X_3$ is S;
$X_4$ is Y, N, S, Q, V, T, H, or D;
$X_5$ is D;
$X_6$ is G;
$X_7$ is S, R, I, T, G, K, H, or N;
$X_8$ is N, Y, S, I, or T;
$X_9$ is K, S, A, or L;
$X_{10}$ is Y, D, or E;
$X_{11}$ is S or Y;
$X_{12}$ is A;
$X_{13}$ is D;
$X_{14}$ is S;
$X_{15}$ is V;
$X_{16}$ is K; and
$X_{17}$ is G;

CDR-H3: (SEQ ID NO: 107)
$X_1$-$X_2$-$X_3$-$X_4$-$X_5$-$X_6$-$X_7$-$X_8$-$X_9$-$X_{10}$, wherein;
$X_1$ is A;
$X_2$ is G, A, or R;
$X_3$ is G;
$X_4$ is G, S, or A;
$X_5$ is N;
$X_6$ is V or M;
$X_7$ is G;
$X_8$ is F, L, Y, or M;

$X_9$ is D; and
$X_{10}$ is I, S, or L;

CDR-L1: (SEQ ID NO: 108)
$X_1-X_2-X_3-X_4-X_5-X_6-X_7-X_8-X_9-X_{10}-X_{11}$, wherein;
$X_1$ is S;
$X_2$ is A or G;
$X_3$ is D;
$X_4$ is K, N, L, Q, M, E, S, T, G, or D;
$X_5$ is L;
$X_6$ is G;
$X_7$ is T, S, N, A, G, or E;
$X_8$ is K, Q, N, or R;
$X_9$ is Y;
$X_{10}$ is V or I; and
$X_{11}$ is S;

CDR-L2: (SEQ ID NO: 109)
$X_1-X_2-X_3-X_4-X_5-X_6-X_7$, wherein:
$X_1$ is Q;
$X_2$ is D;
$X_3$ is A, G, W, S, or D;
$X_4$ is K, M, Q, N, L, T, I, or E;
$X_5$ is R;
$X_6$ is P; and
$X_7$ is S;
and

CDR-L3: (SEQ ID NO: 110)
$X_1-X_2-X_3-X_4-X_5-X_6-X_7-X_8-X_9$, wherein;
$X_1$ is Q;
$X_2$ is S or A;
$X_3$ is W;
$X_4$ is D;
$X_5$ is R, S, Q, P, A, V, W, or M;
$X_6$ is 5, G, I, N, R, or T;
$X_7$ is D or G;
$X_8$ is V, A, P, or E; and
$X_9$ is V.

Preferably, the antigen binding domain of a DLL4 binding protein of the invention comprises at least one CDR comprising an amino acid sequence selected from the group consisting of:
residues 31-35 of SEQ ID NO:112 (CDR-H1); residues 50-66 of SEQ ID NO:112 (CDR-H2); residues 99-108 of SEQ ID NO:112 (CDR-H3);
residues 23-33 of SEQ ID NO:113 (CDR-L1); residues 49-55 of SEQ ID NO:113 (CDR-L2); residues 88-96 of SEQ ID NO:113 (CDR-L3);
residues 31-35 of SEQ ID NO:316 (CDR-H1); residues 50-66 of SEQ ID NO:316 (CDR-H2); residues 99-108 of SEQ ID NO:316 (CDR-H3);
residues 31-35 of SEQ ID NO:317 (CDR-H1); residues 50-66 of SEQ ID NO:317 (CDR-H2); residues 99-108 of SEQ ID NO:317 (CDR-H3);
residues 31-35 of SEQ ID NO:318 (CDR-H1); residues 50-66 of SEQ ID NO:318 (CDR-H2); residues 99-108 of SEQ ID NO:318 (CDR-H3);
residues 31-35 of SEQ ID NO:319 (CDR-H1); residues 50-66 of SEQ ID NO:319 (CDR-H2); residues 99-108 of SEQ ID NO:319 (CDR-H3);
residues 31-35 of SEQ ID NO:320 (CDR-H1); residues 50-66 of SEQ ID NO:320 (CDR-H2); residues 99-108 of SEQ ID NO:320 (CDR-H3);
residues 31-35 of SEQ ID NO:321 (CDR-H1); residues 50-66 of SEQ ID NO:321 (CDR-H2); residues 99-108 of SEQ ID NO:321 (CDR-H3);
residues 31-35 of SEQ ID NO:322 (CDR-H1); residues 50-66 of SEQ ID NO:322 (CDR-H2); residues 99-108 of SEQ ID NO:322 (CDR-H3);
residues 31-35 of SEQ ID NO:323 (CDR-H1); residues 50-66 of SEQ ID NO:323 (CDR-H2); residues 99-108 of SEQ ID NO:323 (CDR-H3);
residues 31-35 of SEQ ID NO:324 (CDR-H1); residues 50-66 of SEQ ID NO:324 (CDR-H2); residues 99-108 of SEQ ID NO:324 (CDR-H3);
residues 31-35 of SEQ ID NO:325 (CDR-H1); residues 50-66 of SEQ ID NO:325 (CDR-H2); residues 99-108 of SEQ ID NO:325 (CDR-H3);
residues 31-35 of SEQ ID NO:326 (CDR-H1); residues 50-66 of SEQ ID NO:326 (CDR-H2); residues 99-108 of SEQ ID NO:326 (CDR-H3);
residues 23-33 of SEQ ID NO:327 (CDR-L1); residues 49-55 of SEQ ID NO:327 (CDR-L2); residues 88-96 of SEQ ID NO:327 (CDR-L3);
residues 23-33 of SEQ ID NO:328 (CDR-L1); residues 49-55 of SEQ ID NO:328 (CDR-L2); residues 88-96 of SEQ ID NO:328 (CDR-L3);
residues 23-33 of SEQ ID NO:329 (CDR-L1); residues 49-55 of SEQ ID NO:329 (CDR-L2); residues 88-96 of SEQ ID NO:329 (CDR-L3);
residues 23-33 of SEQ ID NO:330 (CDR-L1); residues 49-55 of SEQ ID NO:330 (CDR-L2); residues 88-96 of SEQ ID NO:330 (CDR-L3);
residues 23-33 of SEQ ID NO:331 (CDR-L1); residues 49-55 of SEQ ID NO:331 (CDR-L2); residues 88-96 of SEQ ID NO:331 (CDR-L3);
residues 23-33 of SEQ ID NO:332 (CDR-L1); residues 49-55 of SEQ ID NO:332 (CDR-L2); residues 88-96 of SEQ ID NO:332 (CDR-L3);
residues 23-33 of SEQ ID NO:333 (CDR-L1); residues 49-55 of SEQ ID NO:333 (CDR-L2); residues 88-96 of SEQ ID NO:333 (CDR-L3).

In another embodiment, the binding protein comprises at least 3 CDRs disclosed above.

Preferably, a DLL4 binding protein according to the invention comprises one or more CDRs disclosed above. More preferably, the binding protein comprises three or more CDRs disclosed above. Most preferably, a DLL4 binding protein according to the invention comprises six CDRs described above, i.e., a CDR-H1, a CDR-H2, a CDR-H3, a CDR-L1, a CDR-L2, and a CDR-L3 described above.

In a preferred embodiment, the binding protein comprises at least 3 CDRs selected from the group consisting of the sequences disclosed above.

In another preferred embodiment, a binding protein comprises 3 CDRs selected from a set of variable domain CDRs selected from the group below.

VH A10 CDR Set
CDR-H1: residues 31-35 of SEQ ID NO:112
CDR-H2: residues 50-66 of SEQ ID NO:112
CDR-H3: residues 99-108 of SEQ ID NO:112

VL A10 CDR Set
CDR-L1: residues 23-33 of SEQ ID NO:113
CDR-L2: residues 49-55 of SEQ ID NO:113
CDR-L3: residues 88-96 of SEQ ID NO:113
VH A10.3 CDR Set
CDR-H1: residues 31-35 of SEQ ID NO:316
CDR-H2: residues 50-66 of SEQ ID NO:316
CDR-H3: residues 99-108 of SEQ ID NO:316
VL A10.3 CDR Set
CDR-L1: residues 23-33 of SEQ ID NO:327
CDR-L2: residues 49-55 of SEQ ID NO:327
CDR-L3: residues 88-96 of SEQ ID NO:327
VH A10.K30 CDR Set
CDR-H1: residues 31-35 of SEQ ID NO:317
CDR-H2: residues 50-66 of SEQ ID NO:317
CDR-H3: residues 99-108 of SEQ ID NO:317
VH A10.K42 CDR Set
CDR-H1: residues 31-35 of SEQ ID NO:318
CDR-H2: residues 50-66 of SEQ ID NO:318
CDR-H3: residues 99-108 of SEQ ID NO:318
VH A10.9A CDR Set
CDR-H1: residues 31-35 of SEQ ID NO:319
CDR-H2: residues 50-66 of SEQ ID NO:319
CDR-H3: residues 99-108 of SEQ ID NO:319
VH A10.8A CDR Set
CDR-H1: residues 31-35 of SEQ ID NO:320
CDR-H2: residues 50-66 of SEQ ID NO:320
CDR-H3: residues 99-108 of SEQ ID NO:320
VH A10.1A CDR Set
CDR-H1: residues 31-35 of SEQ ID NO:321
CDR-H2: residues 50-66 of SEQ ID NO:321
CDR-H3: residues 99-108 of SEQ ID NO:321
VH A10.5D CDR Set
CDR-H1: residues 31-35 of SEQ ID NO:322
CDR-H2: residues 50-66 of SEQ ID NO:322
CDR-H3: residues 99-108 of SEQ ID NO:322
VH A10.3A CDR Set
CDR-H1: residues 31-35 of SEQ ID NO:323
CDR-H2: residues 50-66 of SEQ ID NO:323
CDR-H3: residues 99-108 of SEQ ID NO:323
VL A10.3A CDR Set
CDR-L1: residues 23-33 of SEQ ID NO:330
CDR-L2: residues 49-55 of SEQ ID NO:330
CDR-L3: residues 88-96 of SEQ ID NO:330
VH A10.6B CDR Set
CDR-H1: residues 31-35 of SEQ ID NO:324
CDR-H2: residues 50-66 of SEQ ID NO:324
CDR-H3: residues 99-108 of SEQ ID NO:324
VL A10.6B CDR Set
CDR-L1: residues 23-33 of SEQ ID NO:331
CDR-L2: residues 49-55 of SEQ ID NO:331
CDR-L3: residues 88-96 of SEQ ID NO:331
VH A10.3D CDR Set
CDR-H1: residues 31-35 of SEQ ID NO:325
CDR-H2: residues 50-66 of SEQ ID NO:325
CDR-H3: residues 99-108 of SEQ ID NO:325
VL A10.3D CDR Set
CDR-L1: residues 23-33 of SEQ ID NO:332
CDR-L2: residues 49-55 of SEQ ID NO:332
CDR-L3: residues 88-96 of SEQ ID NO:332
VH A10.4C CDR Set
CDR-H1: residues 31-35 of SEQ ID NO:326
CDR-H2: residues 50-66 of SEQ ID NO:326
CDR-H3: residues 99-108 of SEQ ID NO:326
VL A10.4C CDR Set
CDR-L1: residues 23-33 of SEQ ID NO:333
CDR-L2: residues 49-55 of SEQ ID NO:333
CDR-L3: residues 88-96 of SEQ ID NO:333
VL A10.L45 CDR Set
CDR-L1: residues 23-33 of SEQ ID NO:328
CDR-L2: residues 49-55 of SEQ ID NO:328
CDR-L3: residues 88-96 of SEQ ID NO:328
VL A10.L73 CDR Set
CDR-L1: residues 23-33 of SEQ ID NO:329
CDR-L2: residues 49-55 of SEQ ID NO:329
CDR-L3: residues 88-96 of SEQ ID NO:329

In another embodiment, a binding protein comprises a variable heavy chain (VH) set of 3 CDRs selected from any VH set of 3 CDRs in the group above and a variable light chain (VL) set of 3 CDRS selected from any VL set of 3 CDRs in the group above.

In still another embodiment a binding protein comprises a named VH set of 3 CDRs and a correspondingly named VL set of 3 CDRs from the group below. Preferably, a binding protein according to the invention comprises at least two variable domain CDR sets selected from the group of variable domain CDR sets consisting of:
VH A10 CDR Set and VL A10 CDR Set;
VH A10.3 CDR Set and VL A10.3 CDR Set:
VH A10.3A CDR Set and VL A10.3A Set;
VH A10.6B CDR Set and VL A10.6B Set;
VH A10.3D CDR Set and VL A10.3D CDR Set;
VH A10.4C CDR Set and VL A10.4C CDR Set;
VH A10.K30 CDR Set and VL A10.3 CDR Set;
VH A10.K42 CDR Set and VL A10.3 CDR Set;
VH A10.3 CDR Set and VL A10.L45 CDR Set;
VH A10.3 CDR Set and VL A10.L73 CDR Set;
VH A10.9A CDR Set and VL A10.3 CDR Set;
VH A10.8A CDR Set and VL A10.3 CDR Set;
VH A10.1A CDR Set and VL A10.3 CDR Set; and
VH A10.5D CDR Set and VL A10.3 CDR Set.

In yet another embodiment, a binding protein described above further comprises a human acceptor framework. Preferably, the human acceptor framework comprises an amino acid sequence selected from the group consisting of:
heavy chain acceptor framework sequences SEQ ID NOS: 6-22,
heavy chain acceptor sequences SEQ ID NOS:35-62,
light chain acceptor sequences SEQ ID NOS:23-34, and
light chain acceptor sequences SEQ ID NOS:63-98.

In another embodiment a binding protein described above comprises a human acceptor framework, which comprises at least one framework region amino acid substitution, wherein the amino acid sequence of the framework is at least 65% identical to the sequence of said human acceptor framework and comprising at least 70 amino acid residues identical to said human acceptor framework.

In another embodiment a binding protein described herein comprises a human acceptor framework that comprises at least one framework region amino acid substitution at a key residue, said key residue selected from the group consisting of:
a residue adjacent to a CDR;
a glycosylation site residue;
a rare residue;
a residue capable of interacting with human DLL4
a canonical residue;
a contact residue between heavy chain variable region and light chain variable region;
a residue within a Vernier zone; and a residue in a region that overlaps between a Chothia-defined variable heavy chain CDR1 and a Kabat-defined first heavy chain framework.

Preferably, the key residue is selected from the group consisting of: 2H, 4H, 24H, 26H, 27H, 29H, 34H, 35H, 37H, 39H, 44H, 45H, 47H, 48H, 49H, 50H, 51H, 58H, 59H, 60H, 63H, 67H, 69H, 71H, 73H, 76H, 78H, 91H, 93H, 94H, 2L, 4L, 25L, 29L, 27bL, 33L, 34L, 36L, 38L, 43L, 44L, 46L, 47L, 48L, 49L, 55L, 58L, 62L, 64L, 71L, 87L, 89L, 90L, 91L, 94L, 95L.

In another embodiment, a binding protein described herein comprises a consensus human variable domain.

In a preferred embodiment, a binding protein described above comprises at least one variable domain having amino acid sequence selected from the group consisting of: SEQ ID NOS:112, 113, 316, 327, 317, 318, 319, 320, 321, 322, 323, 330, 324, 331, 325, 332, 326, 333, 328, and 329.

In another embodiment, a binding protein described above comprises two variable domains, wherein said two variable domains have amino acid sequences selected from the group consisting of: SEQ ID NOS:112 and 113, SEQ ID NOS:316 and 327, SEQ ID NOS:323 and 330, SEQ ID NOS:324 and 331, SEQ ID NOS:325 and 332, and SEQ ID NOS:326 and 333.

In an embodiment, a binding protein according to the invention comprises heavy chain variable domain ($V_H$), preferably wherein the $V_H$ comprises an amino acid sequence selected from the group consisting of:
SEQ ID NOS:112, 316, 317, 318, 319, 320, 321, 322, 323, 324, 325, and 326.

In yet another embodiment, a binding protein according to the invention comprises a light chain variable domain (a $V_L$), preferably wherein the $V_L$ comprises an amino acid sequence selected from the group consisting of:
SEQ ID NOS:113, 327, 328, 329, 330, 331, 332, and 333.

In another embodiment, the invention provides a binding protein capable of binding human DLL-4, said binding protein comprising:
an Ig constant heavy region having an amino acid sequence selected from the group consisting of SEQ ID NO:2 and SEQ ID NO:3;
an Ig constant light region having an amino acid sequence selected from the group consisting of SEQ ID NO:4 and SEQ ID NO:5;
an Ig variable heavy region having an amino acid sequence selected from the group consisting:
SEQ ID NOS: SEQ ID NOS:112, 316, 317, 318, 319, 320, 321, 322, 323, 324, 325, and 326; and
an Ig variable light region having an amino acid sequence selected from the group consisting:
SEQ ID NOS: 113, 327, 328, 329, 330, 331, 332, and 333.

According to the invention, variable heavy (VH) domains and variable light (VL) domains of DLL4 binding proteins described herein may also be shuffled using recombinant techniques available in the art to generate and select for additional DLL4 binding proteins that comprise various combinations of VH and VL domains described herein.

In a preferred embodiment, a DLL4 binding protein according to the invention binds human DLL4 (hu DLL4) and at least one other species of DLL4. More preferably, a DLL4 binding protein described herein binds human DLL4 and a DLL4 selected from the group consisting of: a mouse DLL4 (mu DLL4), a cynomolgus monkey DLL4 (cynomolgus DLL4, cyno DLL4), a rat DLL4, and combinations thereof.

In another embodiment, a DLL4 binding protein is a fully human antibody or antigen binding portion thereof.

In another embodiment, a DLL4 binding protein is a CDR grafted antibody. More preferably, a DLL4 binding protein is a CDR-grafted antibody or antigen binding portion thereof comprising one or more CDRs described above.

Still more preferably, the CDR grafted antibody or antigen binding portion thereof comprise a variable domain described above. More preferably, a CDR grafted antibody or antigen binding portion thereof comprises two variable domains described above. Preferably, the CDR grafted antibody or antigen binding portion thereof comprises a human acceptor framework. More preferably, the human acceptor framework is any one of the human acceptor frameworks described above.

More preferably, a binding protein is capable of neutralizing an activity of a DLL4 selected from the group consisting of human DLL4, mouse DLL4, cynomolgus monkey DLL4, rat DLL4, and combinations thereof. Evaluating the neutralization of activity of DLL4 can be assessed via several in vitro and in vivo assays know in the art. Exemplary parameters for assessing neutralization of DLL4 activity include, but are not limited to, antibodies that inhibit DLL4 interaction with the Notch receptor, and/or Notch-signaling pathway with an $IC_{50}$ values of about at least $10^{-6}$ M; at least $10^{-7}$ M, or at least $10^{-8}$ M.

In one embodiment, the binding protein of the invention has an on rate constant ($K_{on}$) to DLL4 of at least about $10^2 M^{-1} s^{-1}$; at least about $10^3 M^{-1} s^{-1}$; at least about $10^4 M^{-1} s^{-1}$; at least about $10^5 M^{-1} s^{-1}$; or at least about $10^6 M^{-1} s^{-1}$, as measured by surface plasmon resonance. Preferably, the binding protein of the invention has an on rate constant ($K_{on}$) to DLL4 between $10^2 M^{-1} s^{-1}$ to $10^3 M^{-1} s^{-1}$; between $10^3 M^{-1} s^{-1}$ to $10^4 M^{-1} s^{-1}$; between $10^4 M^{-1} s^{-1}$ to $10^5 M^{-1} s^{-1}$; or between $10^5 M^{-1} s^{-1}$ to $10^6 M^{-1} s^{-1}$, as measured by surface plasmon resonance.

In another embodiment, the binding protein of the invention has an off rate constant ($K_{off}$) for DLL4 of at most about $10^{-3} s^{-1}$; at most about $10^{-4} s^{-1}$; at most about $10^{-5} s^{-1}$; or at most about $10^{-6} s^{-1}$, as measured by surface plasmon resonance. Preferably, the binding protein of the invention has an off rate constant ($K_{off}$) to DLL4 of $10^{-3} s^{-1}$ to $10^{-4} s^{-1}$; of $10^{-4} s^{-1}$ to $10^{-5} s^{-1}$; or of $10^{-5} s^{-1}$ to $10^{-6} s^{-1}$, as measured by surface plasmon resonance.

In another embodiment, the binding protein of the invention has a dissociation constant ($K_D$) to DLL4 of at most about $10^{-7}$ M; at most about $10^{-8}$ M; at most about $10^{-9}$ M; at most about $10^{-10}$ M; at most about $10^{-11}$ M; at most about $10^{-12}$ M; or at most $10^{-13}$ M. Preferably, the binding protein of the invention has a dissociation constant ($K_D$) to DLL4 of $10^{-7}$ M to $10^{-8}$ M; of $10^{-8}$ M to $10^{-9}$ M; of $10^{-9}$ M to $10^{-10}$ M; of $10^{-10}$ to $10^{-11}$ M; of $10^{-11}$ M to $10^{-12}$ M; or of $10^{-12}$ to M $10^{-13}$ M.

One embodiment of the invention provides an antibody construct comprising any one of the DLL4 binding proteins disclosed above and a linker polypeptide or an immunoglobulin constant domain. In a preferred embodiment, an antibody construct according to the invention is selected from the group consisting of: an immunoglobulin molecule, a monoclonal antibody, a chimeric antibody, a CDR-grafted antibody, a humanized antibody, a Fab, a Fab', a F(ab')$_2$, a Fv, a disulfide linked Fv, a scFv, a single domain antibody, a diabody, a multispecific antibody, a dual specific antibody, and a bispecific antibody.

In a preferred embodiment, an antibody construct of the invention comprises a heavy chain immunoglobulin constant domain selected from the group consisting of a human IgM constant domain, a human IgG1 constant domain, a human IgG2 constant domain, a human IgG3 constant domain, a human IgG4 constant domain, a human IgE constant domain, and a human IgA constant domain, and mutants of the above Ig isotypes which may alter Fc gamma receptor binding, FcRn binding, C1q binding and may alter pharmacokinetic properties and/or Fc effector functions.

In another embodiment, an antibody construct is glycosylated. Preferably, the glycosylation is a human glycosylation pattern.

In another embodiment, a DLL4 binding protein described herein is conjugated to an agent. Binding protein conjugates of the invention include antibody conjugates in which an antibody construct described herein is conjugated to an agent. Preferably, the agent is selected from the group consisting of: an immunoadhesion molecule, an imaging agent, a therapeutic agent, and a cytotoxic agent. In a preferred embodiment, the imaging agent is selected from the group consisting of a radiolabel, an enzyme, a fluorescent label, a luminescent label, a bioluminescent label, a magnetic label, and biotin. More preferably the imaging agent is a radiolabel selected from the group consisting of: $^{3}$H, $^{14}$C, $^{35}$S, $^{90}$Y, $^{99}$Tc, $^{111}$In, $^{125}$I, $^{131}$I, $^{177}$Lu, $^{166}$Ho, and $^{153}$Sm. In a preferred embodiment, the therapeutic or cytotoxic agent is selected from the group consisting of: an anti-metabolite, an alkylating agent, an antibiotic, a growth factor, a cytokine, an anti-angiogenic agent, an anti-mitotic agent, an anthracycline, toxin, and an apoptotic agent.

In another embodiment, a DLL4 binding protein, an antibody construct, or a binding protein conjugate (including antibody conjugates) disclosed above exists as a crystal. Preferably, the crystal is a carrier-free pharmaceutical controlled release crystal. In a preferred embodiment, such a crystallized binding protein, crystallized antibody construct, or crystallized antibody conjugate has a greater half life in vivo than its soluble counterpart. In another preferred embodiment, the crystallized binding protein, crystallized antibody construct, or crystallized binding protein conjugate (including antibody conjugate) retains biological activity after crystallization.

One aspect of the invention pertains to an isolated nucleic acid encoding a DLL4 binding protein, an antibody construct, a DLL4 binding antibody conjugate, or DLL4 binding portion thereof. Particularly preferred is an isolated nucleic acid that encodes a polypeptide selected from the group consisting of: a polypeptide comprising a heavy chain variable domain, wherein the heavy chain variable domain comprises a CDR-H1, a CDR-H2, or a CDR-H3 described above; a polypeptide comprising a light chain variable domain, wherein the light chain variable domain comprises a CDR-L1, a CDR-L2, or a CDR-L3 as described above; or a combination of both polypeptides.

A further embodiment provides a vector comprising an isolated nucleic acid disclosed above. In a preferred embodiment, the vector is selected from the group consisting of: pcDNA, pTT (Durocher et al., Nucl. Acids Res., 30(2e9): 1-9 (2002)), pTT3 (pTT with additional multiple cloning sites), pEFBOS (Mizushima et al., Nucl. Acids. Res., 18 (17): 5322 (1990)), pHybE, pBV, pJV, and pBJ, and any other expression vectors suitable for prokaryotic or eukaryotic cells.

In another aspect of the invention there is provided a host cell is transformed with the vector disclosed above. The host cell may be prokaryotic or eukaryotic cell. A preferred prokaryotic host cell is *Escherichia coli*. Preferably, the eukaryotic cell is selected from the group consisting of: a protist cell, an animal cell, a plant cell, and a fungal cell. More preferably, the host cell is a mammalian cell including, but not limited to, CHO and COS cells. A preferred fungal cell is, but not limited to, *Saccharomyces cerevisiae*. A preferred insect cell is an Sf9 cell.

Another aspect of the invention provides a method of producing a binding protein that binds human DLL4 comprising the step of culturing any one of the host cells disclosed above in a culture medium under conditions sufficient to produce a binding protein that binds human DLL4. Another embodiment provides a binding protein produced according to the method disclosed above.

One embodiment provides a composition for the release of a DLL4 binding protein according to the invention wherein the composition comprises a formulation which in turn comprises a crystallized DLL4 binding protein, crystallized antibody construct, or crystallized binding protein conjugate (including antibody conjugates) as disclosed above and an ingredient, and further at least one polymeric carrier. Preferably, the polymeric carrier is a polymer selected from one or more of the group consisting of: poly (acrylic acid), poly (cyanoacrylates), poly (amino acids), poly (anhydrides), poly (depsipeptide), poly (esters), poly (lactic acid), poly (lactic-co-glycolic acid) or PLGA, poly (b-hydroxybutryate), poly (caprolactone), poly (dioxanone); poly (ethylene glycol), poly ((hydroxypropyl)methacrylamide, poly [(organo)phosphazene], poly (ortho esters), poly (vinyl alcohol), poly (vinylpyrrolidone), maleic anhydride-alkyl vinyl ether copolymers, pluronic polyols, albumin, alginate, cellulose and cellulose derivatives, collagen, fibrin, gelatin, hyaluronic acid, oligosaccharides, glycaminoglycans, sulfated polyeaccharides, blends and copolymers thereof. Preferably the ingredient is selected from the group consisting of albumin, sucrose, trehalose, lactitol, gelatin, hydroxypropyl-β-cyclodextrin, methoxypolyethylene glycol and polyethylene glycol.

Another embodiment provides a method for treating a mammal comprising the step of administering to the mammal an effective amount of a composition comprising a crystallized DLL4 binding protein, a crystallized antibody construct, or a crystallized protein conjugate (including antibody conjugates) disclosed above.

The invention also provides a pharmaceutical composition comprising a DLL4 binding protein, an antibody construct, or a binding protein conjugate (including antibody conjugates) as disclosed above and a pharmaceutically acceptable carrier. In a further embodiment, the pharmaceutical composition comprises at least one additional agent. The additional agent may be a therapeutic agent for treating a disorder in which DLL4 is detrimental. Preferably, a pharmaceutical composition comprises an additional agent selected from the group consisting of: a therapeutic agent; an imaging agent; an antineoplastic agent; a chemotherapeutic agent (such as a DNA alkylating agent, cisplatin, carboplatin, an anti-tubulin agent, paclitaxel, docetaxel, doxorubicin, gemcitabine, gemzar, an anthracycline, adriamycin, a topoisiomersase I inhibitor, a topoisomerase II inhibitor, 5-fluorouracil (5-FU), leucovorin, irinotecan), and a receptor tyrosine kinase inhibitors (e.g., erlotinib, gefitinib), a COX-2 inhibitor (e.g., celecoxib), a kinase inhibitor, and an angiogenesis inhibitor (including but not limited to an anti-VEGF antibody or VEGF-trap); a co-stimulation molecule blocker (including but not limited to anti-B7.1 antibody, anti-B7.2 antibody, CTLA4-Ig, anti-CD20 antibody); an adhesion molecule blocker (including but not limited to an anti-LFA-1 antibody, an anti-E/L selectin antibody, and a small molecule inhibitor); anti-cytokine antibody or functional fragment thereof (including but not limited to an anti-IL-18, an anti-TNF, and an anti-IL-6/cytokine receptor antibody); methotrexate; cyclosporine; rapamycin; FK506; a detectable label or reporter molecule; a TNF antagonist; an antirheumatic; a muscle relaxant; a narcotic; a non-steroid anti-inflammatory drug (NSAID); an analgesic; an anesthetic; a sedative; a local anesthetic; a neuromuscular blocker; an antimicrobial agent; an antipsoriatic agent; a corticosteroid; an anabolic steroid; an erythropoietin; an immunization; an immunoglobulin; an immunosuppressive agent; a growth hormone; a hormone replacement drug; a radiopharmaceutical drug; an antidepressant; an antipsychotic drug; a stimulant; an asthma medication; a beta agonist; an inhaled steroid; an epinephrine or analog thereof; a cytokine; and a cytokine antagonist.

In another aspect, the invention provides a method for inhibiting human DLL4 activity comprising contacting human DLL4 with a binding protein disclosed above such that human DLL4 is inhibited or neutralized. In a related aspect, the invention provides a method for inhibiting DLL4 activity in a human subject suffering from a disorder in which DLL4 is detrimental, comprising administering to the human subject a binding protein disclosed above such that human DLL4 in the human subject is inhibited and treatment is achieved. Preferably, the disorder is selected from the group comprising primary and metastatic cancers, including carcinomas of breast, colon, rectum, lung, oropharynx, hypopharynx, esophagus, stomach, pancreas, liver, gallbladder and bile ducts, small intestine, urinary tract (including kidney, bladder, and urothelium), female genital tract (including cervix, uterus, and ovaries as well as choriocarcinoma and gestational trophoblastic disease), male genital tract (including prostate, seminal vesicles, testes, and germ cell tumors), endocrine glands (including the thyroid, adrenal, and pituitary glands), and skin, as well as hemangiomas, melanomas, sarcomas (including those arising from bone and soft tissues as well as Kaposi's sarcoma), tumors of the brain, nerves, eyes, and meninges (including astrocytomas, gliomas, glioblastomas, retinoblastomas, neuromas, neuroblastomas, Schwannomas, and meningiomas), solid tumors arising from hematopoietic malignancies such as leukemias and lymphomas (both Hodgkin's and non-Hodgkin's lymphomas), tumor metastases, ocular neovascularization (including diabetic blindness, retinopathies, age-induced macular degeneration and rubeosis), edema, rheumatoid arthritis, multiple sclerosis, atheroscleorotic plaques, Crohn's disease, inflammatory bowel disease, refractory ascites, psoriasis, sarcoidosis, arterial arteriosclerosis, sepsis, peptic ulcers, burns, and pancreatitis, polycystic ovarian disease (POD), endometriosis, uterine fibroids, benign prostate hypertrophy, and other angiogenesis independent and dependent diseases characterized by abberant DLL4 activity.

In another aspect the invention provides a method of treating a patient suffering from a disorder in which human DLL4 is detrimental comprising the step of administering any one of the binding proteins disclosed above before, concurrent, or after the administration of a second agent, as discussed above. In a preferred embodiment, the second agent is selected from the group consisting of: radiotherapeutic agent; an antineoplastic agent; a chemotherapeutic agent (such as a DNA alkylating agent, cisplatin, carboplatin, an anti-tubulin agent, paclitaxel, docetaxel, taxol, doxorubicin, gemcitabine, gemzar, an anthracycline, adriamycin, a topoisomerase I inhibitor, a topoisomerase II inhibitor, 5-fluorouracil (5-FU), leucovorin, irinotecan), a receptor tyrosine kinase inhibitor (e.g., erlotinib, gefitinib), a COX-2 inhibitor (e.g., celecoxib), a kinase inhibitor, and an angiogenesis inhibitor (including but not limited to an anti-VEGF antibody or VEGF-trap); a co-stimulation molecule blocker (including but not limited to anti-B7.1, anti-B7.2, CTLA4-Ig, anti-CD20); an adhesion molecule blocker (including but not limited to an anti-LFA-1 antibody, an anti-E/L selectin antibody, a small molecule inhibitor); anti-cytokine antibody or functional fragment thereof (including but not limited to anti-IL-18, anti-TNF, anti-IL-6/cytokine receptor antibodies); methotrexate; cyclosporine; rapamycin; FK506; detectable label or reporter; a TNF antagonist; an antirheumatic; a muscle relaxant; a narcotic; a non-steroid anti-inflammatory drug (NSAID); an analgesic; an anesthetic; a sedative; a local anesthetic; a neuromuscular blocker; an antimicrobial agent; an antipsoriatic drug; a corticosteroid; an anabolic steroid; an erythropoietin; an immunization; an immunoglobulin; an immunosuppressive agent; a growth hormone; a hormone replacement drug; a radiopharmaceutical drug; an antidepressant; an antipsychotic drug; a stimulant; an asthma medication; a beta agonist; an inhaled steroid; an epinephrine or analog thereof; a cytokine; and a cytokine antagonist.

In a preferred embodiment, the pharmaceutical compositions disclosed above are administered to the subject by at least one mode selected from the group consisting of: parenteral, subcutaneous, intramuscular, intravenous, intrarticular, intrabronchial, intraabdominal, intracapsular, intracartilaginous, intracavitary, intracelial, intracerebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, bolus, vaginal, rectal, buccal, sublingual, intranasal, and transdermal.

Another aspect of the invention provides at least one DLL4 anti-idiotype antibody to at least one DLL4 binding protein of the present invention. The anti-idiotype antibody includes any protein or peptide containing molecule that comprises at least a portion of an immunoglobulin molecule such as, but not limited to, at least one complementarily determining region (CDR) of a heavy or light chain or a ligand binding portion thereof, a heavy chain or light chain variable region, a heavy chain or light chain constant region, a framework region, and any portion thereof, that can be incorporated into a binding protein of the present invention.

Any of a variety of immunodetection assay formats may be adapted to employ a DLL4 binding protein of the invention to detect DLL4 in a mixture, solution, or biological sample. Such immunodetection assay formats include but are not limited to radioimmunoassay (RIA), immunoprecipitation, enzyme-linked immunosorbent assay (ELISA), immunoblot (e.g., Western), immunostrips (e.g., immunodipsticks) comprising a DLL4 binding protein of the invention adsorbed or immobilized to substrate, FACS, and the like. Detection of DLL4 using a DLL4 binding protein of the invention may be conducted in vitro on a mixture, solution, or in biological sample. A biological sample that may be contacted with binding protein of the invention to detect or measure DLL4 in the sample includes, but is not limited to, urine, saliva, oral swab (buccal, lingual, or throat swab), dermal swab, dermal scrape, rectal swab, vaginal swab, whole blood sample, plasma sample, serum sample, tissue biopsy, and any other sample obtained from an individual by a procedure known in the art. In another embodiment, a DLL4 binding protein may be employed to detect DLL4 in vivo such as various tomography and scanning methods, including but not limited to X-ray computer assisted tomography (CT), magnetic resonance imaging (MRI), and positron emission tomography (PET).

DETAILED DESCRIPTION OF THE INVENTION

This invention pertains to DLL4 binding proteins, particularly anti-DLL4 antibodies, or antigen-binding portions thereof that bind DLL4. Various aspects of the invention relate to antibodies and antibody fragments, and pharmaceutical compositions thereof, as well as nucleic acids, recombinant expression vectors, and host cells for making such antibodies and fragments. Methods of using the antibodies of the invention to detect human DLL4 or murine DLL4, methods to inhibit human or mouse DLL4 and/or human or mouse VEGFR2 or VEGR1 activity, either in vitro or in vivo, and methods to regulate gene expression are also encompassed by the invention.

Unless otherwise defined herein, scientific and technical terms used in connection with the present invention shall have the meanings that are commonly understood by those of ordinary skill in the art. The meaning and scope of the terms should be clear, however, in the event of any latent ambiguity, definitions provided herein take precedent over any dictionary or extrinsic definition. Further, unless otherwise required by context, singular terms shall include pluralities and plural terms shall include the singular. In this application, the use of "or" means "and/or" unless stated otherwise. Furthermore, the use of the term "including," as well as other forms, such as "includes" and "included," is not limiting. Also, terms such as "element" or "component" encompass both elements and components comprising one unit and elements and components that comprise more than one subunit unless specifically stated otherwise.

Generally, nomenclatures used in connection with, and techniques of, cell and tissue culture, molecular biology, immunology, microbiology, genetics and protein and nucleic acid chemistry and hybridization described herein are those well known and commonly used in the art. The methods and techniques of the present invention are generally performed according to conventional methods well known in the art and as described in various general and more specific references that are cited and discussed throughout the present specification unless otherwise indicated. Enzymatic reactions and purification techniques are performed according to manufacturer's specifications, as commonly accomplished in the art or as described herein. The nomenclatures used in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

That the present invention may be more readily understood, select terms are defined below.

The term "polypeptide" as used herein, refers to any polymeric chain of amino acids. The terms "peptide" and "protein" are used interchangeably with the term polypeptide and also refer to a polymeric chain of amino acids. The term "polypeptide" encompasses native or artificial proteins, protein fragments and polypeptide analogs of a protein sequence. A polypeptide may be monomeric or polymeric. Use of "polypeptide" herein is intended to encompass polypeptide and fragments and variants (including fragments of variants) thereof, unless otherwise stated. For an antigenic polypeptide, a fragment of polypeptide optionally contains at least one contiguous or nonlinear epitope of polypeptide. The precise boundaries of the at least one epitope fragment can be confirmed using ordinary skill in the art. The fragment comprises at least about 5 contiguous amino acids, such as at least about 10 contiguous amino acids, at least about 15 contiguous amino acids, or at least about 20 contiguous amino acids. A variant of polypeptide is as described herein.

The term "isolated protein" or "isolated polypeptide" is a protein or polypeptide that by virtue of its origin or source of derivation is not associated with naturally associated components that accompany it in its native state; is substantially free of other proteins from the same species; is expressed by a cell from a different species; or does not occur in nature. Thus, a polypeptide that is chemically synthesized or synthesized in a cellular system different from the cell from which it naturally originates will be "isolated" from its naturally associated components. A protein may also be rendered substantially free of naturally associated components by isolation, using protein purification techniques well known in the art.

The term "recovering" as used herein, refers to the process of rendering a chemical species such as a polypeptide substantially free of naturally associated components by isolation, e.g., using protein purification techniques well known in the art.

The term "human DLL4" (abbreviated herein as "hDLL4" or "huDLL4"), as used herein, includes several EGF-like domains and a DSL domain that is required for receptor binding. The term includes a protein comprising about 74-75 kDa. The structure and deduced DNA and protein sequences of human DLL4 is described further in, for example, Shutter et al., Genes & Dev., 4: 1313-1318 (2000). The term "human DLL4" is intended to include recombinant human DLL4 (rh DLL4), which can be prepared by standard recombinant expression methods.

"Biological activity", as used herein with respect to DLL4, refers to all inherent biological properties of DLL4. Biological properties of DLL4 include, but are not limited to, binding a Notch receptor, activating a Notch receptor, negatively regulating VEGF signaling, repressing VEGFR2, and inducing VEGR1.

The terms "specific binding" or "specifically binding", as used herein, in reference to the interaction of an antibody, a protein, or a peptide with a second chemical species, means that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody.

The term "antibody", as used herein, broadly refers to any immunoglobulin (Ig) molecule comprised of four polypeptide chains, two heavy (H) chains and two light (L) chains, or any functional fragment, mutant, variant, or derivation thereof, which retains the essential epitope binding features of an Ig molecule. Such mutant, variant, or derivative antibody formats are known in the art. Nonlimiting embodiments of which are discussed below.

In a full-length antibody, each heavy chain is comprised of a heavy chain variable region (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementary determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, and FR4. Immunoglobulin molecules can be of any type (e.g., IgG, IgE, IgM, IgD, IgA and IgY), class (e.g., IgG 1, IgG2, IgG 3, IgG4, IgA1 and IgA2) or subclass.

The term "Fc region" is used to define the C-terminal region of an immunoglobulin heavy chain, which may be generated by papain digestion of an intact antibody. The Fc region may be a native sequence Fc region or a variant Fc region. The Fc region of an immunoglobulin generally comprises two constant domains, a CH2 domain and a CH3 domain, and optionally comprises a CH4 domain. Replacements of amino acid residues in the Fc portion to alter antibody effector function are known in the art (U.S. Pat. Nos. 5,648,260 and 5,624,821). The Fc portion of an antibody mediates several important effector functions, e.g., cytokine induction, ADCC, phagocytosis, complement dependent cytotoxicity (CDC), and half-life/clearance rate of antibody and antigen-antibody complexes. In some cases these effector functions are desirable for a therapeutic antibody but in other cases might be unnecessary or even deleterious, depending on the therapeutic objectives. Certain human IgG isotypes, particularly IgG1 and IgG3, mediate ADCC and CDC via binding to FcγRs and complement C1q, respectively. Neonatal Fc receptors (FcRn) are the critical components determining the circulating half-life of antibodies. In still another embodiment, at least one amino acid residue is replaced in the constant region of the antibody, for example, the Fc region of the antibody, such that effector functions of the antibody are altered. The dimerization of two identical heavy chains of an immunoglobulin is mediated by the dimerization of CH3 domains and is stabilized by the disulfide bonds within the hinge region (Huber et al., *Nature,* 264: 415-420 (1976); Thies et al., *J. Mol. Biol.,* 293: 67-79 (1999)). Mutation of cysteine residues within the hinge regions to prevent heavy chain-heavy chain disulfide bonds will destabilize dimerization of CH3 domains. Residues responsible for CH3 dimerization have been identified (Dall'Acqua, *Biochem.,* 37: 9266-9273 (1998)). Therefore, it is possible to generate a monovalent half-Ig. Interestingly, these monovalent half Ig molecules have been found in nature for both IgG and IgA subclasses (Seligman, *Ann. Immunol.,* 129: 855-70 (1978); Biewenga et al., *Clin. Exp. Immunol.,* 51: 395-400 (1983)). The stoichiometry of FcRn: Ig Fc region has been determined to be 2:1 (West et al., *Biochem.,* 39: 9698-9708 (2000)), and half Fc is sufficient for mediating FcRn binding (Kim et al., *Eur. J. Immunol.,* 24: 542-548 (1994)). Mutations to disrupt the dimerization of CH3 domain may not have greater adverse effect on its FcRn binding as the residues important for CH3 dimerization are located on the inner interface of CH3 b sheet structure, whereas the region responsible for FcRn binding is located on the outside interface of CH2-CH3 domains. However, the half Ig molecule may have certain advantages in tissue penetration due to its smaller size in comparison to that of a regular antibody. In one embodiment, at least one amino acid residue is replaced in the constant region of a binding protein of the invention, for example the Fc region, such that the dimerization of the heavy chains is disrupted, resulting in half Ig molecules. The anti-inflammatory activity of IgG is completely dependent on sialylation of the N-linked glycan of the IgG Fc fragment. The precise glycan requirements for anti-inflammatory activity has been determined, such that an appropriate IgG1 Fc fragment can be created, thereby generating a fully recombinant, sialylated IgG1 Fc with greatly enhanced potency (Anthony et al., *Science,* 320: 373-376 (2008)).

The term "antigen-binding portion" of an antibody (or simply "antibody portion"), as used herein, refers to one or more fragments of an antibody that retains the ability to bind specifically to an antigen (i.e., to a particular epitope of an antigen, such as an epitope of DLL4). It has been shown that the antigen-binding function of an antibody can be performed by fragments of a full-length antibody. Such antibody embodiments may also be bispecific, dual specific, or multi-specific formats; specifically binding to two or more different antigens (or two or more different epitopes of the same antigen). Examples of binding fragments encompassed within the term "antigen-binding portion" of an antibody include (i) a Fab fragment, a monovalent fragment consisting of the VL, VH, CL, and CH1 domains; (ii) a F(ab')$_2$ fragment, a bivalent fragment comprising two Fab fragments linked by a disulfide bridge at the hinge region; (iii) an Fd fragment consisting of the VH and CH1 domains; (iv) an Fv fragment consisting of the VL and VH domains of a single arm of an antibody; (v) a dAb fragment (Ward et al., *Nature,* 341:544-546 (1989); PCT Publication No. WO 90/05144 A1), which comprises a single variable domain; and (vi) an isolated complementary determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see, e.g., Bird et al., *Science,* 242: 423-426 (1988); Huston et al., *Proc. Natl. Acad. Sci. USA,* 85: 5879-5883 (1988)). Such single chain antibodies are also intended to be encompassed within the term "antigen-binding portion" of an antibody. Other forms of single chain antibodies, such as diabodies, are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see, e.g., Holliger et al., *Proc. Natl. Acad. Sci. USA,* 90: 6444-6448 (1993); Poljak, R. J., *Structure,* 2: 1121-1123 (1994)). Such antibody binding portions are known in the art (see, Kontermann and Dubel eds., *Antibody Engineering* (Springer-Verlag. New York, 2001), p. 790 (ISBN 3-540-41354-5)). In addition, single chain antibodies also include "linear antibodies" comprising a pair of tandem Fv segments (VH-CH1-VH-CH1) which, together with complementary light chain polypeptides, form a pair of antigen binding regions (Zapata et al. *Protein Eng.,* 8(10): 1057-1062 (1995); and U.S. Pat. No. 5,641,870).

The term "antibody construct" (or "DLL4 antibody construct") as used herein refers to a polypeptide comprising one or more the antigen binding portions of the invention linked to a linker polypeptide or an immunoglobulin constant domain. Linker polypeptides comprise two or more amino acid residues joined by peptide bonds and are used to link one or more antigen binding portions. Such linker polypeptides are well known in the art (see e.g., Holliger et al., *Proc. Natl. Acad. Sci. USA,* 90: 6444-6448 (1993); Poljak, R. J., *Structure,* 2: 1121-1123 (1994)). An immunoglobulin constant domain refers to a heavy or light chain constant domain. Human IgG heavy chain and light chain constant domain amino acid sequences are known in the art and represented in Table 1.

TABLE 1

Sequence of human IgG heavy chain constant domain and light chain constant domain

| Protein | Sequence Identifier | Sequence<br>123456789012345678901234567890112 |
|---|---|---|
| Ig gamma-1 constant region | SEQ ID NO: 2 | ASTKGPSVFPLAPSSKSTSGGTAALGCLVKDY<br>FPEPVTVSWNSGALTSGVHTFPAVLQSSGLYS<br>LSSVVTVPSSSLGTQTYICNVNHKPSNTKVDK<br>KVEPKSCDKTHTCPPCPAPELLGGPSVFLFPP<br>KPKDTLMISRTPEVTCVVVDVSHEDPEVKFNW<br>YVDGVEVHNAKTKPREEQYNSTYRVVSVLTVL<br>HQDWLNGKEYKCKVSNKALPAPIEKTISKAKG<br>QPREPQVYTLPPSREEMTKNQVSLTCLVKGFY<br>PSDIAVEWESNGQPENNYKTTPPVLDSDGSFF<br>LYSKLTVDKSRWQQGNVFSCSVMHEALHNHYT<br>QKSLSLSPGK |
| Ig gamma-1 constant region mutant | SEQ ID NO: 3 | ASTKGPSVFPLAPSSKSTSGGTAALGCLVKDY<br>FPEPVTVSWNSGALTSGVHTFPAVLQSSGLYS<br>LSSVVTVPSSSLGTQTYICNVNHKPSNTKVDK<br>KVEPKSCDKTHTCPPCPAPEAAGGPSVFLFPP<br>KPKDTLMISRTPEVTCVVVDVSHEDPEVKFNW<br>YVDGVEVHNAKTKPREEQYNSTYRVVSVLTVL<br>HQDWLNGKEYKCKVSNKALPAPIEKTISKAKG<br>QPREPQVYTLPPSREEMTKNQVSLTCLVKGFY<br>PSDIAVEWESNGQPENNYKTTPPVLDSDGSFF<br>LYSKLTVDKSRWQQGNVFSCSVMHEALHNHYT<br>QKSLSLSPGK |
| Ig Kappa constant region | SEQ ID NO: 4 | TVAAPSVFIFPPSDEQLKSGTASVVCLLNNFY<br>PREAKVQWKVDNALQSGNSQESVTEQDSKDST<br>YSLSSTLTLSKADYEKHKVYACEVTHQGLSSP<br>VTKSFNRGEC |
| Ig Lambda constant region | SEQ ID NO: 5 | QPKAAPSVTLFPPSSEELQANKATLVCLISDF<br>YPGAVTVAWKADSSPVKAGVETTTPSKQSNNK<br>YAASSYLSLTPEQWKSHRSYSCQVTHEGSTVE<br>KTVAPTECS |

Still further, an antibody or antigen-binding portion thereof may be part of a larger immunoadhesion molecules, formed by covalent or noncovalent association of the antibody or antibody portion with one or more other proteins or peptides. Examples of such immunoadhesion molecules include use of the streptavidin core region to make a tetrameric scFv molecule (Kipriyanov et al., *Human Antibodies and Hybridomas*, 6: 93-101 (1995)) and use of a cysteine residue, a marker peptide, and a C-terminal polyhistidine tag to make bivalent and biotinylated scFv molecules (Kipriyanov et al., *Mol. Immunol.*, 31: 1047-1058 (1994)). Antibody portions, such as Fab and F(ab')2 fragments, can be prepared from whole antibodies using conventional techniques, such as papain or pepsin digestion, respectively, of whole antibodies. Moreover, antibodies, antibody portions, and immunoadhesion molecules can be obtained using standard recombinant DNA techniques, as described herein and known in the art.

An "isolated antibody", as used herein, is intended to refer to an antibody that is substantially free of other antibodies having different antigenic specificities (e.g., an isolated antibody that specifically binds hDLL4 is substantially free of antibodies that specifically bind antigens other than hDLL4). An isolated antibody that specifically binds hDLL4 may, however, have cross-reactivity to other antigens, such as DLL4 molecules from other species (e.g., muDLL4). Moreover, an isolated antibody may be substantially free of other cellular material and/or chemicals.

The term "monoclonal antibody" and abbreviations "MAb" and "mAb", as used herein, refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigen. Furthermore, in contrast to polyclonal antibody preparations that typically include different antibodies directed against different determinants (epitopes), each mAb is directed against a single determinant on the antigen. The modifier "monoclonal" is not to be construed as requiring production of the antibody by any particular method.

The term "human antibody", as used herein, is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include antibodies in which CDR sequences derived from the germline of another mammalian species, such as a mouse, have been grafted onto human framework sequences.

The term "recombinant human antibody", as used herein, is intended to include all human antibodies that are prepared, expressed, created, or isolated by recombinant means, such as antibodies expressed using a recombinant expression vector transfected into a host cell, antibodies isolated from a recombinant, combinatorial human antibody library (Hoogenboom, *Trends Biotechnol.*, 15:62-70 (1997); Azzazy and Highsmith, *Clin. Biochem.*, 35: 425-445 (2002); Gavilondo and Larrick, *BioTechniques*, 29: 128-145 (2000); Hoogenboom and Chames, *Immunol. Today,* 21: 371-378 (2000)), antibodies isolated from an animal (e.g., a mouse) that is transgenic for human immunoglobulin genes (see, Taylor et al., *Nucl. Acids Res.,* 20: 6287-6295 (1992); Kellermann and Green, *Curr. Opin. Biotechnol.,* 13: 593-597 (2002); Little et al., *Immunol. Today,* 21: 364-370 (2000)) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

The term "chimeric antibody" refers to antibodies which comprise heavy and light chain variable region sequences from one species and constant region sequences from another species, such as antibodies having murine heavy and light chain variable regions linked to human constant regions.

As used herein, the term "CDR" refers to a complementary determining region within antibody variable sequences. There are three CDRs in each of the variable regions of the heavy chain and the light chain, which are designated "CDR1", "CDR2", and "CDR3", for each of the variable regions. The term "CDR set" as used herein refers to a group of three CDRs that occur in a single variable region that binds the antigen. The exact boundaries of these CDRs have been defined differently according to different systems. The system described by Kabat (Kabat et al., Sequences of Proteins of Immunological Interest (National Institutes of Health, Bethesda, Md. (1987) and (1991)) not only provides an unambiguous residue numbering system applicable to any variable region of an antibody, but also provides precise residue boundaries defining the three CDRs. These CDRs may be referred to as "Kabat CDRs". Chothia and coworkers (Chothia and Lesk, *J. Mol. Biol.,* 196: 901-917 (1987); Chothia et al., *Nature,* 342: 877-883 (1989)) found that certain sub-portions within Kabat CDRs adopt nearly identical peptide backbone conformations, despite having great diversity at the level of amino acid sequence. These sub-portions were designated as "L1", "L2", and "L3", or "H1", "H2", and "H3", where the "L" and the "H" designate the light chain and the heavy chain regions, respectively. These regions may be referred to as "Chothia CDRs", which have boundaries that overlap with Kabat CDRs. Other boundaries defining CDRs overlapping with the Kabat CDRs have been described by Padlan, *FASEB J.,* 9: 133-139 (1995) and MacCallum, *J. Mol. Biol.,* 262(5): 732-745 (1996). Still other CDR boundary definitions may not strictly follow one of the herein systems, but will nonetheless overlap with the Kabat CDRs, although they may be shortened or lengthened in light of prediction or experimental findings that particular residues or groups of residues or even entire CDRs do not significantly impact antigen binding. The methods used herein may utilize CDRs defined according to any of these systems, although certain embodiments use Kabat or Chothia defined CDRs.

The terms "Kabat numbering," "Kabat definitions", and "Kabat labeling" are used interchangeably herein. These terms, which are recognized in the art, refer to a system of numbering amino acid residues which are more variable (i.e., hypervariable) than other amino acid residues in the heavy and light chain variable regions of an antibody, or an antigen binding portion thereof (Kabat et al., *Ann. NY Acad. Sci.,* 190: 382-391 (1971) and Kabat et al., *Sequences of Proteins of Immunological Interest, Fifth Edition,* U.S. Department of Health and Human Services, NIH Publication No. 91-3242 (1991)). For the heavy chain variable region (VH), the hypervariable region ranges from amino acid positions 31 to 35 for CDR1, amino acid positions 50 to 65 for CDR2, and amino acid positions 95 to 102 for CDR3. For the light chain variable region (VL), the hypervariable region ranges from amino acid positions 24 to 34 for CDR1, amino acid positions 50 to 56 for CDR2, and amino acid positions 89 to 97 for CDR3.

The growth and analysis of extensive public databases of amino acid sequences of variable heavy and light regions over the past twenty years have led to the understanding of the typical boundaries between framework regions (FR) and CDR sequences within variable region sequences and enabled persons skilled in this art to accurately determine the CDRs according to Kabat numbering, Chothia numbering, or other systems. See, e.g., Martin, "Protein Sequence and Structure Analysis of Antibody Variable Domains," In Kontermann and Duübel, eds., *Antibody Engineering* (Springer-Verlag, Berlin, 2001), chapter 31, pages 432-433. A useful method of determining the amino acid sequences of Kabat CDRs within the amino acid sequences of variable heavy (VH) and variable light (VL) regions is provided below:

To identify a CDR-L1 amino acid sequence:
Starts approximately 24 amino acid residues from the amino terminus of the VL region;
Residue before the CDR-L1 sequence is always cysteine (C);
Residue after the CDR-L1 sequence is always tryptophan (W) residue, typically Trp-Tyr-Gln (W-Y-Q), but also Trp-Leu-Gln (W-L-Q), Trp-Phe-Gln (W-F-Q), and Trp-Tyr-Leu (W-Y-L);
Length is typically 10 to 17 amino acid residues.
To identify a CDR-L2 amino acid sequence:
Starts always 16 residues after the end of CDR-L1;
Residues before the CDR-L2 sequence are generally Ile-Tyr (I-Y), but also Val-Tyr (V-Y), Ile-Lys (I-K), and Ile-Phe (I-F);
Length is always 7 amino acid residues.
To identify a CDR-L3 amino acid sequence:
Starts always 33 amino acids after the end of CDR-L2;
Residue before the CDR-L3 amino acid sequence is always a cysteine (C);
Residues after are always Phe-Gly-X-Gly (F-G-X-G) (SEQ ID NO:374), where X is any amino acid;
Length is typically 7 to 11 amino acid residues.
To identify a CDR-H1 amino acid sequence:
Starts approximately 31 amino acid residues from amino terminus of VH region and always 9 residues after a cysteine (C);
Residues before are always Cys-X-X-X-X-X-X-X-X (SEQ ID NO:375), where X is any amino acid;
Residue after is always a Trp (W), typically Trp-Val (W-V), but also Trp-Ile (W-I), and Trp-Ala (W-A);
Length is typically 5 to 7 amino acid residues.
To identify a CDR-H2 amino acid sequence:
Starts always 15 amino acid residues after the end of CDR-H1;
Residues before are typically Leu-Glu-Trp-Ile-Gly (L-E-W-I-G) (SEQ ID NO:376), but other variations also;
Residues after are Lys/Arg-Leu/Ile/Val/Phe/Thr/Ala-Thr/Ser/Ile/Ala (K/R-L/I/V/F/T/A-T/S/I/A);
Length is typically 16 to 19 amino acid residues.

To identify a CDR-H3 amino acid sequence:
Starts always 33 amino acid residues after the end of CDR-H2 and always 3 after a cysteine (C)'
Residues before are always Cys-X-X (C-X-X), where X is any amino acid, typically Cys-Ala-Arg (C-A-R);
Residues after are always Trp-Gly-X-Gly (W-G-X-G) (SEQ ID NO:377), where X is any amino acid;
Length is typically 3 to 25 amino acid residues.

The term "CDR-grafted antibody" refers to antibodies which comprise heavy and light chain variable region sequences from one species but in which the sequences of one or more of the CDR regions of VH and/or VL are replaced with CDR sequences of another species, such as antibodies having murine heavy and light chain variable regions in which one or more of the murine CDRs (e.g., CDR3) has been replaced with human CDR sequences.

The term "humanized antibody" refers to antibodies which comprise heavy and light chain variable region sequences from a non-human species (e.g., a mouse) but in which at least a portion of the VH and/or VL sequence has been altered to be more "human-like," i.e., more similar to human germline variable sequences. A "humanized antibody" is an antibody or a variant, derivative, analog, or fragment thereof, which immunospecifically binds to an antigen of interest and which comprises a framework (FR) region having substantially the amino acid sequence of a human antibody and a complementary determining region (CDR) having substantially the amino acid sequence of a non-human antibody. As used herein, the term "substantially" in the context of a CDR refers to a CDR having an amino acid sequence at least 80%, at least 85%, at least 90%, at least 95%, at least 98% or at least 99% identical to the amino acid sequence of a non-human antibody CDR. A humanized antibody comprises substantially all of at least one, and typically two, variable domains (Fab, Fab', F(ab')2, FabC, Fv) in which all or substantially all of the CDR regions correspond to those of a non-human immunoglobulin (i.e., donor antibody) and all or substantially all of the framework regions are those of a human immunoglobulin consensus sequence. In an embodiment, a humanized antibody also comprises at least a portion of an immunoglobulin constant region (Fc), typically that of a human immunoglobulin. In some embodiments, a humanized antibody contains both the light chain as well as at least the variable domain of a heavy chain. The antibody also may include the CH1, hinge, CH2, CH3, and CH4 regions of the heavy chain. In some embodiments, a humanized antibody only contains a humanized light chain. In some embodiments, a humanized antibody only contains a humanized heavy chain. In specific embodiments, a humanized antibody only contains a humanized variable domain of a light chain and/or humanized heavy chain.

A humanized antibody can be selected from any class of immunoglobulins, including IgM, IgG, IgD, IgA, and IgE, and any isotype, including without limitation IgG1, IgG2, IgG3, and IgG4. A humanized antibody may comprise sequences from more than one class or isotype, and particular constant domains may be selected to optimize desired effector functions using techniques well known in the art.

The framework regions and CDRs of a humanized antibody need not correspond precisely to the parental sequences, e.g., the donor antibody CDR or the consensus framework may be mutagenized by substitution, insertion, and/or deletion of at least one amino acid residue so that the CDR or framework residue at that site does not correspond to either the donor antibody or the consensus framework. In a preferred embodiment, such mutations, however, will not be extensive. Usually, at least 80%, preferably at least 85%, more preferably at least 90%, and most preferably at least 95% of the humanized antibody residues will correspond to those of the parental FR and CDR sequences. As used herein, the term "consensus framework" refers to the framework region in the consensus immunoglobulin sequence. As used herein, the term "consensus immunoglobulin sequence" refers to the sequence formed from the most frequently occurring amino acids (or nucleotides) in a family of related immunoglobulin sequences (See, e.g., Winnaker, *From Genes to Clones* (Verlagsgesellschaft, Weinheim, 1987)). A "consensus immunoglobulin sequence" may thus comprise a "consensus framework region(s)" and/or a "consensus CDR(s)". In a family of immunoglobulins, each position in the consensus sequence is occupied by the amino acid occurring most frequently at that position in the family. If two amino acids occur equally frequently, either can be included in the consensus sequence.

An "affinity matured" antibody is an antibody with one or more alterations in one or more CDRs thereof which result in an improvement in the affinity of the antibody for a target antigen, compared to a parent antibody which does not possess the alteration(s). Exemplary affinity matured antibodies will have nanomolar or even picomolar affinities for the target antigen. A variety of procedures for producing affinity matured antibodies are known in the art. For example, Marks et al., *BioTechnology,* 10: 779-783 (1992) describes affinity maturation by VH and VL domain shuffling. Random mutagenesis of CDR and/or framework residues is described by Barbas et al., *Proc. Nat. Acad. Sci. USA,* 91: 3809-3813 (1994); Schier et al., *Gene,* 169: 147-155 (1995); Yelton et al., *J. Immunol.,* 155: 1994-2004 (1995); Jackson et al., *J. Immunol.,* 154(7): 3310-3319 (1995); Hawkins et al, *J. Mol. Biol.,* 226: 889-896 (1992). Selective mutation at selective mutagenesis positions and at contact or hypermutation positions with an activity enhancing amino acid residue is described in U.S. Pat. No. 6,914,128 B1.

The term "multivalent binding protein" denotes a binding protein comprising two or more antigen binding sites (also referred to herein as "antigen binding domains"). A multivalent binding protein is preferably engineered to have three or more antigen binding sites, and is generally not a naturally occurring antibody. The term "multispecific binding protein" refers to a binding protein capable of binding two or more related or unrelated targets, including a binding protein capable of binding two or more different epitopes of the same target molecule.

The term "bispecific antibody", as used herein, refers to full-length antibodies that are generated by quadroma technology (see Milstein et al., *Nature,* 305(5934): 537-540 (1983)), by chemical conjugation of two different monoclonal antibodies (see, Staerz et al., *Nature,* 314(6012): 628-631 (1985)), or by knob-into-hole or similar approaches which introduces mutations in the Fc region (see Holliger et al., *Proc. Natl. Acad. Sci. USA,* 90(14): 6444-6448 (1993)), resulting in multiple different immunoglobulin species of which only one is the functional bispecific antibody. By molecular function, a bispecific antibody binds one antigen (or epitope) on one of its two binding arms (one pair of HC/LC), and binds a different antigen (or epitope) on its second arm (a different pair of HC/LC). By this definition, a bispecific antibody has two distinct antigen binding arms (in both specificity and CDR sequences), and is monovalent for each antigen it binds to.

The term "dual-specific antibody", as used herein, refers to full-length antibodies that can bind two different antigens (or epitopes) in each of its two binding arms (a pair of HC/LC) (see PCT publication WO 02/02773). Accordingly a dual-specific binding protein has two identical antigen binding arms, with identical specificity and identical CDR sequences, and is bivalent for each antigen to which it binds.

"Dual variable domain" ("DVD") binding proteins of the invention comprise two or more antigen binding sites and may be divalent (two antigen binding sites), tetravalent (four antigen binding sites), or multivalent binding proteins. DVDs may be monospecific, i.e., capable of binding one antigen (or one specific epitope), or multispecific, i.e., capable of binding two or more antigens (i.e., two or more epitopes of the same target antigen molecule or two or more epitopes of different target antigens). A preferred DVD binding protein comprises two heavy chain DVD polypeptides and two light chain DVD polypeptides is referred to as a "DVD immunoglobulin" or "DVD-Ig". Such a DVD-Ig binding protein is thus tetrameric and reminiscent of an IgG molecule, but provides more antigen binding site than an IgG molecule. Thus, each half of a tetrameric DVD-Ig molecule is reminiscent of one half of an IgG molecule and comprises a heavy chain DVD polypeptide and a light chain DVD polypeptide, but unlike a pair of heavy and light chains of an IgG molecule that provide a single antigen binding domain, a pair of heavy and light chains of a DVD-Ig provide two or more antigen binding sites.

Each antigen binding site of a DVD-Ig binding protein is derived from a donor ("parental") monoclonal antibody and thus comprises a heavy chain variable domain (VH) and a light chain variable domain (VL) with a total of six CDRs involved in antigen binding per antigen binding site. Accordingly, a DVD-Ig binding protein that binds two different epitopes (i.e., two different epitopes of two different antigen molecules or two different epitopes of the same antigen molecule) comprises an antigen binding site derived from a first parental monoclonal antibody and an antigen binding site of a second parental monoclonal antibody.

A description of the design, expression, and characterization of DVD-Ig binding molecules is provided in PCT Publication No. WO 2007/024715, U.S. Pat. No. 7,612,181, and Wu et al., *Nature Biotech.*, 25: 1290-1297 (2007). A preferred example of such DVD-Ig molecules comprises a heavy chain that comprises the structural formula VD1-(X1)n-VD2-C-(X2)n, wherein VD1 is a first heavy chain variable domain, VD2 is a second heavy chain variable domain, C is a heavy chain constant domain, X1 is a linker with the proviso that it is not CH1, X2 is an Fc region, and n is 0 or 1, but preferably 1; and a light chain that comprises the structural formula VD1-(X1)n-VD2-C-(X2)n, wherein VD1 is a first light chain variable domain, VD2 is a second light chain variable domain, C is a light chain constant domain, X1 is a linker with the proviso that it is not CH1, and X2 does not comprise an Fc region; and n is 0 or 1, but preferably 1. Such a DVD-Ig may comprise two such heavy chains and two such light chains, wherein each chain comprises variable domains linked in tandem without an intervening constant region between variable regions, wherein a heavy chain and a light chain associate to form tandem functional antigen binding sites, and a pair of heavy and light chains may associate with another pair of heavy and light chains to form a tetrameric binding protein with four functional antigen binding sites. In another example, a DVD-Ig molecule may comprise heavy and light chains that each comprise three variable domains (VD1, VD2, VD3) linked in tandem without an intervening constant region between variable domains, wherein a pair of heavy and light chains may associate to form three antigen binding sites, and wherein a pair of heavy and light chains may associate with another pair of heavy and light chains to form a tetrameric binding protein with six antigen binding sites.

In a preferred embodiment, a DVD-Ig binding protein according to the invention not only binds the same target molecules bound by its parental monoclonal antibodies, but also possesses one or more desirable properties of one or more of its parental monoclonal antibodies. Preferably, such an additional property is an antibody parameter of one or more of the parental monoclonal antibodies. Antibody parameters that may be contributed to a DVD-Ig binding protein from one or more of its parental monoclonal antibodies include, but are not limited to, antigen specificity, antigen affinity, potency, biological function, epitope recognition, protein stability, protein solubility, production efficiency, immunogenicity, pharmacokinetics, bioavailability, tissue cross reactivity, and orthologous antigen binding.

A DVD-Ig binding protein according to the invention binds at least one epitope of a human DLL4 protein. Non-limiting examples of a DVD-Ig binding protein according to the invention include a DVD-Ig binding protein that binds one or more epitopes of human DLL4, a DVD-Ig binding protein that binds an epitope of a human DLL4 and an epitope of a DLL4 of another species (for example, mouse), and a DVD-Ig binding protein that binds an epitope of a human DLL4 and an epitope of another target molecule (for example, VEGFR2 or VEGFR1).

A "functional antigen binding site" of a binding protein is one that is capable of binding a target antigen. The antigen binding affinity of the antigen binding site is not necessarily as strong as the parent antibody from which the antigen binding site is derived, but the ability to bind antigen must be measurable using any one of a variety of methods known for evaluating antibody binding to an antigen. Moreover, the antigen binding affinity of each of the antigen binding sites of a multivalent antibody herein need not be quantitatively the same.

As used herein, the terms "acceptor" and "acceptor antibody" refer to an antibody or nucleic acid sequence providing or encoding at least 80%, at least 85%, at least 90%, at least 95%, at least 98%, or 100% of the amino acid sequences of one or more of the framework regions (FRs). In some embodiments, the term "acceptor" refers to the antibody amino acid or nucleic acid sequence providing or encoding the constant region(s). In yet another embodiment, the term "acceptor" refers to the antibody amino acid or nucleic acid sequence providing or encoding one or more of the framework regions and the constant region(s). In a specific embodiment, the term "acceptor" refers to a human antibody amino acid or nucleic acid sequence that provides or encodes at least 80%, preferably, at least 85%, at least 90%, at least 95%, at least 98%, or 100% of the amino acid sequences of one or more of the framework regions. In accordance with this embodiment, an acceptor may contain at least 1, at least 2, at least 3, least 4, at least 5, or at least 10 amino acid residues that does (do) not occur at one or more specific positions of a human antibody. An acceptor framework region and/or acceptor constant region(s) may be, e.g., derived or obtained from a germline antibody gene, a mature antibody gene, a functional antibody (e.g., antibodies well-known in the art, antibodies in development, or antibodies commercially available).

As used herein, the term "canonical" residue refers to a residue in a CDR or framework that defines a particular canonical CDR structure as defined by Chothia et al. (*J. Mol. Biol.*, 196: 901-917 (1987); Chothia et al., *J. Mol. Biol.*, 227: 799-817 (1992), both are incorporated herein by reference). According to Chothia et al., critical portions of the CDRs of many antibodies have nearly identical peptide backbone conformations despite great diversity at the level of amino acid sequence. Each canonical structure specifies primarily a set of peptide backbone torsion angles for a contiguous segment of amino acid residues forming a loop.

As used herein, the terms "donor" and "donor antibody" refer to an antibody providing one or more CDRs. In a preferred embodiment, the donor antibody is an antibody from a species different from the antibody from which the framework regions are obtained or derived. In the context of a humanized antibody, the term "donor antibody" refers to a non-human antibody providing one or more CDRs.

As used herein, the term "framework" or "framework sequence" refers to the remaining sequences of a variable region minus the CDRs. Because the exact definition of a CDR sequence can be determined by different systems (for example, see above), the meaning of a framework sequence is subject to correspondingly different interpretations. The six CDRs (CDR-L1, -L2, and -L3 of light chain and CDR-H1, -H2, and -H3 of heavy chain) also divide the framework regions on the light chain and the heavy chain into four sub-regions (FR1, FR2, FR3, and FR4) on each chain, in which CDR1 is positioned between FR1 and FR2, CDR2 between FR2 and FR3, and CDR3 between FR3 and FR4. Without specifying the particular sub-regions as FR1, FR2, FR3, or FR4, a framework region, as referred by others, represents the combined FR's within the variable region of a single, naturally occurring immunoglobulin chain. As used herein, a FR represents one of the four sub-regions, and FRs represents two or more of the four sub-regions constituting a framework region.

Human heavy chain and light chain acceptor sequences are known in the art. In one embodiment of the invention the human heavy chain and light chain acceptor sequences are selected from the sequences described in Table 2 and Table 3.

TABLE 2

Heavy Chain Acceptor Sequences

| SEQ ID NO.: | Protein region/ Closest Germline Family | Sequence 123456789012345678901234567890012 |
|---|---|---|
| 6 | VH2-70/JH6 FR1 | EVTLRESGPALVKPTQTLTLTCTFSGFSLS |
| 7 | VH2-70/JH6 FR2 | WIRQPPGKALEWLA |
| 8 | VH2-70/JH6 FR3 | RLTISKDTSKNQVVLTMTNMDPVDTATYYCAR |
| 9 | VH2-70/JH6 FR4 | WGQGTTVTVSS |
| 10 | VH2-26/JH6 FR1 | EVTLKESGPVLVKPTETLTLTCTVSGFSLS |
| 7 | VH2-26/JH6 FR2 | WIRQPPGKALEWLA |
| 11 | VH2-26/JH6 FR3 | RLTISKDTSKSQVVLTMTNMDPVDTATYYCAR |
| 9 | VH2-26/JH6 FR4 | WGQGTTVTVSS |
| 12 | VH3-72/JH6 FR1 | EVQLVESGGGLVQPGGSLRLSCAASGFTFS |
| 13 | VH3-72/JH6 FR2 | WVRQAPGKGLEWVG |
| 14 | VH3-72/JH6 FR3 | RFTISRDDSKNSLYLQMNSLKTEDTAVYYCAR |
| 9 | VH3-72/JH6 FR4 | WGQGTTVTVSS |
| 15 | VH3-21/JH6 FR1 | EVQLVESGGGLVKPGGSLRLSCAASGFTFS |
| 16 | VH3-21/JH6 FR2 | WVRQAPGKGLEWVS |
| 17 | VH3-21/JH6 FR3 | RFTISRDNAKNSLYLQMNSLRAEDTAVYYCAR |
| 9 | VH3-21/JH6 FR4 | WGQGTTVTVSS |
| 18 | VH1-69/JH6 FR1 | EVQLVQSGAEVKKPGSSVKVSCKASGGTFS |
| 19 | VH1-69/JH6 FR2 | WVRQAPGQGLEWMG |
| 20 | VH1-69/JH6 FR3 | RVTITADKSTSTAYMELSSLRSEDTAVYYCAR |
| 9 | VH1-69/JH6 FR4 | WGQGTTVTVSS |
| 21 | VH1-18/JH6 FR1 | EVQLVQSGAEVKKPGASVKVSCKASGYTFT |
| 19 | VH1-18/JH6 FR2 | WVRQAPGQGLEWMG |
| 22 | VH1-18/JH6 FR3 | RVTMTTDTSTSTAYMELRSLRSDDTAVYYCAR |
| 9 | VH1-18/JH6 FR4 | WGQGTTVTVSS |
| 35 | IGHV4-59 FR1 | EVQLQESGPGLVKPSETLSLTCTVSGGSIS |
| 36 | IGHV4-59 FR2 | WIRQPPGKGLEWIG |
| 37 | IGHV4-59 FR3 | RVTISVDTSKNQFSLKLSSVTAADTAVYYCAR |
| 38 | IGHV4-59/JH FR4 | WGQGTLVTVSS |

TABLE 2-continued

Heavy Chain Acceptor Sequences

| SEQ ID NO.: | Protein region/ Closest Germline Family | Sequence 1234567890123456789012345678901234567890 |
|---|---|---|
| 39 | IGHV3-66 FW1 | EVQLVESGGGLVQPGGSLRLSCAVSGGSIS |
| 40 | IGHV3-66 FW2 | WIRQAPGKGLEWIG |
| 41 | IGHV3-66 FW3 | RVTISVDTSKNSFYLQMNSLRAEDTAVYYCAR |
| 42 | IGHV3-66/JH FW4 | WGQGTLVTVSS |
| 43 | IGHV4-59 FR1 | EVQLQESGPGLVKPGETLSLTCTVSGGSIS |
| 44 | IGHV4-59 FR2 | WIRQAPGKGLEWIG |
| 45 | IGHV4-59 FR3 | RVTISVDTSKNQFYLKLSSVRAEDTAVYYCAR |
| 46 | IGHV4-59/JH FR4 | WGQGTLVTVSS |
| 47 | IGHV5-51 FR1 | EVQLVQSGTEVKKPGESLKISCKVSGGSIS |
| 48 | IGHV5-51 FR2 | WIRQMPGKGLEWIG |
| 49 | IGHV5-51 FR3 | QVTISVDTSFNTFFLQWSSLKASDTAMYYCAR |
| 50 | IGHV5-51/JH FR4 | WGQGTMVTVSS |
| 51 | IGHV2-70 FR1 | EVTLRESGPALVKPTQTLTLTCTVSGGSIS |
| 52 | IGHV2-70 FR2 | WIRQPPGKGLEWIG |
| 53 | IGHV2-70 FR3 | RVTISVDTSKNQFVLTMTNMDPVDTATYYCAR |
| 54 | IGHV2-70/JH FR4 | WGQGTTVTVSS |
| 55 | IGHV3-15 FR1 | EVQLLESGGGLVKSGGSLRLSCAASGFTFR |
| 56 | IGHV3-15 FR2 | WVRQAPGKGLEWVA |
| 57 | IGHV3-15 FR3 | RFTISRDNSKNTLYLQLNSLRAEDTAVYYCAK |
| 58 | IGHV3-15/JH FR4 | WGQGTMVTVSS |
| 59 | IGHV3-43 FR1 | EVQLVESGGGVVQPGGSLRLSCAASGFTFG |
| 60 | IGHV3-43 FR2 | WVRQAPGKGLEWVA |
| 61 | IGHV3-43 FR3 | RFTISRDNSKNTLYLQLNSLRAEDTAVYYCAK |
| 62 | IGHV3-43/JH FR4 | WGQGTMVTVSS |

TABLE 3

Light Chain Acceptor Sequences

| SEQ ID NO.: | Protein region/ Closest Germline Family | Sequence 1234567890123456789012345678901234567890 |
|---|---|---|
| 23 | B3/JK4 FR1 | DIVMTQSPDSLAVSLGERATINC |
| 24 | B3/JK4 FR2 | WYQQKPGQPPKLLIY |
| 25 | B3/JK4 FR3 | GVPDRFSGSGSGTDFTLTISSLQAEDVAVYYC |
| 26 | B3/JK4 FR4 | FGGGTKVEIKR |
| 27 | L2/JK4 FR1 | EIVMTQSPATLSVSPGERATLSC |
| 28 | L2/JK4 FR2 | WYQQKPGQAPRLLIY |
| 29 | L2/JK4 FR3 | GIPARFSGSGSGTEFTLTISSLQSEDFAVYYC |
| 26 | L2/JK4 FR4 | FGGGTKVEIKR |

TABLE 3-continued

Light Chain Acceptor Sequences

| SEQ ID NO.: | Protein region/ Closest Germline Family | Sequence |
|---|---|---|
| 30 | L15/JK4 FR1 | DIQMTQSPSSLSASVGDRVTITC |
| 31 | L15/JK4 FR2 | WYQQKPEKAPKSLIY |
| 32 | L15/JK4 FR3 | GVPSRFSGSGSGTDFTLTISSLQPEDFATYYC |
| 26 | L15/JK4 FR4 | FGGGTKVEIKR |
| 33 | L5/JK4 FR1 | DIQMTQSPSSVSASVGDRVTITC |
| 34 | L5/JK4 FR2 | WYQQKPGKAPKLLIY |
| 32 | L5/JK4 FR3 | GVPSRFSGSGSGTDFTLTISSLQPEDFATYYC |
| 26 | L5/JK4 FR4 | FGGGTKVEIKR |
| 63 | IGLV3-1 FR1 | SYELTQPPSVSVSPGQTASITC |
| 64 | IGLV3-1 FR2 | WYQQKPGQSPVLVIY |
| 65 | IGLV3-1 FR3 | GIPERFSGSNSGDTATLTISGTQPMDEADYYC |
| 66 | IGLV3-1/JL FR4 | FGYGTKVTVL |
| 67 | IGLV3-1 FR1 | SYELTQPPSVSVSPGQTASITC |
| 68 | IGLV3-1 FR2 | WYQQKPGQSPVLVIY |
| 69 | IGLV3-1 FR3 | GIPERFSGSNSGDTATLTISGTQPMDEADYYC |
| 70 | IGLV3-1/JL FR4 | GGGTKLTVLG |
| 71 | IGLV3-1 FR1 | YELTQPPSVSVSPGQTASITC |
| 72 | IGLV3-1 FR2 | WYQQKPGQSPVLVIY |
| 73 | IGLV3-1 FR3 | GIPERFSGSNSGDTATLTISGTQPMDEADYYC |
| 74 | IGLV3-1/JL FR4 | GGGTKLTVLG |
| 75 | IGLV3-1 FR1 | LYVLTQPPSVSVSPGQTASITC |
| 76 | IGLV3-1 FR2 | WYQQKPGQSPVLVIY |
| 77 | IGLV3-1 FR3 | GIPERFSGSNSGDTATLTISGTQTMDEADYLC |
| 78 | IGLV3-1/JL FR4 | FGGGTKVTVLG |
| 79 | IGKV6D-21 FR1 | EYVLTQSPDFQSVTPKEKVTITC |
| 80 | IGKV6D-21 FR2 | WYQQKPDQSPKLVIY |
| 81 | IGKV6D-21 FR3 | GVPSRFSGSNSGDDATLTINSLEAEDAATYYC |
| 82 | IGKV6D-21/JK FR4 | FGQGTKVEIKR |
| 83 | IGKV3D-15 FR1 | EYVLTQSPATLSVSPGERATLSC |
| 84 | IGKV3D-15 FR2 | WYQQKPGQSPRLVIY |
| 85 | IGKV3D-15 FR3 | DIPARFSGSNSGDEATLTISSLQSEDFAVYYC |
| 86 | IGKV3D-15/JK FR4 | FGQGTRLEIKR |
| 87 | IGKV4-1 FR1 | DYVLTQSPDSLAVSLGERATINC |
| 88 | IGKV4-1 FR2 | WYQQKPGQSPKLVIY |
| 89 | IGKV4-1 FR3 | GIPDRFSGSNSGDDATLTISSLQAEDVAVYYC |
| 90 | IGKV4-1/JK FR4 | FGGGTKVEIKR |
| 91 | IGLV3-1 FR1 | LPVLTQPPSVSVSPGQTASITC |
| 92 | IGLV3-1 FR2 | WYQQKPGQSPVLVIY |

TABLE 3-continued

Light Chain Acceptor Sequences

| SEQ ID NO.: | Protein region/ Closest Germline Family | Sequence 1234567890123456789012345678901 2 |
|---|---|---|
| 93 | IGLV3-1 FR3 | GIPERFSGSNSGNTATLTISGTQTMDEADYLC |
| 94 | IGLV3-1/JL FR4 | FGGGTKVTVL |
| 95 | IGLV3-1 FR1 | SYELTQPPSVSVSPGQTASITC |
| 96 | IGLV3-1 FR2 | WYQQKPGQSPVLVIY |
| 97 | IGLV3-1 FR3 | GIPERFSGSNSGNTATLTISGTQTMDEADYLC |
| 98 | IGLV3-1/JL FR4 | FGGGTKLTVL |

As used herein, the term "germline antibody gene" or "gene fragment" refers to an immunoglobulin sequence encoded by non-lymphoid cells that have not undergone the maturation process that leads to genetic rearrangement and mutation for expression of a particular immunoglobulin. (See, e.g., Shapiro et al., Crit. Rev. Immunol., 22(3): 183-200 (2002); Marchalonis et al., Adv. Exp. Med. Biol., 484:13-30 (2001)). One of the advantages provided by various embodiments of the present invention stems from the recognition that germline antibody genes are more likely than mature antibody genes to conserve essential amino acid sequence structures characteristic of individuals in the species, hence less likely to be recognized as from a foreign source when used therapeutically in that species.

As used herein, the term "key residue" refers to certain residues within the variable region that have more impact on the binding specificity and/or affinity of an antibody, in particular a humanized antibody. A key residue includes, but is not limited to, one or more of the following: a residue that is adjacent to a CDR, a potential glycosylation site (can be either N- or O-glycosylation site), a rare residue, a residue capable of interacting with the antigen, a residue capable of interacting with a CDR, a canonical residue, a contact residue between heavy chain variable region and light chain variable region, a residue within the Vernier zone, and a residue in the region that overlaps between the Chothia definition of a variable heavy chain CDR/and the Kabat definition of the first heavy chain framework.

As used herein, "Vernier" zone refers to a subset of framework residues that may adjust CDR structure and fine-tune the fit to antigen as described by Foote and Winter (J. Mol. Biol., 224: 487-499 (1992)). Vernier zone residues form a layer underlying the CDRs and may impact on the structure of CDRs and the affinity of the antibody.

As used herein, the term "neutralizing" refers to counteracting the biological activity of an antigen when a binding protein specifically binds the antigen. In an embodiment, the neutralizing binding protein binds an antigen reduces its biologically activity by at least about 20%, 40%, 60%, 80%, 85%, or more.

The term "activity" includes activities such as the binding specificity/affinity of an antibody for an antigen, for example, an anti-hDLL4 antibody that binds to an DLL4 antigen and/or the neutralizing potency of an antibody, or an anti-hDLL4 antibody whose binding to hDLL4 inhibits the biological activity of hDLL4, e.g. inhibition of receptor binding in a ligand-receptor binding assay or inhibition of receptor activation in a human Notch reporter assay, or stimulation of endothelial cell proliferation in a endothelial cell sprouting assay.

The term "epitope" includes any polypeptide determinant that specifically binds to an immunoglobulin or T-cell receptor. In certain embodiments, epitope determinants include chemically active surface groupings of molecules such as amino acids, sugar side chains, phosphoryl, or sulfonyl, and, in certain embodiments, may have specific three dimensional structural characteristics, and/or specific charge characteristics. An epitope is a region of an antigen that is bound by an antibody. An epitope thus consists of the amino acid residues of a region of an antigen (or fragment thereof) known to bind to the complementary site on the specific binding partner. An antigen or antigenic fragment can contain more than one epitope. Thus, it is understood by persons skilled in this art that every "antigen binding site" of an antibody molecule binds an epitope of an antigen molecule and every antigen molecule may have one, two, several, or many epitopes. Moreover, it is understood by persons skilled in this art that two independently isolated antibodies to an antigen molecule may bind at the same epitope or at two different epitopes on the antigen molecule.

In certain embodiments, an antibody is said to specifically bind an antigen when it recognizes its target antigen in a complex mixture of proteins and/or macromolecules. Antibodies are said to "bind to the same epitope" if the antibodies cross-compete (one prevents the binding or modulating effect of the other). In addition, structural definitions of epitopes (overlapping, similar, identical) are informative, but functional definitions are often more relevant as they encompass structural (binding) and functional (modulation, competition) parameters.

The term "surface plasmon resonance," as used herein, refers to an optical phenomenon that allows for the analysis of real-time biospecific interactions by detection of alterations in protein concentrations within a biosensor matrix, for example using the BIAcore® system (BIAcore International AB, a GE Healthcare company, Uppsala, Sweden and Piscataway, N.J. US). For further descriptions, see Jönsson et al., Ann. Biol. Clin., 51: 19-26 (1993); Jönsson et al. BioTechniques, 11: 620-627 (1991); Johnsson et al., J. Mol. Recognit., 8: 125-131 (1995); and Johnsson et al., Anal. Biochem., 198: 268-277 (1991).

The term "$K_{on}$", as used herein, is intended to refer to the on rate constant for association of a binding protein (e.g., an antibody) to a cognate partner (e.g., an antigen) to form a binding partner/cognate partner (e.g., antibody/antigen) complex as is known in the art. The "$K_{on}$" also is known by the terms "association rate constant," or "$k_a$," as used interchangeably herein. This value indicating the binding rate of an antibody to its target antigen or the rate of complex formation between an antibody and antigen also is shown by the equation:

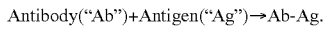

The term "$K_{off}$" as used herein, is intended to refer to the off rate constant for dissociation of a binding protein (e.g., an antibody) from the, e.g., antibody/antigen complex as is known in the art. The "$K_{off}$" also is known by the terms "dissociation rate constant" or "$k_d$" as used interchangeably herein. This value indicates the dissociation rate of an antibody from its target antigen or separation of Ab-Ag complex over time into free antibody and antigen as shown by the equation below:

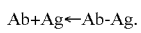

The terms "equilibrium dissociation constant" or "$K_D$", as used interchangeably herein, refer to the value obtained in a titration measurement at equilibrium, or by dividing the dissociation rate constant ($K_{off}$) by the association rate constant ($K_{on}$). The association rate constant, the dissociation rate constant, and the equilibrium dissociation constant are used to represent the binding affinity of an antibody to an antigen. Methods for determining association and dissociation rate constants are well known in the art. Using fluorescence-based techniques offers high sensitivity and the ability to examine samples in physiological buffers at equilibrium. Other experimental approaches and instruments such as a BIAcore® surface plasmon resonance (biomolecular interaction analysis) assay can be used (e.g., instrument available from BIAcore International AB, a GE Healthcare company, Uppsala, Sweden). Additionally, a KinExA® (Kinetic Exclusion Assay) assay, available from Sapidyne Instruments (Boise, Id.) can also be used.

"Label" and "detectable label" mean a moiety attached to a specific binding partner, such as an antibody or an analyte bound by the antibody, e.g., to render the reaction between members of a specific binding pair, such as an antibody and an analyte, detectable. The specific binding partner, e.g., antibody or analyte, so labeled is referred to as "detectably labeled". Thus, the term "labeled binding protein" as used herein, refers to a protein with a label incorporated that provides for the identification of the binding protein. In an embodiment, the label is a detectable marker that can produce a signal that is detectable by visual or instrumental means, e.g., incorporation of a radiolabeled amino acid or attachment to a polypeptide of biotinyl moieties that can be detected by a marked avidin (e.g., an avidin or a streptavidin containing a fluorescent marker or enzymatic activity that can be detected by optical or colorimetric methods). Examples of labels for polypeptides include, but are not limited to, the following: radioisotopes or radionuclides (e.g., $^3H$ $^{14}C$, $^{35}S$, $^{90}Y$, $^{99}Tc$, $^{111}In$, $^{125}I$, $^{131}I$, $^{177}Lu$, $^{166}Ho$, and $^{153}Sm$); chromogens, fluorescent labels (e.g., FITC, rhodamine, and lanthanide phosphors), enzymatic labels (e.g., horseradish peroxidase, luciferase, alkaline phosphatase); chemiluminescent markers; biotinyl groups; predetermined polypeptide epitopes recognized by a secondary reporter (e.g., leucine zipper pair sequences, binding sites for secondary antibodies, metal binding domains, and epitope tags); and magnetic agents, such as gadolinium chelates. Representative examples of labels commonly employed for immunoassays include moieties that produce light, e.g., acridinium compounds, and moieties that produce fluorescence, e.g., fluorescein. Other labels are known in the art or described herein. In this regard, the moiety itself may not be detectably labeled but may become detectable upon reaction with yet another moiety. Use of "detectably labeled" is intended to encompass the latter type of detectable labeling.

The term "antibody conjugate" refers to a binding protein, such as an antibody, chemically linked to a second chemical moiety, such as a therapeutic or cytotoxic agent. The term "agent" is used herein to denote a chemical compound, a mixture of chemical compounds, a biological macromolecule, or an extract made from biological materials. Preferably, the therapeutic or cytotoxic agents include, but are not limited to, pertussis toxin, taxol, cytochalasin B, gramicidin D, ethidium bromide, emetine, mitomycin, etoposide, tenoposide, vincristine, vinblastine, colchicine, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof.

The terms "crystal" and "crystallized" as used herein, refer to a binding protein (e.g., an antibody), or antigen binding portion thereof, that exists in the form of a crystal. Crystals are one form of the solid state of matter, which is distinct from other forms such as the amorphous solid state or the liquid crystalline state. Crystals are composed of regular, repeating, three-dimensional arrays of atoms, ions, molecules (e.g., proteins such as antibodies), or molecular assemblies (e.g., antigen/antibody complexes, including Fab/antigen complexes). These three-dimensional arrays are arranged according to specific mathematical relationships that are well-understood in the field. The fundamental unit, or building block, that is repeated in a crystal is called the asymmetric unit. Repetition of the asymmetric unit in an arrangement that conforms to a given, well-defined crystallographic symmetry provides the "unit cell" of the crystal. Repetition of the unit cell by regular translations in all three dimensions provides the crystal. See, Giegé et al., In *Crystallization of Nucleic Acids and Proteins, a Practical Approach, 2nd ed.*, (Ducruix and Giegé, eds.) (Oxford University Press, New York, 1999), chapter 1, pages 1-16.

The term "polynucleotide" means a polymeric form of two or more nucleotides, either ribonucleotides or deoxyribonucleotides or a modified form of either type of nucleotide. The term includes single and double stranded forms of DNA.

The term "isolated polynucleotide" shall mean a polynucleotide (e.g., of genomic, cDNA, or synthetic origin, or some combination thereof) that, by virtue of its origin, the "isolated polynucleotide" is not associated with all or a portion of a polynucleotide with which the "isolated polynucleotide" is found in nature; is operably linked to a polynucleotide that it is not linked to in nature; or does not occur in nature as part of a larger sequence.

The term "vector," is intended to refer to a nucleic acid molecule capable of transporting another nucleic acid to which it has been linked One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions. RNA versions of vectors (including RNA viral vectors) may also find use in the invention.

The term "operably linked" refers to a juxtaposition wherein the components described are in a relationship permitting them to function in their intended manner. A control sequence "operably linked" to a coding sequence is ligated in such a way that expression of the coding sequence is achieved under conditions compatible with the control sequences. "Operably linked" sequences include expression control sequences that are contiguous with a gene of interest, expression control sequences that act in trans, i.e., located on a different nucleic acid molecule than a gene of interest, as well as expression control sequences that are located on the same nucleic acid molecule as, but at a distance from, a gene of interest. The term "expression control sequence" as used herein refers to polynucleotide sequences which are necessary to effect the expression and processing of coding sequences to which they are ligated. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (i.e., Kozak consensus sequence); sequences that enhance protein stability; and when desired, sequences that enhance protein secretion. The nature of such control sequences differs depending upon the host organism; in prokaryotes, such control sequences generally include a promoter, a ribosomal binding site, and a transcription termination sequence; in eukaryotes, generally, such control sequences include a promoter and a transcription termination sequence. The term "control sequences" is intended to include components whose presence is essential for expression and processing, and can also include additional components whose presence is advantageous, for example, leader sequences and fusion partner sequences.

"Transformation," refers to any process by which exogenous nucleic acid (e.g., a DNA molecule) enters a host cell. Transformation may occur under natural or artificial conditions using various methods well known in the art. Transformation may rely on any known method for the insertion of foreign nucleic acid sequences into a prokaryotic or eukaryotic host cell. The method is selected based on the host cell being transformed and may include, but is not limited to, plasmid uptake across a cellular membrane, viral infection, electroporation, lipofection, and particle bombardment. Such "transformed" cells include stably transformed cells in which the inserted DNA is capable of replication either as an autonomously replicating plasmid or as part of the host chromosome. They also include cells which transiently express the inserted DNA or RNA for limited periods of time.

The term "recombinant host cell" (or simply "host cell"), is intended to refer to a cell into which exogenous DNA has been introduced. In an embodiment, the host cell comprises two or more (e.g., multiple) nucleic acids encoding antibodies, such as, by way of non-limiting example, the host cells described in U.S. Pat. No. 7,262,028. Such terms are intended to refer not only to the particular subject cell, but, also to the progeny of such a cell. Because certain modifications may occur in succeeding generations due to either mutation or environmental influences, such progeny may not, in fact, be identical to the parent cell, but are still included within the scope of the term "host cell" as used herein. In an embodiment, host cells include prokaryotic and eukaryotic cells selected from any of the Kingdoms of life. In another embodiment, eukaryotic cells include protist, fungal, plant and animal cells. In another embodiment, host cells include but are not limited to prokaryotic species, such *Escherichia coli*; mammalian cell lines, such as CHO, HEK 293, COS, NS0, SP2, and PER.C6; the insect cell line Sf9; and fungal cell species, such as *Saccharomyces cerevisiae*.

Standard techniques may be used for recombinant DNA, oligonucleotide synthesis, and tissue culture and transformation (e.g., electroporation, lipofection). Enzymatic reactions and purification techniques may be performed according to manufacturer's specifications or as commonly accomplished in the art or as described herein. The foregoing techniques and procedures may be generally performed according to conventional methods well known in the art and as described in various general and more specific references that are cited and discussed throughout the present specification. See, e.g., Sambrook et al., *Molecular Cloning: A Laboratory Manual, second ed*. (Cold Spring Harbor Laboratory Press, Cold Spring Harbor, 1989).

"Transgenic organism," as known in the art, refers to an organism having cells that contain a transgene, wherein the transgene introduced into the organism (or an ancestor of the organism) expresses a polypeptide not naturally expressed in the organism. A "transgene" is a DNA construct, which is stably and operably integrated into the genome of a cell from which a transgenic organism develops, directing the expression of an encoded gene product in one or more cell types or tissues of the transgenic organism.

The term "regulate" and "modulate" are used interchangeably, and, as used herein, refers to a change or an alteration in the activity of a molecule of interest (e.g., the biological activity of hDLL4). Modulation may be an increase or a decrease in the magnitude of a certain activity or function of the molecule of interest. Exemplary activities and functions of a molecule include, but are not limited to, binding characteristics, enzymatic activity, cell receptor activation, and signal transduction.

Correspondingly, the term "modulator," as used herein, is a compound capable of changing or altering an activity or function of a molecule of interest (e.g., the biological activity of hDLL4). For example, a modulator may cause an increase or decrease in the magnitude of a certain activity or function of a molecule compared to the magnitude of the activity or function observed in the absence of the modulator. In certain embodiments, a modulator is an inhibitor, which decreases the magnitude of at least one activity or function of a molecule. Exemplary inhibitors include, but are not limited to, proteins, peptides, antibodies, peptibodies, carbohydrates or small organic molecules. Peptibodies have been described. See, e.g., PCT Publication No. WO01/83525.

The term "agonist", as used herein, refers to a modulator that, when contacted with a molecule of interest, causes an increase in the magnitude of a certain activity or function of the molecule compared to the magnitude of the activity or function observed in the absence of the agonist. Particular agonists of interest may include, but are not limited to, members of the Notch-signaling pathway, DLL4 polypeptides and nucleic acids, carbohydrates, or any other molecules that bind to DLL4.

The term "antagonist" or "inhibitor", as used herein, refers to a modulator that, when contacted with a molecule of interest causes a decrease in the magnitude of a certain activity or function of the molecule compared to the magnitude of the activity or function observed in the absence of the antagonist. Particular antagonists of interest include those that block or modulate the biological or immunological activity of DLL4, especially human DLL4 (hDLL4). Antagonists and inhibitors of hDLL4 may include, but are not limited to, proteins, nucleic acids, carbohydrates, or any other molecule, which binds to hDLL4 and/or rodent DLL4.

As used herein, the term "effective amount" refers to the amount of a therapy that is sufficient to reduce or ameliorate the severity and/or duration of a disorder or one or more symptoms thereof; inhibit or prevent the advancement of a disorder; cause regression of a disorder; inhibit or prevent the recurrence, development, onset, or progression of one or more symptoms associated with a disorder; detect a disorder; or enhance or improve the prophylactic or therapeutic effect(s) of another therapy (e.g., prophylactic or therapeutic agent).

"Patient" and "subject" may be used interchangeably herein to refer to an animal, such as a mammal, including a primate (for example, a human, a monkey, and a chimpanzee), a non-primate (for example, a cow, a pig, a camel, a llama, a horse, a goat, a rabbit, a sheep, a hamster, a guinea pig, a cat, a dog, a rat, a mouse, and a whale), a bird (e.g., a duck or a goose), and a shark. Preferably, a patient or subject is a human, such as a human being treated or assessed for a disease, disorder, or condition; a human at risk for a disease, disorder, or condition; a human having a disease, disorder, or condition; and/or human being treated for a disease, disorder, or condition. More preferably, a patient or subject is being treated or assessed for cancer or other disease in which the existing aberrant DLL4 expression supports the cancer or other disease and inhibition or disruption of DLL4 activity is desirable to treat the cancer or other disease.

The term "sample," as used herein, is used in its broadest sense. A "biological sample," as used herein, includes, but is not limited to, any quantity of a substance from a living thing or formerly living thing. Such living things include, but are not limited to, humans, mice, rats, monkeys, dogs, rabbits and other animals. Such substances include, but are not limited to, blood, (e.g., whole blood), plasma, serum, urine, amniotic fluid, synovial fluid, endothelial cells, leukocytes, monocytes, other cells, organs, tissues, bone marrow, lymph nodes and spleen.

"Component," "components," and "at least one component," refer generally to a capture antibody, a detection or conjugate antibody, a control, a calibrator, a series of calibrators, a sensitivity panel, a container, a buffer, a diluent, a salt, an enzyme, a co-factor for an enzyme, a detection reagent, a pretreatment reagent/solution, a substrate (e.g., as a solution), a stop solution, and the like that can be included in a kit for assay of a test sample, such as a patient urine, serum or plasma sample, in accordance with the methods described herein and other methods known in the art. Thus, in the context of the present disclosure, "at least one component," "component," and "components" can include a polypeptide or other analyte as above, such as a composition comprising an analyte such as a polypeptide, which is optionally immobilized on a solid support, such as by binding to an anti-analyte (e.g., antipolypeptide) antibody. Some components can be in solution or lyophilized for reconstitution for use in an assay.

"Risk" refers to the possibility or probability of a particular event occurring either presently or at some point in the future. "Risk stratification" refers to an array of known clinical risk factors that allows physicians to classify patients into a low, moderate, high or highest risk of developing a particular disease, disorder or condition.

"Specific" and "specificity" in the context of an interaction between members of a specific binding pair (e.g., an antigen or fragment thereof and an antibody or antigen binding fragment thereof) refer to the selective reactivity of the interaction. The phrase "specifically binds to" and analogous phrases refer to the ability of antibodies (or antigen binding fragments thereof) to bind specifically to a molecule of interest (or a fragment thereof) and not bind specifically to other entities.

"Specific binding partner" is a member of a specific binding pair. A specific binding pair comprises two different molecules, which specifically bind to each other through chemical or physical means. Therefore, in addition to antigen and antibody specific binding pairs, other specific binding pairs can include biotin and avidin (or streptavidin), carbohydrates and lectins, complementary nucleotide sequences, effector and receptor molecules, cofactors and enzymes, enzyme inhibitors and enzymes, and the like. Furthermore, specific binding pairs can include members that are analogs of the original specific binding members, for example, an analyteanalog. Immunoreactive specific binding members include antigens, antigen fragments, and antibodies, including monoclonal and polyclonal antibodies as well as complexes, fragments, and variants (including fragments of variants) thereof, whether isolated or recombinantly produced.

"Variant" as used herein means a polypeptide that differs from a given polypeptide (e.g., DLL4 polypeptide or anti-DLL4 antibody) in amino acid sequence by the addition (e.g., insertion), deletion, or conservative substitution of amino acids, but that retains the biological activity of the given polypeptide (e.g., a variant DLL4 may compete with a wildtype DLL4 for binding with an anti-DLL4 antibody if the variant DLL4 retains the original antibody binding site (epitope) of the wildtype DLL4). A conservative substitution of an amino acid, i.e., replacing an amino acid with a different amino acid of similar properties (e.g., hydrophilicity and degree and distribution of charged regions) is recognized in the art as typically involving a minor change. These minor changes can be identified, in part, by considering the hydropathic index of amino acids, as understood in the art (see, e.g., Kyte et al., *J. Mol. Biol.*, 157: 105-132 (1982)). The hydropathic index of an amino acid is based on a consideration of its hydrophobicity and charge. It is known in the art that amino acids of similar hydropathic indexes can be substituted and still retain protein function. In one aspect, amino acids having hydropathic indexes of ±2 are substituted. The hydrophilicity of amino acids also can be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity (see, e.g., U.S. Pat. No. 4,554,101). Substitution of amino acids having similar hydrophilicity values can result in peptides retaining biological activity, for example immunogenicity, as is understood in the art. In one aspect, substitutions are performed with amino acids having hydrophilicity values within ±2 of each other. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties. "Variant" also can be used to describe a polypeptide or fragment thereof that has been differentially processed, such as by proteolysis, phosphorylation, or other post-translational modification, yet retains its biological activity or antigen reactivity, e.g., the ability to bind to DLL4. Use of "variant" herein is intended to encompass fragments of a variant unless otherwise contradicted by context.

The term "sample", as used herein, is used in its broadest sense. A "biological sample", as used herein, includes, but is not limited to, any quantity of a substance from a living thing or formerly living thing. Such living things include, but are not limited to, humans, mice, rats, monkeys, dogs, rabbits and other animals. Such substances include, but are not limited to, blood, serum, urine, synovial fluid, cells, organs, tissues, bone marrow, lymph nodes, and spleen.

I. Antibodies that Bind Human DLL4.

One aspect of the present invention provides isolated human monoclonal antibodies, or antigen-binding portions thereof, that bind to DLL4 with high affinity, a slow off rate, and/or high neutralizing capacity. Advantageously, such human antibodies or antigen-binding portions thereof that bind DLL4 find use as human therapeutic agents that can be administered to a human patient with minimal or no response by the patient's immune system toward the administered therapeutic DLL4 binding protein. Accordingly, a patient may obtain the benefit of such fully human DLL4 binding proteins over the course of repeated administrations. Other aspects of the invention provide chimeric antibodies that bind DLL4 and CDR grafted antibodies, or antigen-binding portions thereof, that bind DLL4. Preferably, the antibodies, or portions thereof, are isolated antibodies. Preferably, the antibodies of the invention are neutralizing human anti-DLL4 antibodies.

A. Method of Making Anti DLL4 Antibodies.

Antibodies of the present invention may be made by any of a number of techniques known in the art. A preferred method is PROfusion mRNA display technology as exemplified in Example 2 herein. Another method is to immunize a transgenic rodent (e.g., a transgenic mouse) that carries a functional complement of human immunoglobulin genes with human DLL4 or antigenic portion thereof followed by standard hybridoma technology to generate hybridomas that express fully human monoclonal antibodies that bind human DLL4. Recombinant human antibodies obtain by such a method have variable and constant regions derived from human germline immunoglobulin sequences. Such methods provide fully human DLL4 binding proteins and eliminate the need to otherwise carry out one or more rounds of humanization to reduce the sources of non-human antigenicity of the monoclonal DLL4 antibody molecules. Accordingly, techniques utilizing material from multiple species are less preferred but may be used.

It is also noted that the term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

Additional aspects of various techniques that may be employed to obtain DLL4 monoclonal antibody molecules according to the invention are described below.

1. Anti-DLL4 Monoclonal Antibodies Using Hybridoma Technology.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., *Antibodies: A Laboratory Manual, second edition*, (Cold Spring Harbor Laboratory Press, Cold Spring Harbor, 1988); Hammerling, et al., In *Monoclonal Antibodies and T-Cell Hybridomas*, pages 563-681 (Elsevier, New York, 1981) (said references incorporated by reference in their entireties). Methods for producing and screening for specific antibodies using hybridoma technology are routine and well known in the art. In one embodiment, the present invention provides methods of generating monoclonal antibodies as well as antibodies produced by the method comprising culturing a hybridoma cell secreting an antibody of the invention wherein, preferably, the hybridoma is generated by fusing splenocytes isolated from a mouse immunized with an antigen of the invention with myeloma cells and then screening the hybridomas resulting from the fusion for hybridoma clones that secrete an antibody able to bind a polypeptide of the invention. Briefly, mice can be immunized with an DLL4 antigen. In a preferred embodiment, the DLL4 antigen is administered with a adjuvant to stimulate the immune response. Such adjuvants include complete or incomplete Freund's adjuvant, RIBI (muramyl dipeptides) or ISCOM (immunostimulating complexes). Such adjuvants may protect the polypeptide from rapid dispersal by sequestering it in a local deposit, or they may contain substances that stimulate the host to secrete factors that are chemotactic for macrophages and other components of the immune system. Preferably, if a polypeptide is being administered, the immunization schedule will involve two or more administrations of the polypeptide, spread out over several weeks; however, a single administration of the polypeptide may also be used.

After immunization of an animal with a DLL4 antigen, antibodies and/or antibody-producing cells may be obtained from the animal. An anti-DLL4 antibody-containing serum is obtained from the animal by bleeding or sacrificing the animal. The serum may be used as it is obtained from the animal, an immunoglobulin fraction may be obtained from the serum, or the anti-DLL4 antibodies may be purified from the serum. Serum or immunoglobulins obtained in this manner are polyclonal, thus having a heterogeneous array of properties.

Once an immune response is detected, e.g., antibodies specific for the antigen DLL4 are detected in the mouse serum, the mouse spleen is harvested and splenocytes isolated. The splenocytes are then fused by well-known techniques to any suitable myeloma cells, for example cells from cell line SP20 available from the American Type Culture Collection (ATCC, Manassas, Va., US). Hybridomas are selected and cloned by limited dilution. The hybridoma clones are then assayed by methods known in the art for cells that secrete antibodies capable of binding DLL4. Ascites fluid, which generally contains high levels of antibodies, can be generated by immunizing mice with positive hybridoma clones.

In another embodiment, antibody-producing immortalized hybridomas may be prepared from the immunized animal. After immunization, the animal is sacrificed and the splenic B cells are fused to immortalized myeloma cells as is well known in the art. See, e.g., Harlow and Lane, supra. In a preferred embodiment, the myeloma cells do not secrete immunoglobulin polypeptides (a non-secretory cell line). After fusion and antibiotic selection, the hybridomas are screened using DLL4, or a portion thereof, or a cell expressing DLL4. In a preferred embodiment, the initial screening is performed using an enzyme-linked immunosorbent assay (ELISA) or a radioimmunoassay (RIA), preferably an ELISA. An example of ELISA screening is provided in PCT Publication No. WO 00/37504, incorporated herein by reference.

Anti-DLL4 antibody-producing hybridomas are selected, cloned, and further screened for desirable characteristics, including robust hybridoma growth, high antibody production, and desirable antibody characteristics, as discussed further below. Hybridomas may be cultured and expanded in vivo in syngeneic animals, in animals that lack an immune system, e.g., nude mice, or in cell culture in vitro. Methods of selecting, cloning and expanding hybridomas are well known to those of ordinary skill in the art.

In a preferred embodiment, hybridomas are mouse hybridomas, as described above. In another embodiment, hybridomas are produced in a non-human, non-mouse species such as rats, sheep, pigs, goats, cattle, or horses. In yet another preferred embodiment, the hybridomas are human hybridomas, in which a human non-secretory myeloma is fused with a human cell expressing an anti-DLL4 antibody.

Antibody fragments that recognize specific epitopes may be generated by known techniques. For example, Fab and F(ab')2 fragments of the invention may be produced by proteolytic cleavage of immunoglobulin molecules, using enzymes such as papain (to produce Fab fragments) or pepsin (to produce F(ab')2 fragments). F(ab')2 fragments contain the variable region, the light chain constant region, and the CHI domain of the heavy chain.

2. Anti-DLL4 Monoclonal Antibodies Using SLAM.

In another aspect of the invention, recombinant antibodies are generated from single, isolated lymphocytes using a procedure referred to in the art as the selected lymphocyte antibody method (SLAM), as described in U.S. Pat. No. 5,627,052; PCT Publication No. WO 92/02551; and Babcook et al., *Proc. Natl. Acad. Sci. USA*, 93: 7843-7848 (1996). In this method, single cells secreting antibodies of interest, e.g., lymphocytes derived from any one of the immunized animals described in Section I.A.1 (above), are screened using an antigen-specific hemolytic plaque assay, wherein the antigen DLL4, a subunit of DLL4, or a fragment thereof, is coupled to sheep red blood cells using a linker, such as biotin, and used to identify single cells that secrete antibodies with specificity for DLL4. Following identification of antibody-secreting cells of interest, heavy- and light-chain variable region cDNAs are rescued from the cells by reverse transcriptase-PCR (RT-PCR) and these variable regions can then be expressed, in the context of appropriate immunoglobulin constant regions (e.g., human constant regions), in mammalian host cells, such as COS or CHO cells. The host cells transfected with the amplified immunoglobulin sequences, derived from in vivo selected lymphocytes, can then undergo further analysis and selection in vitro, for example by panning the transfected cells to isolate cells expressing antibodies to DLL4. The amplified immunoglobulin sequences further can be manipulated in vitro, such as by in vitro affinity maturation method. See, for example, PCT Publication No. WO 97/29131 and PCT Publication No. WO 00/56772.

3. Anti-DLL4 Monoclonal Antibodies Using Transgenic Animals.

In another embodiment of the instant invention, antibodies are produced by immunizing a non-human animal comprising some, or all, of the human immunoglobulin locus with an DLL4 antigen. In a preferred embodiment, the non-human animal is a XENOMOUSE® transgenic mouse, an engineered mouse strain that comprises large fragments of the human immunoglobulin loci and is deficient in mouse antibody production. See, e.g., Green et al., *Nature Genetics*, 7: 13-21 (1994) and U.S. Pat. Nos. 5,916,771; 5,939,598; 5,985,615; 5,998,209; 6,075,181; 6,091,001; 6,114,598; and 6,130,364. See also PCT Publication Nos. WO 91/10741; WO 94/02602; WO 96/34096; WO 96/33735; WO 98/16654; WO 98/24893; WO 98/50433; WO 99/45031; WO 99/53049; WO 00/09560; and WO 00/37504. The XENOMOUSE® transgenic mouse produces an adult-like human repertoire of fully human antibodies, and generates antigen-specific human monoclonal antibodies. The XENOMOUSE® transgenic mouse contains approximately 80% of the human antibody repertoire through introduction of megabase sized, germline configuration YAC fragments of the human heavy chain loci and x light chain loci. See Mendez et al., *Nature Genetics*, 15: 146-156 (1997), Green and Jakobovits, *J. Exp. Med.*, 188: 483-495 (1998), the disclosures of which are hereby incorporated by reference.

4. Anti-DLL4 Monoclonal Antibodies Using Recombinant Antibody Libraries.

In vitro methods also can be used to make the antibodies of the invention, wherein an antibody library is screened to identify an antibody having the desired DLL4-binding specificity. Methods for such screening of recombinant antibody libraries are well known in the art and include methods described in, for example, U.S. Pat. No. 5,223,409 (Ladner et al.); PCT Publication No. WO 92/18619 (Kang et al.); PCT Publication No. WO 91/17271 (Dower et al.); PCT Publication No. WO 92/20791 (Winter et al.); PCT Publication No. WO 92/15679 (Markland et al.); PCT Publication No. WO 93/01288 (Breitling et al.); PCT Publication No. WO 92/01047 (McCafferty et al.); PCT Publication No. WO 92/09690 (Garrard et al.); Fuchs et al., *Bio/Technology*, 9: 1369-1372 (1991); Hay et al., *Hum. Antibod. Hybridomas*, 3: 81-85 (1992); Huse et al., *Science*, 246: 1275-1281 (1989); McCafferty et al., *Nature*, 348: 552-554 (1990); Griffiths et al., *EMBO T.*, 12: 725-734 (1993); Hawkins et al., *J. Mol. Biol.*, 226: 889-896 (1992); Clackson et al., *Nature*, 352: 624-628 (1991); Gram et al., *Proc. Natl. Acad. Sci. USA*, 89: 3576-3580 (1992); Garrard et al., *Bio/Technology*, 9: 1373-1377 (1991); Hoogenboom et al., *Nucl. Acids Res.*, 19: 4133-4137 (1991); Barbas et al., *Proc. Natl. Acad. Sci. USA*, 88: 7978-7982 (1991); US Patent Application Publication No. 2003/0186374; and PCT Publication No. WO 97/29131, the contents of each of which are incorporated herein by reference.

The recombinant antibody library may be from a subject immunized with DLL4, or a portion of DLL4. Alternatively, the recombinant antibody library may be from a naïve subject, i.e., one who has not been immunized with DLL4, such as a human antibody library from a human subject who has not been immunized with human DLL4. Antibodies of the invention are selected by screening the recombinant antibody library with the peptide comprising human DLL4 to thereby select those antibodies that recognize DLL4. Methods for conducting such screening and selection are well known in the art, such as described in the references in the preceding paragraph. To select antibodies of the invention having particular binding affinities for DLL4, such as those that dissociate from human DLL4 with a particular $K_{off}$ rate constant, the art-known method of surface plasmon resonance can be used to select antibodies having the desired $K_{off}$ rate constant. To select antibodies of the invention having a particular neutralizing activity for hDLL4, such as those with a particular $IC_{50}$, standard methods known in the art for assessing the inhibition of DLL4 activity may be used.

In one aspect, the invention pertains to an isolated antibody, or an antigen-binding portion thereof, that binds human DLL4. Preferably, the antibody is a neutralizing antibody. In various embodiments, the antibody is a recombinant antibody or a monoclonal antibody. For example, the antibodies of the present invention can also be generated using various phage display methods known in the art. In phage display methods, functional antibody domains are displayed on the surface of phage particles which carry the polynucleotide sequences encoding them. Such phage can be utilized to display antigen-binding domains expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage including fd and M13 binding domains expressed from phage with Fab, Fv, or disulfide stabilized Fv antibody domains recombinantly fused to either the phage gene III or gene VIII protein. Examples of phage display methods that can be used to make the antibodies of the present invention include those disclosed in Brinkmann et al., *J. Immunol. Methods,* 182: 41-50 (1995); Ames et al., *J. Immunol. Methods,* 184:177-186 (1995); Kettleborough et al., *Eur. J. Immunol.,* 24: 952-958 (1994); Persic et al., *Gene,* 187: 9-18 (1997); Burton et al., *Advances in Immunology,* 57: 191-280 (1994); PCT Publication No. WO 92/01047; PCT Publication Nos. WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743; and 5,969,108; each of which is incorporated herein by reference in its entirety.

As described in the above references, after phage selection, the antibody coding regions from the phage can be isolated and used to generate whole antibodies including human antibodies or any other desired antigen binding fragment, and expressed in any desired host, including mammalian cells, insect cells, plant cells, yeast, and bacteria, e.g., as described in detail below. For example, techniques to recombinantly produce Fab, Fab', and F(ab')2 fragments can also be employed using methods known in the art such as those disclosed in PCT publication No. WO 92/22324; Mullinax et al., *BioTechniques,* 12(6): 864-869 (1992); Sawai et al., *Am. J. Reprod. Immunol.,* 34: 26-34 (1995); and Better et al., *Science,* 240: 1041-1043 (1988) (said references incorporated by reference in their entireties). Examples of techniques which can be used to produce single-chain Fvs and antibodies include those described in U.S. Pat. Nos. 4,946,778 and 5,258,498; Huston et al., *Methods in Enzymology,* 203: 46-88 (1991); Shu et al., *Proc. Natl. Acad. Sci. USA,* 90: 7995-7999 (1993); and Skerra et al., *Science,* 240: 1038-1041 (1988).

Alternative to screening of recombinant antibody libraries by phage display, other methodologies known in the art for screening large combinatorial libraries can be applied to the identification of antibodies of the invention. One type of alternative expression system is one in which the recombinant antibody library is expressed as RNA-protein fusions, as described in PCT Publication No. WO 98/31700 (Szostak and Roberts), and in Roberts and Szostak, *Proc. Natl. Acad. Sci. USA,* 94:12297-12302 (1997). In this system, a covalent fusion is created between an mRNA and the peptide or protein that it encodes by in vitro translation of synthetic mRNAs that carry puromycin, a peptidyl acceptor antibiotic, at their 3' end. Thus, a specific mRNA can be enriched from a complex mixture of mRNAs (e.g., a combinatorial library) based on the properties of the encoded peptide or protein, e.g., antibody, or portion thereof, such as binding of the antibody, or portion thereof, to the dual specificity antigen. Nucleic acid sequences encoding antibodies, or portions thereof, recovered from screening of such libraries can be expressed by recombinant means as described above (e.g., in mammalian host cells) and, moreover, can be subjected to further affinity maturation by either additional rounds of screening of mRNA-peptide fusions in which mutations have been introduced into the originally selected sequence(s), or by other methods for affinity maturation in vitro of recombinant antibodies, as described above. A preferred example of this methodology, is the PROfusion display technology employed in the Examples (infra).

In another approach the antibodies of the present invention can also be generated using yeast display methods known in the art. In yeast display methods, genetic methods are used to tether antibody domains to the yeast cell wall and display them on the surface of yeast. In particular, such yeast can be utilized to display antigen-binding domains expressed from a repertoire or combinatorial antibody library (e.g., human or murine). Examples of yeast display methods that can be used to make the antibodies of the present invention include those disclosed in U.S. Pat. No. 6,699,658 (Wittrup et al.) incorporated herein by reference.

B. Production of Recombinant DLL4 Antibodies

Antibodies of the present invention may be produced by any of a number of techniques known in the art. For example, expression from host cells, wherein expression vector(s) encoding the heavy and light chains is (are) transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is possible to express the antibodies of the invention in either prokaryotic or eukaryotic host cells, expression of antibodies in eukaryotic cells is preferable, and most preferable in mammalian host cells, because such eukaryotic cells (and in particular mammalian cells) are more likely than prokaryotic cells to assemble and secrete a properly folded and immunologically active antibody.

Preferred mammalian host cells for expressing the recombinant antibodies of the invention include Chinese Hamster Ovary (CHO cells) (including dhfr– CHO cells, described in Urlaub and Chasin, *Proc. Natl. Acad. Sci. USA,* 77: 4216-4220 (1980), used with a DHFR selectable marker, e.g., as described in Kaufman and Sharp, *J. Mol. Biol.,* 159: 601-621 (1982), NS0 myeloma cells, COS cells, and SP2 cells. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Host cells can also be used to produce functional antibody fragments, such as Fab fragments or scFv molecules. It will be understood that variations on the above procedure are within the scope of the present invention. For example, it may be desirable to transfect a host cell with DNA encoding functional fragments of either the light chain and/or the heavy chain of an antibody of this invention. Recombinant DNA technology may also be used to remove some, or all, of the DNA encoding either or both of the light and heavy chains that is not necessary for binding to the antigens of interest. The molecules expressed from such truncated DNA molecules are also encompassed by the antibodies of the invention. In addition, bifunctional antibodies may be produced in which one heavy and one light chain are an antibody of the invention and the other heavy and light chain are specific for an antigen other than the antigens of interest by crosslinking an antibody of the invention to a second antibody by standard chemical crosslinking methods.

In a preferred system for recombinant expression of an antibody, or antigen-binding portion thereof, of the invention, a recombinant expression vector encoding both the antibody heavy chain and the antibody light chain is introduced into dhfr– CHO cells by calcium phosphate-mediated transfection. Within the recombinant expression vector, the antibody heavy and light chain genes are each operatively linked to CMV enhancer/AdMLP promoter regulatory elements to drive high levels of transcription of the genes. The recombinant expression vector also carries a DHFR gene, which allows for selection of CHO cells that have been transfected with the vector using methotrexate selection/amplification. The selected transformant host cells are cultured to allow for expression of the antibody heavy and light chains and intact antibody is recovered from the culture medium. Standard molecular biology techniques are used to prepare the recombinant expression vector, transfect the host cells, select for transformants, culture the host cells and recover the antibody from the culture medium. Still further the invention provides a method of synthesizing a recombinant antibody of the invention by culturing a host cell of the invention in a suitable culture medium until a recombinant antibody of the invention is synthesized. The method can further comprise isolating the recombinant antibody from the culture medium.

1. Anti-DLL4 Antibodies.

Amino acid sequences of VH and VL regions of isolated fully human antibodies that bind human DLL4 are shown for clones E9 and A10 in Table 4 (See, Examples, below). The isolated anti-DLL4 antibody CDR sequences of the E9 and A10 antibodies establish two novel families of DLL4 binding proteins, isolated in accordance with this invention, and comprising polypeptides that include the CDR sequences derived from E9 or affinity matured clones thereof or derived from A10 and affinity matured clones thereof. The variable regions and CDRs of the E9 monoclonal antibody and affinity matured derivatives thereof are listed in Tables 4, 8, 14, 18, and 19. The variable regions and CDRs of the A10 monoclonal antibody and affinity matured derivatives thereof are listed in Table 4, 9, and 10. To generate and to select CDRs for binding proteins according to the invention having preferred DLL4 binding and/or neutralizing activity with respect to human DLL4, standard methods known in the art for generating binding proteins of the present invention and assessing the DLL4 binding and/or neutralizing characteristics of those binding protein may be used, including but not limited to those specifically described herein.

Based on an alignment of the amino acid sequences of the CDRs of the heavy chain variable regions (VH) and the light chain variable regions (VL) of the anti-DLL4 antibody E9 clones described herein, the invention provides a DLL4 binding protein comprising an antigen binding domain capable of binding human DLL4, said antigen binding domain comprising at least one or more CDRs selected from the group consisting of:

CDR-H1: $X_1-X_2-X_3-X_4-X_5-X_6-X_7$, (SEQ ID NO: 99)

wherein;
$X_1$ is S or N;
$X_2$ is S, G or N;
$X_3$ is S, N, T, G or R;
$X_4$ is Y;
$X_5$ is Y or H;
$X_6$ is W; and
$X_7$ is G;

CDR-H2: (SEQ ID NO: 100)
$X_1-X_2-X_3-X_4-X_5-X_6-X_7-X_8-X_9-X_{10}-X_{11}-X_{12}-X_{13}-X_{14}-X_{15}-X_{16}$, wherein;
$X_1$ is D;
$X_2$ is I;
$X_3$ is Y, N, or S;
$X_4$ is Y;
$X_5$ is T, N, A, I, S or R;
$X_6$ is G;
$X_7$ is S, N, T or G;
$X_8$ is T;
$X_9$ is Y;
$X_{10}$ is Y;
$X_{11}$ is N;
$X_{12}$ is P;
$X_{13}$ is S;
$X_{14}$ is L;
$X_{15}$ is K; and
$X_{16}$ is S, N, D or G;

CDR-H3: (SEQ ID NO: 101)
$X_1-X_2-X_3-X_4-X_5-X_6-X_7-X_8-X_9-X_{10}-X_{11}$, wherein;
$X_1$ is E, Y, F, Q, W, L, or A;
$X_2$ is D, A, S, G, V, E or N;
$X_3$ is V, M, L, P, or A;
$X_4$ is I, A, P, R, S, K, Q, V, G, M or E;
$X_5$ is L, Y, F or M;
$X_6$ is R, G, S, Q or A
$X_7$ is G;
$X_8$ is G, A or S;
$X_9$ is S, A, L, V, R or G;
$X_{10}$ is D; and
$X_{11}$ is Y, D, S, N, H, E, R, L, P, C, I M, T, Q, or K;

CDR-L1: (SEQ ID NO: 102)
$X_1-X_2-X_3-X_4-X_5-X_6-X_7-X_8-X_9-X_{10}-X_{11}$, wherein;
$X_1$ is S;
$X_2$ is G;
$X_3$ is Q, E or D;
$X_4$ is R, S, G, M, K, L or T;
$X_5$ is L;
$X_6$ is G;
$X_7$ is D or E;
$X_8$ is K;
$X_9$ is Y;
$X_{10}$ is A or V; and
$X_{11}$ is S;

CDR-L2: $X_1-X_2-X_3-X_4-X_5-X_6-X_7$, (SEQ ID NO: 103)

wherein;
 $X_1$ is E or Q;
 $X_2$ is D;
 $X_3$ is S, L, T, A, E or F;
 $X_4$ is K, T, E, N, Q, S, or M;
 $X_5$ is R;
 $X_6$ is P; and
 $X_7$ is S;
and

CDR-L3: $X_1-X_2-X_3-X_4-X_5-X_6-X_7-X_8-X_9$, (SEQ ID NO: 104)

wherein;
 $X_1$ is Q;
 $X_2$ is A;
 $X_3$ is W;
 $X_4$ is D;
 $X_5$ is R, S, M, E, N, G, or K;
 $X_6$ is D or E
 $X_7$ is T, V, A, S or M;
 $X_8$ is G, A or C; and
 $X_9$ is V.

Preferably, a DLL4 binding protein comprising one or more CDRs described above binds human ("hu", "h") DLL4 and also one or more DLL4 proteins selected from the group consisting of: mouse ("murine", "mu") DLL4, cynomolgus monkey ("cynomolgus", "cyno") DLL4, and rat DLL4.

Based on an alignment of the amino acid sequences of the CDRs of the heavy chain variable regions (VH) and the light chain variable regions (VL) of the anti-DLL4 antibody A10 clones described herein, the invention provides a DLL4 binding protein comprising an antigen binding domain capable of binding human DLL4, said antigen binding domain comprising at least one or more CDRs selected from the group consisting of:

CDR-H1: $X_1-X_2-X_3-X_4-X_5$, (SEQ ID NO: 105)

wherein;
 $X_1$ is S, N, or D;
 $X_2$ is H or Y;
 $X_3$ is W;
 $X_4$ is M; and
 $X_5$ is S or H;

CDR-H2: (SEQ ID NO: 106)
$X_1-X_2-X_3-X_4-X_5-X_6-X_7-X_8-X_9-X_{10}-X_{11}-X_{12}-X_{13}-X_{14}-X_{15}-X_{16}-X_{17}$, wherein;
 $X_1$ is I, D, M, or T;
 $X_2$ is I;
 $X_3$ is S;
 $X_4$ is Y, N, S, Q, V, T, H, or D;
 $X_5$ is D;
 $X_6$ is G;
 $X_7$ is S, R, I, T, G, K, H, or N;
 $X_8$ is N, Y, S, I, or T;
 $X_9$ is K, M, N, Q, E, T, R, S, A, or L;
 $X_{10}$ is Y, D, or E;
 $X_{11}$ is S or Y;
 $X_{12}$ is A;
 $X_{13}$ is D;
 $X_{14}$ is S;
 $X_{15}$ is V;
 $X_{16}$ is K; and
 $X_{17}$ is G;

CDR-H3: $X_1-X_2-X_3-X_4-X_5-X_6-X_7-X_8-X_9-X_{10}$, (SEQ ID NO: 107)

wherein;
 $X_1$ is A;
 $X_2$ is G, A, or R;
 $X_3$ is G;
 $X_4$ is G, S, or A;
 $X_5$ is N;
 $X_6$ is V or M;
 $X_7$ is G;
 $X_8$ is F, L, Y, or M;
 $X_9$ is D; and
 $X_{10}$ is I, S, or L;

CDR-L1: $X_1-X_2-X_3-X_4-X_5-X_6-X_7-X_8-X_9-X_{10}-X_{11}$, (SEQ ID NO: 108)

wherein;
 $X_1$ is S;
 $X_2$ is A or G;
 $X_3$ is D;
 $X_4$ is K, N, L, Q, M, E, S, T, G, or D;
 $X_5$ is L;
 $X_6$ is G;
 $X_7$ is T, S, N, A, G, or E;
 $X_8$ is K, Q, N, or R;
 $X_9$ is Y;
 $X_{10}$ is V or I; and
 $X_{11}$ is S;

CDR-L2: $X_1-X_2-X_3-X_4-X_5-X_6-X_7$, (SEQ ID NO: 109)

wherein;
 $X_1$ is Q;
 $X_2$ is D;
 $X_3$ is A, G, W, S, or D;
 $X_4$ is K, M, Q, N, L, T, I, or E;
 $X_5$ is R;
 $X_6$ is P; and
 $X_7$ is S;
and

CDR-L3: $X_1-X_2-X_3-X_4-X_5-X_6-X_7-X_8-X_9$, (SEQ ID NO: 110)

wherein;
 $X_1$ is Q;
 $X_2$ is S or A;
 $X_3$ is W;
 $X_4$ is D;
 $X_5$ is R, S, Q, P, A, V, W, or M;
 $X_6$ is S, G, I, N, R, or T
 $X_7$ is D or G;
 $X_8$ is V, A, P, or E; and
 $X_9$ is V.

Preferably, a DLL4 binding protein comprising one or more CDRs described above binds human ("hu") DLL4 and also cynomolgus monkey ("cynomolgus", "cyno") DLL4.

2. Anti-DLL4 Chimeric Antibodies.

A chimeric antibody is a molecule in which different portions of the antibody are derived from different animal species, such as antibodies having a variable region derived from a murine monoclonal antibody and a human immunoglobulin constant region. See e.g., Morrison, Science, 229: 1202-1207 (1985); Oi et al., BioTechniques, 4: 214 (1986); Gillies et al., J. Immunol. Methods, 125: 191-202 (1989); U.S. Pat. Nos. 5,807,715; 4,816,567; and 4,816,397, which are incorporated herein by reference in their entireties. In addition, techniques developed for the production of "chimeric antibodies" by splicing genes from a mouse antibody molecule of appropriate antigen specificity together with genes from a human antibody molecule of appropriate biological activity can be used. See, for example, Morrison et al., Proc. Natl. Acad. Sci. USA, 81: 6851-6855 (1984); Neuberger et al., Nature, 312: 604-608 (1984); Takeda et al., Nature, 314: 452-454 (1985), which are incorporated herein by reference in their entireties.

3. Anti-DLL4 CDR Grafted Antibodies.

The isolated anti-DLL4 antibody CDR sequences of the invention may be used to make CDR-grafted antibodies to modulate the properties of the original antibody. Such properties include but are not limited to binding kinetics, affinity, biological activities, species cross-reactivity, molecule cross-reactivity, epitope, physicochemical properties, pharmacokinetic properties, pharmacodynamic properties, or pharmacological properties. CDR-grafted antibodies comprise heavy and light chain variable region sequences from a human antibody or a non-human primate antibody wherein one or more of the CDR regions of VH and/or VL are replaced with CDR sequences of the original anti-DLL4 antibody. A framework sequence from any human or non-human primate antibody may serve as the template for CDR grafting. However, straight chain replacement onto such a framework often leads to some loss of binding affinity to the antigen. The more homologous a human, or other species, antibody is to the original human antibody, the less likely the possibility that combining the CDRs with the new human framework or non-human primate framework will introduce distortions in the CDRs that could reduce affinity or other properties. Therefore, it is preferable that the variable framework that is chosen to replace the human variable region framework apart from the CDRs has at least a 30% sequence identity with the human antibody variable region framework. It is more preferable that the variable region framework that is chosen to replace the human variable region framework apart from the CDRs has at least a 40% sequence identity with the human antibody variable region framework. It is more preferable that the variable region framework that is chosen to replace the human variable framework apart from the CDRs has at least a 50% sequence identity with the human antibody variable region framework. It is more preferable that the variable region framework that is chosen to replace the human variable framework apart from the CDRs has at least a 60% sequence identity with the human antibody variable region framework. It is more preferable that the new human or non-human primate and the original human variable region framework apart from the CDRs has at least 70% sequence identity. It is even more preferable that the new human or non-human primate and the original human variable region framework apart from the CDRs has at least 75% sequence identity. It is most preferable that the new human or non-human primate and the original human variable region framework apart from the CDRs has at least 80% sequence identity. Even using a highly homologous human or non-human primate framework to graft CDRs of the original human anti-DLL4 antibody, the resulting grafted antibody may still lose binding affinity to antigen to some degree. In this case, to regain the affinity it is necessary to include at least one or more key framework residue(s) substitution of the original antibody to the corresponding position of the newly grafted antibody. Such a key residue may be selected from the group consisting of:

- a residue adjacent to a CDR;
- a glycosylation site residue;
- a rare residue;
- a residue capable of interacting with human DLL4
- a canonical residue;
- a contact residue between heavy chain variable region and light chain variable region;
- a residue within a Vernier zone; and
- a residue in a region that overlaps between a Chothia-defined variable heavy chain CDR1 and a Kabat-defined first heavy chain framework.

4. Anti-DLL4 Humanized Antibodies.

While the compositions of the present invention eliminate the requirement to make humanized antibodies, humanized DLL4 antibodies may be prepared using compositions of the invention. Humanized antibodies are antibody molecules from non-human species antibody that binds the desired antigen having one or more complementary determining regions (CDRs) from the non-human species and framework regions from a human immunoglobulin molecule. Known human Ig sequences are disclosed at web sites available via the world wide web (www.), e.g., ncbi.nlm.nih.gov/entrez/query.fcgi; atcc.org/phage/hdb.html; sciquest.com/; abcam.com/; antibodyresource.com/onlinecomp.html; public.iastate.edu/.about.pedro/-/research_tools.html; mgen.uniheidelberg.de/SD/IT/IT.html; whfreeman.com/immunology-/CH05/kuby05.htm; library.thinkquest.org/12429/Immune/Antibody.html; hhmi.org/grants/lectures/1996/vlab/; path.-cam.ac.uk/.about.mrc7/mikeimages.html; antibodyresource.com/; mcb.harvard.edu/BioLinks-/Immunology.html; immunologylink com/; pathbox.wustl.edu/.about.hcenter/index.html; bio-tech.ufl.edu/.about.hcl/; pebio.com/pa/340913-/340913.html; nal.usda.gov/awic/pubs/antibody/; m.ehimeu.acjp/.about.yasuhito-/Elisa.html; biodesign.com/table.asp; icnet.uk/axp/facs/davies/lin-ks.html; biotech.ufl.edu-/.about.fccl/protocol.html; isac-net.org/sites_geo.html; aximtl.imt.uni-marburg.de/.about.rek/AEP-Start.html; baserv.uci.kun.nl/.about.jraats/links1.html; recab.uni-hd.de/immuno.bme.nwu.edu/; mrc-cpe.cam.ac.uk/imt-doc/public/INTRO.html; ibt.unam.mx/-vir/V_mice.html; imgt.cnusc.fr:8104/; biochem.ucl.ac.uk/.about.martin/abs/index.html; antibody.bath.ac.uk/; abgen.cvm.tamu.edu/lab/wwwabgen.html; unizh.ch/.about.honegger/AHO-seminar/Slide01.html; cryst.b-bk.ac.uk/.about. ubcg07s/; nimr.mrc.ac.uk/CC/ccaewg/ccaewg.htm; path.cam.ac.uk/.about.mrc7/ humanisation/TAHH-P.html; ibt.unam.mx/vir/structure/stat_aim.-html; biosci.missouri.edu/smithgp/index.html; cryst.bioc.cam.ac.uk/.about.fmolina/Webpages-/Pept/spottech.html; jerini.de/frroducts.htm; patents.ibm.com/ibm.html. Kabat et al., Sequences of Proteins of Immunological Interest, U.S. Dept. Health (1983), each entirely incorporated herein by reference. Such imported sequences can be used to reduce immunogenicity or reduce, enhance or modify binding, affinity, on-rate, off-rate, avidity, specificity, half-life, or any other suitable characteristic, as known in the art.

Framework residues in the human framework regions may be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., U.S. Pat. No. 5,585,089 (Queen et al.); Riechmann et al., *Nature,* 332: 323-327 (1988), which are incorporated herein by reference in their entireties.) Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequences so that the desired antibody characteristic, such as increased affinity for the target antigen(s), is achieved. In general, the CDR residues are directly and most substantially involved in influencing antigen binding. Antibodies can be humanized using a variety of techniques known in the art, such as but not limited to those described in Jones et al., *Nature,* 321: 522-525 (1986); Verhoeyen et al., *Science,* 239: 1534-1536 (1988), Sims et al., *J. Immunol.,* 151: 2296-2308 (1993); Chothia and Lesk, *J. Mol. Biol.,* 196: 901-917 (1987), Carter et al., *Proc. Natl. Acad. Sci. USA,* 89: 4285-4289 (1992); Presta et al., *J. Immunol.,* 151: 2623-2632 (1993), Padlan, E. A., *Molecular Immunology,* 28(4/5): 489-498 (1991); Studnicka et al., *Protein Engineering,* 7(6): 805-814 (1994); Roguska. et al., *Proc. Natl. Acad. Sci. USA,* 91:969-973 (1994); PCT Publication Nos. WO 91/09967, WO 99/06834 (PCT/US98/16280), WO 97/20032 (PCT/US96/18978), WO 92/11272 (PCT/US91/09630), WO 92/03461 (PCT/US91/05939), WO 94/18219 (PCT/US94/01234), WO 92/01047 (PCT/GB91/01134), WO 93/06213 (PCT/GB92/01755), WO90/14443, WO90/14424, and WO90/14430; European Publication Nos. EP 0 592 106, EP 0 519 596, and EP 0 239 400; U.S. Pat. Nos. 5,565,332; 5,723,323; 5,976,862; 5,824,514; 5,817,483; 5,814,476; 5,763,192; 5,723,323; 5,766,886; 5,714,352; 6,204,023; 6,180,370; 5,693,762; 5,530,101; 5,585,089; 5,225,539; and 4,816,567, each entirely incorporated herein by reference, included references cited therein.

C. Production of Antibodies and Antibody-Producing Cell Lines.

Preferably, anti-DLL4 antibodies of the present invention exhibit a high capacity to reduce or to neutralize tumor angiogenesis activity, e.g., as assessed by any one of several in vitro and in vivo assays known in the art. Evaluating the neutralization of activity of DLL4 can be assessed via several in vitro and in vivo assays know in the art. Exemplary parameters for assessing neutralization of DLL4 activity include, but are not limited to, antibodies that inhibit DLL4 interaction with the Notch receptor, and/or Notch-signaling pathway with an $IC_{50}$ values of about at least $10^{-6}$ M; at least $10^{-7}$ M, or at least $10^{-8}$ M.

Preferably, anti-DLL4 antibodies of the present invention also exhibit a high capacity to reduce or to neutralize DLL4 activity.

In preferred embodiments, the isolated antibody, or antigen-binding portion thereof, binds human DLL4, wherein the antibody, or antigen-binding portion thereof, dissociates from human DLL4 with a $K_{off}$ rate constant of about 0.1 s$^{-1}$ or less, as determined by surface plasmon resonance, or which inhibits DLL4 and/or DLL4 activity with an $IC_{50}$ of about $1\times10^{-6}$M or less. Alternatively, the antibody, or an antigen-binding portion thereof, may dissociate from human DLL4 with a $K_{off}$ rate constant of about $1\times10^{-2}$ s$^{-1}$ or less, as determined by surface plasmon resonance, or may inhibit human DLL4 and/or human DLL4 activity with an $IC_{50}$ of about $1\times10^{-7}$ M or less. Alternatively, the antibody, or an antigen-binding portion thereof, may dissociate from human DLL4 with a $K_{off}$ rate constant of about $1\times10^{-3}$ s$^{-1}$ or less, as determined by surface plasmon resonance, or may inhibit human DLL4 with an $IC_{50}$ of about $1\times10^{-8}$M or less. Alternatively, the antibody, or an antigen-binding portion thereof, may dissociate from human DLL4 with a $K_{off}$ rate constant of about $1\times10^{-4}$ s$^{-1}$ or less, as determined by surface plasmon resonance, or may inhibit DLL4 activity with an $IC_{50}$ of about $1\times10^{-9}$M or less. Alternatively, the antibody, or an antigen-binding portion thereof, may dissociate from human DLL4 with a $K_{off}$ rate constant of about $1\times10^{-5}$ s$^{-1}$ or less, as determined by surface plasmon resonance, or may inhibit DLL4 and/or human DLL4 activity with an $IC_{50}$ of about $1\times10^{-10}$M or less. Alternatively, the antibody, or an antigen-binding portion thereof, may dissociate from human DLL4 with a $K_{off}$ rate constant of about $1\times10^{-5}$ s$^{-1}$ or less, as determined by surface plasmon resonance, or may inhibit DLL4 and/or human DLL4 activity with an $IC_{50}$ of about $1\times10^{-11}$M or less.

In certain embodiments, the antibody comprises a heavy chain constant region, such as an IgG1, IgG2, IgG3, IgG4, IgA, IgE, IgM, or IgD constant region. Preferably, the heavy chain constant region is an IgG1 heavy chain constant region or an IgG4 heavy chain constant region. Furthermore, the antibody can comprise a light chain constant region, either a kappa light chain constant region or a lambda light chain constant region. Preferably, the antibody comprises a kappa light chain constant region. Alternatively, the antibody portion can be, for example, a Fab fragment or a single chain Fv fragment.

Replacements of amino acid residues in the Fc portion to alter antibody effector function are known in the art (see, U.S. Pat. Nos. 5,648,260 and 5,624,821 (Winter et al.)). The Fc portion of an antibody mediates several important effector functions e.g. cytokine induction, ADCC, phagocytosis, complement dependent cytotoxicity (CDC), and half-life/clearance rate of antibody and antigen-antibody complexes. In some cases these effector functions are desirable for therapeutic antibody but in other cases might be unnecessary or even deleterious, depending on the therapeutic objectives. Certain human IgG isotypes, particularly IgG1 and IgG3, mediate ADCC and CDC via binding to FcγRs and complement C1q, respectively. Neonatal Fc receptors (FcRn) are the critical components determining the circulating half-life of antibodies. In still another embodiment at least one amino acid residue is replaced in the constant region of the antibody, for example the Fc region of the antibody, such that effector functions of the antibody are altered.

One embodiment provides a labeled binding protein wherein an antibody or antibody portion of the invention is derivatized or linked to another functional molecule (e.g., another peptide or protein). For example, a labeled binding protein of the invention can be derived by functionally linking an antibody or antibody portion of the invention (by chemical coupling, genetic fusion, noncovalent association or otherwise) to one or more other molecular entities, such as another antibody (e.g., a bispecific antibody or a diabody), a detectable agent, a cytotoxic agent, a pharmaceutical agent, and/or a protein or peptide that can mediate associate of the antibody or antibody portion with another molecule (such as a streptavidin core region or a polyhistidine tag).

Useful detectable agents with which an antibody or antibody portion of the invention may be derivatized include fluorescent compounds. Exemplary fluorescent detectable agents include fluorescein, fluorescein isothiocyanate, rhodamine, 5-dimethylamine-1-napthalenesulfonyl chloride, phycoerythrin and the like. An antibody may also be derivatized with detectable enzymes, such as alkaline phosphatase, horseradish peroxidase, glucose oxidase and the like. When an antibody is derivatized with a detectable enzyme, it is detected by adding additional reagents that the enzyme uses to produce a detectable reaction product. For example, when the detectable agent horseradish peroxidase is present, the addition of hydrogen peroxide and diaminobenzidine leads to a colored reaction product, which is detectable. An antibody may also be derivatized with biotin, and detected through indirect measurement of avidin or streptavidin binding.

Another embodiment of the invention provides a crystallized DLL4 binding protein. Preferably, the invention relates to crystals of DLL4 binding proteins described herein, including whole anti-DLL4 antibodies, fragments thereof, as well as antibody constructs and binding protein conjugates (including antibody conjugates) as disclosed herein, and formulations and compositions comprising such crystals. In one embodiment, the crystallized binding protein has a greater half-life in vivo than the soluble counterpart of the binding protein. In another embodiment the binding protein retains biological activity after crystallization. Crystallized binding proteins of the invention may be produced according methods known in the art and as disclosed in PCT Publication No. WO 02/72636, incorporated herein by reference.

Another embodiment of the invention provides a glycosylated binding protein wherein the antibody or antigen-binding portion thereof comprises one or more carbohydrate residues. Nascent in vivo protein production may undergo further processing, known as post-translational modification. In particular, sugar (glycosyl) residues may be added enzymatically, a process known as glycosylation. The resulting proteins bearing covalently linked oligosaccharide side chains are known as glycosylated proteins or glycoproteins. Protein glycosylation depends on the amino acid sequence of the protein of interest, as well as the host cell in which the protein is expressed. Different organisms may produce different glycosylation enzymes (e.g., glycosyltransferases and glycosidases), and have different substrates (nucleotide sugars) available. Due to such factors, protein glycosylation pattern, and composition of glycosyl residues, may differ depending on the host system in which the particular protein is expressed. Glycosyl residues useful in the invention may include, but are not limited to, glucose, galactose, mannose, fucose, n-acetylglucosamine and sialic acid. Preferably the glycosylated binding protein comprises glycosyl residues such that the glycosylation pattern is human.

It is known to those skilled in the art that differing protein glycosylation may result in differing protein characteristics. For instance, the efficacy of a therapeutic protein produced in a microorganism host, such as yeast, and glycosylated utilizing the yeast endogenous pathway may be reduced compared to that of the same protein expressed in a mammalian cell, such as a CHO cell line. Such glycoproteins may also be immunogenic in humans and show reduced half-life in vivo after administration. Specific receptors in humans and other animals may recognize specific glycosyl residues and promote the rapid clearance of the protein from the bloodstream. Other adverse effects may include changes in protein folding, solubility, susceptibility to proteases, trafficking, transport, compartmentalization, secretion, recognition by other proteins or factors, antigenicity, or allergenicity. Accordingly, a practitioner may prefer a therapeutic protein with a specific composition and pattern of glycosylation, for example glycosylation composition and pattern identical, or at least similar, to that produced in human cells or in the species-specific cells of the intended subject animal.

Expressing glycosylated proteins different from that of a host cell may be achieved by genetically modifying the host cell to express heterologous glycosylation enzymes. Using techniques known in the art a practitioner may generate antibodies or antigen-binding portions thereof exhibiting human protein glycosylation. For example, yeast strains have been genetically modified to express non-naturally occurring glycosylation enzymes such that glycosylated proteins (glycoproteins) produced in these yeast strains exhibit protein glycosylation identical to that of animal cells, especially human cells (US Patent Application Publication Nos. 2004/0018590 and 2002/0137134).

Further, it will be appreciated by one skilled in the art that a protein of interest may be expressed using a library of host cells genetically engineered to express various glycosylation enzymes, such that member host cells of the library produce the protein of interest with variant glycosylation patterns. A practitioner may then select and isolate the protein of interest with particular novel glycosylation patterns. Preferably, the protein having a particularly selected novel glycosylation pattern exhibits improved or altered biological properties.

D. Uses of DLL4 Binding Proteins.

Given their ability to bind to human DLL4 and murine DLL4, the DLL4 binding proteins described herein, including antibodies and portions thereof, can be used to detect or measure DLL4 in a sample (e.g., in a mixture, solution, or biological sample, such as blood, serum, or plasma), using any of the conventional immunoassays known in the art, such as an enzyme linked immunosorbent assays (ELISA), a radioimmunoassay (RIA), or a tissue immunohistochemistry. The invention provides a method for detecting human DLL4 and/or murine DLL4 in a sample comprising contacting a sample with a DLL4 binding protein and detecting either the DLL4 binding protein bound to human DLL4 and/or murine DLL4 or the unbound binding protein to thereby detect human DLL4 and/or murine DLL4 in the sample. A DLL4 binding protein described herein can be directly or indirectly labeled with a detectable substance to facilitate detection of the bound or unbound DLL4 binding protein. Suitable detectable substances include various enzymes, prosthetic groups, fluorescent materials, luminescent materials and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of suitable radioactive material include $^3$H, $^{14}$C, $^{35}$S, $^{99}$Y, $^{99}$TC, $^{111}$In, $^{125}$I, $^{131}$I, $^{177}$Lu, $^{166}$Ho, or $^{153}$Sm.

Biological samples that can be assayed for DLL4 include urine, feces, blood, serum, plasma, perspiration, saliva, oral swab (cheek, tongue, throat), vaginal swab, rectal swab, dermal swab, dermal scrape, tissue biopsy, as well as any other tissue sample that can be obtained by methods available in the art.

Alternative to labeling the binding protein, human DLL4 can be assayed in biological fluids by a competition immunoassay utilizing recombinant human (rh) DLL4 standards labeled with a detectable substance and an unlabeled DLL4 binding protein described herein. In this assay, the biological sample, the labeled rhDLL4 standards, and the DLL4 binding protein are combined and the amount of labeled rhDLL4 standard bound to the unlabeled binding protein is determined. The amount of human DLL4 in the biological sample is inversely proportional to the amount of labeled rhDLL4 standard bound to the DLL4 binding protein. Similarly, human DLL4 can also be assayed in biological fluids by a competition immunoassay utilizing rhDLL4 standards labeled with a detectable substance and an unlabeled DLL4 binding protein described herein.

The DLL4 binding proteins of the invention preferably are capable of neutralizing DLL4 activity, in particular hDLL4 activity, both in vitro and in vivo. Accordingly, such binding proteins of the invention can be used to inhibit DLL4 activity, e.g., in a cell culture containing DLL4, in human subjects, or in other mammalian subjects expressing a DLL4 with which a binding protein of the invention cross-reacts. In one embodiment, the invention provides a method for inhibiting DLL4 activity comprising contacting a DLL4 with a DLL4 antibody or antibody portion of the invention such that DLL4 activity is inhibited. For example, in a cell culture containing or suspected of containing DLL4, an antibody or antibody portion of the invention can be added to the culture medium to inhibit DLL4 activity in the culture.

In another embodiment, the invention provides a method for reducing DLL4 activity in a subject, advantageously from a subject suffering from a disease or disorder in which DLL4 or DLL4 activity is detrimental. The invention provides methods for reducing DLL4 or DLL4 activity in a subject suffering from such a disease or disorder, which method comprises administering to the subject a DLL4 binding protein of the invention such that DLL4 or DLL4 activity in the subject is reduced. Preferably, the DLL4 is human DLL4, and the subject is a human subject. Alternatively, the subject can be a mammal expressing a DLL4 to which a DLL4 binding protein of the invention is capable of binding. Still further, the subject can be a mammal into which DLL4 has been introduced (e.g., by administration of DLL4 or by expression of a DLL4 transgene). An antibody or other DLL4 binding protein of the invention can be administered to a human subject for therapeutic purposes. Moreover, a DLL4 binding protein of the invention can be administered to a non-human mammal expressing a DLL4 with which the binding protein is capable of binding for veterinary purposes or as an animal model of human disease. Regarding the latter, such animal models may be useful for evaluating the therapeutic efficacy of antibodies and other DLL4 binding proteins of the invention (e.g., testing of dosages and time courses of administration).

As used herein, the term "a disorder in which DLL4 and/or Notch signaling activity is detrimental" is intended to include diseases, such as cancer, and other disorders in which the presence of DLL4 and/or Notch signaling activity in a subject suffering from the disorder has been shown to be or is suspected of being either responsible for the pathophysiology of the disorder or a factor that contributes to a worsening of the disorder. Accordingly, a disorder in which DLL4 and/or Notch signaling activity is detrimental is a disorder in which alteration of DLL4 and/or Notch signaling activity is expected to alleviate the symptoms and/or progression of the disorder (e.g., tumor growth). Such disorders may be evidenced, for example, by an increase in angiogenesis in a subject suffering from the disorder (e.g., an increase in the concentration of various proteins known in the art to increase in serum, plasma, synovial fluid, etc., of the subject during tumor growth and formation), which can be detected, for example, using an anti-DLL4 antibody as described above. Non-limiting examples of disorders that can be treated with the antibodies of the invention include those disorders discussed in the section below pertaining to pharmaceutical compositions of the antibodies of the invention.

II. Pharmaceutical Compositions.

The invention also provides pharmaceutical compositions comprising a DLL4 binding protein of the invention and a pharmaceutically acceptable carrier. The pharmaceutical compositions comprising DLL4 binding proteins of the invention are for use in, but not limited to, diagnosing, detecting, or monitoring a disorder; in preventing, treating, managing, or ameliorating a disorder or one or more symptoms thereof; and/or in research. In a specific embodiment, a composition comprises one or more DLL4 binding proteins of the invention. In another embodiment, the pharmaceutical composition comprises one or more binding proteins of the invention and one or more prophylactic or therapeutic agents other than binding proteins of the invention for treating a disorder in which DLL4 and/or DLL4 activity is detrimental. Preferably, the prophylactic or therapeutic agents known to be useful for or having been or currently being used in the prevention, treatment, management, or amelioration of a disorder, such as cancer or a tumor, or one or more symptoms thereof. In accordance with these embodiments, the composition may further comprise of a carrier, diluent, or excipient.

The binding proteins of the invention can be incorporated into pharmaceutical compositions suitable for administration to a subject. Typically, the pharmaceutical composition comprises a DLL4 binding protein (or DLL4 binding portion thereof) of the invention and a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the antibody or antibody portion.

Various delivery systems are known and can be used to administer one or more DLL4 binding proteins of the invention or the combination of one or more binding proteins of the invention and a prophylactic agent or therapeutic agent useful for preventing, managing, treating, or ameliorating a disorder or one or more symptoms thereof, e.g., reducing tumor angiogenesis, encapsulation in liposomes, microparticles, microcapsules, recombinant cells capable of expressing the DLL4 binding protein, receptor-mediated endocytosis (see, e.g., Wu and Wu, *J. Biol. Chem.*, 262: 4429-4432 (1987)), construction of a nucleic acid as part of a retroviral or other vector, etc. Methods of administering a prophylactic or therapeutic agent of the invention include, but are not limited to, parenteral administration (e.g., intradermal, intramuscular, intraperitoneal, intravenous and subcutaneous), epidural administration, intratumoral administration, and mucosal administration (e.g., intranasal and oral routes). In addition, pulmonary administration can be employed, e.g., by use of an inhaler or nebulizer, and formulation with an aerosolizing agent. See, e.g., U.S. Pat. Nos. 6,019,968; 5,985,320; 5,985,309; 5,934,272; 5,874,064; 5,855,913; 5,290,540; and 4,880,078; and PCT Publication Nos. WO 92/19244, WO 97/32572, WO 97/44013, WO 98/31346, and WO 99/66903, each of which is incorporated herein by reference their entireties. In one embodiment, a DLL4 binding protein of the invention, combination therapy, or a composition of the invention is administered using Alkermes AIR® pulmonary drug delivery technology (Alkermes, Inc., Cambridge, Mass., US). In a specific embodiment, prophylactic or therapeutic agents of the invention are administered intramuscularly, intravenously, intratumorally, orally, intranasally, pulmonary, or subcutaneously. The prophylactic or therapeutic agents may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

In a specific embodiment, it may be desirable to administer the prophylactic or therapeutic agents of the invention locally to the area in need of treatment; this may be achieved by, for example, and not by way of limitation, local infusion, by injection, or by means of an implant, said implant being of a porous or non-porous material, including membranes and matrices, such as sialastic membranes, polymers, fibrous matrices (e.g., Tissuel®), or collagen matrices. In one embodiment, an effective amount of one or more DLL4 binding proteins of the invention antagonists is administered locally to the affected area to a subject to prevent, treat, manage, and/or ameliorate a disorder or a symptom thereof. In another embodiment, an effective amount of one or more DLL4 binding proteins of the invention is administered locally to the affected area in combination with an effective amount of one or more therapies (e.g., one or more prophylactic or therapeutic agents) other than a binding protein of the invention of a subject to prevent, treat, manage, and/or ameliorate a disorder or one or more symptoms thereof.

In another embodiment, the prophylactic or therapeutic agent can be delivered in a controlled release or sustained release system. In one embodiment, a pump may be used to achieve controlled or sustained release (see, Langer (*Science*, 249: 1527-1533 (1990)); Sefton, *CRC Crit. Ref. Biomed. Eng.*, 14: 201-240 (1987); Buchwald et al., *Surgery*, 88: 507-516 (1980); Saudek et al., *N. Engl. J. Med.*, 321: 574-579 (1989)). In another embodiment, polymeric materials can be used to achieve controlled or sustained release of the therapies of the invention. See, e.g., Goodson, J. M, In *Medical Applications of Controlled Release, Vol. II, Applications and Evaluations*, (Langer and Wise, eds.), (CRC Press Inc., Boca Raton, 1984), chapter 6, pages 115-138; *Controlled Drug Bioavailability, Drug Product Design and Performance*, Smolen and Ball (eds.) (Wiley, New York, 1984); Langer and Peppas, *J. Macromol. Sci. Rev. Macromol. Chem. Phys.*, C23: 61-126 (1983); see also, Levy et al., *Science*, 228: 190-192 (1985); During et al., *Ann. Neurol.*, 25: 351-356 (1989); Howard et al., *J. Neurosurg.*, 71: 105-112 (1989); U.S. Pat. Nos. 5,679,377; 5,916,597; 5,912,015; 5,989,463; and 5,128,326; and PCT Publication Nos. WO 99/15154 and WO 99/20253. Examples of polymers used in sustained release formulations include, but are not limited to, poly(2-hydroxy ethyl methacrylate), poly(methyl methacrylate), poly(acrylic acid), poly(ethylene-co-vinyl acetate), poly(methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glycolides) (PLGA), and polyorthoesters. In a preferred embodiment, the polymer used in a sustained release formulation is inert, free of leachable impurities, stable on storage, sterile, and biodegradable. In yet another embodiment, a controlled or sustained release system can be placed in proximity of the prophylactic or therapeutic target, thus requiring only a fraction of the systemic dose (see, e.g., Goodson, In *Medical Applications of Controlled Release*, (1984), pages 115-138).

Controlled release systems are discussed in the review by Langer (*Science*, 249: 1527-1533 (1990)). Any technique known to one of skill in the art can be used to produce sustained release formulations comprising one or more therapeutic agents of the invention. See, e.g., U.S. Pat. No. 4,526,938; PCT Publication Nos. WO 91/05548 and WO 96/20698; Ning et al., "Intratumoral Radioimmunotherapy of a Human Colon Cancer Xenograft Using a Sustained-Release Gel," *Radiother. Oncol.*, 39: 179-189 (1996); Song et al., "Antibody Mediated Lung Targeting of Long-Circulating Emulsions," *PDA J. Pharm. Sci. Tech.*, 50: 372-377 (1996); Cleek et al., "Biodegradable Polymeric Carriers for a bFGF Antibody for Cardiovascular Application," *Proceed. Intl. Symp. Control. Rel. Bioact. Mater.*, 24: 853-854 (1997), and Lam et al., "Microencapsulation of Recombinant Humanized Monoclonal Antibody for Local Delivery," *Proceed. Intl. Symp. Control Rel. Bioact. Mater.*: 24: 759-760 (1997), each of which is incorporated herein by reference in their entireties.

In a specific embodiment, where the composition of the invention is a nucleic acid encoding a prophylactic or therapeutic agent, the nucleic acid can be administered in vivo to promote expression of its encoded prophylactic or therapeutic agent, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see, e.g., Joliot et al., *Proc. Natl. Acad. Sci. USA*, 88: 1864-1868 (1991)). Alternatively, a nucleic acid can be introduced intracellularly and incorporated within host cell DNA for expression by homologous recombination.

A pharmaceutical composition of the invention is formulated to be compatible with its intended route of administration. Examples of routes of administration include, but are not limited to, parenteral (e.g., intravenous), intradermal, subcutaneous, oral, intranasal (e.g., inhalation), transdermal (e.g., topical), transmucosal, and rectal administration. In a specific embodiment, the composition is formulated in accordance with routine procedures as a pharmaceutical composition adapted for intravenous, subcutaneous, intramuscular, oral, intranasal, or topical administration to human beings. Typically, compositions for intravenous administration are solutions in sterile isotonic aqueous buffer. Where necessary, the composition may also include a solubilizing agent and a local anesthetic such as lignocamne to ease pain at the site of the injection.

If compositions of the invention are to be administered topically, the compositions can be formulated in the form of an ointment, cream, transdermal patch, lotion, gel, shampoo, spray, aerosol, solution, emulsion, or other form well-known to one of skill in the art. See, e.g., *Remington's Pharmaceutical Sciences and Introduction to Pharmaceutical Dosage Forms*, 19*th ed.*, (Mack Publishing Co., Easton, Pa., 1995). For non-sprayable topical dosage forms, viscous to semisolid or solid forms comprising a carrier or one or more excipients compatible with topical application and having a dynamic viscosity preferably greater than water are typically employed. Suitable formulations include, without limitation, solutions, suspensions, emulsions, creams, ointments, powders, liniments, salves, and the like, which are, if desired, sterilized or mixed with auxiliary agents (e.g., preservatives, stabilizers, wetting agents, buffers, or salts) for influencing various properties, such as, for example, osmotic pressure. Other suitable topical dosage forms include sprayable aerosol preparations wherein the active ingredient, preferably in combination with a solid or liquid inert carrier, is packaged in a mixture with a pressurized volatile (e.g., a gaseous propellant, such as FREON®) or in a squeeze bottle. Moisturizers or humectants can also be added to pharmaceutical compositions and dosage forms if desired. Examples of such additional ingredients are well known in the art.

If a method of the invention comprises intranasal administration of a composition, the composition can be formulated in an aerosol form, spray, mist or in the form of drops. In particular, prophylactic or therapeutic agents for use according to the present invention can be conveniently delivered in the form of an aerosol spray presentation from pressurized packs or a nebulizer, with the use of a suitable propellant (e.g., dichlorodifluoromethane, trichlorofluoromethane, dichlorotetrafluoroethane, carbon dioxide or other suitable gas). In the case of a pressurized aerosol the dosage unit may be determined by providing a valve to deliver a metered amount. Capsules and cartridges (composed of, e.g., gelatin) for use in an inhaler or insufflator may be formulated containing a powder mix of the compound and a suitable powder base such as lactose or starch.

If a method of the invention comprises oral administration, compositions can be formulated orally in the form of tablets, capsules, cachets, gelcaps, solutions, suspensions, and the like. Tablets or capsules can be prepared by conventional means with pharmaceutically acceptable excipients such as binding agents (e.g., pregelatinised maize starch, polyvinylpyrrolidone, or hydroxypropyl methylcellulose); fillers (e.g., lactose, microcrystalline cellulose, or calcium hydrogen phosphate); lubricants (e.g., magnesium stearate, talc, or silica); disintegrants (e.g., potato starch or sodium starch glycolate); or wetting agents (e.g., sodium lauryl sulphate). The tablets may be coated by methods well-known in the art. Liquid preparations for oral administration may take the form of, but not limited to, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives, or hydrogenated edible fats); emulsifying agents (e.g., lecithin or acacia); non-aqueous vehicles (e.g., almond oil, oily esters, ethyl alcohol, or fractionated vegetable oils); and preservatives (e.g., methyl or propyl-p-hydroxybenzoates or sorbic acid). The preparations may also contain buffer salts, flavoring, coloring, and sweetening agents as appropriate. Preparations for oral administration may be suitably formulated for slow release, controlled release, or sustained release of a prophylactic or therapeutic agent(s).

A method of the invention may comprise pulmonary administration, e.g., by use of an inhaler or nebulizer, of a composition formulated with an aerosolizing agent. See, e.g., U.S. Pat. Nos. 6,019,968; 5,985,320; 5,985,309; 5,934,272; 5,874,064; 5,855,913; 5,290,540; and 4,880,078; and PCT Publication Nos. WO 92/19244, WO 97/32572, WO 97/44013, WO 98/31346, and WO 99/66903, each of which is incorporated herein by reference their entireties. In a specific embodiment, an antibody of the invention, combination therapy, and/or composition of the invention is administered using Alkermes AIR® pulmonary drug delivery technology (Alkermes, Inc., Cambridge, Mass., US).

A method of the invention may comprise administration of a composition formulated for parenteral administration by injection (e.g., by bolus injection or continuous infusion). Formulations for injection may be presented in unit dosage form (e.g., in ampoules or in multi-dose containers) with an added preservative. The compositions may take such forms as suspensions, solutions, or emulsions in oily or aqueous vehicles, and may contain formulatory agents such as suspending, stabilizing and/or dispersing agents. Alternatively, the active ingredient may be in powder form for constitution with a suitable vehicle (e.g., sterile pyrogen-free water) before use.

A method of the invention may additionally comprise administration of compositions formulated as depot preparations. Such long acting formulations may be administered by implantation (e.g., subcutaneously or intramuscularly) or by intramuscular injection. Thus, for example, the compositions may be formulated with suitable polymeric or hydrophobic materials (e.g., as an emulsion in an acceptable oil) or ion exchange resins, or as sparingly soluble derivatives (e.g., as a sparingly soluble salt).

Methods of the invention encompass administration of compositions formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

Generally, the ingredients of compositions are supplied either separately or mixed together in unit dosage form, for example, as a dry lyophilized powder or water free concentrate in a hermetically sealed container such as an ampoule or sachette indicating the quantity of active agent. Where the mode of administration is infusion, a composition can be dispensed with an infusion bottle containing sterile pharmaceutical grade water or saline. Where the mode of administration is by injection, an ampoule of sterile water for injection or saline can be provided so that the ingredients may be mixed prior to administration.

In particular, the invention also provides that one or more of the prophylactic or therapeutic agents or pharmaceutical compositions of the invention is packaged in a hermetically sealed container such as an ampoule or sachette indicating the quantity of the agent. In one embodiment, one or more of the prophylactic or therapeutic agents, or pharmaceutical compositions of the invention is supplied as a dry sterilized lyophilized powder or water free concentrate in a hermetically sealed container and can be reconstituted (e.g., with water or saline) to the appropriate concentration for administration to a subject. Preferably, one or more of the prophylactic or therapeutic agents or pharmaceutical compositions of the invention is supplied as a dry sterile lyophilized powder in a hermetically sealed container at a unit dosage of at least 5 mg, more preferably at least 10 mg, at least 15 mg, at least 25 mg, at least 35 mg, at least 45 mg, at least 50 mg, at least 75 mg, or at least 100 mg. The lyophilized prophylactic or therapeutic agents or pharmaceutical compositions of the invention should be stored at between 2° C. and 8° C. in its original container and the prophylactic or therapeutic agents, or pharmaceutical compositions of the invention should be administered within 1 week, preferably within 5 days, within 72 hours, within 48 hours, within 24 hours, within 12 hours, within 6 hours, within 5 hours, within 3 hours, or within 1 hour after being reconstituted. In an alternative embodiment, one or more of the prophylactic or therapeutic agents or pharmaceutical compositions of the invention is supplied in liquid form in a hermetically sealed container indicating the quantity and concentration of the agent. Preferably, the liquid form of the administered composition is supplied in a hermetically sealed container at least 0.25 mg/ml, more preferably at least 0.5 mg/ml, at least 1 mg/ml, at least 2.5 mg/ml, at least 5 mg/ml, at least 8 mg/ml, at least 10 mg/ml, at least 15 mg/kg, at least 25 mg/ml, at least 50 mg/ml, at least 75 mg/ml, or at least 100 mg/ml. The liquid form should be stored at between 2° C. and 8° C. in its original container.

The binding proteins of the invention can be incorporated into a pharmaceutical composition suitable for parenteral administration. Preferably, the binding protein will be prepared as an injectable solution containing 0.1-250 mg/ml antibody. The injectable solution can be composed of either a liquid or lyophilized dosage form in a flint or amber vial, ampoule or pre-filled syringe. The buffer can be L-histidine (1-50 mM), optimally 5-10 mM, at pH 5.0 to 7.0 (optimally pH 6.0). Other suitable buffers include but are not limited to, sodium succinate, sodium citrate, sodium phosphate or potassium phosphate. Sodium chloride can be used to modify the toxicity of the solution at a concentration of 0-300 mM (optimally 150 mM for a liquid dosage form). Cryoprotectants can be included for a lyophilized dosage form, principally 0-10% sucrose (optimally 0.5-1.0%). Other suitable cryoprotectants include trehalose and lactose. Bulking agents can be included for a lyophilized dosage form, principally 1-10% mannitol (optimally 2-4%). Stabilizers can be used in both liquid and lyophilized dosage forms, principally 1-50 mM L-methionine (optimally 5-10 mM). Other suitable bulking agents include glycine, arginine, can be included as 0-0.05% polysorbate-80 (optimally 0.005-0.01%). Additional surfactants include but are not limited to polysorbate 20 and BRIJ surfactants.

The compositions of this invention may be in a variety of forms. These include, for example, liquid, semi-solid and solid dosage forms, such as liquid solutions (e.g., injectable and infusible solutions), dispersions or suspensions, tablets, pills, powders, liposomes and suppositories. The preferred form depends on the intended mode of administration and therapeutic application. Typical preferred compositions are in the form of injectable or infusible solutions, such as compositions similar to those used for passive immunization of humans with other antibodies. The preferred mode of administration is parenteral (e.g., intravenous, subcutaneous, intraperitoneal, intramuscular). In a preferred embodiment, a DLL4 binding protein described herein is administered by intravenous infusion or injection. In another preferred embodiment, a DLL4 binding protein is administered by intramuscular or subcutaneous injection.

Therapeutic compositions typically must be sterile and stable under the conditions of manufacture and storage. The composition can be formulated as a solution, microemulsion, dispersion, liposome, or other ordered structure suitable to high drug concentration. Sterile injectable solutions can be prepared by incorporating the active compound (i.e., antibody or antibody portion) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile, lyophilized powders for the preparation of sterile injectable solutions, the preferred methods of preparation are vacuum drying and spray-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including, in the composition, an agent that delays absorption, for example, monostearate salts and gelatin.

The DLL4 binding proteins of the present invention can be administered by a variety of methods known in the art, although for many therapeutic applications, the preferred route/mode of administration is subcutaneous injection, intravenous injection, or infusion. As will be appreciated by the skilled artisan, the route and/or mode of administration will vary depending upon the desired results. In certain embodiments, the active compound may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., (Marcel Dekker, Inc., New York, 1978).

In certain embodiments, a binding protein of the invention may be orally administered, for example, with an inert diluent or an assimilable edible carrier. The compound (and other ingredients, if desired) may also be enclosed in a hard or soft shell gelatin capsule, compressed into tablets, or incorporated directly into the subject's diet. For oral therapeutic administration, the compounds may be incorporated with excipients and used in the form of ingestible tablets, buccal tablets, troches, capsules, elixirs, suspensions, syrups, wafers, and the like. To administer a compound of the invention by other than parenteral administration, it may be necessary to coat the compound with, or co-administer the compound with, a material to prevent its inactivation.

Supplementary active compounds can also be incorporated into the compositions. In certain embodiments, a binding protein of the invention is coformulated with and/or coadministered with one or more additional therapeutic agents that are useful for treating disorders in which DLL4 activity is detrimental. For example, an anti-huDLL4 antibody or antibody portion of the invention may be coformulated and/or coadministered with one or more additional antibodies that bind other targets (e.g., antibodies that bind other cytokines or that bind cell surface molecules). Furthermore, one or more binding proteins of the invention may be used in combination with two or more of the foregoing therapeutic agents. Such combination therapies may advantageously utilize lower dosages of the administered therapeutic agents, thus avoiding possible toxicities or complications associated with the various monotherapies.

In certain embodiments, a DLL4 binding protein of the invention is linked to a half-life extending vehicle known in the art. Such vehicles include, but are not limited to, the Fc domain, polyethylene glycol, and dextran. Such vehicles are described, e.g., in U.S. Pat. No. 6,660,843 B1 and published PCT Publication No. WO 99/25044, which are hereby incorporated by reference.

In a specific embodiment, nucleic acid sequences comprising nucleotide sequences encoding a binding protein of the invention or another prophylactic or therapeutic agent of the invention are administered to treat, prevent, manage, or ameliorate a disorder or one or more symptoms thereof by way of gene therapy. Gene therapy refers to therapy performed by the administration to a subject of an expressed or expressible nucleic acid. In this embodiment of the invention, the nucleic acids produce their encoded binding protein or prophylactic or therapeutic agent of the invention that mediates a prophylactic or therapeutic effect.

Any of the methods for gene therapy available in the art can be used according to the present invention. For general reviews of the methods of gene therapy, see Goldspiel et al., *Clin. Pharmacy*, 12: 488-505 (1993); Wu and Wu, *Biotherapy*, 3: 87-95 (1991); Tolstoshev, *Ann. Rev. Pharmacol. Toxicol.*, 32: 573-596 (1993); Mulligan, *Science*, 260: 926-932 (1993); and Morgan and Anderson, *Ann. Rev. Biochem.*, 62: 191-217 (1993); Robinson, C., *Trends Biotechnol.*, 11(5): 155 (1993). Methods commonly known in the art of recombinant DNA technology which can be used are described in Ausubel et al. (eds.), *Current Protocols in Molecular Biology* (John Wiley & Sons, New York, 1993); and Kriegler, *Gene Transfer and Expression, A Laboratory Manual*, (Stockton Press, New York, 1990). Detailed descriptions of various methods of gene therapy are disclosed in US Patent Application Publication No. 20050042664 A1, which is incorporated herein by reference.

In another aspect this invention provides a method of treating (e.g. curing, suppressing, ameliorating, delaying, or preventing the onset of, or preventing recurrence or relapse of) or preventing a DLL4-associated tumor in a subject. The method includes administering to a subject a DLL4 binding protein, e.g., an anti-DLL4 antibody or fragment thereof as described herein, in an amount sufficient to treat or prevent the DLL-associated tumor or cancer. The DLL4 antagonist, i.e., the anti-DLL4 antibody or fragment thereof, may be administered to a subject alone or in combination with other therapeutic modalities as described herein.

DLL4 plays a critical role in the pathology associated with a variety of diseases involving immune and inflammatory elements, in particular cancer and tumor angiogenesis. Examples of DLL4-associated disorders include, but are not limited to, those disorders that adversely effect the following biological processes: neuronal function and development; stabilization of arterial endothelial fate and angiogenesis; regulation of crucial cell communication events between endocardium and myocardium during both the formation of the valve primordial and ventricular development and differentiation; cardiac valve homeostasis, as well as implications in other human disorders involving the cardiovascular system; timely cell lineage specification of both endocrine and exocrine pancreas; influencing of binary fate decisions of cells that must choose between the secretory and absorptive lineages in the gut; expansion of the hematopoietic stem cell compartment during bone development and participation in commitment to the osteoblastic lineage such as osteoporosis; regulation of cell-fate decision in mammary glands at several distinct development stages; and certain non-nuclear mechanisms, such as control of the actin cytoskeleton through the tyrosine kinase Abl. More specifically, DLL4-associated disorders include, but are not limited to, cancers, T-ALL (T-cell acute lymphoblastic leukemia), CADASIL (Cerebral Autosomal Dominant Arteriopathy with Sub-cortical Infarcts and Leukoencephalopathy), MS (Multiple Sclerosis), Tetralogy of Fallot, and Alagille syndrome. Preferably, antibodies and antigen-binding portions thereof as described herein are used to treat cancers and tumors.

Binding proteins according to the invention can be used alone or in combination, i.e., more than one DLL4-binding protein described herein, to treat a cancer, a tumor, or other disorder in which binding to, inhibition of, and/or neutralization of DLL4 is considered desirable or otherwise beneficial to the health of an individual.

It should be understood that DLL4 binding proteins of the invention can also be used alone or in combination with an additional agent, e.g., a therapeutic agent, said additional agent being selected by the skilled practitioner for its intended purpose. For example, the additional agent can be a therapeutic agent that is recognized in the art as being useful to treat a cancer, tumor, or other disease or condition in which binding to or inhibition of DLL4 is considered to be desirable or advantageous for treating the cancer, tumor, or other disease or condition. The additional agent also can be an agent that imparts a beneficial attribute to the therapeutic composition e.g., an agent which affects the viscosity of the composition.

It should further be understood that the combinations which are to be included within this invention are those combinations useful for their intended purpose. The agents set forth below are illustrative for purposes and not intended to be limited. The combinations, which are part of this invention, can be the antibodies of the present invention and at least one additional agent selected from the lists below. The combination can also include more than one additional agent, e.g., two or three additional agents, if the combination is such that the formed composition can perform its intended function.

Preferred combinations are non-steroidal anti-inflammatory drug(s) also referred to as NSAIDS, which include drugs like ibuprofen. Other preferred combinations are corticosteroids including prednisolone; the well known side-effects of steroid use can be reduced or even eliminated by tapering the steroid dose required when treating patients in combination with the anti-DLL4 antibodies of this invention. Non-limiting examples of therapeutic agents for rheumatoid arthritis with which an antibody, or antibody portion, of the invention can be combined include the following: cytokine suppressive anti-inflammatory drug(s) (CSAIDs); antibodies to or antagonists of other human cytokines or growth factors, for example, TNF, LT, IL-1, IL-2, IL-3, IL-4, IL-5, IL-6, IL-7, IL-8, IL-15, IL-16, IL-18, IL-21, interferons, EMAP-II, GM-CSF, FGF, and PDGF. Antibodies of the invention, or antigen binding portions thereof, can be combined with antibodies to cell surface molecules such as CD2, CD3, CD4, CD8, CD25, CD28, CD30, CD40, CD45, CD69, CD80 (B7.1), CD86 (B7.2), CD90, CTLA or their ligands including CD154 (gp39 or CD40L).

Preferred combinations of therapeutic agents may interfere at different points in the pro-tumorigenic or pro-angiogenic signaling pathways. Preferred examples therapeutic agents useful in the methods and compositions of the invention include antineoplastic agents, radiotherapy, and chemotherapy such as DNA alkylating agents, cisplatin, carboplatin, anti-tubulin agents, paclitaxel, docetaxel, taxol, doxorubicin, gemcitabine, gemzar, anthracyclines, adriamycin, topoisomerase I inhibitors, topoisomerase II inhibitors, 5-fluorouracil (5-FU), leucovorin, irinotecan, receptor tyrosine kinase inhibitors (e.g., erlotinib, gefitinib), COX-2 inhibitors (e.g., celecoxib), and kinase inhibitors.

The DLL4 binding proteins of the invention may also be combined with agents, such as methotrexate, 6-MP, azathioprine sulphasalazine, mesalazine, olsalazine chloroquinine/hydroxychloroquine, pencillamine, aurothiomalate (intramuscular and oral), azathioprine, colchicine, corticosteroids (oral, inhaled and local injection), beta-2 adrenoreceptor agonists (salbutamol, terbutaline, salmeteral), xanthines (theophylline, aminophylline), cromoglycate, nedocromil, ketotifen, ipratropium and oxitropium, cyclosporin, FK506, rapamycin, mycophenolate mofetil, leflunomide, NSAIDs, for example, ibuprofen, corticosteroids such as prednisolone, phosphodiesterase inhibitors, adensosine agonists, antithrombotic agents, complement inhibitors, adrenergic agents, agents which interfere with signaling by proinflammatory cytokines such as or IL-1 (e.g. IRAK, NIK, IKK, p38 or MAP kinase inhibitors), IL-1b TNFα converting enzyme (TACE) inhibitors, T-cell converting enzyme inhibitors, TNFα signaling inhibitors such as kinase inhibitors, metalloproteinase inhibitors, sulfasalazine, azathioprine, 6-mercaptopurines, angiotensin converting enzyme inhibitors, soluble cytokine receptors and derivatives thereof (e.g. soluble p55 or p75 TNF receptors and the derivatives p75TNFRIgG (Enbrel™ and p55TNFRIgG (Lenercept)), sIL-1RI, sIL-1RII, sIL-6R), antiinflammatory cytokines (e.g., IL-4, IL-10, IL-11, IL-13 and TGFβ), celecoxib, folic acid, hydroxychloroquine sulfate, rofecoxib, etanercept, infliximab, naproxen, valdecoxib, sulfasalazine, methylprednisolone, meloxicam, methylprednisolone acetate, gold sodium thiomalate, aspirin, triamcinolone acetonide, propoxyphene napsylate/apap, folate, nabumetone, diclofenac, piroxicam, etodolac, diclofenac sodium, oxaprozin, oxycodone hcl, hydrocodone bitartrate/apap, diclofenac sodium/misoprostol, fentanyl, anakinra, human recombinant, tramadol hcl, salsalate, sulindac, cyanocobalamin/fa/pyridoxine, acetaminophen, alendronate sodium, prednisolone, morphine sulfate, lidocaine hydrochloride, indomethacin, glucosamine sulf/chondroitin, amitriptyline HCl, sulfadiazine, oxycodone HCl/acetaminophen, olopatadine hcl, misoprostol, naproxen sodium, omeprazole, cyclophosphamide, rituximab, IL-1 TRAP, MRA, CTLA4-IG, IL-18 BP, anti-IL-18, Anti-IL15, BIRB-796, SCIO-469, VX-702, AMG-548, VX-740, Roflumilast, IC-485, CDC-801, and Mesopram. Preferred combinations include methotrexate or leflunomide and in moderate or severe rheumatoid arthritis cases, cyclosporine.

Non-limiting examples of therapeutic agents for cancers with which a DLL4 binding protein of the invention can be combined include the following: budenoside; epidermal growth factor; corticosteroids; cyclosporin; sulfasalazine; aminosalicylates; 6-mercaptopurine; azathioprine; metronidazole; lipoxygenase inhibitors; mesalamine; olsalazine; balsalazide; antioxidants; thromboxane inhibitors; IL-1 receptor antagonists; anti-IL-1β monoclonal antibodies; anti-IL-6 monoclonal antibodies; growth factors; elastase inhibitors; pyridinyl-imidazole compounds; and antibodies to or antagonists of other human cytokines or growth factors, for example, TNF, LT, IL-1, IL-2, IL-6, IL-7, IL-8, IL-15, IL-16, IL-17, IL-18, EMAP-II, GM-CSF, FGF, and PDGF. Antibodies of the invention, or antigen binding portions thereof, can be combined with antibodies to cell surface molecules such as CD2, CD3, CD4, CD8, CD25, CD28, CD30, CD40, CD45, CD69, CD90, or their ligands. The antibodies of the invention, or antigen binding portions thereof, may also be combined with agents, such as methotrexate, cyclosporin, FK506, rapamycin, mycophenolate mofetil, leflunomide, NSAIDs, for example, ibuprofen, corticosteroids such as prednisolone, phosphodiesterase inhibitors, adenosine agonists, antithrombotic agents, complement inhibitors, adrenergic agents, agents which interfere with or IL-1 (e.g., IRAK, NIK, signaling by proinflammatory cytokines such as TNFα IKK, p38 or MAP kinase inhibitors), IL-1β converting enzyme inhibitors, TNFα converting enzyme inhibitors, T-cell signalling inhibitors such as kinase inhibitors, metalloproteinase inhibitors, sulfasalazine, azathioprine, 6-mercaptopurines, angiotensin converting enzyme inhibitors, soluble cytokine receptors and derivatives thereof (e.g., soluble p55 or p75 TNF receptors, sIL-1RI, sIL-1RII, sIL-6R), and anti-inflammatory cytokines (e.g., IL-4, IL-10, IL-11, IL-13, and TGFβ).

Other examples of therapeutic agents with which a DLL4 binding protein of the invention can be combined include the following: TNF antagonists, for example, anti-TNF antibodies, D2E7 (PCT Publication No. WO 97/29131; HUMIRA®), CA2 (REMICADE®), CDP 571, TNFR-Ig constructs, (p75TNFRIgG (ENBREL®) and p55TNFRIgG (LENERCEPT)) and PDE4 inhibitors. Binding proteins of the invention can be combined with corticosteroids, for example, budenoside and dexamethasone. Binding proteins of the invention may also be combined with agents such as sulfasalazine, 5-aminosalicylic acid, and olsalazine, and agents which interfere with synthesis or action of proinflammatory cytokines such as IL-1, for example, IL-1β converting enzyme inhibitors and IL-1ra. DLL4 binding proteins of the invention may also be used with T cell signaling inhibitors, for example, tyrosine kinase inhibitors 6-mercaptopurines. DLL4 binding proteins of the invention can be combined with IL-11. Binding proteins of the invention can be combined with mesalamine, prednisone, azathioprine, mercaptopurine, infliximab, methylprednisolone sodium succinate, diphenoxylate/atrop sulfate, loperamide hydrochloride, methotrexate, omeprazole, folate, ciprofloxacin/dextrose-water, hydrocodone bitartrate/apap, tetracycline hydrochloride, fluocinonide, metronidazole, thimerosal/boric acid, cholestyramine/sucrose, ciprofloxacin hydrochloride, hyoscyamine sulfate, meperidine hydrochloride, midazolam hydrochloride, oxycodone hcl/acetaminophen, promethazine hydrochloride, sodium phosphate, sulfamethoxazole/trimethoprim, celecoxib, polycarbophil, propoxyphene napsylate, hydrocortisone, multivitamins, balsalazide disodium, codeine phosphate/apap, colesevelam hcl, cyanocobalamin, folic acid, levofloxacin, methylprednisolone, natalizumab, and interferon-gamma.

Non-limiting examples of therapeutic agents with which a binding protein of the invention can be combined include the following: aspirin, nitroglycerin, isosorbide mononitrate, metoprolol succinate, atenolol, metoprolol tartrate, amlodipine besylate, diltiazem hydrochloride, isosorbide dinitrate, clopidogrel bisulfate, nifedipine, atorvastatin calcium, potassium chloride, furosemide, simvastatin, verapamil hcl, digoxin, propranolol hydrochloride, carvedilol, lisinopril, spironolactone, hydrochlorothiazide, enalapril maleate, nadolol, ramipril, enoxaparin sodium, heparin sodium, valsartan, sotalol hydrochloride, fenofibrate, ezetimibe, bumetanide, losartan potassium, lisinopril/hydrochlorothiazide, felodipine, captopril, and bisoprolol fumarate.

The pharmaceutical compositions of the invention may include a "therapeutically effective amount" or a "prophylactically effective amount" of a binding protein of the invention. A "therapeutically effective amount" refers to an amount effective, at dosages and for periods of time necessary, to achieve the desired therapeutic result. A therapeutically effective amount of the binding protein may be determined by a person skilled in the art and may vary according to factors such as the disease state, age, sex, and weight of the individual, and the ability of the binding protein to elicit a desired response in the individual. A therapeutically effective amount is also one in which any toxic or detrimental effects of the binding protein are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

Dosage regimens may be adjusted to provide the optimum desired response (e.g., a therapeutic or prophylactic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic or prophylactic effect to be achieved, and (b) the limitations inherent in the art of compounding such an active compound for the treatment of sensitivity in individuals.

An exemplary, non-limiting range for a therapeutically or prophylactically effective amount of a DLL4 binding protein of the invention is 0.1-20 mg/kg, more preferably 1-10 mg/kg. It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

It will be readily apparent to those skilled in the art that other suitable modifications and adaptations of the methods of the invention described herein are obvious and may be made using suitable equivalents without departing from the scope of the invention or the embodiments disclosed herein. Having now described the present invention in detail, the same will be more clearly understood by reference to the following examples, which are included for purposes of illustration only and are not intended to be limiting of the invention.

EXAMPLES

Example 1

In Vitro Assays Used to Determine the Functional Activity of DLL4 Antibodies

Example 1.1

Affinity Determination Using BIACORE® Surface Plasmon Resonance Technology

The BIACORE® surface plasmon resonance assay (Biacore, Inc., Piscataway, N.J. US) determines the affinity of antibodies with kinetic measurements of on-rate and off-rate constants. Binding of DLL4 antibodies to a purified recombinant DLL4 extracellular domain is determined by surface plasmon resonance-based measurements with a Biacore® instrument (either a Biacore 2000, Biacore 3000, or Biacore T100; GE Healthcare, Piscataway, N.J., US) using running buffer HBS-EPB (10 mM HEPES [pH 7.4], 150 mM NaCl, 3 mM EDTA, 0.1 mg/ml BSA and 0.005% surfactant P20) at 25° C. For example, approximately 9000 RU of goat anti-human Fc specific polyclonal antibody (Thermo Fisher Scientific Inc., Rockford, Ill., US) diluted in 10 mM sodium acetate (pH 4.5) is directly immobilized across a CM5 research grade biosensor chip using a standard amine coupling kit according to manufacturer's instructions and procedures at 25 μg/ml. Unreacted moieties on the biosensor surface are blocked with ethanolamine. For kinetic analysis, rate equations derived from the 1:1 Langmuir binding model are fitted simultaneously to multiple antigen injections (using global fit analysis) with the use of Scrubber 2 (BioLogic Software), Biacore Biaevaluation 4.0.1 software or Biacore T100 Evaluation software. Purified antibodies are diluted in running buffer for capture across goat anti-human Fc reaction surfaces. Antibodies to be captured as a ligand (1 μg/ml) are injected over reaction matrices at a flow rate of 10 μl/min. During the assay, all measurements were referenced against the capture surface alone (i.e., with no captured anti-DLL4 antibody). The association and dissociation rate constants, $K_{on}$ ($M^{-1} s^{-1}$) and $K_{off}$ ($s^{-1}$) are determined under a continuous flow rate of 80 μl/min. Rate constants are derived by making kinetic binding measurements at different antigen concentrations ranging from 1.23-900 nM, as a 3-fold dilution series, and included buffer-only injections (to be used for double referencing). The equilibrium dissociation constant $K_D$ (M) of the reaction between antibodies and the target antigen is then calculated from the kinetic rate constants by the following formula: $K_D=K_{off}/K_{on}$. Binding is recorded as a function of time and kinetic rate constants are calculated. In this assay, on-rates as fast as $10^6 M^{-1} s^{-1}$ and off-rates as slow as $10^{-6} s^{-1}$ can be measured.

Example 1.2

Binding of DLL4 Antibodies to Soluble DLL4 Extracellular Domain as Determined by ELISA Method 1 (Capture ELISA).

96-well Nunc-Immuno plates (#439454) were coated with 5 μg/ml antibody against human IgG (Fcg fragment specific, Jackson ImmunoResearch, #109-005-098, 100 μl/well) in D-PBS (Gibco #14190) and incubated overnight at 4° C. ELISA plates were washed 3 times with wash buffer (PBS, 0.05% Tween-20) and then blocked with 200 ml/well blocking buffer (D-PBS, 1% BSA, 1 mM $CaCl_2$, 0.05% Tween-20) for 1 hour at 25° C. Plates were washed 3 times and incubated with 100 μl/well DLL4 antibodies (0.0001-100 nM, 10-fold serial dilution in blocking buffer) for 1 hour at 25° C., and then washed again 3 times. Plates containing captured DLL4 antibody were incubated with biotin-labeled human DLL4 extracellular domain (10 nM in blocking buffer, 100 μl/well) for 1 hour at 25° C., washed 3 times, and incubated with streptavidin conjugated with HRP (KPL #474-3000, 1:10,000 dilution in blocking buffer, 100 μl/well) for 1 hour at 25° C. After the final wash, plates were incubated with 100 μl/well ELISA substrate (1-Step Ultra TMB-ELISA, Pierce #340280). The reaction was stopped after 2 minutes at 25° C. with 100 μl/well 2 N $H_2SO_4$ and the absorbance was read at 450 nm. Data were analyzed using Graphpad Prism software and $EC_{50}$ values were reported.

Method 2 (Copper Coated Plate).

96-well copper-coated plates (Thermo Scientific #15143) were washed 3 times with wash buffer (PBS, 0.05% Tween-20) before use and then incubated with 100 μl/well of human DLL4-his or mouse DLL4-his or cyno DLL4-his at 1 μg/ml in PBS, 1 hour at 25° C. with shaking. Plates were then washed 3 times. 100 μl/well of recombinant rat/human chimeric or recombinant human anti-DLL4 antibodies were then added to the plate (0.00164-27 nM, 4-fold serial dilution in ELISA buffer=PBST, 10% Superblock (Pierce #37515)) for 1 hour at 25° C. with shaking and then washed again 3 times. Plates were incubated with goat anti-human HRP (Pierce #31412) (1:40,000 dilution in ELISA buffer, 100 μl/well) for 1 hour at 25° C. with shaking, then washed 3 times. After the final wash, plates were incubated with 100 µl/well ELISA substrate (Sigma #T8665). The reaction was stopped after 8 minutes at 25° C. with 100 µl/well 1N HCl and the absorbance was read at 450 nm. Data were analyzed using Graphpad Prism software and EC50 values were reported.

Example 1.3

Binding of DLL4 Monoclonal Antibodies to the Surface of Human Tumor Cell Lines as Assessed by Flow Cytometry (FACS)

Stable cell lines overexpressing cell-surface DLL4 were harvested from tissue culture flasks, washed four times and resuspended in phosphate buffered saline (PBS) containing 1% bovine serum albumin and 1 mM $CaCl_2$ (FACS buffer). $1.5 \times 10^5$ cells were incubated with antibodies at various concentrations in FACS buffer for 60 minutes on ice. Cells were washed twice and 50 µL of R-phycoerythrin-conjugated anti-rat IgG, $F(ab')_2$ fragment (1:200 dilution in FACS buffer) (Jackson ImmunoResearch, West Grove, Pa., US, Cat.#112-116-072) was added. Following an incubation on ice (4° C., 60 minutes), cells were washed three times and resuspended in FACS buffer. Fluorescence was measured using a Becton Dickinson FACSCalibur-HTS (Becton Dickinson, San Jose, Calif., US). Data were analyzed using Graphpad Prism software and $EC_{50}$ values were reported as the concentration of antibody to achieve 50% of maximal DLL4 antibodies binding to DLL4 expressing cells.

Example 1.4

Inhibition of Notch-1 Interaction with Soluble DLL4 Extracellular Domain by DLL4 Antibodies (Competition ELISA)

96-well Nunc-Immuno plates (#439454 for huDLL4 ELISA) and 96-well Costar plates (#9018 for muDLL4 ELISA) were coated with 16 nM human Notch-1 (R&D Systems #3647-TK, 100 µl/well in D-PBS) and incubated overnight at 4° C. Plates were then washed 3 times with wash buffer (PBS, 0.05% Tween-20) and blocked with 200 µl/well blocking buffer (D-PBS, 1% BSA, 1 mM $CaCl_2$, 0.05% Tween-20) for 1 hour at 25° C. While blocking, biotin labeled human DLL4 extracellular domain (14 nM) was mixed with antibody (30 pM-66 nM, 3-fold serial dilution in blocking buffer) for 1 hour at 25° C. with shaking. Assay plates were washed after blocking, and incubated with DLL4/antibody mixtures (100 µl/well, 1 hour at 25° C. with shaking). Plates were washed again and 100 µl/well streptavidin conjugated with HRP (Fitzgerald #65R-S104PHRPx, diluted 1:5,000 in blocking buffer) was added for 1 hour at 25° C. with shaking. After a final wash, plates were developed using 100 µl/well substrate (TMB Sigma #T8665), and the reaction was stopped after an 8-minute incubation at 25° C. (for muDLL4 ELISA) and after 20 minute incubation at 25° C. (for huDLL4 ELISA) using 100 µl/well 1N HCl, and the absorbance was read at 450 nm. Data were analyzed using Graphpad Prism software and $IC_{50}$ values were reported as the concentration of antibody to achieve 50% reduction of DLL4 bound to Notch1.

Example 1.5

Blocking of Soluble Notch Binding to DLL4-Overexpressing 293G Cells by Anti-DLL4 Monoclonal Antibodies as Assessed by Flow Cytometry (Competition FACS)

Notch blocking assay: Briefly, stable cell lines overexpressing cell-surface DLL4 were harvested from tissue culture flasks and re-suspended in phosphate buffered saline (PBS) containing 1% bovine serum albumin and 1 mM $CaCl_2$ (FACS buffer). HEK293-hDLL4 or HEK293-mDLL4 cells were dispensed into 96-well plate (v-bottom) at $1.5 \times 10^5$ cells/well in FACS buffer. After spinning down cells and discarding the supernatant, 50 µL of purified IgG with appropriate dilution was added to each well, and incubated on ice at 4° C. for 60 minutes, followed by addition of 50 µL/well of Notch1-biotin at 0.2 µg/mL for hDLL4-293G or 2.0 µg/mL for mDLL4-293G (1.0 or 0.1 µg/mL final) for additional 1 hour incubation ice at 4° C. After washing the cells two times with FACS buffer, 50 µL of R-phycoerythrin-conjugated streptavidin (1:150 dilution in FACS buffer) (Jackson ImmunoResearch, West Grove, Pa., US, catalog no. 016-110-084) were added. Following an incubation on ice (4° C., 60 minutes), cells were washed three times and resuspended in FACS buffer. Fluorescence was measured using a Becton Dickinson FACSCalibur-HTS (Becton Dickinson, San Jose, Calif.). Data were analyzed using Graphpad Prism software and $IC_{50}$ values were reported as the concentration of antibody to achieve 50% reduction of Notch1 bound to DLL4 expressing cells.

Example 1.6

Inhibition of DLL4-Dependent Increase of sVEGFR1 (sFLT1) in EA.hy926 Cells by DLL4 Antibodies Tissue culture plates, 96-well, were coated with 100 µl/well human DLL4 extracellular domain at 1.67 mg/ml in D-PBS (Gibco #14190) and incubated overnight at 4° C. Plates were washed once with D-PBS and 4000 EA.hy926 cells/well were seeded in the absence or presence of antibodies. Cell proliferation was measured four days later using the CyQUANT Cell Proliferation Assay Kit (Invitrogen, #C35007). sVEGFR1 expression in the conditioned media was detected by an ELISA kit per the manufacturer's recommendations (R&D Systems #DVR100B). Levels of sVEGFR1 were normalized to the RFU determined by CyQUANT assay to account for differences in cell proliferation.

Example 1.7

Inhibition of DLL4-Dependent Notch Activation in EA.hy926 Cells by DLL4 Antibodies Using Notch Reporter Assay 96-well black clear-bottom tissue culture plates were seeded overnight with 7000 cells/well engineered EA.hy926 cells expressing luciferase driven by a Notch-responsive promoter. Antibodies serially diluted from 200 nM were mixed for 15 minutes with equal volume of 5000 HEK293G cells/well expressing full-length DLL4. The 293G/DLL4 cells were co-cultured with EA.hy926 Notch reporter cells for 24 hrs in the presence of testing antibodies. Luciferase activity was analyzed by Promega's substrate (Promega # E2940).

Example 1.8

Analytical Methods and Techniques for Molecule Identity and Physicochemical Property Characterizations PEG Precipitation Method.

The use of PEG for inducing phase separation of a solid protein according to principles of volume exclusion represents a feasible approach to assess the solubility of a protein. PEG has several advantages over other precipitants, including minimal denaturation of proteins at ambient temperatures (does not affect tertiary structure of proteins) and within the range of 4° C. to 30° C. temperature control is not required, i.e., precipitation studies can be performed at ambient temperature at the laboratory bench.

Generally, the precipitation of proteins by PEGs is explained on the basis of volume exclusion effects. According to this theory, proteins are sterically excluded from the regions of solvent that are occupied by PEG linear chains. As a result, proteins are concentrated and eventually precipitated when their solubility is exceeded. In thermodynamic terms, the steric exclusion leads to an increase in the chemical potential of the protein until it exceeds that of the pure solid state, resulting in protein precipitation. This happens mainly because of a large unfavorable free energy of interaction between PEG and proteins, reducing the preferential hydration of protein due to steric exclusion effects. In aqueous solutions, preferential hydration helps to maintain the native structure of proteins. Generally, volume exclusion has been shown to become more effective with increasing molecular weight of the PEG, i.e., less PEG is needed to precipitate proteins with increasing PEG molecular weight.

A PEG molecular weight of 3000 was chosen for estimating the solubility of the antibodies covered by this patent. A 50% PEG solution was made by dissolving PEG in deionized water in the ratio of one gram of PEG to 1 mL of water. The PEG solution is then added to a solution of antibody which is initially at a concentration of less than or equal to 0.5 mg/ml and a volume of 0.5 mL. The PEG solution is continually added and mixed until the first instance of cloudiness persists. The percentage of PEG 3000 needed to cause this precipitation is calculated as 50× (volume of PEG 3000 solution added/initial volume of antibody solution before PEG addition).

The percentage of PEG 3000 needed for precipitation is compared to the percentage needed for precipitation of protein with known water solubility. For example, the water solubility of adalimumab exceeds 200 mg/mL. Consequently, if the percentage of PEG 3000 required to precipitate a protein of interest is similar to the percentage needed to precipitate adalimumab then the predicted solubility of that protein will be similar to the solubility adalimumab.

Real Solubility Method.

Real solubility is determined by using Amicon centrifugal filters to concentrate a protein in solution until the protein is observed to precipitate out of solution or until the minimum volume to which the protein can be concentrated within the filter unit is reached. For the latter, 15 mL Amicon centrifugal filters have a minimum volume of approximately 50 µl while 4 mL Amicon centrifugal filters have a minimum volume of approximately 15 µl.

First a protein is dialyzed into a specific formulation(s). For these studies, the antibody amount was 10 mg or much less. Then the protein solution is inserted into the Amicon centrifugal filter retentate chamber. The chamber is lined with a nitrocellulose membrane with pores that permit molecules of less than 10 to 30 kilodaltons to pass when subjected to centrifugal force. Antibodies which are typically above 140 kilodaltons will be retained while water, buffer molecules, small excipients, and salts will pass through. The centrifugal filter is then centrifuged according to manufacturer specifications until the protein is observed to precipitate out of solution or until the minimum volume to which the protein can be concentrated within the filter unit is reached.

After centrifugation, the protein solution is removed from the retentate chamber and the concentration is measured by ultraviolet absorbance. The solution is then kept at 25° C. and 5° C. for 1 to 2 days and is monitored for signs of precipitation.

Near UV-CD Technique.

Near UV-CD spectroscopy provides important information about the tertiary structure of proteins and is one of the most used techniques in this regard. CD refers to the differential absorption of the left and right circularly polarized components of plane polarized radiation. For proteins, the chromophores in the near UVCD region (250-320 nm) are the aromatic amino acids, i.e., tryptophan, tyrosine, and phenylalanine, and the disulfide bonds, and the CD effect occurs when the chromophores are present in an asymmetric (buried) environment. Signals in the region from 250-270 nm are attributable to phenylalanine residues, signals from 270-290 nm are attributable to tyrosine, and those from 280-300 nm are attributable to tryptophan. Disulfide bonds give rise to broad weak signals throughout the near-UV spectrum. The near-UV CD spectrum can be sensitive to small changes in tertiary structure such as those due to protein-protein interactions and/or changes in formulation conditions.

There are a number of other factors that can influence the CD spectra of aromatic amino acids. Among these are: (1) the rigidity of the protein, (2) the nature of hydrogen bonding, and (3) interactions between various aromatic amino acids. Additionally, proteins with large number of such amino acids can have smaller CD bands due to the cancellation of the positive and negative bands.

Briefly, a protein dialyzed into the desired formulation(s) at 1 mg/ml and is scanned from 250-320 nm or 240-320 nm with a Jasco 800 CD spectrometer. The corresponding formulation without protein is also scanned and the readings subtracted from that of the scan of the protein solution. A near UV-CD spectra is a plot of molar ellipticities versus wavelength from 250 or 240 to 320 nm.

For antibodies in general, a near UV-CD spectrum with a semi-sigmoidal profile indicates good tertiary structure folding while a flatter and less featured profile indicates a greater tendency to unfold. Compact folding is associated with good stability while poor folding exposes the hydrophobic interior which may lead to hydrophobic interactions among protein molecules resulting in the formation of undesired aggregates.

DSC Technique.

The thermal stability of the antibodies was assessed using a DSC instrument. The DSC instrument used was an automated VP-DSC equipment with Capillary Cell (Microcal, GE Healthcare Ltd./Microcal, Buckinghamshire, UK). Unfolding of molecules was studied applying a 1° C./minute scan rate over a 25° C.-95° C. temperature range for samples at 1 mg/mL. Additional measurement parameters applied were a fitting period of 16 seconds, a pre-scan wait time of 10 minutes, and measurements were performed in none-feedback mode. Per individual measurement, 420 µL of sample/blank were filled into the DSC measurement sample holder, with a plate fill scheme as provided below. The thermograms obtained were fitted to a non two state model to obtain the midpoint temperatures and enthalpies of the different transitions.

An additional requirement for successful biologics development candidate is that the protein remains its native state and conformation. A protein in aqueous solution is in equilibrium between the native (folded) conformation and its denatured (unfolded) conformation. The stability of the native state is based on the magnitude of the Gibbs free energy (DG) of the system and the thermodynamic relationship between enthalpy (DH) and entropy (DS) changes. A positive DG indicates the native state is more stable than the denatured state—the more positive the DG, the greater the stability. For a protein to unfold, stabilizing forces need to be broken. Conformational entropy overcomes stabilizing forces allowing the protein to unfold at temperatures where entropy becomes dominant. DSC measures DH of protein unfolding due to heat denaturation. As a general rule it can be stated that the higher the transition midpoint (the Tm), the more stable the protein at lower temperatures. During the same experiment DSC also measures the change in heat capacity (DCp) for protein denaturation. Heat capacity changes associated with protein unfolding are primarily due to changes in hydration of side chains that were buries in the native state, but become solvent exposed in the denatured state. DSC has been shown to be a valuable predictor of liquid formulation stability for proteins and other biological macromolecules (Remmele and Gombotz, *BioPharm.*, 13: 36-46 (2000), and Remmele et al., *Pharm. Res.*, 15: 200-208 (1998)).

SEC Technique.

Size exclusion chromatography was used to separate proteins based on size. Proteins are carried in an aqueous mobile phase and through a porous stationary phase resin packed in a column. The retention time in the column is a function of the hydrodynamic size of the protein and the size of the pores in the packed resin bed. Smaller molecules can penetrate into smaller pores in the resin and are retained longer than larger molecules. Upon elution from the column the proteins are detected by UV absorbance. The SEC method used a TSK gel guard (TOSOH Biosciences, Montgomeryville, Pa., US, cat. no. 08543) and a TSK gel G3000SWxL (TOSOH Biosciences, Montgomeryville, Pa., US, cat. no. 08541). The mobile phase was 100 mM $Na_2HPO_4$, 200 mM $Na_2SO_4$, pH 6.8. The flow rate was 0.25 mL/minute. Injection volume was 20 µL of 1 mg/mL sample. The column temperature was room temperature. The autosampler temperature was 2-8° C. The total run time was 55 minutes. The detection was based on UV absorbance at 214 nm wavelength, with band width set at 8 nm, using reference wavelength at 360 nm with band width 100 nm.

Freeze-Thaw Method.

Antibody solutions at 1 mg/ml in the desired formulation(s) are frozen at −80° C. for at least 4 hours and are then thawed at 30° C. in a water bath. The solution is then refrozen at −80° C. This is repeated for 5 cycles. After certain freeze-thaw cycles, e.g., second and fourth, a portion of the solution may be withdrawn for analysis by SEC before refreezing. Freeze-thaw stability testing is done at low protein concentration in order obtain a "worse-case scenario" due to greater exposure of protein molecules to the denaturing ice-water interfaces. At higher concentrations, proportionally less protein encounters the ice-water interface, instead interacting with other protein molecules.

Accelerated Stability Method.

Antibody solutions at 1 mg/ml in the desired formulation(s) are passed through 0.22 µm PVDF filters under sterile conditions and incubated at 40° C. and/or 50° C. for at least 21 days. At 7 days and 21 days, aliquots are withdrawn under sterile conditions and subjected to analysis by SEC. Solutions are then returned to incubation.

Example 2

Generation and Isolation of Anti-DLL4 Human Monoclonal Antibodies E9 and A10 by PROfusion mRNA Display Technology Using PROfusion mRNA display technology (see, Chung-Ming Hsieh et al., US Patent Application Publication No. 2010/0099103), pooled human spleen and lymph node antibody libraries were selected seven rounds against DLL4 antigens: 100 nM biotin-labeled human DLL4 extracellular domain (round 1 and 2), a mixture of 50 nM biotin-labeled human DLL4 extracellular domain, and 50 nM biotin-labeled mouse DLL4 extracellular domain (round 3), 100 nM biotin-labeled human DLL4 extracellular domain (round 4 and 5), 293G cells stably expressing human DLL4 and 100 nM biotin-labeled human DLL4 extracellular domain (round 6), BAF3 cells stably expressing human and mouse DLL4 (round 7). Both A10 and E9 were identified from the round 7 selection of the antibody libraries (Table 4). When constructed in wild type human IgG1, they are renamed A10.1 and E9.1, respectively.

TABLE 4

Anti-DLL4 PROfusion Fully Human Antibody Clones E9 and A10 Sequence Information (Kabat numbered CDRs are indicated by underlining)

| Clone | Source | Isotype | V Region | Germ-line | Sequence |
|---|---|---|---|---|---|
| E9 | Human Lymph Node | huIgG1: VL(λ), VH(L234, 235A) | VH | VH4-39 | 12345678901234567890<br>EVQLQESGPGLVKPSETLSL<br>TCTVSGGSIS<u>SSSYYWG</u>WIR<br>QPPGKGLEWIG<u>DIYYTGSTY</u><br><u>YNPSLKS</u>RVTISVDTSKNQF<br>SLKLSSVTAADTAVYYCAR<u>E</u><br><u>DVILRGGSDY</u>WGQGTLVTVS<br>S (SEQ ID NO: 1) |

TABLE 4-continued

Anti-DLL4 PROfusion Fully Human Antibody Clones
E9 and A10 Sequence Information (Kabat numbered
CDRs are indicated by underlining)

| Clone | Source | Isotype | V Region | Germ-line | Sequence |
|---|---|---|---|---|---|
| | | | VL | V2-1 | SYELTQPPSVSVSPGQTASI TCSGQRLGDKYASWYQQKPG QSPVLVIYEDSKRPSGIPER FSGSNSGDTATLTISGTQPM DEADYYCQAWDRDTGVFGYG TRVTVL (SEQ ID NO: 111) |
| A10 | Human Spleen | huIgG1: VL(λ), VH(L234, 235A) | VH | VH3-30 | EVQLLESGGGLVKSGGSLRL SCAASGFTFRSHWMSWVRQA PGKGLEWVAIISYDGSNKYS ADSVKGRFTISRDNSKNTLY LQLNSLRAEDTAVYYCAKAG GGNVGFDIWGQGTMVTVSS (SEQ ID NO: 112) |
| | | | VL | V2-1 | LPVLTQPPSVSVSPGQTASI TCSADKLGTKYVSWYQQKPG QSPVLVIYQDAKRPSGIPER FSGSNSGNTATLTISGTQTM DEADYLCQSWDRSDVVFGGG TKVTVL (SEQ ID NO: 113) |

Example 3

In Vitro Characterization of PROfusion Antibodies E9 and A10

The DLL4 antigen binding affinities for E9 and A10 were determined by the BIACORE technology as described in Example 1.1. As shown in Table 5, below, E9 and A10 have similar equilibrium dissociation constant values against human DLL4 ($K_D$ of 3.36 and 6.68 nM, respectively) and cynomolgus monkey DLL4 ($K_D$ of 4.2 and 7.8 nM, respectively). E9 also cross-reacts with mouse and rat DLL4 ($K_D$ of 16 and 15 nM, respectively).

Antibody-antigen binding activity was also evaluated using ELISA and FACS based assays (described in Example 1.2, 1.3 and $EC_{50}$ values reported in Table 3). In addition to binding to recombinant DLL4 extracellular domain (ECD), E9 and A10 can both bind DLL4 expressed at cell surface (Table 6).

The ability of the antibodies to block DLL4 interaction with its receptor Notch1 was assessed with ELISA and FACS based competition assays as described in Example 1.4 and 1.5. As shown in Table 6, E9 and A10 efficiently blocked the interaction of Notch1 with DLL4 (ECD and cell-bound form). In addition, cell-based functional assays were developed to further determine the ability of the antibodies to neutralize DLL4-mediated cellular activity in vitro (as described in Examples 1.6 and 1.7). Both E9 and A10 inhibited DLL4-induced Notch activation and sVEGFR1 expression in EA.hy926 cells (Table 6).

TABLE 5

Biacore Kinetics on Anti-DLL4 PROfusion Antibodies.

| | Kinetics on Biacore | | | | | | | | | | | |
|---|---|---|---|---|---|---|---|---|---|---|---|---|
| | huDLL4 ECD | | | cynoDLL4 ECD | | | muDLL4 ECD | | | ratDLL4 ECD | | |
| MAb | Ka | Kd | $K_D$ | Ka | Kd | $K_D$ | Ka | Kd | $K_D$ | Ka | Kd | $K_D$ |
| E9 | 2.0E+04 | 6.6E−05 | 3.36 | 1.8E+04 | 7.4E−05 | 4.2 | 1.8E+04 | 2.6E−04 | 16 | 1.9E+04 | 2.9E+04 | 15 |
| A10 | 2.2E+04 | 1.5E−04 | 6.68 | 1.9E+04 | 1.5E−04 | 7.8 | — | — | NB | — | — | NB |

MAb = monoclonal antibody;
E = multiply by 10 to indicated exponent;
Ka ($M^{-1}s^{-1}$);
Kd ($s^{-1}$);
$K_D$ (nM);
NB = no binding (900 nM DLL4)

TABLE 6

PROfusion DLL4 antibody in vitro potency.

| | Direct Binding Assays | | | | | Functional Blockade Assays | | | | | | | |
|---|---|---|---|---|---|---|---|---|---|---|---|---|---|
| | | | | | | Competition ELISA | | | Competition FACS | | sVEGFR1 Inhibition | | Inhibition of Notch |
| | Capture ELISA (EC$_{50}$, nM) DLL4 ECD | | | FACS (EC$_{50}$, nM) DLL4 Cells | | (IC$_{50}$, nM) DLL4 ECD/ huNotch-1 | | | (IC$_{50}$, nM) huNotch-1/ DLL4 cells | | (IC$_{50}$, nM) DLL4 ECD/ EaHy cells | | activation via huDLL4 cells, coculture |
| MAb | hu | mu | cyno | hu | mu | hu | mu | cyno | hu | mu | hu | mu | (IC$_{50}$, nM) |
| E9 | 0.17 | 0.18 | 0.40 | 7.23 | 0.32 | 1.7 | 2.1 | 2.1 | 23.4 | 3.2 | 1.0 | 0.4 | 6.2 |
| A10 | 0.17 | — | 0.44 | 0.93 | — | 2.6 | — | 5.1 | 4.4 | — | 1.5 | — | 7.3 |

MAb = monoclonal antibody;
hu = human;
mu = murine;
cyno = cynomolgus monkey

Example 4

Affinity Maturation of PROfusion Antibodies E9 and A10

Anti-DLL4 E9 Affinity Maturation.

Sequence alignment showed that the DLL4 antibody E9 shares the highest identity to human germlines VH4-39/JH4 and V2-1/JL6. To improve the affinity of E9 to DLL4, hypermutated CDR residues were identified from other human antibody sequences in the IgBLAST database that also shared high identity to germlines VH4-39 and V2-1. The corresponding E9 CDR residues were then subjected to limited mutagenesis by PCR with primers having low degeneracy at these positions to create three antibody libraries in the scFv format suitable for use an affinity maturation procedure. The first library contained mutations at residues 30, 31, 32, 33, 50, 54, 56, and 65 in the VH CDR1 and 2 (Kabat numbering); the second library at residues 95 to 100, 100a, 100b, 100c, and 102 in VH CDR3; and the third library at residues 27, 30, 31, 33, 52, 53, 93 to 96 in the three VL CDRs. To further increase the identity of E9 to the human germline framework sequences, an Arg at VL position 103 was mutated to a Lys and a binary degeneracy at VL positions 80 (A/P) and 100 (S/Y) was also introduced into the third library (Table 7).

TABLE 7

Mutations in E9 VH and VL Amino Acid Sequences for Affinity Maturation.

Mutated E9 VH Sequence (SEQ ID NO: 114):

```
EVQLQESGPGLVKPSETLSLTCTVSGGSISSSSYYWGWIRQPPGKGLEWIGDIYYTGSTYY
                            NNGN        S              N N N
                            G NT        L              A T
                            R   G                      I G
                                R                      S
                                                       R

NPSLKSRVTISVDTSKNQFSLKLSSVTAADTAVYYCAREDVILRGGSDYWGQGTLVTVSS
      N                           E      YAMAYGGAA D
      D                                  FSLPFS   SL S
      G                                  QGPRMQ   V  N
                                         WV  S A  R  H
                                         LE  K       E
                                         AN  Q       R
                                             V       L
                                             G       P
                                             M       C
                                             E       I
                                                     M
```

Mutated E9 VL Sequence (SEQ ID NO: 115):

```
SYELTQPPSVSVSPGQTASITCSGQRLGDKYASWYQQKPGQSPVLVIYEDSKRPSGIPER
                       ES    E V                    Q LT
                       DG                             TE
                       M                              AN
                       K                              EQ
                       L                              FS
                       T                              M
```

TABLE 7-continued

Mutations in E9 VH and VL Amino Acid Sequences for Affinity Maturation.

```
FSGSNSGDTATLTISGTQPMDEADYYCQAWDRDTGVFGYGTRVTVL
         A              SEVA    S       K
                        M AC
                        E  S
                        N  M
                        K
```

These E9 libraries were transformed into cells and displayed on cell surfaces to be selected against a low concentration of biotinylated DLL4 extracellular domain by magnetic then fluorescence activated cell sorting (FACS). Selection for improved on-rate, off-rate, or both were carried out and antibody protein sequences of affinity-modulated E9 clones (Table 8) were recovered for converting back to IgG format for further characterization.

Table 8. Protein Sequences of Antibody Clones Identified from Affinity Maturation Libraries for Anti-DLL4 Antibody E9.

TABLE 8

Affinity Matured Clones: Heavy Chain (VH) Regions

E9.4   EVQLQESGPGLVKPSETLSLTCTVSGGSISSSSYYWGWIRQPPGKGLEWIGDIYY
       TGSTYYNPSLKSRVTISVDTSKNQFSLKLSSVTAADTAVYYCARYDVSLGGSSDH
       WGQGTLVTVSS (SEQ ID NO: 116)

CDR1                CDR2                    CDR3
       SSSYYWG             DIYYTGSTYYNPSLKS        YDVSLGGSSDH
       (SEQ ID NO: 117)    (SEQ ID NO: 118)        (SEQ ID NO: 119)

E9.11  EVQLQESGPGLVKPSETLSLTCTVSGGSISSSSYYWGWIRQPPGKGLEWIGDIYY
       TGSTYYNPSLKSRVTISVDTSKNQFSLKLSSVTAADTAVYYCAREAVPLGGGSDY
       WGQGTLVTVSS (SEQ ID NO: 120)

CDR1                CDR2                    CDR3
       SSSYYWG             DIYYTGSTYYNPSLKS        EAVPLGGGSDY
       (SEQ ID NO: 121)    (SEQ ID NO: 122)        (SEQ ID NO: 123)

E9.14  EVQLQESGPGLVKPSETLSLTCTVSGGSISNSRYHWGWIRQSPGKGLEWIGDIYY
       TGSTYYNPSLKSRVTISVDTSKNQFSLKLSSVTAEDTAVYYCAREDVILRGGSDY
       WGQGTLVTVSS (SEQ ID NO: 124)

CDR1                CDR2                    CDR3
       NSRYHWG             DIYYTGSTYYNPSLKS        EDVILRGGSDY
       (SEQ ID NO: 125)    (SEQ ID NO: 126)        (SEQ ID NO: 127)

E9.17  EVQLQESGPGLVKPSETLSLTCTVSGGSISSSSYYWGWIRQPPGKGLEWIGDIYY
       TGSTYYNPSLKSRVTISVDTSKNQFSLKLSSVTAADTAVYYCAREEAILGGGSDY
       WGQGTLVTVSS (SEQ ID NO: 128)

CDR1                CDR2                    CDR3
       SSSYYWG             DIYYTGSTYYNPSLKS        EEAILGGGSDY
       (SEQ ID NO: 129)    (SEQ ID NO: 130)        (SEQ ID NO: 131)

E9.18  EVQLQESGPGLVKPSETLSLTCTVSGGSISSSGYYWGWIRQPPGKGLEWIGDINY
       AGSTYYNPSLKSRVTISVDTSKNQFSLKLSSVTAADTAVYYCAREDVILRGGSDY
       WGQGTLVTVSS (SEQ ID NO: 132)

CDR1                CDR2                    CDR3
       SSGYYWG             DINYAGSTYYNPSLKS        EDVILRGGSDY
       (SEQ ID NO: 133)    (SEQ ID NO: 134)        (SEQ ID NO: 135)

E9.19  EVQLQESGPGLVKPSETLSLTCTVSGGSISSSSYYWGWIRQPPGKGLEWIGDIYY
       TGSTYYNPSLKSRVTISVDTSKNQFSLKLSSVTAADTAVYYCARFDVSLGGGSDT
       WGQGTLVTVSS (SEQ ID NO: 136)

CDR1                CDR2                    CDR3
       SSSYYWG             DIYYTGSTYYNPSLKS        FDVSLGGGSDT
       (SEQ ID NO: 137)    (SEQ ID NO: 138)        (SEQ ID NO: 139)

TABLE 8-continued

E9.22  EVQLQESGPGLVKPSETLSLTCTVSGGSISNSRYHWGWIRQPPGKGLEWIGDIYY
       TGSTYYNPSLKGRVTISVDTSKNQFSLKLSSVTAADTAVYYCAREDVILRGGSDY
       WGQGTLVTVSS (SEQ ID NO: 140)

CDR1              CDR2                CDR3
       NSRYHWG           DIYYTGSTYYNPSLKG    EDVILRGGSDY
       (SEQ ID NO: 141)  (SEQ ID NO: 142)    (SEQ ID NO: 143)

E9.48  EVQLQESGPGLVKPSETLSLTCTVSGGSISSSGYYWGWIRQPPGKGLEWIGDINY
       RGSTYYNPSLKSRVTISVDTSKNQFSLKLSSVTAADTAVYYCAREDVILRGGSDY
       WGQGTLVTVSS (SEQ ID NO: 144)

CDR1              CDR2                CDR3
       SSGYYWG           DINYRGSTYYNPSLKS    EDVILRGGSDY
       (SEQ ID NO: 145)  (SEQ ID NO: 146)    (SEQ ID NO: 147)

E9.65  EVQLQESGPGLVKPSETLSLTCTVSGGSIRNSRYHWGWIRQPPGKGLEWIGDIYY
       TGSTYYNPSLKGRVTISVDTSKNQFSLKLSSVTAADTAVYYCAREDVILRGGSDY
       WGQGTLVTVSS (SEQ ID NO: 148)

CDR1              CDR2                CDR3
       NSRYHWG           DIYYTGSTYYNPSLKG    EDVILRGGSDY
       (SEQ ID NO: 149)  (SEQ ID NO: 150)    (SEQ ID NO: 151)

E9.66  EVQLQESGPGLVKPSETLSLTCTVSGGSISSSSYYWGWIRQPPGKGLEWIGDIYY
       TGSTYYNPSLKSRVTISVDTSKNQFSLKLSSVTAADTAVYYCAREGVPLGGGADK
       WGQGTLVTVSS (SEQ ID NO: 152)

CDR1              CDR2                CDR3
       SSSYYWG           DIYYTGSTYYNPSLKS    EGVPLGGGADK
       (SEQ ID NO: 153)  (SEQ ID NO: 154)    (SEQ ID NO: 155)

E9.71  EVQLQESGPGLVKPSETLSLTCTVSGGSISSSSYYWGWIRQPPGKGLEWIGDIYY
       TGSTYYNPSLKSRVTISVDTSKNQFSLKLSSVTAADTAVYYCARQALAMGGGSDK
       WGQGTLVTVSS (SEQ ID NO: 156)

CDR1              CDR2                CDR3
       SSSYYWG           DIYYTGSTYYNPSLKS    QALAMGGGSDK
       (SEQ ID NO: 157)  (SEQ ID NO: 158)    (SEQ ID NO: 159)

E9.13  EVQLQESGPGLVKPSETLSLTCTVSGGSISSSSYYWGWIRQPPGKGLEWIGDIYY
       TGSTYYNPSLKSRVTISVDTSKNQFSLKLSSVTAADTAVYYCAREDVILRGGSDY
       WGQGTLVTVSS (SEQ ID NO: 160)

CDR1              CDR2                CDR3
       SSSYYWG           DIYYTGSTYYNPSLKS    EDVILRGGSDY
       (SEQ ID NO: 161)  (SEQ ID NO: 162)    (SEQ ID NO: 163)

E9.16  EVQLQESGPGLVKPSETLSLTCTVSGGSISSSSYYWGWIRQPPGKGLEWIGDIYY
       TGSTYYNPSLKSRVTISVDTSKNQFSLKLSSVTAADTAVYYCAREDVILRGGSDY
       WGQGTLVTVSS (SEQ ID NO: 164)

CDR1              CDR2                CDR3
       SSSYYWG           DIYYTGSTYYNPSLKS    EDVILRGGSDY
       (SEQ ID NO: 165)  (SEQ ID NO: 166)    (SEQ ID NO: 167)

E9.38  EVQLQESGPGLVKPSETLSLTCTVSGGSISSSSYYWGWIRQPPGKGLEWIGDIYY
       TGSTYYNPSLKSRVTISVDTSKNQFSLKLSSVTAADTAVYYCAREDVILRGGSDY
       WGQGTLVTVSS (SEQ ID NO: 168)

CDR1              CDR2                CDR3
       SSSYYWG           DIYYTGSTYYNPSLKS    EDVILRGGSDY
       (SEQ ID NO: 169)  (SEQ ID NO: 170)    (SEQ ID NO: 171)

E9.2B  EVQLQESGPGLVKPSETLSLTCTVSGGSISSSNYYWGWIRQPPGKGLEWIGDINY
       NGNTYYNPSLKSRVTISVDTSKNQFSLKLSSVTAADTAVYYCAREAVALGGGADD
       WGQGTLVTVSS (SEQ ID NO: 172)

CDR1              CDR2                CDR3
       SSNYYWG           DINYNGNTYYNPSLKS    EAVALGGGADD
       (SEQ ID NO: 173)  (SEQ ID NO: 174)    (SEQ ID NO: 175)

E9.1F  EVQLQESGPGLVKPSETLSLTCTVSGGSISSGYYWGWIRQPPGKGLEWIGDINY
       IGSTYYNPSLKSRVTISVDTSKNQFSLKLSSVTAADTAVYYCAREAVSFGGGADS
       WGQGTLVTVSS (SEQ ID NO: 176)

CDR1              CDR2                CDR3
       SGSYYWG           DINYIGSTYYNPSLKS    EAVSFGGGADS
       (SEQ ID NO: 177)  (SEQ ID NO: 178)    (SEQ ID NO: 179)

TABLE 8-continued

E9.10H EVQLQESGPGLVKPSETLSLTCTVSGGSISSSGYYWGWIRQPPGKGLEWIG**DIYY
TGNTYYNPSLKNRVTISVDTSKNQFSLKLSSVTAADTAVYYCAREEVILGGGADQ**
WGQGTLVTVSS (SEQ ID NO: 180)

CDR1               CDR2               CDR3
    SSGYYWG           DIYYTGNTYYNPSLKN   EEVILGGGADQ
    (SEQ ID NO: 181)  (SEQ ID NO: 182)  (SEQ ID NO: 183)

E9.5E  EVQLQESGPGLVKPSETLSLTCTVSGGSISSSSYYWGWIRQPPGKGLEWIG**DINY
IGSTYYNPSLKSRVTISVDTSKNQFSLKLSSVTAADTAVYYCARESVPLGGGADE**
WGQGTLVTVSS (SEQ ID NO: 184)

CDR1               CDR2               CDR3
    SSSYYWG           DINYIGSTYYNPSLKS   ESVPLGGGADE
    (SEQ ID NO: 185)  (SEQ ID NO: 186)  (SEQ ID NO: 187)

E9.10C EVQLQESGPGLVKPSETLSLTCTVSGGSISSGSYYWGWIRQPPGKGLEWIG**DIYY
TGSTYYNPSLKSRVTISVDTSKNQFSLKLSSVTAADTAVYYCARQAVMYGGGSDN**
WGQGTLVTVSS (SEQ ID NO: 188)

CDR1               CDR2               CDR3
    SGSYYWG           DIYYTGSTYYNPSLKS   QAVMYGGGSDN
    (SEQ ID NO: 189)  (SEQ ID NO: 190)  (SEQ ID NO: 191)

E9.7E  EVQLQESGPGLVKPSETLSLTCTVSGGSISSSSYYWGWIRQPPGKGLEWIG**DIYY
AGSTYYNPSLKDRVTISVDTSKNQFSLKLSSVTAADTAVYYCAREDMILGGGADN**
WGQGTLVTVSS (SEQ ID NO: 192)

CDR1               CDR2               CDR3
    SSSYYWG           DIYYAGSTYYNPSLKD   EDMILGGGADN
    (SEQ ID NO: 193)  (SEQ ID NO: 194)  (SEQ ID NO: 195)

E9.12B EVQLQESGPGLVKPSETLSLTCTVSGGSISSSNYYWGWIRQPPGKGLEWIG**DIYY
TGSTYYNPSLKSRVTISVDTSKNQFSLKLSSVTAADTAVYYCAREAVSFGGGADS**
WGQGTLVTVSS (SEQ ID NO: 196)

CDR1               CDR2               CDR3
    SSNYYWG           DIYYTGSTYYNPSLKS   EAVSFGGGADS
    (SEQ ID NO: 197)  (SEQ ID NO: 198)  (SEQ ID NO: 199)

E9.10E EVQLQESGPGLVKPSETLSLTCTVSGGSINSGNYYWGWIRQPPGKGLEWIG**DISY
TGSTYYNPSLKSRVTISVDTSKNQFSLKLSSVTAADTAVYYCAREDVMYGGGGDS**
WGQGTLVTVSS (SEQ ID NO: 200)

CDR1               CDR2               CDR3
    SGNYYWG           DISYTGSTYYNPSLKS   EDVMYGGGGDS
    (SEQ ID NO: 201)  (SEQ ID NO: 202)  (SEQ ID NO: 203)

E9.6A  EVQLQESGPGLVKPSETLSLTCTVSGGSISSSSYYWGWIRQPPGKGLEWIG**DINY
AGSTYYNPSLKNRVTISVDTSKNQFSLKLSSVTAADTAVYYCAREAVLGGGADS**
WGQGTLVTVSS (SEQ ID NO: 204)

CDR1               CDR2               CDR3
    SSSYYWG           DINYAGSTYYNPSLKN   EAVLGGGADS
    (SEQ ID NO: 205)  (SEQ ID NO: 206)  (SEQ ID NO: 207)

E9.7A  EVQLQESGPGLVKPSETLSLTCTVSGGSISSSSYYWGWIRQPPGKGLEWIG**DINY
AGSTYYNPSLKSRVTISVDTSKNQFSLKLSSVTAADTAVYYCAREDVKFGGGADL**
WGQGTLVTVSS (SEQ ID NO: 208)

CDR1               CDR2               CDR3
    SSSYYWG           DINYAGSTYYNPSLKS   EDVKFGGGADL
    (SEQ ID NO: 209)  (SEQ ID NO: 210)  (SEQ ID NO: 211)

E9.8H  EVQLQESGPGLVKPSETLSLTCTVSGGSISSGSYYWGWIRQPPGKGLEWIG**DIYY
TGSTYYNPSLKNRVTISVDTSKNQFSLKLSSVTAADTAVYYCARESVPLGGGADN**
WGQGTLVTVSS (SEQ ID NO: 212)

CDR1               CDR2               CDR3
    SGSYYWG           DIYYTGSTYYNPSLKN   ESVPLGGGADN
    (SEQ ID NO: 213)  (SEQ ID NO: 214)  (SEQ ID NO: 215)

TABLE 8-continued

Affinity Matured Clones: Light Chain (VL) Regions

E9.13 SYELTQPPSVSVSPGQTASITCSGDTLGDKYVSWYQQKPGQSPVLVIYEDSERPS
GIPERFSGSNSGDTATLTISGTQPMDEADYYCQAWDSETGVFGSGTKVTVL
(SEQ ID NO: 216)

CDR1              CDR2              CDR3
    SGDTLGDKYVS     EDSERPS       QAWDSETGV
    (SEQ ID NO: 217) (SEQ ID NO: 218) (SEQ ID NO: 219)

E9.16 SYELTQPPSVSVSPGQTASITCSGERLGDKYVSWYQQKPGQSPVLVIYEDFKRPS
GIPERFSGSNSGDTATLTISGTQPMDEADYYCQAWDRDTGVFGYGTKVTVL
(SEQ ID NO: 220)

CDR1              CDR2              CDR3
    SGERLGDKYVS     EDFKRPS       QAWDRDTGV
    (SEQ ID NO: 221) (SEQ ID NO: 222) (SEQ ID NO: 223)

E9.38 SYELTQPPSVSVSPGQTASITCSGQRLGDKYVSWYQQKPGQSPVLVIYEDSKRPS
GIPERFSGSNSGDTATLTISGTQPMDEADYYCQAWDRDVGVFGSGTKVTVL
(SEQ ID NO: 224)

CDR1              CDR2              CDR3
    SGQRLGDKYVS     EDSKRPS       QAWDRDVGV
    (SEQ ID NO: 225) (SEQ ID NO: 226) (SEQ ID NO: 227)

E9.4 SYELTQPPSVSVSPGQTASITCSGQRLGDKYASWYQQKPGQSPVLVIYEDSKRPS
GIPERFSGSNSGDTATLTISGTQPMDEADYYCQAWDRDTGVFGYGTKVTVL
(SEQ ID NO: 228)

CDR1              CDR2              CDR3
    SGQRLGDKYAS     EDSKRPS       QAWDRDTGV
    (SEQ ID NO: 229) (SEQ ID NO: 230) (SEQ ID NO: 231)

E9.11 SYELTQPPSVSVSPGQTASITCSGQRLGDKYASWYQQKPGQSPVLVIYEDSKRPS
GIPERFSGSNSGDTATLTISGTQPMDEADYYCQAWDRDTGVFGYGTKVTVL
(SEQ ID NO: 232)

CDR1              CDR2              CDR3
    SGQRLGDKYAS     EDSKRPS       QAWDRDTGV
    (SEQ ID NO: 233) (SEQ ID NO: 234) (SEQ ID NO: 235)

E9.14 SYELTQPPSVSVSPGQTASITCSGQRLGDKYASWYQQKPGQSPVLVIYEDSKRPS
GIPERFSGSNSGDTATLTISGTQPMDEADYYCQAWDRDTGVFGYGTKVTVL
(SEQ ID NO: 236)

CDR1              CDR2              CDR3
    SGQRLGDKYAS     EDSKRPS       QAWDRDTGV
    (SEQ ID NO: 237) (SEQ ID NO: 238) (SEQ ID NO: 239)

E9.17 SYELTQPPSVSVSPGQTASITCSGQRLGDKYASWYQQKPGQSPVLVIYEDSKRPS
GIPERFSGSNSGDTATLTISGTQPMDEADYYCQAWDRDTGVFGYGTKVTVL
(SEQ ID NO: 240)

CDR1              CDR2              CDR3
    SGQRLGDKYAS     EDSKRPS       QAWDRDTGV
    (SEQ ID NO: 241) (SEQ ID NO: 242) (SEQ ID NO: 243)

E9.18 SYELTQPPSVSVSPGQTASITCSGQRLGDKYASWYQQKPGQSPVLVIYEDSKRPS
GIPERFSGSNSGDTATLTISGTQPMDEADYYCQAWDRDTGVFGYGTKVTVL
(SEQ ID NO: 244)

CDR1              CDR2              CDR3
    SGQRLGDKYAS     EDSKRPS       QAWDRDTGV
    (SEQ ID NO: 245) (SEQ ID NO: 246) (SEQ ID NO: 247)

E9.19 SYELTQPPSVSVSPGQTASITCSGQRLGDKYASWYQQKPGQSPVLVIYEDSKRPS
GIPERFSGSNSGDTATLTISGTQPMDEADYYCQAWDRDTGVFGYGTKVTVL
(SEQ ID NO: 248)

CDR1              CDR2              CDR3
    SGQRLGDKYAS     EDSKRPS       QAWDRDTGV
    (SEQ ID NO: 249) (SEQ ID NO: 250) (SEQ ID NO: 251)

TABLE 8-continued

E9.22  SYELTQPPSVSVSPGQTASITCSGQRLGDKYASWYQQKPGQSPVLVIYEDSKRPS
       GIPERFSGSNSGDTATLTISGTQPMDEADYYCQAWDRDTGVFGYGTKVTVL
       (SEQ ID NO: 252)

CDR1            CDR2            CDR3
       SGQRLGDKYAS     EDSKRPS         QAWDRDTGV
       (SEQ ID NO: 253) (SEQ ID NO: 254) (SEQ ID NO: 255)

E9.48  SYELTQPPSVSVSPGQTASITCSGQRLGDKYASWYQQKPGQSPVLVIYEDSKRPS
       GIPERFSGSNSGDTATLTISGTQPMDEADYYCQAWDRDTGVFGYGTKVTVL
       (SEQ ID NO: 256)

CDR1            CDR2            CDR3
       SGQRLGDKYAS     EDSKRPS         QAWDRDTGV
       (SEQ ID NO: 257) (SEQ ID NO: 258) (SEQ ID NO: 259)

E9.65  SYELTQPPSVSVSPGQTASITCSGQRLGDKYASWYQQKPGQSPVLVIYEDS
       KRPSGIPERFSGSNSGDTATLTISGTQPMDEADYYCQAWDRDTGVFGYGT
       KVTVL (SEQ ID NO: 260)

CDR1            CDR2            CDR3
       SGQRLGDKYAS     EDSKRPS         QAWDRDTGV
       (SEQ ID NO: 261) (SEQ ID NO: 262) (SEQ ID NO: 263)

E9.66  SYELTQPPSVSVSPGQTASITCSGQRLGDKYASWYQQKPGQSPVLVIYEDSKRPS
       GIPERFSGSNSGDTATLTISGTQPMDEADYYCQAWDRDTGVFGYGTKVTVL
       (SEQ ID NO: 264)

CDR1            CDR2            CDR3
       SGQRLGDKYAS     EDSKRPS         QAWDRDTGV
       (SEQ ID NO: 265) (SEQ ID NO: 266) (SEQ ID NO: 267)

E9.71  SYELTQPPSVSVSPGQTASITCSGQRLGDKYASWYQQKPGQSPVLVIYEDSKRPS
       GIPERFSGSNSGDTATLTISGTQPMDEADYYCQAWDRDTGVFGYGTKVTVL
       (SEQ ID NO: 268)

CDR1            CDR2            CDR3
       SGQRLGDKYAS     EDSKRPS         QAWDRDTGV
       (SEQ ID NO: 269) (SEQ ID NO: 270) (SEQ ID NO: 271)

E9.2B  SYELTQPPSVSVSPGQTASITCSGEGLGDKYVSWYQQKPGQSPVLVIYEDSTRPS
       GIPERFSGSNSGDTATLTISGTQPMDEADYYCQAWDSETGVFGSGTKVTVL
       (SEQ ID NO: 272)

CDR1            CDR2            CDR3
       SGEGLGDKYVS     EDSTRPS         QAWDSETGV
       (SEQ ID NO: 273) (SEQ ID NO: 274) (SEQ ID NO: 275)

E9.1F  SYELTQPPSVSVSPGQTASITCSGDRLGDKYVSWYQQKPGQSPVLVIYEDSQRPS
       GIPERFSGSNSGDTATLTISGTQAMDEADYYCQAWDMEAGVFGSGTKVTVL
       (SEQ ID NO: 276)

CDR1            CDR2            CDR3
       SGDRLGDKYVS     EDSQRPS         QAWDMEAGV
       (SEQ ID NO: 277) (SEQ ID NO: 278) (SEQ ID NO: 279)

E9.10C SYELTQPPSVSVSPGQTASITCSGDSLGDKYVSWYQQKPGQSPVLVIYEDSERPS
       GIPERFSGSNSGDTATLTISGTQAMDEADYYCQAWDSETGVFGSGTKVT
       (SEQ ID NO: 280)

CDR1            CDR2            CDR3
       SGDSLGDKYVS     EDSERPS         QAWDSETGV
       (SEQ ID NO: 281) (SEQ ID NO: 282) (SEQ ID NO: 283)

E9.10E SYELTQPPSVSVSPGQTASITCSGEGLGDKYVSWYQQKPGQSPVLVIYEDSERPS
       GIPERFSGSNSGDTATLTISGTQAMDEADYYCQAWDSEAGVFGSGTKVT
       (SEQ ID NO: 284)

CDR1            CDR2            CDR3
       SGEGLGDKYVS     EDSERPS         QAWDSEAGV
       (SEQ ID NO: 285) (SEQ ID NO: 286) (SEQ ID NO: 287)

E9.7E  SYELTQPPSVSVSPGQTASITCSGDRLGDKYVSWYQQKPGQSPVLVIY**ED
       SERPSGIPERFSGSNSGDTAILTISGTQAMDEADYYCQAWDSEAGV**FGSG
       TKVT (SEQ ID NO: 288)

CDR1            CDR2            CDR3
       SGDRLGDKYVS     EDSERPS         QAWDSEAGV
       (SEQ ID NO: 289) (SEQ ID NO: 290) (SEQ ID NO: 291)

TABLE 8-continued

```
E9.5E   SYELTQPPSVSVSPGQTASITCSGDMLGDKYVSWYQQKPGQSPVLVIYEDSQRPS
        GIPERFSGSNSGDTATLTISGTQPMDEADYYCQAWDSETGVFGSGTKVT
        (SEQ ID NO: 292)

CDR1             CDR2              CDR3
        SGDMLGDKYVS       EDSQRPS           QAWDSETGV
        (SEQ ID NO: 293)  (SEQ ID NO: 294)  (SEQ ID NO: 295)

E9.12   SYELTQPPSVSVSPGQTASITCSGDGLGDKYVSWYQQKPGQSPVLVIYEDSTRPS
B       GIPERFSGSNSGDTATLTISGTQPMDEADYYCQAWDSESGVFGSGTKVT
        (SEQ ID NO: 296)

CDR1             CDR2              CDR3
        SGDGLGDKYVS       EDSTRPS           QAWDSESGV
        (SEQ ID NO: 297)  (SEQ ID NO: 298)  (SEQ ID NO: 299)

E9.10   SYELTQPPSVSVSPGQTASITCSGESLGDKYVSWYQQKPGQSPVLVIYEDSKRPS
H       GIPERFSGSNSGDTATLTISGTQAMDEADYYCQAWDGETGVFGSGTKVT
        (SEQ ID NO: 300)

CDR1             CDR2              CDR3
        SGESLGDKYVS       EDSKRPS           QAWDGETGV
        (SEQ ID NO: 301)  (SEQ ID NO: 302)  (SEQ ID NO: 303)

E9.6A   SYELTQPPSVSVSPGQTASITCSGDMLGDKYVSWYQQKPGQSPVLVIYEDTNRPS
        GIPERFSGSNSGDTATLTISGTQAMDEADYYCQAWDSETGVFGSGTKVT
        (SEQ ID NO: 304)

CDR1             CDR2              CDR3
        SGDMLGDKYVS       EDTNRPS           QAWDSETGV
        (SEQ ID NO: 305)  (SEQ ID NO: 306)  (SEQ ID NO: 307)

E9.7A   SYELTQPPSVSVSPGQTASITCSGESLGDKYVSWYQQKPGQSPVLVIYQDAMRPS
        GIPERFSGSNSGDTATLTISGTQAMDEADYYCQAWDMETGVFGSGTKVT
        (SEQ ID NO: 308)

CDR1             CDR2              CDR3
        SGESLGDKYVS       QDAMRPS           QAWDMETGV
        (SEQ ID NO: 309)  (SEQ ID NO: 310)  (SEQ ID NO: 311)

E9.8H   SYELTQPPSVSVSPGQTASITCSGESLGDKYVSWYQQKPGQSPVLVIYEDSMRPS
        GIPERFSGSNSGDTATLTISGTQPMDEADYYCQAWDSEVGVFGSGTKVT
        (SEQ ID NO: 312)

CDR1             CDR2              CDR3
        SGESLGDKYVS       EDSMRPS           QAWDSEVGV
        (SEQ ID NO: 313)  (SEQ ID NO: 314)  (SEQ ID NO: 315)
```

Anti-DLL4 A10 Affinity Maturation.

In a manner similar to E9 affinity maturation described above, sequence alignment showed that the DLL4 antibody A10 shared the highest identity to human germlines VH3-30 and V2-1. Human VH and Vλ sequences derived from VH3-30 and V2-1, respectively, were downloaded from NCBI IgBlast database to generate sequence logos. These sequence logos were used to decide which positions would be doped to generate the affinity matured libraries.

The A10 libraries were transformed into cells and displayed on the cell surface to be selected against low concentration of biotinylated DLL4 extracellular domain by magnetic then fluorescence activated cell sorting. Selection for improved on-rate or off-rate or both were carried out and antibody protein sequences of affinity-modulated A10 clones were recovered for converting back to IgG format for further characterization. The heavy chain (VH) regions of the affinity matured clones are shown below in Table 9 and the light chain (VL) regions of the affinity matured clones are shown below in Table 10.

TABLE 9

Variable Heavy Chain Regions (VH) of Affinity Matured A10 Clones.

| Protein Region | Sequence<br>123456789012345678901234567890 |
|---|---|
| A10.3<br>VH | EVQLVESGGGLVKSGGSLRLSCAASGFTFR<br>SHWMSWVRQAPGKGLEWVAIISYDGSNKYS<br>ADSVKGRFTISRDNSKNTLYLQLNSLRAED<br>TAVYYCAKAGGGNVGFDIWGQGTMVTVSS<br>(SEQ ID NO: 316) |

TABLE 9-continued

Variable Heavy Chain Regions (VH) of Affinity Matured A10 Clones.

| Protein | Region | Sequence<br>12345678901234567890 |
|---|---|---|
| A10.3 VH | CDR-H1 Residues 31-35 of SEQ ID NO.: 316 | SHWMS |
| A10.3 VH | CDR-H2 Residues 50-66 of SEQ ID NO.: 316 | IISYDGSNKYSADSVKG |
| A10.3 VH | CDR-H3 Residues 99-108 of SEQ ID NO.: 316 | AGGGNVGFDI |
| A10.K30 VH | | EVQLVESGGGVVQPGGSLRLSCAASGFTFGNHWMSWVRQAPGKGLEWVADISSDGRYKYYADSVKGRFTISRDNSKNTLYLQLNSLRAEDTAVYYCAKAGGGNVGFDIWGQGTMVTVSS (SEQ ID NO: 317) |
| A10.K30 VH | CDR-H1 Residues 31-35 of SEQ ID NO.: 317 | NHWMS |
| A10.K30 VH | CDR-H2 Residues 50-66 of SEQ ID NO.: 317 | DISSDGRYKYYADSVKG |
| A10.K30 VH | CDR-H3 Residues 99-108 of SEQ ID NO.: 317 | AGGGNVGFDI |
| A10.K42 VH | | EVQLVESGGGLVQPGGSLRLSCAASGFTFQSHWMSWVRQAPGKGLEWVAMISYDGTIKYYADSVKGRFTISRDNSKNTLYLQLNSLRAEDTAVYYCAKAGGGNVGFDIWGQGTMVTVSS (SEQ ID NO: 318) |
| A10.K42 VH | CDR-H1 Residues 31-35 of SEQ ID NO.: 318 | SHWMS |
| A10.K42 VH | CDR-H2 Residues 50-66 of SEQ ID NO.: 318 | MISYDGTIKYYADSVKG |
| A10.K42 VH | CDR-H3 Residues 99-108 of SEQ ID NO.: 318 | AGGGNVGFDI |
| A10.9A VH | | EVQLVESGGGVVQPGRSLRLSCAASGFTFRSYWMSWVRQAPGKGLEWVATISYDGRNKDYADSVKGRFTISRDNSKNTLYLQLNSLRAEDTAVYYCAKAGGGNVGFDIWGQGTMVTVSS (SEQ ID NO: 319) |
| A10.9A VH | Residues 31-35 of SEQ ID NO.: 319 | SYWMS |
| A10.9A VH | Residues 50-66 of SEQ ID NO.: 319 | TISYDGRNKDYADSVKG |
| A10.9A VH | Residues 99-108 of SEQ ID NO.: 319 | AGGGNVGFDI |
| A10.8A VH | | EVQLVESGGGVVQPGGSLRLSCAASGFTFGNHWMSWVRQAPGKGLEWVADISSDGRYKYYADSVKGRFTISRDNSKNTLYLQLNSLRAEDTAVYYCAKAGGGNVGFDIWGQGTMVTVSS (SEQ ID NO: 320) |

TABLE 9-continued

Variable Heavy Chain Regions (VH) of Affinity Matured A10 Clones.

| Protein Region | | Sequence<br>12345678901234567890123456789 0 |
|---|---|---|
| A10.8A VH | Residues 31-35 of SEQ ID NO.: 320 | NHWMS |
| A10.8A VH | Residues 50-66 of SEQ ID NO.: 320 | DISSDGRYKYYADSVKG |
| A10.8A VH | Residues 99-108 of SEQ ID NO.: 320 | AGGGNVGFDI |
| A10.1A VH | | EVQLVESGGGVVQPGGSLRLSCAASGFTFH SHWMSWVRQAPGKGLEWVAMISDDGRNKDY ADSVKGRFTISRDNSKNTLYLQLNSLRAED TAVYYCARAAGGNVGLDIWGQGTMVTVSS (SEQ ID NO: 321) |
| A10.1A VH | Residues 31-35 of SEQ ID NO.: 321 | SHWMS |
| A10.1A VH | Residues 50-66 of SEQ ID NO.: 321 | MISDDGRNKDYADSVKG |
| A10.1A VH | Residues 99-108 of SEQ ID NO.: 321 | AAGGNVGLDI |
| A10.5D VH | | EVQLVESGGGVVQSGGSLRLSCAASGFTFG SHWMSWVRQAPGKGLEWVADISVDGSNKYS ADSVKGRFTISRDNSKNTLYLQMNSLRAED TAVYYCARAAGGNVGLDSWGQGTMVTVSS (SEQ ID NO: 322) |
| A10.5D VH | Residues 31-35 of SEQ ID NO.: 322 | SHWMS |
| A10.5D VH | Residues 50-66 of SEQ ID NO.: 322 | DISVDGSNKYSADSVKG |
| A10.5D VH | Residues 99-108 of SEQ ID NO.: 322 | AAGGNVGLDS |
| A10.3A VH | | EVQLVESGGGVVQPGGSLRLSCAASGFTFG NHWMSWVRQAPGKGLEWVADISSDGRYKYY ADSVKGRFTISRDNSKNTLYLQLNSLRAED TAVYYCAKAGGGNVGFDIWGQGTMVTVSS (SEQ ID NO: 323) |
| A10.3A VH | Residues 31-35 of SEQ ID NO.: 323 | NHWMS |
| A10.3A VH | Residues 50-66 of SEQ ID NO.: 323 | DISSDGRYKYYADSVKG |
| A10.3A VH | Residues 99-108 of SEQ ID NO.: 323 | AGGGNVGFDI |
| A10.6B VH | | EVQLVESGGGVVQPGGSLRLSCAASGFTFG NHWMSWVRQAPGKGLEWVADISSDGRYKYY ADSVKGRFTISRDNSKNTLYLQLNSLRAED TAVYYCAKAGGGNVGFDIWGQGTMVTVSS (SEQ ID NO: 324) |

TABLE 9-continued

Variable Heavy Chain Regions (VH) of Affinity Matured A10 Clones.

| Protein Region | | Sequence<br>12345678901234567890123456 7890 |
|---|---|---|
| A10.6B VH | Residues 31-35 of SEQ ID NO.: 324 | NHWMS |
| A10.6B VH | Residues 50-66 of SEQ ID NO.: 324 | DISSDGRYKYYADSVKG |
| A10.6B VH | Residues 99-108 of SEQ ID NO.: 324 | AGGGNVGFDI |
| A10.3D VH | | EVQLVESGGGVVQPGRSLRLSCAASGFTFRSHWMSWVRQAPGKGLEWVADISQDGSYKYYADSVKGRFTISRDNSKNTLYLQMNSLRAEDTAVYYCARAAGGGNVGFDIWGQGTMVTVSS<br>(SEQ ID NO: 325) |
| A10.3D VH | Residues 31-35 of SEQ ID NO.: 325 | SHWMS |
| A10.3D VH | Residues 50-66 of SEQ ID NO.: 325 | DISQDGSYKYYADSVKG |
| A10.3D VH | Residues 99-108 of SEQ ID NO.: 325 | AAGGGNVGFDI |
| A10.4C VH | | EVQLVESGGGVVQPGGSLRLSCAASGFTFGSHWMSWVRQAPGKGLEWVADISNDGRYAYSADSVKGRFTISRDNSKNTLYLQLNSLRAEDTAVYYCAKAGGGNVGFDIWGQGTMVTVSS<br>(SEQ ID NO:326) |
| A10.4C VH | Residues 31-35 of SEQ ID NO.: 326 | SHWMS |
| A10.4C VH | Residues 50-66 of SEQ ID NO.: 326 | DISNDGRYAYSADSVKG |
| A10.4C VH | Residues 99-108 of SEQ ID NO.: 326 | AGGGNVGFDI |

TABLE 10

Variable Light Chain Regions (VL) of Affinity Matured A10 Clones.

| Protein region | | Sequence<br>12345678901234567890123456 7890 |
|---|---|---|
| A10.3 VL | | SYELTQPPSVSVSPGQTASITCSADKLGTKYVSWYQQKPGQSPVLVIYQDAKRPSGIPERFSGSNSGNTATLTISGTQTMDEADYLCQSWDRSDVVFGGGTKLTVL (SEQ ID NO: 327) |
| A10.3 VL | CDR-L1 Residues 23-33 of SEQ ID NO.: 327 | SADKLGTKYVS |
| A10.3 VL | CDR-L2 Residues 49-55 of SEQ ID NO.: 327 | QDAKRPS |

TABLE 10-continued

Variable Light Chain Regions (VL) of Affinity Matured A10 Clones.

| Protein region | | Sequence 12345678901234567890123456 7890 |
|---|---|---|
| A10.3 VL | CDR-L3 Residues 88-96 of SEQ ID NO.: 327 | QSWDRSDVV |
| A10.L45 VL | | SYELTQPPSVSVSPGQTASITCSADELGTQ YVSWYQQKPGQSPVLVIYQDATRPSGIPER FSGSNSGNTATLTISGTQAMDEADYYCQAW DRSGVVFGGGTKLTVL (SEQ ID NO: 328) |
| A10.L45 VL | CDR-L1 Residues 23-33 of SEQ ID NO.: 328 | SADELGTQYVS |
| A10.L45 VL | CDR-L2 Residues 49-55 of SEQ ID NO.: 328 | QDATRPS |
| A10.L45 VL | CDR-L3 Residues 88-96 of SEQ ID NO.: 328 | QAWDRSGVV |
| A10.L73 VL | | SYELTQPPSVSVSPGQTASITCSGDNLGSQ YVSWYQQKPGQSPVLVIYQDATRPSGIPER FSGSNSGNTATLTISGTQAMDEADYYCQAW DRSGVVFGGGTKLTVL (SEQ ID NO: 329) |
| A10.L73 VL | CDR-L1 Residues 23-33 of SEQ ID NO.: 329 | SGDNLGSQYVS |
| A10.L73 VL | CDR-L2 Residues 49-55 of SEQ ID NO.: 329 | QDAQRPS |
| A10.L73 VL | CDR-L3 Residues 88-96 of SEQ ID NO.: 329 | QAWDRSGVV |
| A10.3A VL | | SYELTQPPSVSVSPGQTASITCSADNLGEK YVSWYQQKPGQSPVLVIYQDATRPSGIPER FSGSNSGNTATLTISGTQAMDEADYYCQSW DSSGAVFGGGTKLTVL (SEQ ID NO: 330) |
| A10.3A VL | CDR-L1 Residues 23-33 of SEQ ID NO.: 330 | SADNLGEKYVS |

TABLE 10-continued

Variable Light Chain Regions (VL) of Affinity Matured A10 Clones.

| Protein | region | | Sequence<br>12345678901234567890123456 7890 |
|---|---|---|---|
| A10.3A VL | CDR-L2 | Residues 49-55 of SEQ ID NO.: 330 | QDATRPS |
| A10.3A VL | CDR-L3 | Residues 88-96 of SEQ ID NO.: 330 | QSWDSSGAV |
| A10.6B VL | | | SYELTQPPSVSVSPGQTASITCSADNLGNQ YVSWYQQKPGQSPVLVIYQDGMRPSGIPER FSGSNSGNTATLTISGTQAMDEADYYCQAW DWSGEVFGGGTKLTVL (SEQ ID NO: 331) |
| A10.6B VL | CDR-L1 | Residues 23-33 of SEQ ID NO.: 331 | SADNLGNQYVS |
| A10.6B VL | CDR-L2 | Residues 49-55 of SEQ ID NO.: 331 | QDGMRPS |
| A10.6B VL | CDR-L3 | Residues 88-96 of SEQ ID NO.: 331 | QAWDWSGEV |
| A10.3D VL | | | SYELTQPPSVSVSPGQTASITCSADKLGTK YVSWYQQKPGQSPVLVIYQDGNRPSGIPER FSGSNSGNTATLTISGTQAMDEADYYCQSW DQSGAVFGGGTKLTVL (SEQ ID NO: 332) |
| A10.3D VL | CDR-L1 | Residues 23-33 of SEQ ID NO.: 332 | SADKLGTKYVS |
| A10.3D VL | CDR-L2 | Residues 49-55 of SEQ ID NO.: 332 | QDGNRPS |
| A10.3D VL | CDR-L3 | Residues 88-96 of SEQ ID NO.: 332 | QSWDQSGAV |
| A10.4C VL | | | SYELTQPPSVSVSPGQTASITCSADNLGNQ YVSWYQQKPGQSPVLVIYQDGMRPSGIPER FSGSNSGNTATLTISGTQAMDEADYYCQAW DSSGAVFGGGTKLTVL (SEQ ID NO: 333) |
| A10.4C VL | CDR-L1 | Residues 23-33 of SEQ ID NO.: 333 | SADNLGNQYVS |
| A10.4C VL | CDR-L2 | Residues 49-55 of SEQ ID NO.: 333 | QDGMRPS |
| A10.4C VL | CDR-L3 | Residues 88-96 of SEQ ID NO.: 333 | QAWDSSGAV |

Example 5

Construction of CDR-Grafted E9 Antibodies

CDRs of E9 VH were grafted onto VH3 consensus framework (grafted VH=E9vh3g2) and CDRs of E9 VL were grafted onto VL2-1 framework of anti-DLL4 A10 antibody (grafted VL=E9a10vlg2) and onto VK framework of A10 germline (the closest germline in homology to the E9 VL) (grafted VL=E9AVK). Alternatively framework (FW) repairing was also performed with the E9 VH; its FW was maintained but amino acids that may cause antibody instability were replaced, (repaired VH=E9VH4r2). Framework back-mutations were incorporated in both CDR-grafting and FWrepairing to maintain antibody structure and functionality (Table 11 and Table 14).

CDRs of E9 were also grafted on the frameworks of anti-IL-18 and anti-IL-12 antibodies. Specifically CDRs of E9 VH were grafted onto VH5-51 framework of anti-IL-18 (grafted VH=E9VH325) and onto VH2-70 framework of anti-IL-12 (grafted VH=E9VH1D4.1). CDRs of E9 VL were grafted onto VK L2/L16 framework of anti-IL-12 (grafted VL=E9VL325) and onto VK B3 framework of anti-IL-12 (grafted VL=E9VL1D4.1). Framework back-mutations were incorporated in the CDR-grafting to maintain antibody structure and functionality (Table 15 and Table 18).

In silico constructed CDR grafted antibodies described above were synthesized directly in the plasmid of choice by Blue Heron Biotechnology. The variable heavy region was inserted in-frame onto a cDNA fragment encoding the wild type human IgG1 constant region and onto the human IgG1 constant region containing two hinge-region amino acid mutations. These mutations are a leucine to alanine change at position 234 (EU numbering) and a leucine to alanine change at position 235 (Lund et al., *J. Immunol.*, 147: 2657 (1991)). The variable light chain region was inserted in-frame with the human lambda constant region and with the human kappa constant region. Upon receipt of synthesized constructs from Blue Heron, DNA was scaled up and sequence confirmed. Correct CDR-grafted heavy and light chains corresponding to each antibody (Tables 11 and 14) (Tables 15 and 18) were co-transfected into HEK-293-6E cells to transiently produce full-length CDR-grafted anti-human DLL4 antibodies. Table 11 summarizes all the E9 antibody variants generated and HEK-293-6e expression data. Cell supernatants containing recombinant human antibody were purified by Protein A Sepharose chromatography and bound antibody eluted by addition of acid buffer. Antibodies were dialyzed into PBS.

The ability of purified CDR grafted antibodies to bind to DLL4 or to inhibit DLL4 activity was determined using different types of assays like ELISA (Example 1.2, Method 2), Biacore (Example 1.2) and Flow Cytometry (FACS) (Example 1.3). Table 12 and Table 16 show EC50 values from the ELISA assays and the FACS assays and the affinity determined by Biacore of the CDR grafted antibodies described respectively in Table 11 and Table 15 for human DLL4, murine DLL4 and cynomolgus DLL4. Table 13 and Table 17 show IC50 values from the blocking ELISA (Example 1.4) and blocking FACS (Example 1.5) with human DLL4 and murine DLL4 for the CDR-grafted antibodies described respectively in Table 11 and Table 15.

TABLE 11

Summary of the E9 antibody variants generated and expression data

| Antibody | VH name | VL name | HEK-293-6e titer (mg/L) |
|---|---|---|---|
| E9-SE1 | E9vh3g2 | E9a10vlg2 | 104 |
| E9-SE2 | E9vh3g2 | E9.1 | 87 |
| E9-SE3 | E9vh4r2 | E9.1 | 89 |
| E9-SE4 | E9.1 | E9a10vlg2 | 66 |
| E9-SE5 | E9.1 | E9AVK | 79 |
| E9-SE6 | E9vh4r2 | E9a10vlg2 | 125 |
| E9-SE7 | E9vh3g2 | E9AVK | 56 |
| E9-SE8 | E9vh4r2 | E9AVK | 85 |

TABLE 12

Binding affinities of the E9 antibody variants for human, mouse, and cynomolgus DLL4 as determined by ELISA, Biacore, and FACS.

Binding Data

| | Human DLL4 | | | Mouse DLL4 | | | Cyno DLL4 | |
|---|---|---|---|---|---|---|---|---|
| Antibody | Binding ELISA (EC50, nM) | Biacore (Kd, nM) | Binding FACS (Kd, nM) | Binding ELISA (EC50, nM) | Biacore (Kd, nM) | Binding FACS (Kd, nM) | Binding ELISA (EC50, nM) | Biacore (Kd, nM) |
| E9-SE1 | 0.16 | 15.2* | 3.45 | 0.19 | 12.83 | 1.34 | 0.14 | 5.42 |
| E9-SE2 | 0.18 | 2.43 | 5.2 | 0.20 | 15.09 | 0.87 | 0.14 | 3.68 |
| E9-SE3 | 0.18 | 2.26 | 2.29 | 0.20 | 12.1 | 0.74 | 0.14 | 3.42 |
| E9-SE4 | 0.17 | 2.38 | nc | 0.20 | 10.52 | 1.15 | 0.14 | 3.92 |
| E9-SE5 | 0.16 | 1.57 | 7.81 | 0.19 | 12.77 | 2.9 | 0.13 | 6.7 |
| E9-SE6 | 0.17 | 0.64 | 4.25 | 0.19 | 10.04 | 1.18 | 0.13 | 6.55 |
| E9-SE7 | 0.17 | 1.69 | 2.28 | 0.17 | 16.22 | 2.24 | 0.12 | 7.53 |
| E9-SE8 | 0.18 | 2.00 | 2.67 | 0.19 | 13.03 | 2.32 | 0.14 | 3.41 |
| E9.1 | 0.29 | 2.38 | 0.35 | 0.34 | 12.77 | 1.6* | 0.24 | 4.08 |

*historic data;

nc = not calculaed

TABLE 13

Neutralizing activities of the E9 antibody variants for human and mouse DLL4 as determined by ELISA and FACS. Functional Data

| Antibody | Human DLL4 | | Mouse DLL4 | |
|---|---|---|---|---|
| | Blocking ELISA (IC50, nM) | Blocking FACS (IC50, nM) | Blocking ELISA (IC50, nM) | Blocking FACS (IC50, nM) |
| E9-SE1 | 2.7 | 8.51 | 2.9 | 1.71 |
| E9-SE2 | 2.6 | 5.61 | 2.2 | 1.23 |
| E9-SE3 | 2.5 | 6.75 | 2.1 | 1.25 |
| E9-SE4 | 2.7 | 5.82 | 2.9 | 1.71 |
| E9-SE5 | 2.6 | 6.38 | 2.4 | 1.76 |
| E9-SE6 | 2.5 | 8.16 | 2.9 | 1.53 |
| E9-SE7 | 2.4 | 7.81 | 2.4 | 1.94 |
| E9-SE8 | 2.5 | 9.25 | 2.6 | 2.3 |
| E9.1 | 2.5 | 4.55 | 2.5 | 1.02 |

TABLE 14

VH and VL amino acid sequences of human CDR-grafted E9 antibodies.

| SEQ ID No. | Protein region | | Sequence 12345678901234567890123456 7890 |
|---|---|---|---|
| 334 | VH E9.1 | | EVQLQESGPGLVKPSETLSLTCTVSGGSISSSSYYWGWIRQPPGKGLEWIGDIYYTGSTY YNPSLKSRVTISVDTSKNQFSLKLSSVTAA DTAVYYCAREDVILRGGSDYWGQGTLVTVS S |
| | VH E9.1 CDR-H1 | Residues 31-37 of SEQ ID NO.: 334 | SSSYYWG |
| | VH E9.1 CDR-H2 | Residues 52-67 of SEQ ID NO.: 334 | DIYYTGSTYYNPSLKS |
| | VH E9.1 CDR-H3 | Residues 100-110 of SEQ ID NO.: 334 | EDVILRGGSDY |
| 335 | VL E9.1 | | SYELTQPPSVSVSPGQTASITCSGQRLGDK YASWYQQKPGQSPVLVIYEDSKRPSGIPER FSGSNSGDTATLTISGTQPMDEADYYCQAW DRDTGVFGYGTRVTVLG |
| | VL E9.1 CDR-L1 | Residues 23-33 of SEQ ID NO.: 335 | SGQRLGDKYAS |
| | VL E9.1 CDR-L2 | Residues 49-55 of SEQ ID NO.: 335 | EDSKRPS |
| | VL E9.1 CDR-L3 | Residues 88-96 of SEQ ID NO.: 335 | QAWDRDTGV |
| 336 | VH E9-SE1 | | EVQLVESGGGLVQPGGSLRLSCAVSGGSISSSSYYWGWIRQAPGKGLEWIGDIYYTGSTY YNPSLKSRVTISVDTSKNSFYLQMNSLRAE DTAVYYCAREDVILRGGSDYWGQGTLVTVS S |
| | VH E9-SE1 CDR-H1 | Residues 31-37 of SEQ ID NO.: 336 | SSSYYWG |
| | VH E9-SE1 CDR-H2 | Residues 52-67 of SEQ ID NO.: 336 | DIYYTGSTYYNPSLKS |

TABLE 14-continued

VH and VL amino acid sequences of human CDR-grafted E9 antibodies.

| SEQ ID No. | Protein region | | Sequence 123456789012345678901234567890 |
|---|---|---|---|
| | VH E9-SE1 CDR-H3 | Residues 100-110 of SEQ ID NO.: 336 | EDVILRGGSDY |
| 337 | VL E9-SE1 | | LYVLTQPPSVSVSPGQTASITCSGQRLGDK YASWYQQKPGQSPVLVIYEDSKRPSGIPER FSGSNSGDTATLTISGTQTMDEADYLCQAW DRDTGVFGGGTKVTVLG |
| | VL E9-SE1 CDR-L1 | Residues 23-33 of SEQ ID NO.: 337 | SGQRLGDKYAS |
| | VL E9-SE1 CDR-L2 | Residues 49-55 of SEQ ID NO.: 337 | EDSKRPS |
| | VL E9-SE1 CDR-L3 | Residues 88-96 of SEQ ID NO.: 337 | QAWDRDTGV |
| 338 | VH E9-SE2 | | EVQLVESGGGLVQPGGSLRLSCAVSGGSIS SSSYYWGWIRQAPGKGLEWIGDIYYTGSTY YNPSLKSRVTISVDTKNSFYLQMNSLRAE DTAVYYCAREDVILRGGSDYWGQGTLVTVS S |
| | VH E9-SE2 CDR-H1 | Residues 31-37 of SEQ ID NO.: 338 | SSSYYWG |
| | VH E9-SE2 CDR-H2 | Residues 52-67 of SEQ ID NO.: 338 | DIYYTGSTYYNPSLKS |
| | VH E9-SE2 CDR-H3 | Residues 100-110 of SEQ ID NO.: 338 | EDVILRGGSDY |
| 339 | VL E9-SE2 | | SYELTQPPSVSVSPGQTASITCSGQRLGDK YASWYQQKPGQSPVLVIYEDSKRPSGIPER FSGSNSGDTATLTISGTQPMDEADYYCQAW DRDTGVFGYGTRVTVLG |
| | VL E9-SE2 CDR-L1 | Residues 23-33 of SEQ ID NO.: 339 | SGQRLGDKYAS |
| | VL E9-SE2 CDR-L2 | Residues 49-55 of SEQ ID NO.: 339 | EDSKRPS |
| | VL E9-SE2 CDR-L3 | Residues 88-96 of SEQ ID NO.: 339 | QAWDRDTGV |
| 340 | VH E9-SE3 | | EVQLQESGPGLVKPGETLSLTCTVSGGSIS SSSYYWGWIRQAPGKGLEWIGDIYYTGSTY YNPSLKSRVTISVDTSKNQFYLKLSSVRAE DTAVYYCAREDVILRGGSDYWGQGTLVTVS S |
| | VH E9-SE3 CDR-H1 | Residues 31-37 of SEQ ID NO.: 340 | SSSYYWG |
| | VH E9-SE3 CDR-H2 | Residues 52-67 of SEQ ID NO.: 340 | DIYYTGSTYYNPSLKS |

TABLE 14-continued

VH and VL amino acid sequences of human CDR-grafted E9 antibodies.

| SEQ ID No. | Protein region | | Sequence 123456789012345678901234567890 |
|---|---|---|---|
| | VH E9-SE3 CDR-H3 | Residues 100-110 of SEQ ID NO.: 340 | EDVILRGGSDY |
| 341 | VL E9-SE3 | | SYELTQPPSVSVSPGQTASITCSGQRLGDK YASWYQQKPGQSPVLVIYEDSKRPSGIPER FSGSNSGDTATLTISGTQPMDEADYYCQAW DRDTGVFGYGTRVTVLG |
| | VL E9-SE3 CDR-L1 | Residues 23-33 of SEQ ID NO.: 341 | SGQRLGDKYAS |
| | VL E9-SE3 CDR-L2 | Residues 49-55 of SEQ ID NO.: 341 | EDSKRPS |
| | VL E9-SE3 CDR-L3 | Residues 88-96 of SEQ ID NO.: 341 | QAWDRDTGV |
| 342 | VH E9-SE4 | | EVQLQESGPGLVKPSETLSLTCTVSGGSIS SSSYYWGWIRQPPGKGLEWIGDIYYTGSTY YNPSLKSRVTISVDTSKNQFSLKLSSVTAA DTAVYYCAREDVILRGGSDYWGQGTLVTVS S |
| | VH E9-SE4 CDR-H1 | Residues 31-37 of SEQ ID NO.: 342 | SSSYYWG |
| | VH E9-SE4 CDR-H2 | Residues 52-67 of SEQ ID NO.: 342 | DIYYTGSTYYNPSLKS |
| | VH E9-SE4 CDR-H3 | Residues 100-110 of SEQ ID NO.: 342 | EDVILRGGSDY |
| 343 | VL E9-SE4 | | LYVLTQPPSVSVSPGQTASITCSGQRLGDK YASWYQQKPGQSPVLVIYEDSKRPSGIPER FSGSNSGDTATLTISGTQTMDEADYLCQAW DRDTGVFGGGTKVTVLG |
| | VL E9-SE4 CDR-L1 | Residues 23-33 of SEQ ID NO.: 343 | SGQRLGDKYAS |
| | VL E9-SE4 CDR-L2 | Residues 49-55 of SEQ ID NO.: 343 | EDSKRPS |
| | VL E9-SE4 CDR-L3 | Residues 88-96 of SEQ ID NO.: 343 | QAWDRDTGV |
| 344 | VH E9-SE5 | | EVQLQESGPGLVKPSETLSLTCTVSGGSIS SSSYYWGWIRQPPGKGLEWIGDIYYTGSTY YNPSLKSRVTISVDTSKNQFSLKLSSVTAA DTAVYYCAREDVILRGGSDYWGQGTLVTVS S |
| | VH E9-SE5 CDR-H1 | Residues 31-37 of SEQ ID NO.: 344 | SSSYYWG |
| | VH E9-SE5 CDR-H2 | Residues 52-67 of SEQ ID NO.: 344 | DIYYTGSTYYNPSLKS |

TABLE 14-continued

VH and VL amino acid sequences of human CDR-grafted E9 antibodies.

| SEQ ID No. | Protein region | | Sequence 123456789012345678901234567890 |
|---|---|---|---|
| | VH E9-SE5 CDR-H3 | Residues 100-110 of SEQ ID NO.: 344 | EDVILRGGSDY |
| 345 | VL E9-SE5 | | EYVLTQSPDFQSVTPKEKVTITCSGQRLGD KYASWYQQKPDQSPKLVIYEDSKRPSGVPS RFSGSNSGDDATLTINSLEAEDAATYYCQA WDRDTGVFGQGTKVEIKR |
| | VL E9-SE5 CDR-L1 | Residues 24-34 of SEQ ID NO.: 345 | SGQRLGDKYAS |
| | VL E9-SE5 CDR-L2 | Residues 50-56 of SEQ ID NO.: 345 | EDSKRPS |
| | VL E9-SE5 CDR-L3 | Residues 89-97 of SEQ ID NO.: 345 | QAWDRDTGV |
| 346 | VH E9-SE6 | | EVQLQESGPGLVKPSETLSLTCTVSGGSIS SSSYYWGWIRQAPGKGLEWIGDIYYTGSTY YNPSLKSRVTISVDTSKNQFYLKLSSVRAE DTAVYYCAREDVILRGGSDYWGQGTLVTVS S |
| | VH E9-SE6 CDR-H1 | Residues 31-37 of SEQ ID NO.: 346 | SSSYYWG |
| | VH E9-SE6 CDR-H2 | Residues 52-67 of SEQ ID NO. 346 | DIYYTGSTYYNPSLKS |
| | VH E9-SE6 CDR-H3 | Residues 100-110 of SEQ ID NO.: 346 | EDVILRGGSDY |
| 347 | VL E9-SE6 | | LYVLTQPPSVSVSPGQTASITCSGQRLGDK YASWYQQKPGQSPVLVIYEDSKRPSGIPER FSGSNSGDTATLTISGTQTMDEADYLCQAW DRDTGVFGGGTKVTVLG |
| | VL E9-SE6 CDR-L1 | Residues 23-33 of SEQ ID NO.: 347 | SGQRLGDKYAS |
| | VL E9-SE6 CDR-L2 | Residues 49-55 of SEQ ID NO.: 347 | EDSKRPS |
| | VL E9-SE6 CDR-L3 | Residues 88-96 of SEQ ID NO.: 347 | QAWDRDTGV |
| 348 | VH E9-SE7 | | EVQLVESGGGLVQPGGSLRLSCAVSGGSIS SSSYYWGWIRQAPGKGLEWIGDIYYTGSTY YNPSLKSRVTISVDTSKNSFYLQMNSLRAE DTAVYYCAREDVILRGGSDYWGQGTLVTVS S |
| | VH E9-SE7 CDR-H1 | Residues 31-37 of SEQ ID NO.: 348 | SSSYYWG |
| | VH E9-SE7 CDR-H2 | Residues 52-67 of SEQ ID NO.: 348 | DIYYTGSTYYNPSLKS |

TABLE 14-continued

VH and VL amino acid sequences of human CDR-grafted E9 antibodies.

| SEQ ID No. | Protein region | | Sequence 123456789012345678901234567890 |
|---|---|---|---|
| | VH E9-SE7 CDR-H3 | Residues 100-110 of SEQ ID NO.: 348 | EDVILRGGSDY |
| 349 | VL E9-SE7 | | EYVLTQSPDFQSVTPKEKVTITCSGQRLGD KYASWYQQKPDQSPKLVIYEDSKRPSGVPS RFSGSNSGDDATLTINSLEAEDAATYYCQA WDRDTGVFGQGTKVEIKR |
| | VL E9-SE7 CDR-L1 | Residues 24-34 of SEQ ID NO.: 349 | SGQRLGDKYAS |
| | VL E9-SE7 CDR-L2 | Residues 50-56 of SEQ ID NO.: 349 | EDSKRPS |
| | VL E9-SE7 CDR-L3 | Residues 89-97 of SEQ ID NO.: 349 | QAWDRDTGV |
| 350 | VH E9-SE8 | | EVQLQESGPGLVKPGETLSLTCTVSGGSIS SSSYYWGWIRQAPGKGLEWIGDIYYTGSTY YNPSLKSRVTISVDTSKNQFYLKLSSVRAE DTAVYYCAREDVILRGGSDYWGQGTLVTVS S |
| | VH E9-SE8 CDR-H1 | Residues 31-37 of SEQ ID NO.: 350 | SSSYYWG |
| | VH E9-SE8 CDR-H2 | Residues 52-67 of SEQ ID NO.: 350 | DIYYTGSTYYNPSLKS |
| | VH E9-SE8 CDR-H3 | Residues 100-110 of SEQ ID NO.: 350 | EDVILRGGSDY |
| 351 | VL E9-SE8 | | EYVLTQSPDFQSVTPKEKVTITCSGQRLGD KYASWYQQKPDQSPKLVIYEDSKRPSGVPS RFSGSNSGDDATLTINSLEAEDAATYYCQA WDRDTGVFGQGTKVEIKR |
| | VL E9-SE8 CDR-L1 | Residues 24-34 of SEQ ID NO.: 351 | SGQRLGDKYAS |
| | VL E9-SE8 CDR-L2 | Residues 50-56 of SEQ ID NO.: 351 | EDSKRPS |
| | VL E9-SE8 CDR-L3 | Residues 89-97 of SEQ ID NO.: 351 | QAWDRDTGV |

TABLE 15

Summary of the E9 antibody variants generated and expression data.

| Antibody | VH name | VL name | HEK-293-6e titer (mg/L) |
|---|---|---|---|
| E9-FR1 | E9VH325 | E9VL325 | 29 |
| E9-FR2 | E9VH1D4.1 | E9VL1D4.1 | 44 |

TABLE 16

Binding affinities of the E9 CDR-grafted antibodies for human, mouse and cynomolgus DLL4 as determined by ELISA, Biacore and FACS.
Binding Data

| MAb | Human DLL4 Binding ELISA (EC50, nM) | Human DLL4 Biacore (Kd, nM) | Human DLL4 Binding FACS (Kd, nM) | Mouse DLL4 Binding ELISA (EC50, nM) | Mouse DLL4 Biacore (Kd, nM) | Mouse DLL4 Binding FACS (Kd, nM) | Cyno DLL4 Binding ELISA (EC50, nM) | Cyno DLL4 Biacore (Kd, nM) |
|---|---|---|---|---|---|---|---|---|
| E9-FR1 | 0.11 | 0.72 | 4 | 0.13 | 1.6 | 2.51 | 0.12 | 0.74 |
| E9-FR2 | 0.105 | 0.31 | 6.2 | 0.125 | 0.69 | 3.57 | 0.12 | 0.3 |
| E9.1 | 0.03 | 0.52 | 3.62 | 0.04 | 1.1 | 1.66 | 0.035 | 0.47 |

TABLE 17

Neutralizing activities of the E9 CDR-grafted antibodies for human and mouse DLL4 as determined by ELISA and FACS.
Functional Data

| MAb | Human DLL4 Blocking ELISA (IC50, nM) | Human DLL4 Blocking FACS (IC50, nM) | Mouse DLL4 Blocking ELISA (IC50, nM) | Mouse DLL4 Blocking FACS (IC50, nM) |
|---|---|---|---|---|
| E9-FR1 | 1.54 | 1.57 | 3.35 | 0.98 |
| E9-FR2 | 1.52 | 3.03 | 4.35 | 1.07 |
| E9.1 | 2.2 | 1.62 | 5.85 | 1.06 |

TABLE 18

VH and VL amino acid sequences of human CDR-grafted E9 antibodies.

| SEQ ID No. | Protein region | | Sequence 123456789012345678901234567890 |
|---|---|---|---|
| 352 | VH E9-FR1 | | EVQLVQSGTEVKKPGESLKISCKVSGGSISSSSYYWGWIRQMPGKGLEWIGDIYYTGSTYYNPSLKSQVTISVDTSFNTFFLQWSSLKASDTAMYYCAREDVILRGGSDYWGQGTMVTVSS |
| | VH E9-FR1 CDR-H1 | Residues 31-37 of SEQ ID NO.: 352 | SSSYYWG |
| | VH E9-FR1 CDR-H2 | Residues 52-67 of SEQ ID NO.: 352 | DIYYTGSTYYNPSLKS |
| | VH E9-FR1 CDR-H3 | Residues 100-110 of SEQ ID NO.: 352 | EDVILRGGSDY |

TABLE 18-continued

VH and VL amino acid sequences of human CDR-grafted E9 antibodies.

| SEQ ID No. | Protein region | | Sequence 12345678901234567890123456 7890 |
|---|---|---|---|
| 353 | VL E9-FR1 | | EYVLTQSPATLSVSPGERATLSCSGQRLGD KYASWYQQKPGQSPRLVIYEDSKRPSDIPA RFSGSNSGDEATLTISSLQSEDFAVYYCQA WDRDTGVFGQGTRLEIKR |
| | VL E9-FR1 CDR-L1 | Residues 24-34 of SEQ ID NO.: 353 | SGQRLGDKYAS |
| | VL E9-FR1 CDR-L2 | Residues 50-56 of SEQ ID NO.: 353 | EDSKRPS |
| | VL E9-FR1 CDR-L3 | Residues 89-97 of SEQ ID NO.: 353 | QAWDRDTGV |
| 354 | VH E9-FR2 | | EVTLRESGPALVKPTQTLTLTCTVSGGSIS SSSYYWGWIRQPPGKGLEWIGDIYYTGSTY YNPSLKSRVTISVDTSKNQFVLTMTNMDPV DTATYYCAREDVILRGGSDYWGQGTTVTVS S |
| | VH E9-FR2 CDR-H1 | Residues 31-37 of SEQ ID NO.: 354 | SSSYYWG |
| | VH E9-FR2 CDR-H2 | Residues 52-67 of SEQ ID NO.: 354 | DIYYTGSTYYNPSLKS |
| | VH E9-FR2 CDR-H3 | Residues 100-110 of SEQ ID NO.: 354 | EDVILRGGSDY |
| 355 | VL E9-FR2 | | DYVLTQSPDSLAVSLGERATINCSGQRLGD KYASWYQQKPGQSPKLVIYEDSKRPSGIPD RFSGSNSGDDATLTISSLQAEDVAVYYCQA WDRDTGVFGGGTKVEIKR |
| | VL E9-FR2 CDR-L1 | Residues 24-34 of SEQ ID NO.: 355 | SGQRLGDKYAS |
| | VL E9-FR2 CDR-L2 | Residues 50-56 of SEQ ID NO.: 355 | EDSKRPS |
| | VL E9-FR2 CDR-L3 | Residues 89-97 of SEQ ID NO.: 355 | QAWDRDTGV |

Example 6

Further Engineering of Affinity-Matured Antibody E9-71

E9-71(M) and E9-71(L).

Both heavy chain and light chain of affinity-matured anti-DLL4 antibody E9-71 were further engineered. The methionine (M) in CDR-H3 of E9-71 heavy chain was mutated to leucine (L) by designing forward and reverse overlapping primers containing the mutated nucleotides. Polymerase chain reaction (PCR) was performed in two sequential steps to amplify the entire variable region gene using the two primers carrying the mutated nucleotides and two outermost primers containing overhanging sequences complementary to the receiving vector.

The signal peptide used for the light chain of E9-71(M) and E9-71(L) is called lambda 1a signal peptide. The framework 4 (FW4) region hJL-1 of E9-71 light chain was changed to hJL2 to be more compatible with the huCL2 constant region of the antibody. Forward and reverse primers were designed containing the mutated nucleotides. Polymerase chain reaction (PCR) was performed in two sequential steps to amplify the entire variable region gene using the two primers carrying the mutated nucleotides and two outermost primers containing overhanging sequences complementary to the receiving vector.

The PCR products derived from each cDNA assembly was separated on an agarose gel and the band corresponding to the predicted variable region cDNA size excised and purified. The variable heavy region were inserted in-frame onto a cDNA fragment encoding the human IgG1 constant region containing two hinge-region amino acid mutations by homologous recombination in bacteria. These mutations are a leucine to alanine change at position 234 (EU numbering) and a leucine to alanine change at position 235 (Lund et al., *J. Immunol.*, 147: 2657 (1991)). The variable light chain region were inserted in-frame between the human lambda 1a signal peptide and the human lambda constant region by homologous recombination. Bacterial colonies were isolated and plasmid DNA extracted; cDNA inserts were sequenced in their entirety. Correct heavy and light chains corresponding to each antibody (Table 19) were co-transfected into HEK-293-6E cells to transiently produce full-length E9-71(M) or E9-71(L) anti-human DLL4 antibodies. Both E9.71(M) and E9.71(L) share the same light chain. Cell supernatants containing recombinant human antibody may be purified by Protein A Sepharose chromatography and bound antibody eluted by addition of acid buffer. Antibodies were neutralized and dialyzed into PBS.

TABLE 19

VH and VL Amino Acid Sequences of Human E9.71 engineered antibodies

| SEQ ID No. | Protein region | | Sequence 12345678901234567890123456 7890 |
|---|---|---|---|
| 356 | VH E9.71 | | EVQLQESGPGLVKPSETLSLTCTVSGGSIS SSSYYWGWIRQPPGKGLEWIGDIYYTGSTY YNPSLKSRVTISVDTSKNQFSLKLSSVTAA DTAVYYCARQALAMGGGSDKWGQGTLVTVS S |
| | VH E9.71 CDR-H1 | Residues 31-37 of SEQ ID NO.: 356 | SSSYYWG |
| | VH E9.71 CDR-H2 | Residues 52-67 of SEQ ID NO.: 356 | DIYYTGSTYYNPSLKS |
| | VH E9.71 CDR-H3 | Residues 100-110 of SEQ ID NO.: 356 | QALAMGGGSDK |
| 357 | VL E9.71 | | SYELTQPPSVSVSPGQTASITCSGQRLGDK YASWYQQKPGQSPVLVIYEDSKRPSGIPER FSGSNSGDTATLTISGTQPMDEADYYCQAW DRDTGVFGYGTKVTVLG |
| | VL E9.71 CDR-L1 | Residues 23-33 of SEQ ID NO.: 357 | SGQRLGDKYAS |
| | VL E9.71 CDR-L2 | Residues 49-55 of SEQ ID NO.: 357 | EDSKRPS |
| | VL E9.71 CDR-L3 | Residues 88-96 of SEQ ID NO.: 357 | QAWDRDTGV |
| 358 | VH E9.71 (M) | | EVQLQESGPGLVKPSETLSLTCTVSGGSIS SSSYYWGWIRQPPGKGLEWIGDIYYTGSTY YNPSLKSRVTISVDTSKNQFSLKLSSVTAA DTAVYYCARQALAMGGGSDKWGQGTLVTVS S |
| | VH E9.71(M) CDR-H1 | Residues 31-37 of SEQ ID NO.: 358 | SSSYYWG |
| | VH E9.71(M) CDR-H2 | Residues 52-67 of SEQ ID NO.: 358 | DIYYTGSTYYNPSLKS |
| | VH E9.71(M) CDR-H3 | Residues 100-110 of SEQ ID NO.: 358 | QALAMGGGSDK |

TABLE 19-continued

VH and VL Amino Acid Sequences of Human E9.71 engineered antibodies

| SEQ ID No. | Protein region | | Sequence 123456789012345678901234567890 |
|---|---|---|---|
| 359 | VL E9.71 (M) | | SYELTQPPSVSVSPGQTASITCSGQRLGDKYASWYQQKPGQSPVLVIYEDSKRPSGIPERFSGSNSGDTATLTISGTQPMDEADYYCQAWDRDTGVFGGGTKLTVLG |
| | VL E9.71(M) CDR-L1 | Residues 23-33 of SEQ ID NO.: 359 | SGQRLGDKYAS |
| | VL E9.71(M) CDR-L2 | Residues 49-55 of SEQ ID NO.: 359 | EDSKRPS |
| | VL E9.71(M) CDR-L3 | Residues 88-96 of SEQ ID NO.: 359 | QAWDRDTGV |
| 360 | VH E9.71(L) | | EVQLQESGPGLVKPSETLSLTCTVSGGSISSSSYYWGWIRQPPGKGLEWIGDIYYTGSTYYNPSLKSRVTISVDTSKNQFSLKLSSVTAADTAVYYCARQALALGGGSDKWGQGTLVTVSS |
| | VH E9.71(L) CDR-H1 | Residues 31-37 of SEQ ID NO.: 360 | SSSYYWG |
| | VH E9.71(L) CDR-H2 | Residues 52-67 of SEQ ID NO.: 360 | DIYYTGSTYYNPSLKS |
| | VH E9.71(L) CDR-H3 | Residues 100-110 of SEQ ID NO.: 360 | QALALGGGSDK |
| 361 | VL E9.71(L) | | SYELTQPPSVSVSPGQTASITCSGQRLGDKYASWYQQKPGQSPVLVIYEDSKRPSGIPERFSGSNSGDTATLTISGTQPMDEADYYCQAWDRDTGVFGGGTKLTVLG |
| | VL E9.71(L) CDR-L1 | Residues 23-33 of SEQ ID NO.: 361 | SGQRLGDKYAS |
| | VL E9.71(L) CDR-L2 | Residues 49-55 of SEQ ID NO.: 361 | EDSKRPS |
| | VL E9.71(L) CDR-L3 | Residues 88-96 of SEQ ID NO.: 361 | QAWDRDTGV |

Example 7

E9-71(M) Signal Peptide Engineering

Signal peptide lambda 1a was used for the generation of anti-DLL4 antibody E9-71(M). Alternative signal peptides were also investigated. The prediction of the percentage of the correct antibody cleavage during mammalian expression of in silico constructed amino acid sequences of E9-71(M) N-terminal variable region with different signal peptides from the lambda and kappa signal peptide families is known in the art using the Signal IP 3.0 Server available on the Internet (e.g., worldwide website cbs.dtu.dk/services/SignalP/) or numerous other equivalent software. The signal peptides with the highest predicted percentages of correct cleavage, one from each family were chosen: the lambda 3p from the lambda family and the L23 from the kappa family. A mutated version of the original lambda 1a signal peptide was also selected, with two amino acid changes (glycine to arginine and serine to valine). For the construction of the light chain containing the lambda 1a signal peptide polymerase chain reaction (PCR) was performed in one step to amplify the entire variable region gene using the two outermost primers containing overhanging sequences complementary to the receiving vector with one of them containing the mutated nucleotide sequence. For the construction of the light chain containing the lambda 3p signal peptide and the kappa L23 signal peptide two overlapping primers were designed to construct the signal peptide region then polymerase chain reaction (PCR) was performed to amplify the entire variable region gene using the two outermost primers containing overhanging sequences complementary to the receiving vector. Two versions of the E9-71 variable regions were generated using the lambda 3p and the kappa L23 signal peptides: one with the full length variable region and another one with the first serine (S) at the variable region N-terminus missing. Only the full length variable region was generated with the lambda 1a signal peptide. The PCR products derived from each cDNA assembly were separated on an agarose gel and the band corresponding to the predicted variable region cDNA size excised and purified. The variable heavy region was inserted in-frame onto a cDNA fragment encoding the human IgG1 constant region containing two hinge-region amino acid mutations by homologous recombination in bacteria. These mutations are a leucine to alanine change at position 234 (EU numbering) and a leucine to alanine change at position 235 (Lund et al., *J. Immunol.*, 147: 2657 (1991)). The variable light chain region was inserted in-frame with the human lambda constant region by homologous recombination. Bacterial colonies were isolated, plasmid DNA extracted, and cDNA inserts were sequenced in their entirety. Correct heavy and light chains corresponding to each antibody were co-transfected into HEK-293-6E cells to transiently produce full-length E9-71(M) anti-human DLL4 antibodies. Cell supernatants containing recombinant human antibody were purified by Protein A Sepharose chromatography and bound antibody eluted by addition of acid buffer. Antibodies were dialyzed into PBS. Purified E9.71(M) antibodies were analyzed by Mass Spectrometry (MS) for confirmation of intact antibody sequence. Table 20, below, shows the amino acid sequence of the different signal peptides used for the generation of E9.71(M). Table 21, below, shows the E9.71(M) cleavage sites analyzed by Mass Spectrometry.

TABLE 20

Amino acid sequence of the signal peptides used for the generation of E9.71(M)

| Antibody | Signal Peptide | Signal Peptide Sequence | VL Region |
|---|---|---|---|
| E9.71(M) | λ 1a | MAWSPLFLTLITHCAGSWA (SEQ ID NO: 362) | Full Length |
| E9.71(M)-1λ | 1a (GS to RV) | MAWSPLFLTLITHCARVWA (SEQ ID NO: 363) | Full Length |
| E9.71(M)-2λ | 3p | MAWTPLLLPLLTFCTVSEA (SEQ ID NO: 364) | Full Length |
| E9.71(M)-3λ | 3p | MAWTPLLLPLLTFCTVSEA (SEQ ID NO: 365) | N-terminus S missing |
| E9.71(M)-4 | Kappa L23 | MDMRVPAQRLGLLLLWFPGARC (SEQ ID NO: 366) | Full Length |
| E9.71(M)-5 | Kappa L23 | MDMRVPAQRLGLLLLWFPGARC (SEQ ID NO: 367) | N-terminus S missing |

TABLE 21

E9.71(M) antibody cleavage sites analyzed by Mass Spectrometry (MS)

| Antibody | Antibody Major Cleavage Site | % Major Peak (↓) |
|---|---|---|
| E9.71(M) | MAWSPLFLTLITHCAG↓SWA↓SYELTQPPSVS (SEQ ID NO: 368) | 95 |
| E9.71(M)-1 | MAWSPLFLTLITHCARVWA↓SYELTQPPSVS (SEQ ID NO: 369) | 96 |
| E9.71(M)-2 | MAWTPLLLPLLTFCTVSEA↓SYELTQPPSVS (SEQ ID NO: 370) | 96 |
| E9.71(M)-3 | MAWTPLLLPLLTFCTVSEA↓YELTQPPSVS (SEQ ID NO: 371) | 97 |
| E9.71(M)-4 | MDMRVPAQRLGLLLLWFPGARC↓SYELTQPPSVS (SEQ ID NO: 372) | Not determined |
| E9.71(M)-5 | MDMRVPAQRLGLLLLWFPGARC↓YELTQPPSVS (SEQ ID NO: 373) | Not determined |

Example 8

In Vitro Characterization of Engineered PROfusion Antibodies

The antigen binding affinities of these engineered PROfusion antibodies were determined by the BIACORE technology as described in Example 1.1, and are shown in Table 22. The in vitro activities of the representative ones were further evaluated using other methods described in Example 1, with results shown in Table 23.

TABLE 22

Biacore kinetics of engineered anti-DLL4 PROfusion antibodies.

| | Binding kinetics | | | | | | | | |
|---|---|---|---|---|---|---|---|---|---|
| | Human DLL4 ECD | | | Mouse DLL4 ECD | | | Cyno DLL4 ECD | | |
| Antibody | $K_a$ ($M^{-1}S^{-1}$) E+04 | $K_d$ ($S^{-1}$) E−05 | $K_D$ (nM) | $K_a$ ($M^{-1}S^{-1}$) E+04 | $K_d$ ($S^{-1}$) E−05 | $K_D$ (nM) | $K_a$ ($M^{-1}S^{-1}$) E+04 | $K_d$ ($S^{-1}$) E−05 | $K_D$ (nM) |
| E9.4    | 5.67 | 3.31 | 0.58  | 5.38 | 6.01 | 1.12 | 1.37 | 3.44 | 0.25 |
| E9.11   | 3.63 | 1.74 | 0.48  | 2.77 | 1.39 | 0.5  | 5.31 | 0.89 | 0.17 |
| E9.14   | 3.99 | 36.5 | 9.14  | 3.89 | 13.6 | 3.49 | 5.72 | 38.6 | 6.75 |
| E9.17   | 4.39 | 0.44 | 0.1   | 3.7  | 1.41 | 0.38 | 7.51 | 1.23 | 0.16 |
| E9.18   | 1.57 | 1.84 | 1.18  | 2.32 | 1.68 | 0.73 | 2.63 | 2.63 | 1    |
| E9.19   | 7.49 | 5.17 | 0.69  | 6.7  | 20.6 | 3.07 | 1.92 | 4.86 | 0.25 |
| E9.22   | 3.91 | 33.1 | 8.46  | 3.78 | 13.3 | 3.5  | 5.62 | 35.2 | 6.26 |
| E9.48   | 1.1  | 7.59 | 6.92  | 1.65 | 4.17 | 2.53 | 1.68 | 7.91 | 4.71 |
| E9.65   | 2.59 | 36.3 | 14    | 2.57 | 13.6 | 5.27 | 3.21 | 41.4 | 12.9 |
| E9.66   | 3.26 | 0.25 | 0.078 | 2.89 | 1.44 | 0.50 | 6.55 | 0.91 | 0.14 |
| E9.71   | 3.88 | 3.51 | 0.91  | 3.55 | 21.6 | 6.08 | 7.75 | 3.79 | 0.49 |
| E9.13   | 3.74 | 4.97 | 1.33  | 4.34 | 21.2 | 4.89 | 7.92 | 4.95 | 0.63 |
| E9.16   | 1.29 | 3.15 | 2.45  | 1.83 | 14.8 | 8.1  | 2.49 | 3.79 | 1.52 |
| E9.38   | 1.27 | 3.48 | 2.75  | 1.84 | 17.1 | 9.27 | 2.42 | 3.47 | 1.44 |
| E9.2B   | 35.6 | 0.79 | 0.02  | N/D  | N/D  | N/D  | N/D  | N/D  | N/D  |
| E9.1F   | 21.8 | 1.16 | 0.05  | N/D  | N/D  | N/D  | N/D  | N/D  | N/D  |
| E9-12B  | 15.1 | 0.31 | 0.02  | 8.35 | 1.47 | 0.18 | N/D  | N/D  | N/D  |
| E9-10H  | 10.4 | 5.9  | 0.57  | 6.53 | 2.23 | 0.34 | N/D  | N/D  | N/D  |
| E9-5E   | 15   | 0.6  | 0.04  | 8.9  | 0.2  | 0.02 | N/D  | N/D  | N/D  |
| E9-10C  | 12   | 4.59 | 0.38  | 7.37 | 12.1 | 1.6  | N/D  | N/D  | N/D  |
| E9-10E  | 21.8 | 4.62 | 0.21  | 15.1 | 9.41 | 0.62 | N/D  | N/D  | N/D  |
| E9-7E   | 15.2 | 4.12 | 0.27  | 9.53 | 22.1 | 2.3  | N/D  | N/D  | N/D  |
| A10.K30 | 3.57 | 27.4 | 7.69  | NB   | NB   | NB   | N/D  | N/D  | N/D  |
| A10.K42 | 10   | 40.6 | 4.06  | NB   | NB   | NB   | N/D  | N/D  | N/D  |
| A10.L45 | 4.4  | 3.16 | 0.72  | NB   | NB   | NB   | N/D  | N/D  | N/D  |
| A10.L73 | 5.07 | 0.95 | 0.19  | NB   | NB   | NB   | N/D  | N/D  | N/D  |

MAb = monoclonal antibody;
N/D = not determined,
NB = no binding

TABLE 23

Characterization of selected engineered PROfusion DLL4 antibody.

| | Direct Binding Assays | | | | | | Functional Blockade Assays | | | | | |
|---|---|---|---|---|---|---|---|---|---|---|---|---|
| | Capture ELISA ($EC_{50}$, nM) DLL4 ECD | | | FACS ($EC_{50}$, nM) DLL4 Cells | | | Competition ELISA ($IC_{50}$, nM) DLL4 ECD/ huNotch-1 | | | Competition FACS ($IC_{50}$ nM) huNotch-1/ DLL4 cells | | Inhibition of Notch activation via huDLL4 cells, coculture |
| Antibody | hu | mu | cyno | hu | mu | hu | mu | cyno | hu | mu | ($IC_{50}$ nM) |
| E9-2B  | 0.16 | 0.16 | 0.45 | 1.78  | 0.35  | 2.3 | 2.8 | 2.2 | 2.63  | 0.34 | 2.1 |
| E9-71  | 0.16 | 0.17 | 0.44 | 1.82  | 0.32  | 2.0 | 1.3 | 2.0 | 3.22  | 0.24 | 2.1 |
| E9-19  | 0.17 | 0.17 | 0.46 | 2.79  | 0.54  | 1.8 | 1.3 | 1.5 | 4.90  | 0.44 | 4.4 |
| E9-4   | N/D  | N/D  | N/D  | 1.63  | 0.63  | N/D | N/D | N/D | 4.3   | 0.3  | N/D |
| E9-11  | N/D  | N/D  | N/D  | 4.46  | 1.45  | N/D | N/D | N/D | 14.75 | 2.06 | N/D |
| E9-16  | N/D  | N/D  | N/D  | 1.7   | >50   | N/D | N/D | N/D | 12.6  | 1.1  | N/D |
| E9-17  | N/D  | N/D  | N/D  | 8     | 2.57  | N/D | N/D | N/D | 19.79 | N/D  | 1   |
| E9-22  | N/D  | N/D  | N/D  | 34.34 | 37.35 | N/D | N/D | N/D | 21.05 | 2.63 | N/D |
| E9-38  | N/D  | N/D  | N/D  | 1.66  | 0.13  | N/D | N/D | N/D | 7.76  | 1.2  | N/D |

TABLE 23-continued

Characterization of selected engineered PROfusion DLL4 antibody.

| | Direct Binding Assays | | | | | | Functional Blockade Assays | | | | |
| | Capture ELISA ($EC_{50}$, nM) DLL4 ECD | | | FACS ($EC_{50}$, nM) DLL4 Cells | | Competition ELISA ($IC_{50}$, nM) DLL4 ECD/ huNotch-1 | | | Competition FACS ($IC_{50}$ nM) huNotch-1/ DLL4 cells | | Inhibition of Notch activation via huDLL4 cells, coculture |
|---|---|---|---|---|---|---|---|---|---|---|---|
| Antibody | hu | mu | cyno | hu | mu | hu | mu | cyno | hu | mu | ($IC_{50}$ nM) |
| E9-48 | N/D | N/D | N/D | N/D | N/D | N/D | N/D | N/D | 9.12 | 1.3 | N/D |
| E9-66 | N/D | N/D | N/D | 2.02 | 0.7 | N/D | N/D | N/D | 5.03 | 0.99 | N/D |
| E9-1F | N/D | N/D | N/D | 2.65 | 0.37 | N/D | N/D | N/D | 6.55 | 0.65 | N/D |
| E9-5E | N/D | N/D | N/D | 2.7 | 0.89 | N/D | N/D | N/D | 3.76 | 0.34 | N/D |
| E9-7E | N/D | N/D | N/D | 4.46 | 1.94 | N/D | N/D | N/D | 4 | 0.33 | 0.41 |
| E9-10C | N/D | N/D | N/D | 3.15 | 0.88 | N/D | N/D | N/D | 3.03 | 0.26 | 0.85 |
| E9-10E | N/D | N/D | N/D | 5.1 | 1.19 | N/D | N/D | N/D | 3.83 | 0.36 | N/D |
| E9-10H | N/D | N/D | N/D | 3.52 | 0.82 | N/D | N/D | N/D | 5.65 | 0.6 | N/D |
| E9-12B | N/D | N/D | N/D | 3.34 | 0.71 | N/D | N/D | N/D | 4.44 | 0.37 | N/D |
| E9-71(M) | N/D | N/D | N/D | 0.27 | 0.29 | N/D | N/D | N/D | 2.12 | 0.18 | N/D |
| E9-71(L) | N/D | N/D | N/D | 0.22 | 0.47 | N/D | N/D | N/D | 1.82 | 0.21 | 2.4 |
| E9-71(M)-3 | N/D | N/D | N/D | N/D | N/D | N/D | N/D | N/D | N/D | N/D | 0.65 | hu = human;
mu = murine;
cyno = cynomolgus monkey;
N/D = not determined

Example 8

Physicochemical Properties of Selected PROfusion Antibodies

The identity of monoclonal antibodies specific to DLL4 was determined by mass spectrometry as below.

Mass Spectrometry Analysis of E9-71.

Light chain and heavy chain molecular weight analysis: E9-71 sample was diluted to 1 mg/mL with Milli-Q water. 1 µL of 1 M DTT was added to 20 µL of diluted sample. The sample was incubated at 37° C. for 30 minutes. 1 µL of the reduced samples was injected onto the Agilent 6510 Q-TOF LC/MS system with a Varian Diphenyl column. Buffer A was 0.02% trifluoroacetic acid (TFA), 0.08% formic acid (FA) in water. Buffer B was 0.02% TFA, 0.08% FA in acetonitrile. The gradient started at 5% B, increased to 35% B in 5 minutes, and increased to 38% B in 15 minutes. The gradient then increased to 95% B in 1 minute and stayed at 95% B for 4 minutes, and decreased to 5% B in 1 minute. The flow rate was 50 µL/min. The mass spectrometer was operated at 5 kvolts spray voltage and scan range was from 600 to 3200 mass to charge ratio. The light chain molecular weight of 22649 Dalton matched well with the theoretical value with the amino acid Y being the N-terminus. Three minor peaks were observed at molecular weight 22014 Dalton, 22737 Dalton, and 22937 Dalton. The peak at 22014 Dalton was consistent with N-terminal-6 amino acid fragment. This peak was most probably caused by the in-source fragmentation from the full length light chain, as lowering the mass spectrometer "fragmentor value" can lead to the disappearance of this peak. The 22737 Dalton was consistent with the theoretical value with the amino acid S being the N-terminus. The 22937 Dalton was consistent with the light chain with signal peptide extension of amino acids "LS" on the N-terminal. The heavy chain molecular weights matched well with the theoretical values. The observed molecular weights were 50263 Dalton, 50426 Dalton, and 50588 Dalton, with the difference corresponding to 162 Dalton as result of different glycosylation.

Mass Spectrometry Analysis of E9-71(M).

The same method described in "Mass spectrometry analysis of E9-71" was used to analyze the E9-71(M) sample. The light chain molecular weight of 22645 Dalton matched well with the theoretical value with the amino acid S being the N-terminus. A small peak with molecular weight 22989 Dalton was observed, corresponding to the light chain with signal peptide extension of amino acids "SWA" on the N-terminal. A very small peak with molecular weight 21923 Dalton was also observed, although it was highly likely caused by in-source fragmentation as lowering the mass spectrometer "fragmentor value" led to disappearance of this peak. The heavy chain molecular weights matched well with the theoretical values. The observed molecular weights were 50263 Dalton, 50426 Dalton, and 50588 Dalton, with the difference corresponding to 162 Dalton as result of different glycosylation.

Mass Spectrometry Analysis of E9-71(L).

The same method described in "Mass spectrometry analysis of E9-71" was used to analyze the E9-71(L) sample. The light chain molecular weight of 22645 Dalton matched well with the theoretical value with the amino acid S being the N-terminus. A small peak with molecular weight 22989 Dalton was observed, corresponding to the light chain with signal peptide extension of amino acids "SWA" on the N-terminal. A very small peak with molecular weight 21923 Dalton was also observed, although it was highly likely caused by in-source fragmentation as lowering the mass spectrometer "fragmentor value" led to disappearance of this peak. The heavy chain molecular weights matched well with the theoretical values. The observed molecular weights were 50245 Dalton, 50407 Dalton, and 50569 Dalton, with the difference corresponding to 162 Dalton as result of different glycosylation.

Mass Spectrometry Analysis of E9-71(M)-3.

The same method described in "Mass spectrometry analysis of E9-71" was used to analyze the E9-71(M)-3 sample. The light chain molecular weight of 22558 Dalton matched well with the theoretical value. A very small peak with molecular weight 21923 Dalton was also observed, although it was highly likely caused by in-source fragmentation as lowering the mass spectrometer "fragmentor value" led to disappearance of this peak. The heavy chain molecular weights matched well with the theoretical values. The observed molecular weights were 50263 Dalton, 50426 Dalton, and 50588 Dalton, with the difference corresponding to 162 Dalton as result of different glycosylation.

The solubilities of the antibodies were estimated by polyethylene glycol (PEG) 3000 precipitation. They were also directly determined, i.e., real solubility, by concentrating the antibodies in a specific solution and/or buffer with Amicon centrifugal filters and then observed for any precipitation at 25° C. and 5° C. Stability was inferred by near ultra-violet circular (UV-CD) and differential scanning calorimetry (DSC). Stability to freezing and thawing and at elevated temperatures (accelerated stability) was assessed by size exclusion chromatography (SEC). The detail techniques were described in Example 1.8 and the results are described below: Solubility Estimation by PEG Precipitation Results.

Tables 24 and 26 shows the percentage of PEG 3000 needed to induce precipitation for a series of E9 clones. The clones and the Adalimumab reference were formulated at 0.2 mg/ml. According to the results, clones such as E9-4, E9-14, E9-22, and E9-19 are estimated to have solubilities similar to that of adalimumab (approximately 200 mg/ml) while clones such as E9-11 and E9-17 are estimated to have much lower solubilities.

Table 25 shows the percentage of PEG 3000 needed to induce precipitation for a series of stability engineered E9 clones. The clones and the adalimumab reference were formulated at 0.2 mg/ml. According to the results, clones such as E9-SE1 have the highest solubilities in the series but are not expected to have solubilities similar to that of adalimumab (approximately 200 mg/ml) while clones such as E9-SE5 are estimated to have much lower solubilities.

TABLE 24

Percentage of PEG 3000 needed to induce precipitation for a series of E9 antibodies. (The antibodies were formulated at 0.2 mg/ml.)

| A-Number | Lot # | Antibody | % PEG 3000 |
|---|---|---|---|
| A-1242367.0 | 1718299 | DLL4-E9-11 hIgG1/L | 3.00 |
| A-1242368.0 | 1718300 | DLL4-E9-17 hIgG1/L | 3.00 |
|  |  | E9.1 IgG2 | 3.00 |
| A-1242369.0 | 1718301 | DLL4-E9-18 hIgG1/L | 4.00 |
| A-1242370.0 | 1718302 | DLL4-E9-48 hIgG1/L | 4.00 |
|  |  | E9.1 IgG4 | 5.00 |
|  |  | DLL4-E9-3 hIgG/L | 6.00 |
| A-1242371.0 | 1718303 | DLL4-E9-66 hIgG1/L | 8.00 |
| A-1241120.0 | 1716682 | DLL4-E9-16 hIgG1/L | 10.00 |
| A-1242795.0 | 1718785 | DLL4-E9-13 hIgG1/L | 10.00 |
| A-1241121.0 | 1716683 | DLL4-E9-38 hIgG1/L | 11.00 |
| A-1242800.0 | 1718790 | DLL4-E9-71 hIgG1/L | 11.00 |
| A-1242794.0 | 1718784 | DLL4-E9-4 hIgG1/L | 12.00 |
| A-1242796.0 | 1718786 | DLL4-E9-14 hIgG1/L | 12.00 |
| A-1242798.0 | 1718788 | DLL4-E9-22 hIgG1/L | 12.00 |
| A-1242797.0 | 1718787 | DLL4-E9-19 hIgG1/L | 14.00 |
|  |  | adalimumab | 14.00 |

TABLE 25

Percentage of PEG 3000 needed to induce precipitation for a series of E9 stability engineered antibodies. (The antibodies were formulated at 0.2 mg/ml.)

| Antibody | % PEG 3000 |
|---|---|
| E9-SE5 | 6.00 |
| E9-SE7 | 7.00 |
| E9-SE4 | 7.50 |
| E9-SE8 | 7.50 |
| E9-SE2 | 9.00 |
| E9-SE3 | 9.00 |
| E9-SE6 | 9.50 |
| E9-SE1 | 10.00 |
| (+) E9.1 | 9.00 |
| (+) E9 | 10.50 |
| adalimumab | 13.00 |

TABLE 26

Percentage of PEG 3000 needed to induce precipitation for a series of E9 antibodies. (The antibodies were formulated at 0.2 mg/ml.)

| Antibody | % PEG 3000 |
|---|---|
| E9-2B | 8.00 |
| E9-1F | 8.00 |
| E9 | 10 |
| adalimumab | 14 |

Real Solubility Screening Results: E9, E9-19, E9-71, E9-2B, E9-1F.

Solutions containing 12 mg of E9, E9-71, E9-1F, and E9-19 and 5.5 mg of E9-2B were obtained. E9 is the IgG1 mutant isotype. The volumes of all solutions were reduced below 1 ml by ultra-centrifugation with Amicon 30K 15 ml tubes.

After this step, the following was observed: E9-2B and E9-19 were clear. E9, E9-71, and E9-1F were slightly cloudy.

10 ml of 15 mM histidine buffer at pH 5.03 was added to each tube and the solutions re-concentrated to 1 ml. The solutions were then transferred to Amicon 30K 4 ml tubes and concentrated to as low a volume as possible.

After this step, the following was observed at room temperature:
E9: 163 mg/ml; vol=0.05 ml; pH=5.12
E9-19: 132 mg/ml; vol=0.05 ml; pH=5.06
E9-71: 193 mg/ml; vol=0.05 ml; pH=5.32
E9-2B: 64 mg/ml; vol=0.1 ml; pH=5.29
E9-1F: 100 mg/ml; vol=0.1 ml; pH=5.31

Both E9-2B and E9-1F required much longer to concentrate than the other three. This may suggest that their viscosity is high under the formulation conditions.

The solutions were then placed at 5° C. for two days to assess solubility at this temperature. The following was observed:
E9: remained clear at 5° C. and when brought back to room temperature
E9-71: remained clear at 5° C. and when brought back to room temperature
E9-1F: showed an extremely slight amount of cloudiness at 5° C. that cleared when brought to room temperature after 20 minutes
E9-2B: showed a slight amount of cloudiness at 5° C. that cleared when brought to room temperature after 20 minutes
E9-19: showed apparent cloudiness at 5° C. that cleared when brought to room temperature after 20 minutes.

Real Solubility Screening Results for E9-71.

For E9-71, 4 mg in solution was concentrated with Amicon centrifugal filters to 60 mg/ml. No precipitation or cloudiness was observed at 25° C. nor after storage for 1 day at 5° C.

Tertiary Structure Characterization by Near UV-CD Results.

Near UV-CD was performed on E9, E9-19, E9-71, E9-2B, and E9-1F samples at 1 mg/ml. The profiles of the spectra show a sigmoidal pattern typically observed for properly folded antibodies. From this technique, no indication of misfolding is observed for the antibodies.

Intrinsic Stability Characterization by Differential Scanning Calorimetry (DSC).

DSC was performed on E9, E9-19, E9-71, E9-2B, and E9-1F samples at 1 mg/ml. The results are given in Table 27. The onset is the temperature at which unfolding initiates. Also, an IgG antibody typically shows three unfolding transitions (Tm): unfolding of the intact antibody is associated with the melting of the CH2 domain in the Fc fragment, melting of the CH3 domain in the Fc fragment, and melting of the Fab fragment. Onset values suggest E9, E9-19, and E9-71 are most stable. Typically, clones with higher Tm values are preferred over those with lower values.

TABLE 27

Intrinsic stability of anti-DLL4 E9 clones via DSC at 1 mg/ml.

| Antibody | Tm1 (° C.) | Tm2 (° C.) | Tm3 (° C.) | Onset (° C.) |
|---|---|---|---|---|
| E9 | 64.45 | 72.12 | 80.04 | 54 |
| E9-19 | 65.66 | 77 | — | 56 |
| E9-71 | 65.65 | 75.36 | 81.24 | 54 |
| E9-2B | 64.74 | 80.58 | 83.27 | 52.5 |
| E9-1F | 63.84 | 80.51 | 83.26 | 51.3 |

Evaluation of Stability to Freeze-Thaw Stress

Stability to freeze-thaw stress was evaluated for E9, E9-19, E9-71, E9-2B, and E9-1F samples at 1 mg/ml. Table 28 shows the results of SEC analysis of samples after five freeze-thaw cycles. All the antibodies tested were stable to freeze-thaw stress. No apparent loss of monomer was observed even after 5 freeze-thaw cycles.

TABLE 28

Percentage of monomer species quantitated by SEC before freezing at −80° C. and after five cycles of freezing at −80° C. and thawing at 30° C. in water bath for anti-DLL4 clones.

| Antibody | % monomer before freezing | % monomer after 5th freeze-thaw cycle |
|---|---|---|
| E9 | 99.2 | 99.3 |
| E9-19 | 99.3 | 99.1 |
| E9-71 | 96.9 | 96.8 |
| E9-2B | 99.0 | 98.9 |
| E9-1F | 98.6 | 98.5 |

Evaluation of Stability at Elevated Temperatures (Accelerated Stability).

Stability at elevated temperatures was evaluated for E9, E9-19, E9-71, E9-2B, and E9-1F samples at 1 mg/ml. Table 29 shows the results of SEC analysis of samples at time zero and after 7 and 21 days at 40° C. and 50° C. The degradation kinetics for all of the antibodies revealed an approximately 8% reduction in monomer percentage after 21 days 50° C.

TABLE 29

Percentage of different species quantitated by SEC for anti-DLL4 clones at time zero and after incubation for 7 and 21 days at 40° C. and 50° C. (Samples were formulated at 1 mg/ml.)

| Antibody | % monomer at time zero | % monomer at 7 days at 40° C. | % monomer at 7 days at 50° C. | % monomer at 21 days at 40° C. | % monomer at 21 days at 50° C. |
|---|---|---|---|---|---|
| E9 | 99.2 | 98.6 | 86.8 | 90.9 | 88.1 |
| E9-19 | 99.3 | 98.7 | 96.8 | 97.4 | 91.9 |
| E9-71 | 96.9 | 96.4 | 95.4 | 95.0 | 91.0 |
| E9-2B | 99.0 | 98.6 | 97.0 | 97.1 | 92.4 |
| E9-1F | 98.6 | 98.2 | 96.5 | 96.8 | 91.9 |

| Antibody | % aggregate at time zero | % aggregate at 7 days at 40° C. | % aggregate at 7 days at 50° C. | % aggregate at 21 days at 40° C. | % aggregate at 21 days at 50° C. |
|---|---|---|---|---|---|
| E9 | 0.3 | 0.3 | 0.3 | 0.5 | 0.6 |
| E9-19 | 0.3 | 0.3 | 0.4 | 0.7 | 1.4 |
| E9-71 | 2.4 | 2.3 | 1.8 | 2.9 | 2.8 |
| E9-2B | 0.5 | 0.4 | 0.5 | 0.9 | 1.7 |
| E9-1F | 0.3 | 0.3 | 0.3 | 0.6 | 1.6 |

| Antibody | % fragment at time zero | % fragment at 7 days at 40° C. | % fragment at 7 days at 50° C. | % fragment at 21 days at 40° C. | % fragment at 21 days at 50° C. |
|---|---|---|---|---|---|
| E9 | 0.5 | 1.2 | 12.9 | 8.7 | 11.3 |
| E9-19 | 0.4 | 1.0 | 2.8 | 1.9 | 6.7 |
| E9-71 | 0.7 | 1.3 | 2.8 | 2.1 | 6.2 |
| E9-2B | 0.6 | 1.0 | 2.5 | 2.0 | 5.9 |
| E9-1F | 1.1 | 1.5 | 3.2 | 2.5 | 6.5 |

Example 9

Rodent PK Assessment of Anti-DLL4 Antibodies

To assess pharmacokinetics properties of anti-DLL4 antibodies, SCID-Beige mice (n=3 per antibody) were administered a single intraperitoneal (IP) dose of antibody at either 5 or 30 mg/kg concentration, depending on cross-reactivity of antibody to murine DLL4. Longitudinal serum samples (5 µl of whole blood diluted 1:50 in HBS-EP+ buffer per time point) were collected from each animal over 21 days. Serum concentrations were determined using a DLL4-specific Biacore platform. Briefly, human DLL4 was immobilized to a sensorchip and samples were injected over the flowcell at 5 µl per minute for 5 minutes with the resulting binding levels measured and compared to standards. Serum concentration time profiles were used to estimate the pharmacokinetic parameters of $C_{max}$ (peak serum concentration), CL (clearance), and $t_{1/2}$ (antibody half life), summarized in Table 30. For both E9 and A10 PROfusion antibodies, their pharmacokinetics properties were improved through CDR-engineering during the process of affinity maturation.

TABLE 30

Pharmacokinetic parameters of anti-DLL4 antibodies in SCID-beige mice.

| Antibody | Dose (mg/kg) | Cmax (µg/mL) | CL (mL/hr/kg) | $t_{1/2}$ (d) |
|---|---|---|---|---|
| E9 | 30 | 201 | 3.10 | 1.3 |
| E9-10C | 30 | 165 | 0.82 | 5.2 |
| E9-10E | 30 | 263 | 0.97 | 3.8 |
| E9-10H | 30 | 235 | 1.49 | 3.1 |
| E9-12B | 30 | 146 | 1.32 | 3.8 |
| E9-19 | 30 | 179 | 1.08 | 4.4 |
| E9-1F | 30 | 269 | 0.89 | 4.2 |
| E9-2B | 30 | 165 | 0.65 | 5.5 |
| E9-5E | 30 | 234 | 0.95 | 3.0 |
| E9-66 | 30 | 114 | 2.90 | 1.9 |
| E9-71 | 30 | 102 | 1.10 | 4.2 |
| E9-71(L) | 30 | 145 | 0.83 | 4.1 |
| E9-71(M) | 30 | 113 | 1.07 | 4.3 |
| E9-7E | 30 | 130 | 1.23 | 5.8 |
| A10 | 5 | 10.5 | 5.80 | 3.1 |
| A10.K30 | 5 | 15.6 | 0.69 | 17.7 |
| A10.K42 | 5 | 12.5 | 0.93 | 13.8 |
| A10.L45 | 5 | 18.6 | 0.65 | 13.4 |

Example 10

Anti-DLL4 Antibody Treatment Increased Endothelial Cell Sprouting In Vitro

Fibrin gel beads sprouting assay was carried out to examine the in vitro angiogenesis activity of HUVEC (passage 2-3, Lonza) as described (Nakatsu et al., *Microvasc. Res.*, 66: 102-112 (2003)). Briefly, fibrinogen solution was reconstituted with aprotinin (4 U/ml) and thrombin (50 U/ml). Cytodex 3 beads (Amersham Pharmacia Biotech) were coated with 350 to 400 HUVECs per bead for overnight. About 20 HUVEC-coated beads were imbedded in the fibrin clot per well of a 96-well tissue culture plate. Conditioned medium derived from normal human fibroblasts (NHLF, Lonza) at 80% confluence was plated on top of the gel. DLL4 antibody and control antibody KLH at 15 µg/ml were added onto the well. At day 10 and 12, images were taken with inverted microscope and Nikon CCD camera. DLL4 inhibition with E9 and A10 antibodies results in enhancement of endothelial cell sprouting in vitro (data not shown).

Example 11

DLL4 Antibody Treatment Inhibited Tumor Growth In Vivo

The effect of anti-DLL4 antibodies on tumor growth was evaluated on subcutaneous Calu-6 xenograft tumors implanted in SCID-Beige mice. Briefly, $2 \times 10^6$ cells were inoculated subcutaneously into the right hind flank of female SCID-Beige mice. Tumors were allowed to establish for 14-18 days, at which point tumor volume was determined using electronic caliper measurements. Tumor size was calculated using the formula: $L \times W^2/2$. Mice were allocated into treatment groups (n=10 per group) so that each cohort of animals had equivalent mean tumor volume prior to initiation of therapy (typically between 180 and 250 mm³) Animals were then dosed intraperitoneally twice a week for two weeks (total of 4 doses) with anti-DLL4 antibodies. Tumor volume was measured on average twice a week for the duration of the experiment until the mean tumor volume in each group reached an endpoint of ≥2,000 mm³. Results are shown in Table 31. For E9 series of PROfusion antibodies, those with improved pharmacokinetics (as shown in Example 9) tend to have stronger anti-tumor activity in vivo.

TABLE 31

Efficacy of anti-DLL4 antibodies in the Calu-6 human non-small cell lung cancer xenograft model.

| Treatment | Dose Route, Regimen | % T/C a | % ILS b |
|---|---|---|---|
| E9 | 10 mg/kg IP, 2X/week X2 | 43** | 52** |
| E9-10C | 10 mg/kg IP, 2X/week X2 | 26** | 81** |
| E9-2B | 10 mg/kg IP, 2X/week X2 | 28** | 76** |
| E9-10E | 10 mg/kg IP, 2X/week X2 | 30** | 70** |
| E9-19 | 10 mg/kg IP, 2X/week X2 | 31** | 64** |
| E9-5E | 10 mg/kg IP, 2X/week X2 | 30** | 57** |
| E9-71 | 10 mg/kg IP, 2X/week X2 | 34** | 63** |
| E9-1F | 10 mg/kg IP, 2X/week X2 | 34** | 57** |
| E9-12B | 10 mg/kg IP, 2X/week X2 | 38** | 52** |
| E9-7E | 10 mg/kg IP, 2X/week X2 | 38** | 44** |
| E9-10H | 10 mg/kg IP, 2X/week X2 | 41** | 52** |
| E9-66 | 10 mg/kg IP, 2X/week X2 | 43** | 32* | a. % T/C = mean tumor volume of treatment group/tumor volume of treatment control group × 100. P values (as indicated by asterisks) are derived from Student's T test comparison of treatment group vs. treatment control group. Based on day 25/26/27 measurements.
b. % ILS = (T − C)/C × 100, where T = median time to endpoint of treatment group and C = median time to endpoint of treatment control group. P values (as indicated by asterisks) derived from Kaplan Meier log-rank comparison of treatment group vs. treatment control group. Based on an endpoint of 2000 mm³.
*p < 0.05;
**p < 0.01

The contents of all cited references (including literature references, patents, patent applications, and websites) that maybe cited throughout this application are hereby expressly incorporated by reference in their entirety for any purpose, as are the references cited therein.

EQUIVALENTS

The invention may be embodied in other specific forms without departing from the spirit or essential characteristics thereof. The foregoing embodiments are therefore to be considered in all respects illustrative rather than limiting of the invention described herein. Scope of the invention is thus indicated by the appended claims rather than by the foregoing description, and all changes that come within the meaning and range of equivalency of the claims are therefore intended to be embraced herein.

What is claimed is:

1. A method for treating a subject having a disease or a disorder characterized by aberrant DLL4 expression or in which DLL4 is detrimental, said method comprising administering to said subject an effective amount of a binding protein capable of binding human DLL4, said binding protein comprising an antigen binding domain comprising six complementarity determining regions (CDRs): CDR-H1, CDR-H2, CDR-H3, CDR-L1, CDR-L2, and CDR-L3, wherein:

CDR-H1 is selected from the group consisting of:
  residues 31-37 of SEQ ID NO:1;
  SEQ ID NO:117;
  SEQ ID NO:121;
  SEQ ID NO:125;
  SEQ ID NO:129;
  SEQ ID NO:133;
  SEQ ID NO:137;
  SEQ ID NO:141;
  SEQ ID NO:145;
  SEQ ID NO:149;
  SEQ ID NO:153;
  SEQ ID NO:157;
  SEQ ID NO:161;
  SEQ ID NO:165;
  SEQ ID NO:169;
  SEQ ID NO:173;
  SEQ ID NO:177;
  SEQ ID NO:181;
  SEQ ID NO:185;
  SEQ ID NO:189;
  SEQ ID NO:193;
  SEQ ID NO:197;
  SEQ ID NO:201;
  SEQ ID NO:205;
  SEQ ID NO:209;
  SEQ ID NO:213;
  residues 31-37 of SEQ ID NO:334;
  residues 31-37 of SEQ ID NO:336;
  residues 31-37 of SEQ ID NO:338;
  residues 31-37 of SEQ ID NO:340;
  residues 31-37 of SEQ ID NO:342;
  residues 31-37 of SEQ ID NO:344;
  residues 31-37 of SEQ ID NO:346;
  residues 31-37 of SEQ ID NO:348;
  residues 31-37 of SEQ ID NO:350;
  residues 31-37 of SEQ ID NO:352;
  residues 31-37 of SEQ ID NO:354;
  residues 31-37 of SEQ ID NO:356;
  residues 31-37 of SEQ ID NO:358; and
  residues 31-37 of SEQ ID NO:360;

CDR-H2 is selected from the group consisting of:
  residues 52-67 of SEQ ID NO:1;
  SEQ ID NO:118;
  SEQ ID NO:122;
  SEQ ID NO:126;
  SEQ ID NO:130;
  SEQ ID NO:134;
  SEQ ID NO:138;
  SEQ ID NO:142;
  SEQ ID NO:146;
  SEQ ID NO:150;
  SEQ ID NO:154;
  SEQ ID NO:158;
  SEQ ID NO:162;
  SEQ ID NO:166;
  SEQ ID NO:170;
  SEQ ID NO:174;
  SEQ ID NO:178;
  SEQ ID NO:182;
  SEQ ID NO:186;
  SEQ ID NO:190;
  SEQ ID NO:194;
  SEQ ID NO:198;
  SEQ ID NO:202;
  SEQ ID NO:206;
  SEQ ID NO:210;
  SEQ ID NO:214;
  residues 52-67 of SEQ ID NO:334;
  residues 52-67 of SEQ ID NO:336;
  residues 52-67 of SEQ ID NO:338;
  residues 52-67 of SEQ ID NO:340;
  residues 52-67 of SEQ ID NO:342;
  residues 52-67 of SEQ ID NO:344;
  residues 52-67 of SEQ ID NO:346;
  residues 52-67 of SEQ ID NO:348;
  residues 52-67 of SEQ ID NO:350;
  residues 52-67 of SEQ ID NO:352;
  residues 52-67 of SEQ ID NO:354;
  residues 52-67 of SEQ ID NO:356;
  residues 52-67 of SEQ ID NO:358; and
  residues 52-67 of SEQ ID NO:360;

CDR-H3 is selected from the group consisting of:
  residues 100-110 of SEQ ID NO:1;
  SEQ ID NO:119;
  SEQ ID NO:123;
  SEQ ID NO:127;
  SEQ ID NO:131;
  SEQ ID NO:135;
  SEQ ID NO:139;
  SEQ ID NO:143;
  SEQ ID NO:147;
  SEQ ID NO:151;
  SEQ ID NO:155;
  SEQ ID NO:159;
  SEQ ID NO:163;
  SEQ ID NO:167;
  SEQ ID NO:171;
  SEQ ID NO:175;
  SEQ ID NO:179;

SEQ ID NO:183;
SEQ ID NO:187;
SEQ ID NO:191;
SEQ ID NO:195;
SEQ ID NO:199;
SEQ ID NO:203;
SEQ ID NO:207;
SEQ ID NO:211;
SEQ ID NO:215;
residues 100-110 of SEQ ID NO:334;
residues 100-110 of SEQ ID NO:336;
residues 100-110 of SEQ ID NO:338;
residues 100-110 of SEQ ID NO:340;
residues 100-110 of SEQ ID NO:342;
residues 100-110 of SEQ ID NO:344;
residues 100-110 of SEQ ID NO:346;
residues 100-110 of SEQ ID NO:348;
residues 100-110 of SEQ ID NO:350;
residues 100-110 of SEQ ID NO:352;
residues 100-110 of SEQ ID NO:354;
residues 100-110 of SEQ ID NO:356;
residues 100-110 of SEQ ID NO:358; and
residues 100-110 of SEQ ID NO:360;
CDR-L1 is selected from the group consisting of:
residues 23-33 of SEQ ID NO:111;
SEQ ID NO:217;
SEQ ID NO:221;
SEQ ID NO:225;
SEQ ID NO:229;
SEQ ID NO:233;
SEQ ID NO:237;
SEQ ID NO:241;
SEQ ID NO:245;
SEQ ID NO:249;
SEQ ID NO:253;
SEQ ID NO:257;
SEQ ID NO:261;
SEQ ID NO:265;
SEQ ID NO:269;
SEQ ID NO:273;
SEQ ID NO:277;
SEQ ID NO:281;
SEQ ID NO:285;
SEQ ID NO:289;
SEQ ID NO:293;
SEQ ID NO:297;
SEQ ID NO:301;
SEQ ID NO:305;
SEQ ID NO:309;
SEQ ID NO:313;
residues 23-33 of SEQ ID NO:335;
residues 23-33 of SEQ ID NO:337;
residues 23-33 of SEQ ID NO:339;
residues 23-33 of SEQ ID NO:341;
residues 23-33 of SEQ ID NO:343;
residues 24-34 of SEQ ID NO:345;
residues 23-33 of SEQ ID NO:347;
residues 24-34 of SEQ ID NO:349;
residues 24-34 of SEQ ID NO:351;
residues 24-34 of SEQ ID NO:353;
residues 24-34 of SEQ ID NO:355;
residues 23-33 of SEQ ID NO:357;
residues 23-33 of SEQ ID NO:359; and
residues 23-33 of SEQ ID NO:361;
CDR-L2 is selected from the group consisting of:
residues 49-55 of SEQ ID NO:111;
SEQ ID NO:230;
SEQ ID NO:234;
SEQ ID NO:238;
SEQ ID NO:242;
SEQ ID NO:246;
SEQ ID NO:250;
SEQ ID NO:254;
SEQ ID NO:258;
SEQ ID NO:262;
SEQ ID NO:266;
SEQ ID NO:270;
SEQ ID NO:218;
SEQ ID NO:222;
SEQ ID NO:226;
SEQ ID NO:274;
SEQ ID NO:278;
SEQ ID NO:302;
SEQ ID NO:294;
SEQ ID NO:282;
SEQ ID NO:290;
SEQ ID NO:298;
SEQ ID NO:286;
SEQ ID NO:306;
SEQ ID NO:310;
SEQ ID NO:314;
residues 49-55 of SEQ ID NO:335;
residues 49-55 of SEQ ID NO:337;
residues 49-55 of SEQ ID NO:339;
residues 49-55 of SEQ ID NO:341;
residues 49-55 of SEQ ID NO:343;
residues 50-56 of SEQ ID NO:345;
residues 49-55 of SEQ ID NO:347;
residues 50-56 of SEQ ID NO:349;
residues 50-56 of SEQ ID NO:351;
residues 50-56 of SEQ ID NO:353;
residues 50-56 of SEQ ID NO:355;
residues 49-55 of SEQ ID NO:357;
residues 49-55 of SEQ ID NO:359; and
residues 49-55 of SEQ ID NO:361;
and
CDR-L3 is selected from the group consisting of:
residues 88-96 of SEQ ID NO:111;
SEQ ID NO:231;
SEQ ID NO:235;
SEQ ID NO:239;
SEQ ID NO:243;
SEQ ID NO:247;
SEQ ID NO:251;
SEQ ID NO:255;
SEQ ID NO:259;
SEQ ID NO:263;
SEQ ID NO:267;
SEQ ID NO:271;
SEQ ID NO:219;
SEQ ID NO:223;
SEQ ID NO:227;
SEQ ID NO:275;
SEQ ID NO:279;
SEQ ID NO:303;
SEQ ID NO:295;
SEQ ID NO:283;
SEQ ID NO:291;
SEQ ID NO:299;
SEQ ID NO:287;
SEQ ID NO:307;
SEQ ID NO:311;
SEQ ID NO:315;
residues 88-96 of SEQ ID NO:335;

residues 88-96 of SEQ ID NO:337;
residues 88-96 of SEQ ID NO:339;
residues 88-96 of SEQ ID NO:341;
residues 88-96 of SEQ ID NO:343;
residues 89-97 of SEQ ID NO:345;
residues 88-96 of SEQ ID NO:347;
residues 89-97 of SEQ ID NO:349;
residues 89-97 of SEQ ID NO:351;
residues 89-97 of SEQ ID NO:353;
residues 89-97 of SEQ ID NO:355;
residues 88-96 of SEQ ID NO:357;
residues 88-96 of SEQ ID NO:359; and
residues 88-96 of SEQ ID NO:361.

2. The method according to claim 1, wherein said binding protein comprises a variable domain CDR set of three CDRs, wherein the variable domain CDR set is selected from the group of variable domain CDR sets consisting of:

VH E9 CDR Set
  CDR-H1: residues 31-37 of SEQ ID NO:1
  CDR-H2: residues 52-67 of SEQ ID NO:1 and
  CDR-H3: residues 100-110 of SEQ ID NO:1
VL E9 CDR Set
  CDR-L1: residues 23-33 of SEQ ID NO:111
  CDR-L2: residues 49-55 of SEQ ID NO:111 and
  CDR-L3: residues 88-96 of SEQ ID NO:111
VH E9.4 CDR Set
  CDR-H1: SEQ ID NO:117
  CDR-H2: SEQ ID NO:118 and
  CDR-H3: SEQ ID NO:119
VL E9.4 CDR Set
  CDR-L1: SEQ ID NO:229
  CDR-L2: SEQ ID NO:230 and
  CDR-L3: SEQ ID NO:231
VH E9.11 CDR Set
  CDR-H1: SEQ ID NO:121
  CDR-H2: SEQ ID NO:122 and
  CDR-H3: SEQ ID NO:123
VL E9.11 CDR Set
  CDR-L1: SEQ ID NO:233
  CDR-L2: SEQ ID NO:234 and
  CDR-L3: SEQ ID NO:235
VH E9.14 CDR Set
  CDR-H1: SEQ ID NO:125
  CDR-H2: SEQ ID NO:126 and
  CDR-H3: SEQ ID NO:127
VL E9.14 CDR Set
  CDR-L1: SEQ ID NO:237
  CDR-L2: SEQ ID NO:238 and
  CDR-L3: SEQ ID NO:239
VH E9.17 CDR Set
  CDR-H1: SEQ ID NO:129
  CDR-H2: SEQ ID NO:130 and
  CDR-H3: SEQ ID NO:131
VL E9.17 CDR Set
  CDR-L1: SEQ ID NO:241
  CDR-L2: SEQ ID NO:242 and
  CDR-L3: SEQ ID NO:243
VH E9.18 CDR Set
  CDR-H1: SEQ ID NO:133
  CDR-H2: SEQ ID NO:134 and
  CDR-H3: SEQ ID NO:135
VL E9.18 CDR Set
  CDR-L1: SEQ ID NO:245
  CDR-L2: SEQ ID NO:246 and
  CDR-L3: SEQ ID NO:247
VH E9.19 CDR Set
  CDR-H1: SEQ ID NO:137
  CDR-H2: SEQ ID NO:138 and
  CDR-H3: SEQ ID NO:139
VL E9.19 CDR Set
  CDR-L1: SEQ ID NO:249
  CDR-L2: SEQ ID NO:250 and
  CDR-L3: SEQ ID NO:251
VH E9.22 CDR Set
  CDR-H1: SEQ ID NO:141
  CDR-H2: SEQ ID NO:142 and
  CDR-H3: SEQ ID NO:143
VL E9.22 CDR Set
  CDR-L1: SEQ ID NO:253
  CDR-L2: SEQ ID NO:254 and
  CDR-L3: SEQ ID NO:255
VH E9.48 CDR Set
  CDR-H1: SEQ ID NO:145
  CDR-H2: SEQ ID NO:146 and
  CDR-H3: SEQ ID NO:147
VL E9.48 CDR Set
  CDR-L1: SEQ ID NO:257
  CDR-L2: SEQ ID NO:258 and
  CDR-L3: SEQ ID NO:259
VH E9.65 CDR Set
  CDR-H1: SEQ ID NO:149
  CDR-H2: SEQ ID NO:150 and
  CDR-H3: SEQ ID NO:151
VL E9.65 CDR Set
  CDR-L1: SEQ ID NO:261
  CDR-L2: SEQ ID NO:262 and
  CDR-L3: SEQ ID NO:263
VH E9.66 CDR Set
  CDR-H1: SEQ ID NO:153
  CDR-H2: SEQ ID NO:154 and
  CDR-H3: SEQ ID NO:155
VL E9.66 CDR Set
  CDR-L1: SEQ ID NO:265
  CDR-L2: SEQ ID NO:266 and
  CDR-L3: SEQ ID NO:267
VH E9.71 CDR Set
  CDR-H1: SEQ ID NO:157
  CDR-H2: SEQ ID NO:158 and
  CDR-H3: SEQ ID NO:159
VL E9.71 CDR Set
  CDR-L1: SEQ ID NO:269
  CDR-L2: SEQ ID NO:270 and
  CDR-L3: SEQ ID NO:271
VH E9.13 CDR Set
  CDR-H1: SEQ ID NO:161
  CDR-H2: SEQ ID NO:162 and
  CDR-H3: SEQ ID NO:163
VL E9.13 CDR Set
  CDR-L1: SEQ ID NO:217
  CDR-L2: SEQ ID NO:218 and
  CDR-L3: SEQ ID NO:219
VH E9.16 CDR Set
  CDR-H1: SEQ ID NO:165
  CDR-H2: SEQ ID NO:166 and
  CDR-H3: SEQ ID NO:167
VL E9.16 CDR Set
  CDR-L1: SEQ ID NO:221
  CDR-L2: SEQ ID NO:222 and
  CDR-L3: SEQ ID NO:223
VH E9.38 CDR Set
  CDR-H1: SEQ ID NO:169
  CDR-H2: SEQ ID NO:170 and
  CDR-H3: SEQ ID NO:171
VL E9.38 CDR Set CDR-L1: SEQ ID NO:225
CDR-L2: SEQ ID NO:226 and
CDR-L3: SEQ ID NO:227
VH E9.2B CDR Set
 CDR-H1: SEQ ID NO:173
 CDR-H2: SEQ ID NO:174 and
 CDR-H3: SEQ ID NO:175
VL E9.2B CDR Set
 CDR-L1: SEQ ID NO:273
 CDR-L2: SEQ ID NO:274 and
 CDR-L3: SEQ ID NO:275
VH E9.1F CDR Set
 CDR-H1: SEQ ID NO:177
 CDR-H2: SEQ ID NO:178 and
 CDR-H3: SEQ ID NO:179
VL E9.1F CDR Set
 CDR-L1: SEQ ID NO:277
 CDR-L2: SEQ ID NO:278 and
 CDR-L3: SEQ ID NO:279
VH E9.10H CDR Set
 CDR-H1: SEQ ID NO:181
 CDR-H2: SEQ ID NO:182 and
 CDR-H3: SEQ ID NO:183
VL E9.10H CDR Set
 CDR-L1: SEQ ID NO:301
 CDR-L2: SEQ ID NO:302 and
 CDR-L3: SEQ ID NO:303
VH E9.5E CDR Set
 CDR-H1: SEQ ID NO:185
 CDR-H2: SEQ ID NO:186 and
 CDR-H3: SEQ ID NO:187
VL E9.5E CDR Set
 CDR-L1: SEQ ID NO:293
 CDR-L2: SEQ ID NO:294 and
 CDR-L3: SEQ ID NO:295
VH E9.10C CDR Set
 CDR-H1: SEQ ID NO:189
 CDR-H2: SEQ ID NO:190 and
 CDR-H3: SEQ ID NO:191
VL E9.10C CDR Set
 CDR-L1: SEQ ID NO:281
 CDR-L2: SEQ ID NO:282 and
 CDR-L3: SEQ ID NO:283
VH E9.7E CDR Set
 CDR-H1: SEQ ID NO:193
 CDR-H2: SEQ ID NO:194 and
 CDR-H3: SEQ ID NO:195
VL E9.7E CDR Set
 CDR-L1: SEQ ID NO:289
 CDR-L2: SEQ ID NO:290 and
 CDR-L3: SEQ ID NO:291
VH E9.12B CDR Set
 CDR-H1: SEQ ID NO:197
 CDR-H2: SEQ ID NO:198 and
 CDR-H3: SEQ ID NO:199
VL E9.12B CDR Set
 CDR-L1: SEQ ID NO:297
 CDR-L2: SEQ ID NO:298 and
 CDR-L3: SEQ ID NO:299
VH E9.10E CDR Set
 CDR-H1: SEQ ID NO:201
 CDR-H2: SEQ ID NO:202 and
 CDR-H3: SEQ ID NO:203
VL E9.10E CDR Set
 CDR-L1: SEQ ID NO:285
 CDR-L2: SEQ ID NO:286 and
 CDR-L3: SEQ ID NO:287
VH E9.6A CDR Set
 CDR-H1: SEQ ID NO:205
 CDR-H2: SEQ ID NO:206 and
 CDR-H3: SEQ ID NO:207
VL E9.6A CDR Set
 CDR-L1: SEQ ID NO:305
 CDR-L2: SEQ ID NO:306 and
 CDR-L3: SEQ ID NO:307
VH E9.7A CDR Set
 CDR-H1: SEQ ID NO:209
 CDR-H2: SEQ ID NO:210 and
 CDR-H3: SEQ ID NO:211
VL E9.7 A CDR Set
 CDR-L1: SEQ ID NO:309
 CDR-L2: SEQ ID NO:310 and
 CDR-L3: SEQ ID NO:311
VH E9.8H CDR Set
 CDR-H1: SEQ ID NO:213
 CDR-H2: SEQ ID NO:214 and
 CDR-H3: SEQ ID NO:215
VL E9.8H CDR Set
 CDR-L1: SEQ ID NO:313
 CDR-L2: SEQ ID NO:314 and
 CDR-L3: SEQ ID NO:315
VH E9.1 CDR Set
 CDR-H1: residues 31-37 of SEQ ID NO:334
 CDR-H2: residues 52-67 of SEQ ID NO:334 and
 CDR-H3: residues 100-110 of SEQ ID NO:334
VL E9.1 CDR Set
 CDR-L1: residues 23-33 of SEQ ID NO:335
 CDR-L2: residues 49-55 of SEQ ID NO:335 and
 CDR-L3: residues 88-96 of SEQ ID NO:335
VH E9-SE1 CDR Set
 CDR-H1: residues 31-37 of SEQ ID NO:336
 CDR-H2: residues 52-67 of SEQ ID NO:336 and
 CDR-H3: residues 100-110 of SEQ ID NO:336
VL E9-SE1 CDR Set
 CDR-L1: residues 23-33 of SEQ ID NO:337
 CDR-L2: residues 49-55 of SEQ ID NO:337 and
 CDR-L3: residues 88-96 of SEQ ID NO:337
VH E9-SE2 CDR Set
 CDR-H1: residues 31-37 of SEQ ID NO:338
 CDR-H2: residues 52-67 of SEQ ID NO:338 and
 CDR-H3: residues 100-110 of SEQ ID NO:338
VL E9-SE2 CDR Set
 CDR-L1: residues 23-33 of SEQ ID NO:339
 CDR-L2: residues 49-55 of SEQ ID NO:339 and
 CDR-L3: residues 88-96 of SEQ ID NO:339
VH E9-SE3 CDR Set
 CDR-H1: residues 31-37 of SEQ ID NO:340
 CDR-H2: residues 52-67 of SEQ ID NO:340 and
 CDR-H3: residues 100-110 of SEQ ID NO:340
VL E9-SE3 CDR Set
 CDR-L1: residues 23-33 of SEQ ID NO:341
 CDR-L2: residues 49-55 of SEQ ID NO:341 and
 CDR-L3: residues 88-96 of SEQ ID NO:341
VH E9-SE4 CDR Set
 CDR-H1: residues 31-37 of SEQ ID NO:342
 CDR-H2: residues 52-67 of SEQ ID NO:342 and
 CDR-H3: residues 100-110 of SEQ ID NO:342
VL E9-SE4 CDR Set
 CDR-L1: residues 23-33 of SEQ ID NO:343
 CDR-L2: residues 49-55 of SEQ ID NO:343 and
 CDR-L3: residues 88-96 of SEQ ID NO:343
VH E9-SE5 CDR Set
 CDR-H1: residues 31-37 of SEQ ID NO:344
 CDR-H2: residues 52-67 of SEQ ID NO:344 and CDR-H3: residues 100-110 of SEQ ID NO:344
VL E9-SE5 CDR Set
  CDR-L1: residues 24-34 of SEQ ID NO:345
  CDR-L2: residues 50-56 of SEQ ID NO:345 and
  CDR-L3: residues 89-97 of SEQ ID NO:345
VH E9-SE6 CDR Set
  CDR-H1: residues 31-37 of SEQ ID NO:346
  CDR-H2: residues 52-67 of SEQ ID NO:346 and
  CDR-H3: residues 100-110 of SEQ ID NO:346
VL E9-SE6 CDR Set
  CDR-L1: residues 23-33 of SEQ ID NO:347
  CDR-L2: residues 49-55 of SEQ ID NO:347 and
  CDR-L3: residues 88-96 of SEQ ID NO:347
VH E9-SE7 CDR Set
  CDR-H1: residues 31-37 of SEQ ID NO:348
  CDR-H2: residues 52-67 of SEQ ID NO:348 and
  CDR-H3: residues 100-110 of SEQ ID NO:348
VL E9-SE7 CDR Set
  CDR-L1: residues 24-34 of SEQ ID NO:349
  CDR-L2: residues 50-56 of SEQ ID NO:349 and
  CDR-L3: residues 89-97 of SEQ ID NO:349
VH E9-SE8 CDR Set
  CDR-H1: residues 31-37 of SEQ ID NO:350
  CDR-H2: residues 52-67 of SEQ ID NO:350 and
  CDR-H3: residues 100-110 of SEQ ID NO:350
VL E9-SE8 CDR Set
  CDR-L1: residues 24-34 of SEQ ID NO:351
  CDR-L2: residues 50-56 of SEQ ID NO:351 and
  CDR-L3: residues 89-97 of SEQ ID NO:351
VH E9-FR1 CDR Set
  CDR-H1: residues 31-37 of SEQ ID NO:352
  CDR-H2: residues 52-67 of SEQ ID NO:352 and
  CDR-H3: residues 100-110 of SEQ ID NO:352
VL E9-FR1 CDR Set
  CDR-L1: residues 24-34 of SEQ ID NO:353
  CDR-L2: residues 50-56 of SEQ ID NO:353 and
  CDR-L3: residues 89-97 of SEQ ID NO:353
VH E9-FR2 CDR Set
  CDR-H1: residues 31-37 of SEQ ID NO:354
  CDR-H2: residues 52-67 of SEQ ID NO:354 and
  CDR-H3: residues 100-110 of SEQ ID NO:354
VL E9-FR2 CDR Set
  CDR-L1: residues 24-34 of SEQ ID NO:355
  CDR-L2: residues 50-56 of SEQ ID NO:355 and
  CDR-L3: residues 89-97 of SEQ ID NO:355
VH E9.71 CDR Set
  CDR-H1: residues 31-37 of SEQ ID NO:356
  CDR-H2: residues 52-67 of SEQ ID NO:356 and
  CDR-H3: residues 100-110 of SEQ ID NO:356
VL E9.71 CDR Set
  CDR-L1: residues 23-33 of SEQ ID NO:357
  CDR-L2: residues 49-55 of SEQ ID NO:357 and
  CDR-L3: residues 88-96 of SEQ ID NO:357
VH E9.71(M) CDR Set
  CDR-H1: residues 31-37 of SEQ ID NO:358
  CDR-H2: residues 52-67 of SEQ ID NO:358 and
  CDR-H3: residues 100-110 of SEQ ID NO:358
VL E9.71(M) CDR Set
  CDR-L1: residues 23-33 of SEQ ID NO:359
  CDR-L2: residues 49-55 of SEQ ID NO:359 and
  CDR-L3: residues 88-96 of SEQ ID NO:359
VH E9.71(L) CDR Set
  CDR-H1: residues 31-37 of SEQ ID NO:360
  CDR-H2: residues 52-67 of SEQ ID NO:360 and
  CDR-H3: residues 100-110 of SEQ ID NO:360 and
VL E9.71(L) CDR Set
  CDR-L1: residues 23-33 of SEQ ID NO:361
  CDR-L2: residues 49-55 of SEQ ID NO:361 and
  CDR-L3: residues 88-96 of SEQ ID NO:361.

3. The method according to claim 2, wherein said binding protein comprises at least two variable domain CDR sets selected from the group consisting of:
  VH E9 CDR Set and VL E9 CDR Set,
  VH E9.4 CDR Set and VL E9.4 CDR Set,
  VH E9.11 CDR Set and VL E9.11 CDR Set,
  VH E9.14 CDR Set and VL E9.14 CDR Set,
  VH E9.17 CDR Set and VL E9.17 CDR Set,
  VH E9.18 CDR Set and VL E9.18 CDR Set,
  VH E9.19 CDR Set and VL E9.19 CDR Set,
  VH E9.22 CDR Set and VL E9.22 CDR Set,
  VH E9.48 CDR Set and VL E9.48 CDR Set,
  VH E9.65 CDR Set and VL E9.65 CDR Set,
  VH E9.66 CDR Set and VL E9.66 CDR Set,
  VH E9.71 CDR Set and VL E9.71 CDR Set,
  VH E9.13 CDR Set and VL E9.13 CDR Set,
  VH E9.16 CDR Set and VL E9.16 CDR Set,
  VH E9.38 CDR Set and VL E9.38 CDR Set,
  VH E9.2B CDR Set and VL E9.2B CDR Set,
  VH E9.1F CDR Set and VL E9.1F CDR Set,
  VH E9.10H CDR Set and VL E9.10H CDR Set,
  VH E9.5E CDR Set and VL E9.5E CDR Set,
  VH E9.10C CDR Set and VL E9.10C CDR Set,
  VH E9.7E CDR Set and VL E9.7E CDR Set,
  VH E9.12B CDR Set and VL E9.12B CDR Set,
  VH E9.10E CDR Set and VL E9.10E CDR Set,
  VH E9.6A CDR Set and VL E9.6A CDR Set,
  VH E9.7A CDR Set and VL E9.7A CDR Set,
  VH E9.8H CDR Set and VL E9.8H CDR Set,
  VH E9-SE1 CDR Set and VL E9-SE1 CDR Set,
  VH E9-SE2 CDR Set and VL E9-SE2 CDR Set,
  VH E9-SE3 CDR Set and VL E9-SE3 CDR Set,
  VH E9-SE4 CDR Set and VL E9-SE4 CDR Set,
  VH E9-SE5 CDR Set and VL E9-SE5 CDR Set,
  VH E9-SE6 CDR Set and VL E9-SE6 CDR Set,
  VH E9-SE7 CDR Set and VL E9-SE7 CDR Set,
  VH E9-SE8 CDR Set and VL E9-SE8 CDR Set,
  VH E9-FR1 CDR Set and VL E9-FR1 CDR Set,
  VH E9-FR2 CDR Set and VL E9-FR2 CDR Set,
  VH E9.71 CDR Set and VL E9.71 CDR Set,
  VH E9.71(M) CDR Set and VL E9.71(M) CDR Set, and
  VH E9.71(L) CDR Set and VL E9.71(L) CDR Set.

4. The method according to claim 1, wherein said binding protein further comprises a human acceptor framework, said human acceptor framework comprising an amino acid sequence selected from the group consisting of:
  SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62,
  SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 88, SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 96, SEQ ID NO: 97, and SEQ ID NO: 98.

5. The method according to claim 4, wherein said human acceptor framework further comprises at least one amino acid substitution relative to a human germline acceptor framework at a key residue selected from the group consisting of:
   a residue adjacent to a CDR;
   a glycosylation site residue;
   a rare residue;
   a residue capable of interacting with human DLL4
   a canonical residue;
   a contact residue between heavy chain variable region and light chain variable region;
   a residue within a Vernier zone; and
   a residue in a region that overlaps between a Chothia-defined variable heavy chain CDR1 and a Kabat-defined first heavy chain framework.

6. The method according to claim 5, wherein said key residue is selected from the group consisting of: 2H, 4H, 24H, 26H, 27H, 29H, 34H, 35H, 37H, 39H, 44H, 45H, 47H, 48H, 49H, 50H, 51H, 58H, 59H, 60H, 63H, 67H, 69H, 71H, 73H, 76H, 78H, 91H, 93H, 94H, 2L, 4L, 25L, 29L, 27bL, 33L, 34L, 36L, 38L, 43L, 44L, 46L, 47L, 48L, 49L, 55L, 58L, 62L, 64L, 71L, 87L, 89L, 90L, 91L, 94L, and 95L.

7. The method according to claim 1, wherein said binding protein comprises at least one variable domain having amino acid sequence selected from the group consisting of: SEQ ID NOS:1, 111, 116, 228, 120, 232, 124, 236, 128, 240, 132, 244, 136, 248, 140, 252, 144, 256, 148, 260, 152, 264, 156, 268, 160, 216, 164, 220, 168, 224, 172, 272, 176, 276, 180, 300, 184, 292, 188, 280, 192, 288, 196, 296, 200, 284, 204, 304, 208, 308, 212, 312, 334, 335, 336, 337, 338, 339, 340, 341, 342, 343, 344, 345, 346, 347, 348, 349, 350, 351, 352, 353, 354, 355, 356, 357, 358, 359, 360, and 361.

8. The method according to claim 7, wherein said binding protein comprises two variable domains, wherein said two variable domains have amino acid sequences selected from the group consisting of: SEQ ID NOS:1 and 111, SEQ ID NOS:116 and 228, SEQ ID NOS:120 and 232, SEQ ID NOS: 124 and 236, SEQ ID NOS: 128 and 240, SEQ ID NOS: 132 and 244, SEQ ID NOS: 136 and 248, SEQ ID NOS:140 and 252, SEQ ID NOS:144 and 256, SEQ ID NOS:148 and 260, SEQ ID NOS:152 and 264, SEQ ID NOS:156 and 268, SEQ ID NOS: 160 and 216, SEQ ID NOS: 164 and 220, SEQ ID NOS:168 and 224, SEQ ID NOS:172 and 272, SEQ ID NOS: 176 and 276, SEQ ID NOS:180 and 300, SEQ ID NOS:184 and 292, SEQ ID NOS:188 and 280, SEQ ID NOS:192 and 288, SEQ ID NOS:196 and 296, SEQ ID NOS:200 and 284, SEQ ID NOS:204 and 304, SEQ ID NOS:208 and 308, SEQ ID NOS:212 and 312, SEQ ID NOS:334 and 335, SEQ ID NOS:336 and 337, SEQ ID NOS:338 and 339, SEQ ID NOS: 340 and 341, SEQ ID NOS:342 and 343, SEQ ID NOS:344 and 345, SEQ ID NOS:346 and 347, SEQ ID NOS:348 and 349, SEQ ID NOS:350 and 351, SEQ ID NOS:352 and 353, SEQ ID NOS:354 and 355, SEQ ID NOS:356 and 357, SEQ ID NOS:358 and 359, and SEQ ID NOS:360 and 361.

9. The method according to claim 8, wherein the binding protein further comprises a heavy chain immunoglobulin constant domain selected from the group consisting of: a human IgM constant domain; a human IgG1 constant domain; a human IgG2 constant domain; a human IgG3 constant domain; a human IgG4 constant domain; a human IgE constant domain; and a human IgA constant domain.

10. The method according to claim 9, wherein said heavy chain immunoglobulin constant domain is a human IgG1 constant domain, said human IgG1 constant domain comprising an amino acid sequence selected from the group consisting of SEQ ID NO:2 and SEQ ID NO:3.

11. The method according to claim 8, wherein the binding protein further comprises a light chain immunoglobulin constant domain, wherein said light chain immunoglobulin constant domain is a human Ig kappa constant domain, said Ig kappa constant domain comprising amino acid sequence SEQ ID NO:4.

12. The method according to claim 8, wherein the binding protein further comprises a light chain immunoglobulin constant domain, wherein said light chain immunoglobulin constant domain is a human Ig lambda constant domain, said Ig lambda constant domain comprising amino acid sequence SEQ ID NO:5.

13. The method according to claim 1, wherein said binding protein is selected from the group consisting of: an immunoglobulin molecule, an scFv, a monoclonal antibody, a human antibody, a chimeric antibody, a humanized antibody, a single domain antibody, a Fab fragment, a Fab' fragment, an F(ab')2, an Fv, a disulfide linked Fv, a single domain antibody, a diabody, a multispecific antibody, a bispecific antibody, a dual variable domain immunoglobulin (DVD-Ig) binding protein, and a dual specific antibody.

14. The method according to claim 1, wherein said binding protein comprises:
   an Ig constant heavy region having an amino acid sequence selected from the group consisting of SEQ ID NO:2 and SEQ ID NO:3;
   an Ig constant light region having an amino acid sequence selected from the group consisting of SEQ ID NO:4 and SEQ ID NO:5;
   an Ig variable heavy region having an amino acid sequence selected from the group consisting of:
   SEQ ID NOS:1, 116, 120, 124, 128, 132, 136, 140, 144, 148, 152, 156, 160, 164, 168, 172, 176, 180, 184, 188, 192, 196, 200, 204, 208, 212, 334, 336, 338, 340, 342, 344, 346, 348, 350, 352, 354, 356, 358, and 360; and
   an Ig variable light region having an amino acid sequence selected from the group consisting of:
   SEQ ID NOS:111, 228, 232, 236, 240, 244, 248, 252, 256, 260, 264, 268, 216, 220, 224, 272, 276, 300, 292, 280, 288, 296, 284, 304, 308, 312, 335, 337, 339, 341, 343, 345, 347, 349, 351, 353, 355, 357, 359, and 361.

15. The method according to claim 14, wherein the binding protein comprises:
   an Ig variable heavy region comprising the amino acid sequence of SEQ ID NO:156, and
   an Ig variable light region comprising the amino acid sequence of SEQ ID NO:268.

16. The method of claim 15, wherein the binding protein further comprises:
   a heavy chain immunoglobulin constant domain comprising an amino acid sequence selected from the group consisting of SEQ ID NO:2 and SEQ ID NO:3, and
   a light chain immunoglobulin constant domain comprising an amino acid sequence selected from the group consisting of SEQ ID NO:4 and SEQ ID NO:5.

17. The method according to claim 14, wherein the binding protein comprises:

an Ig variable heavy region comprising the amino acid sequence of SEQ ID NO:360, and
an Ig variable light region comprising the amino acid sequence of SEQ ID NO:361.

18. The method of claim 17, wherein the binding protein further comprises:
a heavy chain immunoglobulin constant domain comprising an amino acid sequence selected from the group consisting of SEQ ID NO:2 and SEQ ID NO:3, and
a light chain immunoglobulin constant domain comprising an amino acid sequence selected from the group consisting of SEQ ID NO:4 and SEQ ID NO:5.

19. The method according to claim 14, wherein the binding protein comprises:
an Ig variable heavy region comprising the amino acid sequence of SEQ ID NO:156, and
an Ig variable light region comprising the amino acid sequence of SEQ ID NO:359.

20. The method of claim 19, wherein the binding protein further comprises:
a heavy chain immunoglobulin constant domain comprising an amino acid sequence selected from the group consisting of SEQ ID NO:2 and SEQ ID NO:3, and
a light chain immunoglobulin constant domain comprising an amino acid sequence selected from the group consisting of SEQ ID:NO 4 and SEQ ID NO:5.

21. The method of claim 1, wherein the binding protein is capable of blocking DLL4 interaction with a Notch protein selected from the group consisting of Notch-1, Notch-2, Notch-3, Notch-4, and combinations thereof.

22. The method of claim 21, wherein the binding protein is capable of blocking DLL4 interaction with Notch-1 and Notch-4.

23. The method of claim 1, wherein the binding protein is capable of modulating a biological function of DLL4.

24. The method of claim 1, wherein said binding protein is capable of neutralizing a DLL4.

25. The method of claim 1, wherein said binding protein is capable of reducing angiogenesis.

26. The method of claim 1, wherein said binding protein has a dissociation constant (KD) selected from the group consisting of: at most about $10^{-7}$ M; at most about $10^{-8}$ M; at most about $10^{-9}$ M; at most about $10^{-10}$ M; at most about $10^{-11}$ M; at most about $10^{-12}$ M; and at most about $10^{-13}$ M.

27. The method of claim 1, wherein said binding protein has an on rate selected from the group consisting of: at least about $10^2$ $M^{-1}$ $s^{-1}$; at least about $10^3$ $M^{-1}$ $s^{-1}$; at least about $10^4$ $M^{-1}$ $s^{-1}$; at least about $10^5$ $M^{-1}$ $s^{-1}$; and at least about $10^6$ $M^{-1}$ $s^{-1}$.

28. The method of claim 1, wherein said binding protein has an off rate selected from the group consisting of: at most about $10^{-3}$ $s^{-1}$; at most about $10^{-4}$ $s^{-1}$; at most about $10^{-5}$ $s^{-1}$; and at most about $10^{-6}$ $s^{-1}$.

29. The method of claim 1, wherein said binding protein is administered as a binding protein construct, said binding protein construct being selected from the group consisting of:
an immunoglobulin molecule,
a monoclonal antibody,
a chimeric antibody,
a CDR-grafted antibody,
a humanized antibody,
a Fab,
a Fab',
a F(ab')2,
a Fv,
a disulfide linked Fv,
a scFv,
a single domain antibody,
a diabody,
a multispecific antibody,
a dual specific antibody,
a dual variable domain immunoglobulin (DVD-Ig) binding protein, and
a bispecific antibody.

30. The method of claim 1, wherein said binding protein is administered as a binding protein construct, said binding protein construct being conjugated to a therapeutic or cytotoxic agent.

31. The method of claim 1, wherein said binding protein is administered as a pharmaceutical composition, said pharmaceutical composition comprising the binding protein and a pharmaceutically acceptable carrier.

32. The method of claim 31, wherein said pharmaceutical composition further comprises at least one additional therapeutic agent, said additional therapeutic agent selected from the group consisting of an antibody or fragment thereof capable of binding human VEGFR2; an antibody or fragment thereof capable of binding human VEGFR1, an antibody or fragment thereof capable of binding human VEGF; methotrexate; an antibody or fragment thereof capable of binding human TNF; angiogenesis inhibitors; kinase inhibitors; co-stimulation molecule blockers; adhesion molecule blockers; anti-cytokine antibody or functional fragment thereof; methotrexate; corticosteroids; cyclosporine; rapamycin; FK506; and non-steroidal anti-inflammatory agents.

33. The method of claim 1, wherein the disease or disorder is selected from the group consisting of: breast cancer, colon cancer, rectal cancer, lung cancer, oropharynx cancer, hypopharynx cancer, esophageal cancer, stomach cancer, pancreas cancer, liver cancer, gallbladder cancer, bile duct cancer, small intestine cancer, urinary tract cancer, female genital tract cancer, male genital tract cancer, endocrine gland cancer, skin cancer, hemangiomas, melanomas, sarcomas, brain tumor, nerve cancer, eye tumor, meninges cancer, solid tumors from hematopoietic malignancies, tumor metastases, ocular neovascularization, edema, rheumatoid arthritis, multiple sclerosis, atheroscleorotic plaques, Crohn's disease, inflammatory bowel disease, refractory ascites, psoriasis, sarcoidosis, arterial arteriosclerosis, sepsis, peptic ulcers, burns, and pancreatitis, polycystic ovarian disease (POD), endometriosis, uterine fibroids, benign prostate hypertrophy, and other angiogenesis independent and dependent diseases characterized by abberant DLL4 activity.

34. The method according to claim 33, wherein the disease or disorder is a primary cancer or a metastatic cancer.

35. The method according to claim 33, wherein the urinary tract cancer is selected from the group consisting of renal cancer, bladder cancer, and urothelium cancer.

36. The method according to claim 33, wherein the female genital tract cancer is selected from the group consisting of cervical cancer, uterine cancer, ovarian cancer, choriocarcinoma, and gestational trophoblastic disease.

37. The method according to claim 33, wherein the male genital tract cancer is selected from the group consisting of prostate cancer, seminal vesicles cancer, testicular cancer, and germ cell tumor.

38. The method according to claim 33, wherein the endocrine gland cancer is selected from the group consisting of thyroid cancer, adrenal cancer, and pituitary gland cancer.

39. The method according to claim 33, wherein the sarcoma is selected from the group consisting of a bone sarcoma, a soft tissue sarcoma, and Kaposi's sarcoma.

40. The method according to claim 33, wherein the meninges cancer is selected from the group consisting of an astrocytoma, a glioma, a glioblastoma, a retinoblastoma, a neuroma, a neuroblastoma, a Schwannoma, and a meningiomas.

41. The method according to claim 33, wherein the solid tumor from a hematopoietic malignancy is a leukemia, a Hodgkin's leukemia, a non-Hodgkin's leukemia, a lymphoma, a Hodgkin's lymphoma, and a non-Hodgkin's lymphoma.

42. The method according to claim 33, wherein the ocular neovascularization is selected from the group consisting of diabetic blindness, a retinopathy, an age induced macular degeneration, and a rubeosis.

43. The method according to claim 33, wherein the disease or disorder is a non-small cell lung cancer.

44. The method according to claim 43, wherein the tumor size in the treated subject is at least 50% smaller than the tumor size in a control subject not treated with said binding protein.

45. A method of treating a subject having a disease or a disorder characterized by aberrant DLL4 expression or in which DLL4 is detrimental, said method comprising administering to said subject an effective amount of a binding protein in combination with at least one additional agent, said at least one additional agent selected from the group consisting of an antibody or fragment thereof capable of binding human VEGFR2; an antibody or fragment thereof capable of binding human VEGFR1, an antibody or fragment thereof capable of binding human VEGF; methotrexate; an antibody or fragment thereof capable of binding human TNF; corticosteroids; cyclosporine; rapamycin; FK506; and non-steroidal anti-inflammatory agents; wherein said binding protein comprises an antigen binding domain comprising six CDRs: CDR-H1, CDR-H2, CDR-H3, CDR-L1, CDR-L2, and CDR-L3, wherein:

CDR-H1 is selected from the group consisting of:
residues 31-37 of SEQ ID NO:1;
SEQ ID NO:117;
SEQ ID NO:121;
SEQ ID NO:125;
SEQ ID NO:129;
SEQ ID NO:133;
SEQ ID NO:137;
SEQ ID NO:141;
SEQ ID NO:145;
SEQ ID NO:149;
SEQ ID NO:153;
SEQ ID NO:157;
SEQ ID NO:161;
SEQ ID NO:165;
SEQ ID NO:169;
SEQ ID NO:173;
SEQ ID NO:177;
SEQ ID NO:181;
SEQ ID NO:185;
SEQ ID NO:189;
SEQ ID NO:193;
SEQ ID NO:197;
SEQ ID NO:201;
SEQ ID NO:205;
SEQ ID NO:209;
SEQ ID NO:213;
residues 31-37 of SEQ ID NO:334;
residues 31-37 of SEQ ID NO:336;
residues 31-37 of SEQ ID NO:338;
residues 31-37 of SEQ ID NO:340;
residues 31-37 of SEQ ID NO:342;
residues 31-37 of SEQ ID NO:344;
residues 31-37 of SEQ ID NO:346;
residues 31-37 of SEQ ID NO:348;
residues 31-37 of SEQ ID NO:350;
residues 31-37 of SEQ ID NO:352;
residues 31-37 of SEQ ID NO:354;
residues 31-37 of SEQ ID NO:356;
residues 31-37 of SEQ ID NO:358; and
residues 31-37 of SEQ ID NO:360;

CDR-H2 is selected from the group consisting of:
residues 52-67 of SEQ ID NO:1;
SEQ ID NO:118;
SEQ ID NO:122;
SEQ ID NO:126;
SEQ ID NO:130;
SEQ ID NO:134;
SEQ ID NO:138;
SEQ ID NO:142;
SEQ ID NO:146;
SEQ ID NO:150;
SEQ ID NO:154;
SEQ ID NO:158;
SEQ ID NO:162;
SEQ ID NO:166;
SEQ ID NO:170;
SEQ ID NO:174;
SEQ ID NO:178;
SEQ ID NO:182;
SEQ ID NO:186;
SEQ ID NO:190;
SEQ ID NO:194;
SEQ ID NO:198;
SEQ ID NO:202;
SEQ ID NO:206;
SEQ ID NO:210;
SEQ ID NO:214;
residues 52-67 of SEQ ID NO:334;
residues 52-67 of SEQ ID NO:336;
residues 52-67 of SEQ ID NO:338;
residues 52-67 of SEQ ID NO:340;
residues 52-67 of SEQ ID NO:342;
residues 52-67 of SEQ ID NO:344;
residues 52-67 of SEQ ID NO:346;
residues 52-67 of SEQ ID NO:348;
residues 52-67 of SEQ ID NO:350;
residues 52-67 of SEQ ID NO:352;
residues 52-67 of SEQ ID NO:354;
residues 52-67 of SEQ ID NO:356;
residues 52-67 of SEQ ID NO:358; and
residues 52-67 of SEQ ID NO:360;

CDR-H3 is selected from the group consisting of:
residues 100-110 of SEQ ID NO:1;
SEQ ID NO:119;
SEQ ID NO:123;
SEQ ID NO:127;
SEQ ID NO:131;
SEQ ID NO:135;
SEQ ID NO:139;
SEQ ID NO:143;
SEQ ID NO:147;
SEQ ID NO:151;
SEQ ID NO:155;
SEQ ID NO:159;
SEQ ID NO:163;
SEQ ID NO:167;
SEQ ID NO:171;
SEQ ID NO:175;
SEQ ID NO:179;
SEQ ID NO:183;
SEQ ID NO:187;
SEQ ID NO:191;
SEQ ID NO:195;
SEQ ID NO:199;
SEQ ID NO:203;
SEQ ID NO:207;
SEQ ID NO:211;
SEQ ID NO:215;
residues 100-110 of SEQ ID NO:334;
residues 100-110 of SEQ ID NO:336;

residues 100-110 of SEQ ID NO:338;
residues 100-110 of SEQ ID NO:340;
residues 100-110 of SEQ ID NO:342;
residues 100-110 of SEQ ID NO:344;
residues 100-110 of SEQ ID NO:346;
residues 100-110 of SEQ ID NO:348;
residues 100-110 of SEQ ID NO:350;
residues 100-110 of SEQ ID NO:352;
residues 100-110 of SEQ ID NO:354;
residues 100-110 of SEQ ID NO:356;
residues 100-110 of SEQ ID NO:358; and
residues 100-110 of SEQ ID NO:360;
CDR-L1 is selected from the group consisting of:
residues 23-33 of SEQ ID NO:111;
SEQ ID NO:217;
SEQ ID NO:221;
SEQ ID NO:225;
SEQ ID NO:229;
SEQ ID NO:233;
SEQ ID NO:237;
SEQ ID NO:241;
SEQ ID NO:245;
SEQ ID NO:249;
SEQ ID NO:253;
SEQ ID NO:257;
SEQ ID NO:261;
SEQ ID NO:265;
SEQ ID NO:269;
SEQ ID NO:273;
SEQ ID NO:277;
SEQ ID NO:281;
SEQ ID NO:285;
SEQ ID NO:289;
SEQ ID NO:293;
SEQ ID NO:297;
SEQ ID NO:301;
SEQ ID NO:305;
SEQ ID NO:309;
SEQ ID NO:313;
residues 23-33 of SEQ ID NO:335;
residues 23-33 of SEQ ID NO:337;
residues 23-33 of SEQ ID NO:339;
residues 23-33 of SEQ ID NO:341;
residues 23-33 of SEQ ID NO:343;
residues 24-34 of SEQ ID NO:345;
residues 23-33 of SEQ ID NO:347;
residues 24-34 of SEQ ID NO:349;
residues 24-34 of SEQ ID NO:351;
residues 24-34 of SEQ ID NO:353;
residues 24-34 of SEQ ID NO:355;
residues 23-33 of SEQ ID NO:357;
residues 23-33 of SEQ ID NO:359; and
residues 23-33 of SEQ ID NO:361;
CDR-L2 is selected from the group consisting of:
residues 49-55 of SEQ ID NO:111;
SEQ ID NO:230;
SEQ ID NO:234;
SEQ ID NO:238;
SEQ ID NO:242;
SEQ ID NO:246;
SEQ ID NO:250;
SEQ ID NO:254;
SEQ ID NO:258;
SEQ ID NO:262;
SEQ ID NO:266;
SEQ ID NO:270;
SEQ ID NO:218;
SEQ ID NO:222;
SEQ ID NO:226;
SEQ ID NO:274;
SEQ ID NO:278;
SEQ ID NO:302;
SEQ ID NO:294;
SEQ ID NO:282;
SEQ ID NO:290;
SEQ ID NO:298;
SEQ ID NO:286;
SEQ ID NO:306;
SEQ ID NO:310;
SEQ ID NO:314;
residues 49-55 of SEQ ID NO:335;
residues 49-55 of SEQ ID NO:337;
residues 49-55 of SEQ ID NO:339;
residues 49-55 of SEQ ID NO:341;
residues 49-55 of SEQ ID NO:343;
residues 50-56 of SEQ ID NO:345;
residues 49-55 of SEQ ID NO:347;
residues 50-56 of SEQ ID NO:349;
residues 50-56 of SEQ ID NO:351;
residues 50-56 of SEQ ID NO:353;
residues 50-56 of SEQ ID NO:355;
residues 49-55 of SEQ ID NO:357;
residues 49-55 of SEQ ID NO:359; and
residues 49-55 of SEQ ID NO:361;
and
CDR-L3 is selected from the group consisting of:
residues 88-96 of SEQ ID NO:111;
SEQ ID NO:231;
SEQ ID NO:235;
SEQ ID NO:239;
SEQ ID NO:243;
SEQ ID NO:247;
SEQ ID NO:251;
SEQ ID NO:255;
SEQ ID NO:259;
SEQ ID NO:263;
SEQ ID NO:267;
SEQ ID NO:271;
SEQ ID NO:219;
SEQ ID NO:223;
SEQ ID NO:227;
SEQ ID NO:275;
SEQ ID NO:279;
SEQ ID NO:303;
SEQ ID NO:295;
SEQ ID NO:283;
SEQ ID NO:291;
SEQ ID NO:299;
SEQ ID NO:287;
SEQ ID NO:307;
SEQ ID NO:311;
SEQ ID NO:315;
residues 88-96 of SEQ ID NO:335;
residues 88-96 of SEQ ID NO:337;
residues 88-96 of SEQ ID NO:339;
residues 88-96 of SEQ ID NO:341;
residues 88-96 of SEQ ID NO:343;
residues 89-97 of SEQ ID NO:345;
residues 88-96 of SEQ ID NO:347;
residues 89-97 of SEQ ID NO:349;
residues 89-97 of SEQ ID NO:351;
residues 89-97 of SEQ ID NO:353;
residues 89-97 of SEQ ID NO:355;
residues 88-96 of SEQ ID NO:357;
residues 88-96 of SEQ ID NO:359; and
residues 88-96 of SEQ ID NO:361.

46. A method for reducing human DLL4 activity in a subject, said method comprising administering to said subject an effective amount of a binding protein capable of binding human DLL4 such that human DLL4 activity in said subject is reduced, said binding protein comprising an antigen binding domain comprising six CDRs: CDR-H1, CDR-H2, CDR-H3, CDR-L1, CDR-L2, and CDR-L3, wherein:
CDR-H1 is selected from the group consisting of:
residues 31-37 of SEQ ID NO:1;
SEQ ID NO:117;
SEQ ID NO:121;
SEQ ID NO:125;
SEQ ID NO:129;
SEQ ID NO:133;
SEQ ID NO:137;
SEQ ID NO:141;
SEQ ID NO:145;
SEQ ID NO:149;
SEQ ID NO:153;
SEQ ID NO:157;
SEQ ID NO:161;
SEQ ID NO:165;
SEQ ID NO:169;
SEQ ID NO:173;
SEQ ID NO:177;
SEQ ID NO:181;
SEQ ID NO:185;
SEQ ID NO:189;
SEQ ID NO:193;
SEQ ID NO:197;
SEQ ID NO:201;
SEQ ID NO:205;
SEQ ID NO:209;
SEQ ID NO:213;
residues 31-37 of SEQ ID NO:334;
residues 31-37 of SEQ ID NO:336;
residues 31-37 of SEQ ID NO:338;
residues 31-37 of SEQ ID NO:340;
residues 31-37 of SEQ ID NO:342;
residues 31-37 of SEQ ID NO:344;
residues 31-37 of SEQ ID NO:346;
residues 31-37 of SEQ ID NO:348;
residues 31-37 of SEQ ID NO:350;
residues 31-37 of SEQ ID NO:352;
residues 31-37 of SEQ ID NO:354;
residues 31-37 of SEQ ID NO:356;
residues 31-37 of SEQ ID NO:358; and
residues 31-37 of SEQ ID NO:360;
CDR-H2 is selected from the group consisting of:
residues 52-67 of SEQ ID NO:1;
SEQ ID NO:118;
SEQ ID NO:122;
SEQ ID NO:126;
SEQ ID NO:130;
SEQ ID NO:134;
SEQ ID NO:138;
SEQ ID NO:142;
SEQ ID NO:146;
SEQ ID NO:150;
SEQ ID NO:154;
SEQ ID NO:158;
SEQ ID NO:162;
SEQ ID NO:166;
SEQ ID NO:170;
SEQ ID NO:174;
SEQ ID NO:178;
SEQ ID NO:182;
SEQ ID NO:186;
SEQ ID NO:190;
SEQ ID NO:194;
SEQ ID NO:198;
SEQ ID NO:202;
SEQ ID NO:206;
SEQ ID NO:210;
SEQ ID NO:214;
residues 52-67 of SEQ ID NO:334;
residues 52-67 of SEQ ID NO:336;
residues 52-67 of SEQ ID NO:338;
residues 52-67 of SEQ ID NO:340;
residues 52-67 of SEQ ID NO:342;
residues 52-67 of SEQ ID NO:344;
residues 52-67 of SEQ ID NO:346;
residues 52-67 of SEQ ID NO:348;
residues 52-67 of SEQ ID NO:350;
residues 52-67 of SEQ ID NO:352;
residues 52-67 of SEQ ID NO:354;
residues 52-67 of SEQ ID NO:356;
residues 52-67 of SEQ ID NO:358; and
residues 52-67 of SEQ ID NO:360;
CDR-H3 is selected from the group consisting of:
residues 100-110 of SEQ ID NO:1;
SEQ ID NO:119;
SEQ ID NO:123;
SEQ ID NO:127;
SEQ ID NO:131;
SEQ ID NO:135;
SEQ ID NO:139;
SEQ ID NO:143;
SEQ ID NO:147;
SEQ ID NO:151;
SEQ ID NO:155;
SEQ ID NO:159;
SEQ ID NO:163;
SEQ ID NO:167;
SEQ ID NO:171;
SEQ ID NO:175;
SEQ ID NO:179;
SEQ ID NO:183;
SEQ ID NO:187;
SEQ ID NO:191;
SEQ ID NO:195;
SEQ ID NO:199;
SEQ ID NO:203;
SEQ ID NO:207;
SEQ ID NO:211;
SEQ ID NO:215;
residues 100-110 of SEQ ID NO:334;
residues 100-110 of SEQ ID NO:336;
residues 100-110 of SEQ ID NO:338;
residues 100-110 of SEQ ID NO:340;
residues 100-110 of SEQ ID NO:342;
residues 100-110 of SEQ ID NO:344;
residues 100-110 of SEQ ID NO:346;
residues 100-110 of SEQ ID NO:348;
residues 100-110 of SEQ ID NO:350;
residues 100-110 of SEQ ID NO:352;
residues 100-110 of SEQ ID NO:354;
residues 100-110 of SEQ ID NO:356;
residues 100-110 of SEQ ID NO:358; and
residues 100-110 of SEQ ID NO:360;
CDR-L1 is selected from the group consisting of:
residues 23-33 of SEQ ID NO:111;
SEQ ID NO:217;
SEQ ID NO:221;
SEQ ID NO:225;
SEQ ID NO:229;
SEQ ID NO:233;
SEQ ID NO:237;
SEQ ID NO:241;
SEQ ID NO:245;
SEQ ID NO:249;
SEQ ID NO:253;
SEQ ID NO:257;

SEQ ID NO:261;
SEQ ID NO:265;
SEQ ID NO:269;
SEQ ID NO:273;
SEQ ID NO:277;
SEQ ID NO:281;
SEQ ID NO:285;
SEQ ID NO:289;
SEQ ID NO:293;
SEQ ID NO:297;
SEQ ID NO:301;
SEQ ID NO:305;
SEQ ID NO:309;
SEQ ID NO:313;
residues 23-33 of SEQ ID NO:335;
residues 23-33 of SEQ ID NO:337;
residues 23-33 of SEQ ID NO:339;
residues 23-33 of SEQ ID NO:341;
residues 23-33 of SEQ ID NO:343;
residues 24-34 of SEQ ID NO:345;
residues 23-33 of SEQ ID NO:347;
residues 24-34 of SEQ ID NO:349;
residues 24-34 of SEQ ID NO:351;
residues 24-34 of SEQ ID NO:353;
residues 24-34 of SEQ ID NO:355;
residues 23-33 of SEQ ID NO:357;
residues 23-33 of SEQ ID NO:359; and
residues 23-33 of SEQ ID NO:361;
CDR-L2 is selected from the group consisting of:
residues 49-55 of SEQ ID NO:111;
SEQ ID NO:230;
SEQ ID NO:234;
SEQ ID NO:238;
SEQ ID NO:242;
SEQ ID NO:246;
SEQ ID NO:250;
SEQ ID NO:254;
SEQ ID NO:258;
SEQ ID NO:262;
SEQ ID NO:266;
SEQ ID NO:270;
SEQ ID NO:218;
SEQ ID NO:222;
SEQ ID NO:226;
SEQ ID NO:274;
SEQ ID NO:278;
SEQ ID NO:302;
SEQ ID NO:294;
SEQ ID NO:282;
SEQ ID NO:290;
SEQ ID NO:298;
SEQ ID NO:286;
SEQ ID NO:306;
SEQ ID NO:310;
SEQ ID NO:314;
residues 49-55 of SEQ ID NO:335;
residues 49-55 of SEQ ID NO:337;
residues 49-55 of SEQ ID NO:339;
residues 49-55 of SEQ ID NO:341;
residues 49-55 of SEQ ID NO:343;
residues 50-56 of SEQ ID NO:345;
residues 49-55 of SEQ ID NO:347;
residues 50-56 of SEQ ID NO:349;
residues 50-56 of SEQ ID NO:351;
residues 50-56 of SEQ ID NO:353;
residues 50-56 of SEQ ID NO:355;
residues 49-55 of SEQ ID NO:357;
residues 49-55 of SEQ ID NO:359; and
residues 49-55 of SEQ ID NO:361;
and
CDR-L3 is selected from the group consisting of:
residues 88-96 of SEQ ID NO:111;
SEQ ID NO:231;
SEQ ID NO:235;
SEQ ID NO:239;
SEQ ID NO:243;
SEQ ID NO:247;
SEQ ID NO:251;
SEQ ID NO:255;
SEQ ID NO:259;
SEQ ID NO:263;
SEQ ID NO:267;
SEQ ID NO:271;
SEQ ID NO:219;
SEQ ID NO:223;
SEQ ID NO:227;
SEQ ID NO:275;
SEQ ID NO:279;
SEQ ID NO:303;
SEQ ID NO:295;
SEQ ID NO:283;
SEQ ID NO:291;
SEQ ID NO:299;
SEQ ID NO:287;
SEQ ID NO:307;
SEQ ID NO:311;
SEQ ID NO:315;
residues 88-96 of SEQ ID NO:335;
residues 88-96 of SEQ ID NO:337;
residues 88-96 of SEQ ID NO:339;
residues 88-96 of SEQ ID NO:341;
residues 88-96 of SEQ ID NO:343;
residues 89-97 of SEQ ID NO:345;
residues 88-96 of SEQ ID NO:347;
residues 89-97 of SEQ ID NO:349;
residues 89-97 of SEQ ID NO:351;
residues 89-97 of SEQ ID NO:353;
residues 89-97 of SEQ ID NO:355;
residues 88-96 of SEQ ID NO:357;
residues 88-96 of SEQ ID NO:359; and
residues 88-96 of SEQ ID NO:361.

* * * * *

SEQUENCE LISTING

<160> NUMBER OF SEQ ID NOS: 377

<210> SEQ ID NO 1
<211> LENGTH: 121
<212> TYPE: PRT
<213> ORGANISM: Homo sapiens

<400> SEQUENCE: 1

Glu Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Asp Ile Tyr Tyr Thr Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Glu Asp Val Ile Leu Arg Gly Gly Ser Asp Tyr Trp Gly
            100                 105                 110

Gln Gly Thr Leu Val Thr Val Ser Ser
        115                 120

<210> SEQ ID NO 2
<211> LENGTH: 330
<212> TYPE: PRT
<213> ORGANISM: Homo sapiens

<400> SEQUENCE: 2

Ala Ser Thr Lys Gly Pro Ser Val Phe Phe Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

```
His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 3
<211> LENGTH: 330
<212> TYPE: PRT
<213> ORGANISM: Artificial Sequence
<220> FEATURE:
<223> OTHER INFORMATION: IgG1 constant region mutant

<400> SEQUENCE: 3

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
            130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220
```

```
Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
        260                 265                 270

Asn Tyr Lys Thr Thr Pro Pro Val Leu Asp Ser Asp Gly Ser Phe Phe
    275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 4
<211> LENGTH: 106
<212> TYPE: PRT
<213> ORGANISM: Homo sapiens

<400> SEQUENCE: 4

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 5
<211> LENGTH: 105
<212> TYPE: PRT
<213> ORGANISM: Homo sapiens

<400> SEQUENCE: 5

Gln Pro Lys Ala Ala Pro Ser Val Thr Leu Phe Pro Pro Ser Ser Glu
1               5                   10                  15

Glu Leu Gln Ala Asn Lys Ala Thr Leu Val Cys Leu Ile Ser Asp Phe
            20                  25                  30

Tyr Pro Gly Ala Val Thr Val Ala Trp Lys Ala Asp Ser Ser Pro Val
        35                  40                  45

Lys Ala Gly Val Glu Thr Thr Thr Pro Ser Lys Gln Ser Asn Asn Lys
    50                  55                  60

Tyr Ala Ala Ser Ser Tyr Leu Ser Leu Thr Pro Glu Gln Trp Lys Ser
65                  70                  75                  80

His Arg Ser Tyr Ser Cys Gln Val Thr His Glu Gly Ser Thr Val Glu
                85                  90                  95

Lys Thr Val Ala Pro Thr Glu Cys Ser
            100                 105
```

```
<210> SEQ ID NO 6
<211> LENGTH: 30
<212> TYPE: PRT
<213> ORGANISM: Artificial Sequence
<220> FEATURE:
<223> OTHER INFORMATION: VH2-70/JH6 FR1 heavy chain acceptor sequence

<400> SEQUENCE: 6

Glu Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser
            20                  25                  30

<210> SEQ ID NO 7
<211> LENGTH: 14
<212> TYPE: PRT
<213> ORGANISM: Artificial Sequence
<220> FEATURE:
<223> OTHER INFORMATION: VH2-70/JH6 FR2 heavy chain acceptor sequence

<400> SEQUENCE: 7

Trp Ile Arg Gln Pro Pro Gly Lys Ala Leu Glu Trp Leu Ala
1               5                   10

<210> SEQ ID NO 8
<211> LENGTH: 32
<212> TYPE: PRT
<213> ORGANISM: Artificial Sequence
<220> FEATURE:
<223> OTHER INFORMATION: VH2-70/JH6 FR3 heavy chain acceptor sequence

<400> SEQUENCE: 8

Arg Leu Thr Ile Ser Lys Asp Thr Ser Lys Asn Gln Val Val Leu Thr
1               5                   10                  15

Met Thr Asn Met Asp Pro Val Asp Thr Ala Thr Tyr Tyr Cys Ala Arg
            20                  25                  30

<210> SEQ ID NO 9
<211> LENGTH: 11
<212> TYPE: PRT
<213> ORGANISM: Artificial Sequence
<220> FEATURE:
<223> OTHER INFORMATION: VH2-70/JH6 FR4 heavy chain acceptor sequence

<400> SEQUENCE: 9

Trp Gly Gln Gly Thr Thr Val Thr Val Ser Ser
1               5                   10

<210> SEQ ID NO 10
<211> LENGTH: 30
<212> TYPE: PRT
<213> ORGANISM: Artificial Sequence
<220> FEATURE:
<223> OTHER INFORMATION: VH2-26/JH6 FR1 heavy chain acceptor sequence

<400> SEQUENCE: 10

Glu Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Ser
            20                  25                  30

<210> SEQ ID NO 11
<211> LENGTH: 32
<212> TYPE: PRT
```

```
<213> ORGANISM: Artificial Sequence
<220> FEATURE:
<223> OTHER INFORMATION: VH2-26/JH6 FR3 heavy chain acceptor sequence

<400> SEQUENCE: 11

Arg Leu Thr Ile Ser Lys Asp Thr Ser Lys Ser Gln Val Val Leu Thr
1               5                   10                  15

Met Thr Asn Met Asp Pro Val Asp Thr Ala Thr Tyr Tyr Cys Ala Arg
            20                  25                  30

<210> SEQ ID NO 12
<211> LENGTH: 30
<212> TYPE: PRT
<213> ORGANISM: Artificial Sequence
<220> FEATURE:
<223> OTHER INFORMATION: VH3-72/JH6 FR1 heavy chain acceptor sequence

<400> SEQUENCE: 12

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser
            20                  25                  30

<210> SEQ ID NO 13
<211> LENGTH: 14
<212> TYPE: PRT
<213> ORGANISM: Artificial Sequence
<220> FEATURE:
<223> OTHER INFORMATION: VH3-72/JH6 FR2 heavy chain acceptor sequence

<400> SEQUENCE: 13

Trp Val Arg Gln Ala Pro Gly Lys Gly Leu Glu Trp Val Gly
1               5                   10

<210> SEQ ID NO 14
<211> LENGTH: 32
<212> TYPE: PRT
<213> ORGANISM: Artificial Sequence
<220> FEATURE:
<223> OTHER INFORMATION: VH3-72/JH6 FR3 heavy chain acceptor sequence

<400> SEQUENCE: 14

Arg Phe Thr Ile Ser Arg Asp Asp Ser Lys Asn Ser Leu Tyr Leu Gln
1               5                   10                  15

Met Asn Ser Leu Lys Thr Glu Asp Thr Ala Val Tyr Tyr Cys Ala Arg
            20                  25                  30

<210> SEQ ID NO 15
<211> LENGTH: 30
<212> TYPE: PRT
<213> ORGANISM: Artificial Sequence
<220> FEATURE:
<223> OTHER INFORMATION: VH3-21/JH6 FR1 heavy chain acceptor sequence

<400> SEQUENCE: 15

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser
            20                  25                  30

<210> SEQ ID NO 16
<211> LENGTH: 14
<212> TYPE: PRT
<213> ORGANISM: Artificial Sequence
<220> FEATURE:
```

<223> OTHER INFORMATION: VH3-21/JH6 FR2 heavy chain acceptor sequence

<400> SEQUENCE: 16

Trp Val Arg Gln Ala Pro Gly Lys Gly Leu Glu Trp Val Ser
1               5                   10

<210> SEQ ID NO 17
<211> LENGTH: 32
<212> TYPE: PRT
<213> ORGANISM: Artificial Sequence
<220> FEATURE:
<223> OTHER INFORMATION: VH3-21/JH6 FR3 heavy chain acceptor sequence

<400> SEQUENCE: 17

Arg Phe Thr Ile Ser Arg Asp Asn Ala Lys Asn Ser Leu Tyr Leu Gln
1               5                   10                  15
Met Asn Ser Leu Arg Ala Glu Asp Thr Ala Val Tyr Tyr Cys Ala Arg
                20                  25                  30

<210> SEQ ID NO 18
<211> LENGTH: 30
<212> TYPE: PRT
<213> ORGANISM: Artificial Sequence
<220> FEATURE:
<223> OTHER INFORMATION: VH1-69/JH6 FR1 heavy chain acceptor sequence

<400> SEQUENCE: 18

Glu Val Gln Leu Val Gln Ser Gly Ala Glu Val Lys Lys Pro Gly Ser
1               5                   10                  15
Ser Val Lys Val Ser Cys Lys Ala Ser Gly Gly Thr Phe Ser
                20                  25                  30

<210> SEQ ID NO 19
<211> LENGTH: 14
<212> TYPE: PRT
<213> ORGANISM: Artificial Sequence
<220> FEATURE:
<223> OTHER INFORMATION: VH1-69/JH6 FR2 heavy chain acceptor sequence

<400> SEQUENCE: 19

Trp Val Arg Gln Ala Pro Gly Gln Gly Leu Glu Trp Met Gly
1               5                   10

<210> SEQ ID NO 20
<211> LENGTH: 32
<212> TYPE: PRT
<213> ORGANISM: Artificial Sequence
<220> FEATURE:
<223> OTHER INFORMATION: VH1-69/JH6 FR3 heavy chain acceptor sequence

<400> SEQUENCE: 20

Arg Val Thr Ile Thr Ala Asp Lys Ser Thr Ser Thr Ala Tyr Met Glu
1               5                   10                  15
Leu Ser Ser Leu Arg Ser Glu Asp Thr Ala Val Tyr Tyr Cys Ala Arg
                20                  25                  30

<210> SEQ ID NO 21
<211> LENGTH: 30
<212> TYPE: PRT
<213> ORGANISM: Artificial Sequence
<220> FEATURE:
<223> OTHER INFORMATION: VH1-18/JH6 FR1 heavy chain acceptor sequence

<400> SEQUENCE: 21

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr
            20                  25                  30

<210> SEQ ID NO 22
<211> LENGTH: 32
<212> TYPE: PRT
<213> ORGANISM: Artificial Sequence
<220> FEATURE:
<223> OTHER INFORMATION: VH1-18/JH6 FR3 heavy chain acceptor sequence

<400> SEQUENCE: 22

Arg Val Thr Met Thr Thr Asp Thr Ser Thr Ser Thr Ala Tyr Met Glu
1               5                   10                  15

Leu Arg Ser Leu Arg Ser Asp Asp Thr Ala Val Tyr Tyr Cys Ala Arg
            20                  25                  30

<210> SEQ ID NO 23
<211> LENGTH: 23
<212> TYPE: PRT
<213> ORGANISM: Artificial Sequence
<220> FEATURE:
<223> OTHER INFORMATION: B3/JK4 FR1 light chain acceptor sequence

<400> SEQUENCE: 23

Asp Ile Val Met Thr Gln Ser Pro Asp Ser Leu Ala Val Ser Leu Gly
1               5                   10                  15

Glu Arg Ala Thr Ile Asn Cys
            20

<210> SEQ ID NO 24
<211> LENGTH: 15
<212> TYPE: PRT
<213> ORGANISM: Artificial Sequence
<220> FEATURE:
<223> OTHER INFORMATION: B3/JK4 FR2 light chain acceptor sequence

<400> SEQUENCE: 24

Trp Tyr Gln Gln Lys Pro Gly Gln Pro Pro Lys Leu Leu Ile Tyr
1               5                   10                  15

<210> SEQ ID NO 25
<211> LENGTH: 32
<212> TYPE: PRT
<213> ORGANISM: Artificial Sequence
<220> FEATURE:
<223> OTHER INFORMATION: B3/JK4 FR3 light chain acceptor sequence

<400> SEQUENCE: 25

Gly Val Pro Asp Arg Phe Ser Gly Ser Gly Ser Gly Thr Asp Phe Thr
1               5                   10                  15

Leu Thr Ile Ser Ser Leu Gln Ala Glu Asp Val Ala Val Tyr Tyr Cys
            20                  25                  30

<210> SEQ ID NO 26
<211> LENGTH: 11
<212> TYPE: PRT
<213> ORGANISM: Artificial Sequence
<220> FEATURE:
<223> OTHER INFORMATION: B3/JK4 FR4 light chain acceptor sequence

<400> SEQUENCE: 26

Phe Gly Gly Gly Thr Lys Val Glu Ile Lys Arg
1               5                   10

<210> SEQ ID NO 27
<211> LENGTH: 23
<212> TYPE: PRT
<213> ORGANISM: Artificial Sequence
<220> FEATURE:
<223> OTHER INFORMATION: L2/JK4 FR1 light chain acceptor sequence

<400> SEQUENCE: 27

Glu Ile Val Met Thr Gln Ser Pro Ala Thr Leu Ser Val Ser Pro Gly
1               5                   10                  15

Glu Arg Ala Thr Leu Ser Cys
            20

<210> SEQ ID NO 28
<211> LENGTH: 15
<212> TYPE: PRT
<213> ORGANISM: Artificial Sequence
<220> FEATURE:
<223> OTHER INFORMATION: L2/JK4 FR2 light chain acceptor sequence

<400> SEQUENCE: 28

Trp Tyr Gln Gln Lys Pro Gly Gln Ala Pro Arg Leu Leu Ile Tyr
1               5                   10                  15

<210> SEQ ID NO 29
<211> LENGTH: 32
<212> TYPE: PRT
<213> ORGANISM: Artificial Sequence
<220> FEATURE:
<223> OTHER INFORMATION: L2/JK4 FR3 light chain acceptor sequence

<400> SEQUENCE: 29

Gly Ile Pro Ala Arg Phe Ser Gly Ser Gly Ser Gly Thr Glu Phe Thr
1               5                   10                  15

Leu Thr Ile Ser Ser Leu Gln Ser Glu Asp Phe Ala Val Tyr Tyr Cys
            20                  25                  30

<210> SEQ ID NO 30
<211> LENGTH: 23
<212> TYPE: PRT
<213> ORGANISM: Artificial Sequence
<220> FEATURE:
<223> OTHER INFORMATION: L15/JK4 FR1 light chain acceptor sequence

<400> SEQUENCE: 30

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 31
<211> LENGTH: 15
<212> TYPE: PRT
<213> ORGANISM: Artificial Sequence
<220> FEATURE:
<223> OTHER INFORMATION: L15/JK4 FR2 light chain acceptor sequence

<400> SEQUENCE: 31

Trp Tyr Gln Gln Lys Pro Glu Lys Ala Pro Lys Ser Leu Ile Tyr
1               5                   10                  15

<210> SEQ ID NO 32
<211> LENGTH: 32
<212> TYPE: PRT
<213> ORGANISM: Artificial Sequence
<220> FEATURE:
<223> OTHER INFORMATION: L15/JK4 FR3 light chain acceptor sequence

<400> SEQUENCE: 32

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 33
<211> LENGTH: 23
<212> TYPE: PRT
<213> ORGANISM: Artificial Sequence
<220> FEATURE:
<223> OTHER INFORMATION: L5/JK4 FR1 light chain acceptor sequence

<400> SEQUENCE: 33

Asp Ile Gln Met Thr Gln Ser Pro Ser Ser Val Ser Ala Ser Val Gly
1               5                   10                  15

Asp Arg Val Thr Ile Thr Cys
            20

<210> SEQ ID NO 34
<211> LENGTH: 15
<212> TYPE: PRT
<213> ORGANISM: Artificial Sequence
<220> FEATURE:
<223> OTHER INFORMATION: L5/JK4 FR2 light chain acceptor sequence

<400> SEQUENCE: 34

Trp Tyr Gln Gln Lys Pro Gly Lys Ala Pro Lys Leu Leu Ile Tyr
1               5                   10                  15

<210> SEQ ID NO 35
<211> LENGTH: 30
<212> TYPE: PRT
<213> ORGANISM: Artificial Sequence
<220> FEATURE:
<223> OTHER INFORMATION: IGHV4-59 FR1 heavy chain acceptor sequence

<400> SEQUENCE: 35

Glu Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser
            20                  25                  30

<210> SEQ ID NO 36
<211> LENGTH: 14
<212> TYPE: PRT
<213> ORGANISM: Artificial Sequence
<220> FEATURE:
<223> OTHER INFORMATION: IGHV4-59 FR2 heavy chain acceptor sequence

<400> SEQUENCE: 36

Trp Ile Arg Gln Pro Pro Gly Lys Gly Leu Glu Trp Ile Gly
1               5                   10

<210> SEQ ID NO 37
<211> LENGTH: 32
<212> TYPE: PRT

<213> ORGANISM: Artificial Sequence
<220> FEATURE:
<223> OTHER INFORMATION: IGHV4-59 FR3 heavy chain acceptor sequence

<400> SEQUENCE: 37

Arg Val Thr Ile Ser Val Asp Thr Ser Lys Asn Gln Phe Ser Leu Lys
1               5                   10                  15

Leu Ser Ser Val Thr Ala Ala Asp Thr Ala Val Tyr Tyr Cys Ala Arg
            20                  25                  30

<210> SEQ ID NO 38
<211> LENGTH: 11
<212> TYPE: PRT
<213> ORGANISM: Artificial Sequence
<220> FEATURE:
<223> OTHER INFORMATION: IGHV4-59/JH FR4 heavy chain acceptor sequence

<400> SEQUENCE: 38

Trp Gly Gln Gly Thr Leu Val Thr Val Ser Ser
1               5                   10

<210> SEQ ID NO 39
<211> LENGTH: 30
<212> TYPE: PRT
<213> ORGANISM: Artificial Sequence
<220> FEATURE:
<223> OTHER INFORMATION: IGHV3-66 FW1 heavy chain acceptor sequence

<400> SEQUENCE: 39

Glu Val Gln Leu Val Glu Ser Gly Gly Gly Leu Val Gln Pro Gly Gly
1               5                   10                  15

Ser Leu Arg Leu Ser Cys Ala Val Ser Gly Gly Ser Ile Ser
            20                  25                  30

<210> SEQ ID NO 40
<211> LENGTH: 14
<212> TYPE: PRT
<213> ORGANISM: Artificial Sequence
<220> FEATURE:
<223> OTHER INFORMATION: IGHV3-66 FW2 heavy chain acceptor sequence

<400> SEQUENCE: 40

Trp Ile Arg Gln Ala Pro Gly Lys Gly Leu Glu Trp Ile Gly
1               5                   10

<210> SEQ ID NO 41
<211> LENGTH: 32
<212> TYPE: PRT
<213> ORGANISM: Artificial Sequence
<220> FEATURE:
<223> OTHER INFORMATION: IGHV3-66 FW3 heavy chain acceptor sequence

<400> SEQUENCE: 41

Arg Val Thr Ile Ser Val Asp Thr Ser Lys Asn Ser Phe Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 42
<211> LENGTH: 11
<212> TYPE: PRT
<213> ORGANISM: Artificial Sequence
<220> FEATURE:
<223> OTHER INFORMATION: IGHV3-66/JH FW4 heavy chain acceptor sequence

<400> SEQUENCE: 42

```
Trp Gly Gln Gly Thr Leu Val Thr Val Ser Ser
1               5                   10

<210> SEQ ID NO 43
<211> LENGTH: 30
<212> TYPE: PRT
<213> ORGANISM: Artificial Sequence
<220> FEATURE:
<223> OTHER INFORMATION: IGHV4-59 FR1 heavy chain acceptor sequence

<400> SEQUENCE: 43

Glu Val Gln Leu Gln Glu Ser Gly Pro Gly Leu Val Lys Pro Gly Glu
1               5                   10                  15

Thr Leu Ser Leu Thr Cys Thr Val Ser Gly Gly Ser Ile Ser
            20                  25                  30

<210> SEQ ID NO 44
<211> LENGTH: 14
<212> TYPE: PRT
<213> ORGANISM: Artificial Sequence
<220> FEATURE:
<223> OTHER INFORMATION: IGHV4-59 FR2 heavy chain acceptor sequence

<400> SEQUENCE: 44

Trp Ile Arg Gln Ala Pro Gly Lys Gly Leu Glu Trp Ile Gly
1               5                   10

<210> SEQ ID NO 45
<211> LENGTH: 32
<212> TYPE: PRT
<213> ORGANISM: Artificial Sequence
<220> FEATURE:
<223> OTHER INFORMATION: IGHV4-59 FR3 heavy chain acceptor sequence

<400> SEQUENCE: 45

Arg Val Thr Ile Ser Val Asp Thr Ser Lys Asn Gln Phe Tyr Leu Lys
1               5                   10                  15

Leu Ser Ser Val Arg Ala Glu Asp Thr Ala Val Tyr Tyr Cys Ala Arg
            20                  25                  30

<210> SEQ ID NO 46
<211> LENGTH: 11
<212> TYPE: PRT
<213> ORGANISM: Artificial Sequence
<220> FEATURE:
<223> OTHER INFORMATION: IGHV4-59/JH FR4 heavy chain acceptor sequence

<400> SEQUENCE: 46

Trp Gly Gln Gly Thr Leu Val Thr Val Ser Ser
1               5                   10

<210> SEQ ID NO 47
<211> LENGTH: 30
<212> TYPE: PRT
<213> ORGANISM: Artificial Sequence
<220> FEATURE:
<223> OTHER INFORMATION: IGHV5-51 FR1 heavy chain acceptor sequence

<400> SEQUENCE: 47

Glu Val Gln Leu Val Gln Ser Gly Thr Glu Val Lys Lys Pro Gly Glu
1               5                   10                  15

Ser Leu Lys Ile Ser Cys Lys Val Ser Gly Gly Ser Ile Ser
            20                  25                  30
```

<210> SEQ ID NO 48
<211> LENGTH: 14
<212> TYPE: PRT
<213> ORGANISM: Artificial Sequence
<220> FEATURE:
<223> OTHER INFORMATION: IGHV5-51 FR2 heavy chain acceptor sequence

<400> SEQUENCE: 48

Trp Ile Arg Gln Met Pro Gly Lys Gly Leu Glu Trp Ile Gly
1               5                   10

<210> SEQ ID NO 49
<211> LENGTH: 32
<212> TYPE: PRT
<213> ORGANISM: Artificial Sequence
<220> FEATURE:
<223> OTHER INFORMATION: IGHV5-51 FR3 heavy chain acceptor sequence

<400> SEQUENCE: 49

Gln Val Thr Ile Ser Val Asp Thr Ser Phe Asn Thr Phe Phe Leu Gln
1               5                   10                  15

Trp Ser Ser Leu Lys Ala Ser Asp Thr Ala Met Tyr Tyr Cys Ala Arg
            20                  25                  30

<210> SEQ ID NO 50
<211> LENGTH: 11
<212> TYPE: PRT
<213> ORGANISM: Artificial Sequence
<220> FEATURE:
<223> OTHER INFORMATION: IGHV5-51/JH FR4 heavy chain acceptor sequence

<400> SEQUENCE: 50

Trp Gly Gln Gly Thr Met Val Thr Val Ser Ser
1               5                   10

<210> SEQ ID NO 51
<211> LENGTH: 30
<212> TYPE: PRT
<213> ORGANISM: Artificial Sequence
<220> FEATURE:
<223> OTHER INFORMATION: IGHV2-70 FR1 heavy chain acceptor sequence

<400> SEQUENCE: 51

Glu Val Thr Leu Arg Glu Ser Gly Pro Ala Leu Val Lys Pro Thr Gln
1               5                   10                  15

Thr Leu Thr Leu Thr Cys Thr Val Ser Gly Gly Ser Ile Ser
            20                  25                  30

<210> SEQ ID NO 52
<211> LENGTH: 14
<212> TYPE: PRT
<213> ORGANISM: Artificial Sequence
<220> FEATURE:
<223> OTHER INFORMATION: IGHV2-70 FR2 heavy chain acceptor sequence

<400> SEQUENCE: 52

Trp Ile Arg Gln Pro Pro Gly Lys Gly Leu Glu Trp Ile Gly
1               5                   10

<210> SEQ ID NO 53
<211> LENGTH: 32
<212> TYPE: PRT
<213> ORGANISM: Artificial Sequence
<220> FEATURE:
<223> OTHER INFORMATION: IGHV2-70 FR3 heavy chain acceptor sequence

<400> SEQUENCE: 53

```
Arg Val Thr Ile Ser Val Asp Thr Ser Lys Asn Gln Phe Val Leu Thr
1               5                   10                  15

Met Thr Asn Met Asp Pro Val Asp Thr Ala Thr Tyr Tyr Cys Ala Arg
            20                  25                  30

<210> SEQ ID NO 54
<211> LENGTH: 11
<212> TYPE: PRT
<213> ORGANISM: Artificial Sequence
<220> FEATURE:
<223> OTHER INFORMATION: IGHV2-70/JH FR4 heavy chain acceptor sequence

<400> SEQUENCE: 54

Trp Gly Gln Gly Thr Thr Val Thr Val Ser Ser
1               5                   10

<210> SEQ ID NO 55
<211> LENGTH: 30
<212> TYPE: PRT
<213> ORGANISM: Artificial Sequence
<220> FEATURE:
<223> OTHER INFORMATION: IGHV3-15 FR1 heavy chain acceptor sequence

<400> SEQUENCE: 55

Glu Val Gln Leu Leu Glu Ser Gly Gly Gly Leu Val Lys Ser Gly Gly
1               5                   10                  15

Ser Leu Arg Leu Ser Cys Ala Ala Ser Gly Phe Thr Phe Arg
            20                  25                  30

<210> SEQ ID NO 56
<211> LENGTH: 14
<212> TYPE: PRT
<213> ORGANISM: Artificial Sequence
<220> FEATURE:
<223> OTHER INFORMATION: IGHV3-15 FR2 heavy chain acceptor sequence

<400> SEQUENCE: 56

Trp Val Arg Gln Ala Pro Gly Lys Gly Leu Glu Trp Val Ala
1               5                   10

<210> SEQ ID NO 57
<211> LENGTH: 32
<212> TYPE: PRT
<213> ORGANISM: Artificial Sequence
<220> FEATURE:
<223> OTHER INFORMATION: IGHV3-15 FR3 heavy chain acceptor sequence

<400> SEQUENCE: 57

Arg Phe Thr Ile Ser Arg Asp Asn Ser Lys Asn Thr Leu Tyr Leu Gln
1               5                   10                  15

Leu Asn Ser Leu Arg Ala Glu Asp Thr Ala Val Tyr Tyr Cys Ala Lys
            20                  25                  30

<210> SEQ ID NO 58
<211> LENGTH: 11
<212> TYPE: PRT
<213> ORGANISM: Artificial Sequence
<220> FEATURE:
<223> OTHER INFORMATION: IGHV3-15/JH FR4 heavy chain acceptor sequence

<400> SEQUENCE: 58

Trp Gly Gln Gly Thr Met Val Thr Val Ser Ser
1               5                   10
```

```
<210> SEQ ID NO 59
<211> LENGTH: 30
<212> TYPE: PRT
<213> ORGANISM: Artificial Sequence
<220> FEATURE:
<223> OTHER INFORMATION: IGHV3-43 FR1 heavy chain acceptor sequence

<400> SEQUENCE: 59

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Gly
            20                  25                  30

<210> SEQ ID NO 60
<211> LENGTH: 14
<212> TYPE: PRT
<213> ORGANISM: Artificial Sequence
<220> FEATURE:
<223> OTHER INFORMATION: IGHV3-43 FR2 heavy chain acceptor sequence

<400> SEQUENCE: 60

Trp Val Arg Gln Ala Pro Gly Lys Gly Leu Glu Trp Val Ala
1               5                   10

<210> SEQ ID NO 61
<211> LENGTH: 32
<212> TYPE: PRT
<213> ORGANISM: Artificial Sequence
<220> FEATURE:
<223> OTHER INFORMATION: IGHV3-43 FR3 heavy chain acceptor sequence

<400> SEQUENCE: 61

Arg Phe Thr Ile Ser Arg Asp Asn Ser Lys Asn Thr Leu Tyr Leu Gln
1               5                   10                  15

Leu Asn Ser Leu Arg Ala Glu Asp Thr Ala Val Tyr Tyr Cys Ala Lys
            20                  25                  30

<210> SEQ ID NO 62
<211> LENGTH: 11
<212> TYPE: PRT
<213> ORGANISM: Artificial Sequence
<220> FEATURE:
<223> OTHER INFORMATION: IGHV3-43/JH FR4 heavy chain acceptor sequence

<400> SEQUENCE: 62

Trp Gly Gln Gly Thr Met Val Thr Val Ser Ser
1               5                   10

<210> SEQ ID NO 63
<211> LENGTH: 22
<212> TYPE: PRT
<213> ORGANISM: Artificial Sequence
<220> FEATURE:
<223> OTHER INFORMATION: IGLV3-1 FR1 light chain acceptor sequence

<400> SEQUENCE: 63

Ser Tyr Glu Leu Thr Gln Pro Pro Ser Val Ser Val Ser Pro Gly Gln
1               5                   10                  15

Thr Ala Ser Ile Thr Cys
            20

<210> SEQ ID NO 64
<211> LENGTH: 15
<212> TYPE: PRT
<213> ORGANISM: Artificial Sequence
<220> FEATURE:
```

```
<223> OTHER INFORMATION: IGLV3-1 FR2 light chain acceptor sequence

<400> SEQUENCE: 64

Trp Tyr Gln Gln Lys Pro Gly Gln Ser Pro Val Leu Val Ile Tyr
1               5                   10                  15

<210> SEQ ID NO 65
<211> LENGTH: 32
<212> TYPE: PRT
<213> ORGANISM: Artificial Sequence
<220> FEATURE:
<223> OTHER INFORMATION: IGLV3-1 FR3 light chain acceptor sequence

<400> SEQUENCE: 65

Gly Ile Pro Glu Arg Phe Ser Gly Ser Asn Ser Gly Asp Thr Ala Thr
1               5                   10                  15

Leu Thr Ile Ser Gly Thr Gln Pro Met Asp Glu Ala Asp Tyr Tyr Cys
            20                  25                  30

<210> SEQ ID NO 66
<211> LENGTH: 10
<212> TYPE: PRT
<213> ORGANISM: Artificial Sequence
<220> FEATURE:
<223> OTHER INFORMATION: IGLV3-1/JL FR4 light chain acceptor sequence

<400> SEQUENCE: 66

Phe Gly Tyr Gly Thr Lys Val Thr Val Leu
1               5                   10

<210> SEQ ID NO 67
<211> LENGTH: 22
<212> TYPE: PRT
<213> ORGANISM: Artificial Sequence
<220> FEATURE:
<223> OTHER INFORMATION: IGLV3-1 FR1 light chain acceptor sequence

<400> SEQUENCE: 67

Ser Tyr Glu Leu Thr Gln Pro Pro Ser Val Ser Val Ser Pro Gly Gln
1               5                   10                  15

Thr Ala Ser Ile Thr Cys
            20

<210> SEQ ID NO 68
<211> LENGTH: 15
<212> TYPE: PRT
<213> ORGANISM: Artificial Sequence
<220> FEATURE:
<223> OTHER INFORMATION: IGLV3-1 FR2 light chain acceptor sequence

<400> SEQUENCE: 68

Trp Tyr Gln Gln Lys Pro Gly Gln Ser Pro Val Leu Val Ile Tyr
1               5                   10                  15

<210> SEQ ID NO 69
<211> LENGTH: 32
<212> TYPE: PRT
<213> ORGANISM: Artificial Sequence
<220> FEATURE:
<223> OTHER INFORMATION: IGLV3-1 FR3 light chain acceptor sequence

<400> SEQUENCE: 69

Gly Ile Pro Glu Arg Phe Ser Gly Ser Asn Ser Gly Asp Thr Ala Thr
1               5                   10                  15

Leu Thr Ile Ser Gly Thr Gln Pro Met Asp Glu Ala Asp Tyr Tyr Cys
```

```
            20                  25                  30

<210> SEQ ID NO 70
<211> LENGTH: 10
<212> TYPE: PRT
<213> ORGANISM: Artificial Sequence
<220> FEATURE:
<223> OTHER INFORMATION: IGLV3-1/JL FR4 light chain acceptor sequence

<400> SEQUENCE: 70

Gly Gly Gly Thr Lys Leu Thr Val Leu Gly
1               5                   10

<210> SEQ ID NO 71
<211> LENGTH: 21
<212> TYPE: PRT
<213> ORGANISM: Artificial Sequence
<220> FEATURE:
<223> OTHER INFORMATION: IGLV3-1 FR1 light chain acceptor sequence

<400> SEQUENCE: 71

Tyr Glu Leu Thr Gln Pro Pro Ser Val Ser Val Ser Pro Gly Gln Thr
1               5                   10                  15

Ala Ser Ile Thr Cys
            20

<210> SEQ ID NO 72
<211> LENGTH: 15
<212> TYPE: PRT
<213> ORGANISM: Artificial Sequence
<220> FEATURE:
<223> OTHER INFORMATION: IGLV3-1 FR2 light chain acceptor sequence

<400> SEQUENCE: 72

Trp Tyr Gln Gln Lys Pro Gly Gln Ser Pro Val Leu Val Ile Tyr
1               5                   10                  15

<210> SEQ ID NO 73
<211> LENGTH: 32
<212> TYPE: PRT
<213> ORGANISM: Artificial Sequence
<220> FEATURE:
<223> OTHER INFORMATION: IGLV3-1 FR3 light chain acceptor sequence

<400> SEQUENCE: 73

Gly Ile Pro Glu Arg Phe Ser Gly Ser Asn Ser Gly Asp Thr Ala Thr
1               5                   10                  15

Leu Thr Ile Ser Gly Thr Gln Pro Met Asp Glu Ala Asp Tyr Tyr Cys
            20                  25                  30

<210> SEQ ID NO 74
<211> LENGTH: 10
<212> TYPE: PRT
<213> ORGANISM: Artificial Sequence
<220> FEATURE:
<223> OTHER INFORMATION: IGLV3-1/JL FR4 light chain acceptor sequence

<400> SEQUENCE: 74

Gly Gly Gly Thr Lys Leu Thr Val Leu Gly
1               5                   10

<210> SEQ ID NO 75
<211> LENGTH: 22
<212> TYPE: PRT
<213> ORGANISM: Artificial Sequence
<220> FEATURE:
```

-continued

<223> OTHER INFORMATION: IGLV3-1 FR1 light chain acceptor sequence

<400> SEQUENCE: 75

Leu Tyr Val Leu Thr Gln Pro Pro Ser Val Ser Val Ser Pro Gly Gln
1               5                   10                  15

Thr Ala Ser Ile Thr Cys
            20

<210> SEQ ID NO 76
<211> LENGTH: 15
<212> TYPE: PRT
<213> ORGANISM: Artificial Sequence
<220> FEATURE:
<223> OTHER INFORMATION: IGLV3-1 FR2 light chain acceptor sequence

<400> SEQUENCE: 76

Trp Tyr Gln Gln Lys Pro Gly Gln Ser Pro Val Leu Val Ile Tyr
1               5                   10                  15

<210> SEQ ID NO 77
<211> LENGTH: 32
<212> TYPE: PRT
<213> ORGANISM: Artificial Sequence
<220> FEATURE:
<223> OTHER INFORMATION: IGLV3-1 FR3 light chain acceptor sequence

<400> SEQUENCE: 77

Gly Ile Pro Glu Arg Phe Ser Gly Ser Asn Ser Gly Asp Thr Ala Thr
1               5                   10                  15

Leu Thr Ile Ser Gly Thr Gln Thr Met Asp Glu Ala Asp Tyr Leu Cys
            20                  25                  30

<210> SEQ ID NO 78
<211> LENGTH: 11
<212> TYPE: PRT
<213> ORGANISM: Artificial Sequence
<220> FEATURE:
<223> OTHER INFORMATION: IGLV3-1/JL FR4 light chain acceptor sequence

<400> SEQUENCE: 78

Phe Gly Gly Gly Thr Lys Val Thr Val Leu Gly
1               5                   10

<210> SEQ ID NO 79
<211> LENGTH: 23
<212> TYPE: PRT
<213> ORGANISM: Artificial Sequence
<220> FEATURE:
<223> OTHER INFORMATION: IGKV6D-21 FR1 light chain acceptor sequence

<400> SEQUENCE: 79

Glu Tyr Val Leu Thr Gln Ser Pro Asp Phe Gln Ser Val Thr Pro Lys
1               5                   10                  15

Glu Lys Val Thr Ile Thr Cys
            20

<210> SEQ ID NO 80
<211> LENGTH: 15
<212> TYPE: PRT
<213> ORGANISM: Artificial Sequence
<220> FEATURE:
<223> OTHER INFORMATION: IGKV6D-21 FR2 light chain acceptor sequence

<400> SEQUENCE: 80

Trp Tyr Gln Gln Lys Pro Asp Gln Ser Pro Lys Leu Val Ile Tyr

-continued

```
1               5                   10                  15

<210> SEQ ID NO 81
<211> LENGTH: 32
<212> TYPE: PRT
<213> ORGANISM: Artificial Sequence
<220> FEATURE:
<223> OTHER INFORMATION: IGKV6D-21 FR3 light chain acceptor sequence

<400> SEQUENCE: 81

Gly Val Pro Ser Arg Phe Ser Gly Ser Asn Ser Gly Asp Asp Ala Thr
1               5                   10                  15

Leu Thr Ile Asn Ser Leu Glu Ala Glu Asp Ala Ala Thr Tyr Tyr Cys
            20                  25                  30

<210> SEQ ID NO 82
<211> LENGTH: 11
<212> TYPE: PRT
<213> ORGANISM: Artificial Sequence
<220> FEATURE:
<223> OTHER INFORMATION: IGKV6D-21/JK FR4 light chain acceptor sequence

<400> SEQUENCE: 82

Phe Gly Gln Gly Thr Lys Val Glu Ile Lys Arg
1               5                   10

<210> SEQ ID NO 83
<211> LENGTH: 23
<212> TYPE: PRT
<213> ORGANISM: Artificial Sequence
<220> FEATURE:
<223> OTHER INFORMATION: IGKV3D-15 FR1 light chain acceptor sequence

<400> SEQUENCE: 83

Glu Tyr Val Leu Thr Gln Ser Pro Ala Thr Leu Ser Val Ser Pro Gly
1               5                   10                  15

Glu Arg Ala Thr Leu Ser Cys
            20

<210> SEQ ID NO 84
<211> LENGTH: 15
<212> TYPE: PRT
<213> ORGANISM: Artificial Sequence
<220> FEATURE:
<223> OTHER INFORMATION: IGKV3D-15 FR2 light chain acceptor sequence

<400> SEQUENCE: 84

Trp Tyr Gln Gln Lys Pro Gly Gln Ser Pro Arg Leu Val Ile Tyr
1               5                   10                  15

<210> SEQ ID NO 85
<211> LENGTH: 32
<212> TYPE: PRT
<213> ORGANISM: Artificial Sequence
<220> FEATURE:
<223> OTHER INFORMATION: IGKV3D-15 FR3 light chain acceptor sequence

<400> SEQUENCE: 85

Asp Ile Pro Ala Arg Phe Ser Gly Ser Asn Ser Gly Asp Glu Ala Thr
1               5                   10                  15

Leu Thr Ile Ser Ser Leu Gln Ser Glu Asp Phe Ala Val Tyr Tyr Cys
            20                  25                  30

<210> SEQ ID NO 86
<211> LENGTH: 11
```

```
<212> TYPE: PRT
<213> ORGANISM: Artificial Sequence
<220> FEATURE:
<223> OTHER INFORMATION: IGKV3D-15/JK FR4 light chain acceptor sequence

<400> SEQUENCE: 86

Phe Gly Gln Gly Thr Arg Leu Glu Ile Lys Arg
1               5                   10

<210> SEQ ID NO 87
<211> LENGTH: 23
<212> TYPE: PRT
<213> ORGANISM: Artificial Sequence
<220> FEATURE:
<223> OTHER INFORMATION: IGKV4-1 FR1 light chain acceptor sequence

<400> SEQUENCE: 87

Asp Tyr Val Leu Thr Gln Ser Pro Asp Ser Leu Ala Val Ser Leu Gly
1               5                   10                  15

Glu Arg Ala Thr Ile Asn Cys
            20

<210> SEQ ID NO 88
<211> LENGTH: 15
<212> TYPE: PRT
<213> ORGANISM: Artificial Sequence
<220> FEATURE:
<223> OTHER INFORMATION: IGKV4-1 FR2 light chain acceptor sequence

<400> SEQUENCE: 88

Trp Tyr Gln Gln Lys Pro Gly Gln Ser Pro Lys Leu Val Ile Tyr
1               5                   10                  15

<210> SEQ ID NO 89
<211> LENGTH: 32
<212> TYPE: PRT
<213> ORGANISM: Artificial Sequence
<220> FEATURE:
<223> OTHER INFORMATION: IGKV4-1 FR3 light chain acceptor sequence

<400> SEQUENCE: 89

Gly Ile Pro Asp Arg Phe Ser Gly Ser Asn Ser Gly Asp Asp Ala Thr
1               5                   10                  15

Leu Thr Ile Ser Ser Leu Gln Ala Glu Asp Val Ala Val Tyr Tyr Cys
            20                  25                  30

<210> SEQ ID NO 90
<211> LENGTH: 11
<212> TYPE: PRT
<213> ORGANISM: Artificial Sequence
<220> FEATURE:
<223> OTHER INFORMATION: IGKV4-1/JK FR4 light chain acceptor sequence

<400> SEQUENCE: 90

Phe Gly Gly Gly Thr Lys Val Glu Ile Lys Arg
1               5                   10

<210> SEQ ID NO 91
<211> LENGTH: 22
<212> TYPE: PRT
<213> ORGANISM: Artificial Sequence
<220> FEATURE:
<223> OTHER INFORMATION: IGLV3-1 FR1 light chain acceptor sequence

<400> SEQUENCE: 91

Leu Pro Val Leu Thr Gln Pro Pro Ser Val Ser Val Ser Pro Gly Gln
```

```
                               1               5                  10                  15
Thr Ala Ser Ile Thr Cys
            20

<210> SEQ ID NO 92
<211> LENGTH: 15
<212> TYPE: PRT
<213> ORGANISM: Artificial Sequence
<220> FEATURE:
<223> OTHER INFORMATION: IGLV3-1 FR2 light chain acceptor sequence

<400> SEQUENCE: 92

Trp Tyr Gln Gln Lys Pro Gly Gln Ser Pro Val Leu Val Ile Tyr
1               5                  10                  15

<210> SEQ ID NO 93
<211> LENGTH: 32
<212> TYPE: PRT
<213> ORGANISM: Artificial Sequence
<220> FEATURE:
<223> OTHER INFORMATION: IGLV3-1 FR3 light chain acceptor sequence

<400> SEQUENCE: 93

Gly Ile Pro Glu Arg Phe Ser Gly Ser Asn Ser Gly Asn Thr Ala Thr
1               5                  10                  15

Leu Thr Ile Ser Gly Thr Gln Thr Met Asp Glu Ala Asp Tyr Leu Cys
            20                  25                  30

<210> SEQ ID NO 94
<211> LENGTH: 10
<212> TYPE: PRT
<213> ORGANISM: Artificial Sequence
<220> FEATURE:
<223> OTHER INFORMATION: IGLV3-1/JL FR4 light chain acceptor sequence

<400> SEQUENCE: 94

Phe Gly Gly Gly Thr Lys Val Thr Val Leu
1               5                  10

<210> SEQ ID NO 95
<211> LENGTH: 22
<212> TYPE: PRT
<213> ORGANISM: Artificial Sequence
<220> FEATURE:
<223> OTHER INFORMATION: IGLV3-1 FR1 light chain acceptor sequence

<400> SEQUENCE: 95

Ser Tyr Glu Leu Thr Gln Pro Pro Ser Val Ser Val Ser Pro Gly Gln
1               5                  10                  15

Thr Ala Ser Ile Thr Cys
            20

<210> SEQ ID NO 96
<211> LENGTH: 15
<212> TYPE: PRT
<213> ORGANISM: Artificial Sequence
<220> FEATURE:
<223> OTHER INFORMATION: IGLV3-1 FR2 light chain acceptor sequence

<400> SEQUENCE: 96

Trp Tyr Gln Gln Lys Pro Gly Gln Ser Pro Val Leu Val Ile Tyr
1               5                  10                  15

<210> SEQ ID NO 97
<211> LENGTH: 32
```

```
<212> TYPE: PRT
<213> ORGANISM: Artificial Sequence
<220> FEATURE:
<223> OTHER INFORMATION: IGLV3-1 FR3 light chain acceptor sequence

<400> SEQUENCE: 97

Gly Ile Pro Glu Arg Phe Ser Gly Ser Asn Ser Gly Asn Thr Ala Thr
1               5                   10                  15

Leu Thr Ile Ser Gly Thr Gln Thr Met Asp Glu Ala Asp Tyr Leu Cys
            20                  25                  30

<210> SEQ ID NO 98
<211> LENGTH: 10
<212> TYPE: PRT
<213> ORGANISM: Artificial Sequence
<220> FEATURE:
<223> OTHER INFORMATION: IGLV3-1/JL FR4 light chain acceptor sequence

<400> SEQUENCE: 98

Phe Gly Gly Gly Thr Lys Leu Thr Val Leu
1               5                   10

<210> SEQ ID NO 99
<211> LENGTH: 7
<212> TYPE: PRT
<213> ORGANISM: Artificial Sequence
<220> FEATURE:
<223> OTHER INFORMATION: DLL4 antibody CDR-H1 consensus sequence
<220> FEATURE:
<221> NAME/KEY: MISC_FEATURE
<222> LOCATION: (1)..(1)
<223> OTHER INFORMATION: X is S or N
<220> FEATURE:
<221> NAME/KEY: MISC_FEATURE
<222> LOCATION: (2)..(2)
<223> OTHER INFORMATION: X is S, G or N
<220> FEATURE:
<221> NAME/KEY: MISC_FEATURE
<222> LOCATION: (3)..(3)
<223> OTHER INFORMATION: X is S, N, T, G or R
<220> FEATURE:
<221> NAME/KEY: MISC_FEATURE
<222> LOCATION: (5)..(5)
<223> OTHER INFORMATION: X is Y or H

<400> SEQUENCE: 99

Xaa Xaa Xaa Tyr Xaa Trp Gly
1               5

<210> SEQ ID NO 100
<211> LENGTH: 16
<212> TYPE: PRT
<213> ORGANISM: Artificial Sequence
<220> FEATURE:
<223> OTHER INFORMATION: DLL4 antibody CDR-H2 consensus sequence
<220> FEATURE:
<221> NAME/KEY: MISC_FEATURE
<222> LOCATION: (3)..(3)
<223> OTHER INFORMATION: X is Y, N or S
<220> FEATURE:
<221> NAME/KEY: MISC_FEATURE
<222> LOCATION: (5)..(5)
<223> OTHER INFORMATION: X is T, N, A, I, S or R
<220> FEATURE:
<221> NAME/KEY: MISC_FEATURE
<222> LOCATION: (7)..(7)
<223> OTHER INFORMATION: X is S, N, T or G
<220> FEATURE:
<221> NAME/KEY: MISC_FEATURE
<222> LOCATION: (16)..(16)
<223> OTHER INFORMATION: X is S, N, D or G
```

```
<400> SEQUENCE: 100

Asp Ile Xaa Tyr Xaa Gly Xaa Thr Tyr Tyr Asn Pro Ser Leu Lys Xaa
1               5                   10                  15

<210> SEQ ID NO 101
<211> LENGTH: 11
<212> TYPE: PRT
<213> ORGANISM: Artificial Sequence
<220> FEATURE:
<223> OTHER INFORMATION: DLL4 antibody CDR-H3 consensus sequence
<220> FEATURE:
<221> NAME/KEY: MISC_FEATURE
<222> LOCATION: (1)..(1)
<223> OTHER INFORMATION: X is E, Y, F, Q, W, L or A
<220> FEATURE:
<221> NAME/KEY: MISC_FEATURE
<222> LOCATION: (2)..(2)
<223> OTHER INFORMATION: X is D, A, S, G, V, E or N
<220> FEATURE:
<221> NAME/KEY: MISC_FEATURE
<222> LOCATION: (3)..(3)
<223> OTHER INFORMATION: X is V, M, L, P or A
<220> FEATURE:
<221> NAME/KEY: MISC_FEATURE
<222> LOCATION: (4)..(4)
<223> OTHER INFORMATION: X is I, A, P, R, S, K, Q, V, G, M, or E
<220> FEATURE:
<221> NAME/KEY: MISC_FEATURE
<222> LOCATION: (5)..(5)
<223> OTHER INFORMATION: X is L, Y, F or M
<220> FEATURE:
<221> NAME/KEY: MISC_FEATURE
<222> LOCATION: (6)..(6)
<223> OTHER INFORMATION: X is R, G, S, Q or A
<220> FEATURE:
<221> NAME/KEY: MISC_FEATURE
<222> LOCATION: (8)..(8)
<223> OTHER INFORMATION: X is G, A or S
<220> FEATURE:
<221> NAME/KEY: MISC_FEATURE
<222> LOCATION: (9)..(9)
<223> OTHER INFORMATION: X is S, A, L, V, R or G
<220> FEATURE:
<221> NAME/KEY: MISC_FEATURE
<222> LOCATION: (11)..(11)
<223> OTHER INFORMATION: X is Y, D, S, N, H, E, R, L, P, C, I, M, T,
      Q or K

<400> SEQUENCE: 101

Xaa Xaa Xaa Xaa Xaa Xaa Gly Xaa Xaa Asp Xaa
1               5                   10

<210> SEQ ID NO 102
<211> LENGTH: 11
<212> TYPE: PRT
<213> ORGANISM: Artificial Sequence
<220> FEATURE:
<223> OTHER INFORMATION: DLL4 antibody CDR-L1 consensus sequence
<220> FEATURE:
<221> NAME/KEY: MISC_FEATURE
<222> LOCATION: (3)..(3)
<223> OTHER INFORMATION: X is Q, E or D
<220> FEATURE:
<221> NAME/KEY: MISC_FEATURE
<222> LOCATION: (4)..(4)
<223> OTHER INFORMATION: X is R, S, G, M, K, L or T
<220> FEATURE:
<221> NAME/KEY: MISC_FEATURE
<222> LOCATION: (7)..(7)
<223> OTHER INFORMATION: X is D or E
<220> FEATURE:
<221> NAME/KEY: MISC_FEATURE
<222> LOCATION: (10)..(10)
<223> OTHER INFORMATION: X is A or V
```

```
<400> SEQUENCE: 102

Ser Gly Xaa Xaa Leu Gly Xaa Lys Tyr Xaa Ser
1               5                   10

<210> SEQ ID NO 103
<211> LENGTH: 7
<212> TYPE: PRT
<213> ORGANISM: Artificial Sequence
<220> FEATURE:
<223> OTHER INFORMATION: DLL4 antibody CDR-L2 consensus sequence
<220> FEATURE:
<221> NAME/KEY: MISC_FEATURE
<222> LOCATION: (1)..(1)
<223> OTHER INFORMATION: X is E or Q
<220> FEATURE:
<221> NAME/KEY: MISC_FEATURE
<222> LOCATION: (3)..(3)
<223> OTHER INFORMATION: X is S, L, T, A, E or F
<220> FEATURE:
<221> NAME/KEY: MISC_FEATURE
<222> LOCATION: (4)..(4)
<223> OTHER INFORMATION: X is K, T, E, N, Q, S, or M

<400> SEQUENCE: 103

Xaa Asp Xaa Xaa Arg Pro Ser
1               5

<210> SEQ ID NO 104
<211> LENGTH: 9
<212> TYPE: PRT
<213> ORGANISM: Artificial Sequence
<220> FEATURE:
<223> OTHER INFORMATION: DLL4 antibody CDR-L3 consensus sequence
<220> FEATURE:
<221> NAME/KEY: MISC_FEATURE
<222> LOCATION: (5)..(5)
<223> OTHER INFORMATION: X is R, S, M, E, N, G or K
<220> FEATURE:
<221> NAME/KEY: MISC_FEATURE
<222> LOCATION: (6)..(6)
<223> OTHER INFORMATION: X is D or E
<220> FEATURE:
<221> NAME/KEY: MISC_FEATURE
<222> LOCATION: (7)..(7)
<223> OTHER INFORMATION: X is T, V, A, S or M
<220> FEATURE:
<221> NAME/KEY: MISC_FEATURE
<222> LOCATION: (8)..(8)
<223> OTHER INFORMATION: X is G, A or C

<400> SEQUENCE: 104

Gln Ala Trp Asp Xaa Xaa Xaa Xaa Val
1               5

<210> SEQ ID NO 105
<211> LENGTH: 5
<212> TYPE: PRT
<213> ORGANISM: Artificial Sequence
<220> FEATURE:
<223> OTHER INFORMATION: DLL4 antibody CDR-H1 consensus sequence
<220> FEATURE:
<221> NAME/KEY: MISC_FEATURE
<222> LOCATION: (1)..(1)
<223> OTHER INFORMATION: X is S, N or D
<220> FEATURE:
<221> NAME/KEY: MISC_FEATURE
<222> LOCATION: (2)..(2)
<223> OTHER INFORMATION: X is H or Y
<220> FEATURE:
<221> NAME/KEY: MISC_FEATURE
<222> LOCATION: (5)..(5)
<223> OTHER INFORMATION: X is S or H
```

```
<400> SEQUENCE: 105

Xaa Xaa Trp Met Xaa
1               5

<210> SEQ ID NO 106
<211> LENGTH: 17
<212> TYPE: PRT
<213> ORGANISM: Artificial Sequence
<220> FEATURE:
<223> OTHER INFORMATION: DLL4 antibody CDR-H2 consensus sequence
<220> FEATURE:
<221> NAME/KEY: MISC_FEATURE
<222> LOCATION: (1)..(1)
<223> OTHER INFORMATION: X is I, D, M or T
<220> FEATURE:
<221> NAME/KEY: MISC_FEATURE
<222> LOCATION: (4)..(4)
<223> OTHER INFORMATION: X is Y, N, S, Q, V, T, H or D
<220> FEATURE:
<221> NAME/KEY: MISC_FEATURE
<222> LOCATION: (7)..(7)
<223> OTHER INFORMATION: X is S, R, I, T, G, K, H or N
<220> FEATURE:
<221> NAME/KEY: MISC_FEATURE
<222> LOCATION: (8)..(8)
<223> OTHER INFORMATION: X is N, Y, S, I or T
<220> FEATURE:
<221> NAME/KEY: MISC_FEATURE
<222> LOCATION: (9)..(9)
<223> OTHER INFORMATION: X is K, M, N, Q, E, T, R, S, A or L
<220> FEATURE:
<221> NAME/KEY: MISC_FEATURE
<222> LOCATION: (10)..(10)
<223> OTHER INFORMATION: X is Y, D or E
<220> FEATURE:
<221> NAME/KEY: MISC_FEATURE
<222> LOCATION: (11)..(11)
<223> OTHER INFORMATION: X is S or Y

<400> SEQUENCE: 106

Xaa Ile Ser Xaa Asp Gly Xaa Xaa Xaa Xaa Ala Asp Ser Val Lys
1               5                   10                  15

Gly

<210> SEQ ID NO 107
<211> LENGTH: 10
<212> TYPE: PRT
<213> ORGANISM: Artificial Sequence
<220> FEATURE:
<223> OTHER INFORMATION: DLL4 antibody CDR-H3 consensus sequence
<220> FEATURE:
<221> NAME/KEY: MISC_FEATURE
<222> LOCATION: (2)..(2)
<223> OTHER INFORMATION: X is G, A or R
<220> FEATURE:
<221> NAME/KEY: MISC_FEATURE
<222> LOCATION: (4)..(4)
<223> OTHER INFORMATION: X is G, S or A
<220> FEATURE:
<221> NAME/KEY: MISC_FEATURE
<222> LOCATION: (6)..(6)
<223> OTHER INFORMATION: X is V or M
<220> FEATURE:
<221> NAME/KEY: MISC_FEATURE
<222> LOCATION: (8)..(8)
<223> OTHER INFORMATION: X is F, L, Y or M
<220> FEATURE:
<221> NAME/KEY: MISC_FEATURE
<222> LOCATION: (10)..(10)
<223> OTHER INFORMATION: X is I, S or L

<400> SEQUENCE: 107

Ala Xaa Gly Xaa Asn Xaa Gly Xaa Asp Xaa
```

```
1               5                    10
```

```
<210> SEQ ID NO 108
<211> LENGTH: 11
<212> TYPE: PRT
<213> ORGANISM: Artificial Sequence
<220> FEATURE:
<223> OTHER INFORMATION: DLL4 antibody CDR-L1 consensus sequence
<220> FEATURE:
<221> NAME/KEY: MISC_FEATURE
<222> LOCATION: (2)..(2)
<223> OTHER INFORMATION: X is A or G
<220> FEATURE:
<221> NAME/KEY: MISC_FEATURE
<222> LOCATION: (4)..(4)
<223> OTHER INFORMATION: X is K, N, L, Q, M, E, S, T, G or D
<220> FEATURE:
<221> NAME/KEY: MISC_FEATURE
<222> LOCATION: (7)..(7)
<223> OTHER INFORMATION: X is T, S, N, A, G or E
<220> FEATURE:
<221> NAME/KEY: MISC_FEATURE
<222> LOCATION: (8)..(8)
<223> OTHER INFORMATION: X is K, Q, N or R
<220> FEATURE:
<221> NAME/KEY: MISC_FEATURE
<222> LOCATION: (10)..(10)
<223> OTHER INFORMATION: X is V or I

<400> SEQUENCE: 108

Ser Xaa Asp Xaa Leu Gly Xaa Xaa Tyr Xaa Ser
 1               5                   10

<210> SEQ ID NO 109
<211> LENGTH: 7
<212> TYPE: PRT
<213> ORGANISM: Artificial Sequence
<220> FEATURE:
<223> OTHER INFORMATION: DLL4 antibody CDR-L2 consensus sequence
<220> FEATURE:
<221> NAME/KEY: MISC_FEATURE
<222> LOCATION: (3)..(3)
<223> OTHER INFORMATION: X is A, G, W, S or D
<220> FEATURE:
<221> NAME/KEY: MISC_FEATURE
<222> LOCATION: (4)..(4)
<223> OTHER INFORMATION: X is K, M, Q, N, L, T, I or E

<400> SEQUENCE: 109

Gln Asp Xaa Xaa Arg Pro Ser
 1               5

<210> SEQ ID NO 110
<211> LENGTH: 9
<212> TYPE: PRT
<213> ORGANISM: Artificial Sequence
<220> FEATURE:
<223> OTHER INFORMATION: DLL4 antibody CDR-L3 consensus sequence
<220> FEATURE:
<221> NAME/KEY: MISC_FEATURE
<222> LOCATION: (2)..(2)
<223> OTHER INFORMATION: X is S or A
<220> FEATURE:
<221> NAME/KEY: MISC_FEATURE
<222> LOCATION: (5)..(5)
<223> OTHER INFORMATION: X is R, S, Q, P, A, V, W or M
<220> FEATURE:
<221> NAME/KEY: MISC_FEATURE
<222> LOCATION: (6)..(6)
<223> OTHER INFORMATION: X is S, G, I, N, R or T
<220> FEATURE:
<221> NAME/KEY: MISC_FEATURE
<222> LOCATION: (7)..(7)
<223> OTHER INFORMATION: X is D or G
```

<220> FEATURE:
<221> NAME/KEY: MISC_FEATURE
<222> LOCATION: (8)..(8)
<223> OTHER INFORMATION: X is V, A, P or E

<400> SEQUENCE: 110

```
Gln Xaa Trp Asp Xaa Xaa Xaa Val
1               5
```

<210> SEQ ID NO 111
<211> LENGTH: 106
<212> TYPE: PRT
<213> ORGANISM: Homo sapiens

<400> SEQUENCE: 111

```
Ser Tyr Glu Leu Thr Gln Pro Pro Ser Val Ser Val Ser Pro Gly Gln
1               5                   10                  15

Thr Ala Ser Ile Thr Cys Ser Gly Gln Arg Leu Gly Asp Lys Tyr Ala
            20                  25                  30

Ser Trp Tyr Gln Gln Lys Pro Gly Gln Ser Pro Val Leu Val Ile Tyr
        35                  40                  45

Glu Asp Ser Lys Arg Pro Ser Gly Ile Pro Glu Arg Phe Ser Gly Ser
50                  55                  60

Asn Ser Gly Asp Thr Ala Thr Leu Thr Ile Ser Gly Thr Gln Pro Met
65                  70                  75                  80

Asp Glu Ala Asp Tyr Tyr Cys Gln Ala Trp Asp Arg Asp Thr Gly Val
                85                  90                  95

Phe Gly Tyr Gly Thr Arg Val Thr Val Leu
            100                 105
```

<210> SEQ ID NO 112
<211> LENGTH: 119
<212> TYPE: PRT
<213> ORGANISM: Homo sapiens

<400> SEQUENCE: 112

```
Glu Val Gln Leu Leu Glu Ser Gly Gly Gly Leu Val Lys Ser Gly Gly
1               5                   10                  15

Ser Leu Arg Leu Ser Cys Ala Ala Ser Gly Phe Thr Phe Arg Ser His
            20                  25                  30

Trp Met Ser Trp Val Arg Gln Ala Pro Gly Lys Gly Leu Glu Trp Val
        35                  40                  45

Ala Ile Ile Ser Tyr Asp Gly Ser Asn Lys Tyr Ser Ala Asp Ser Val
50                  55                  60

Lys Gly Arg Phe Thr Ile Ser Arg Asp Asn Ser Lys Asn Thr Leu Tyr
65                  70                  75                  80

Leu Gln Leu Asn Ser Leu Arg Ala Glu Asp Thr Ala Val Tyr Tyr Cys
                85                  90                  95

Ala Lys Ala Gly Gly Gly Asn Val Gly Phe Asp Ile Trp Gly Gln Gly
            100                 105                 110

Thr Met Val Thr Val Ser Ser
        115
```

<210> SEQ ID NO 113
<211> LENGTH: 106
<212> TYPE: PRT
<213> ORGANISM: Homo sapiens

<400> SEQUENCE: 113

```
Leu Pro Val Leu Thr Gln Pro Pro Ser Val Ser Val Ser Pro Gly Gln
1               5                   10                  15

Thr Ala Ser Ile Thr Cys Ser Ala Asp Lys Leu Gly Thr Lys Tyr Val
            20                  25                  30

Ser Trp Tyr Gln Gln Lys Pro Gly Gln Ser Pro Val Leu Val Ile Tyr
        35                  40                  45

Gln Asp Ala Lys Arg Pro Ser Gly Ile Pro Glu Arg Phe Ser Gly Ser
50                  55                  60

Asn Ser Gly Asn Thr Ala Thr Leu Thr Ile Ser Gly Thr Gln Thr Met
65                  70                  75                  80

Asp Glu Ala Asp Tyr Leu Cys Gln Ser Trp Asp Arg Ser Asp Val Val
                85                  90                  95

Phe Gly Gly Gly Thr Lys Val Thr Val Leu
            100                 105

<210> SEQ ID NO 114
<211> LENGTH: 121
<212> TYPE: PRT
<213> ORGANISM: Artificial Sequence
<220> FEATURE:
<223> OTHER INFORMATION: mutations of antibody E9 VH sequence
<220> FEATURE:
<221> NAME/KEY: MISC_FEATURE
<222> LOCATION: (30)..(30)
<223> OTHER INFORMATION: X is S, N, G or R
<220> FEATURE:
<221> NAME/KEY: MISC_FEATURE
<222> LOCATION: (31)..(31)
<223> OTHER INFORMATION: X is S or N
<220> FEATURE:
<221> NAME/KEY: MISC_FEATURE
<222> LOCATION: (32)..(32)
<223> OTHER INFORMATION: X is S, G or N
<220> FEATURE:
<221> NAME/KEY: MISC_FEATURE
<222> LOCATION: (33)..(33)
<223> OTHER INFORMATION: X is S, N, T, G or R
<220> FEATURE:
<221> NAME/KEY: MISC_FEATURE
<222> LOCATION: (42)..(42)
<223> OTHER INFORMATION: X is P, S or L
<220> FEATURE:
<221> NAME/KEY: MISC_FEATURE
<222> LOCATION: (54)..(54)
<223> OTHER INFORMATION: X is Y or N
<220> FEATURE:
<221> NAME/KEY: MISC_FEATURE
<222> LOCATION: (56)..(56)
<223> OTHER INFORMATION: X is T, N, A, I, S or R
<220> FEATURE:
<221> NAME/KEY: MISC_FEATURE
<222> LOCATION: (58)..(58)
<223> OTHER INFORMATION: X is S, N, T or G
<220> FEATURE:
<221> NAME/KEY: MISC_FEATURE
<222> LOCATION: (67)..(67)
<223> OTHER INFORMATION: X is S, N, D or G
<220> FEATURE:
<221> NAME/KEY: MISC_FEATURE
<222> LOCATION: (90)..(90)
<223> OTHER INFORMATION: X is A or E
<220> FEATURE:
<221> NAME/KEY: MISC_FEATURE
<222> LOCATION: (100)..(100)
<223> OTHER INFORMATION: X is E, Y, F, Q, W, L or A
<220> FEATURE:
<221> NAME/KEY: MISC_FEATURE
<222> LOCATION: (101)..(101)
<223> OTHER INFORMATION: X is D, A, S, G, V, E or N
<220> FEATURE:
<221> NAME/KEY: MISC_FEATURE
<222> LOCATION: (102)..(102)
```

```
<223> OTHER INFORMATION: X is V, M, L or P
<220> FEATURE:
<221> NAME/KEY: MISC_FEATURE
<222> LOCATION: (103)..(103)
<223> OTHER INFORMATION: X is I, A, P, R, S, K, Q, V, G, M or E
<220> FEATURE:
<221> NAME/KEY: MISC_FEATURE
<222> LOCATION: (104)..(104)
<223> OTHER INFORMATION: X is L, Y, F or M
<220> FEATURE:
<221> NAME/KEY: MISC_FEATURE
<222> LOCATION: (105)..(105)
<223> OTHER INFORMATION: X is R, G, S, Q or A
<220> FEATURE:
<221> NAME/KEY: MISC_FEATURE
<222> LOCATION: (107)..(107)
<223> OTHER INFORMATION: X is G, S or A
<220> FEATURE:
<221> NAME/KEY: MISC_FEATURE
<222> LOCATION: (108)..(108)
<223> OTHER INFORMATION: X is S, A, L, V or R
<220> FEATURE:
<221> NAME/KEY: MISC_FEATURE
<222> LOCATION: (110)..(110)
<223> OTHER INFORMATION: X is Y, D, S, N, H, E, R, L, P, C, I or M

<400> SEQUENCE: 114

Glu Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Xaa Xaa Xaa
            20                  25                  30

Xaa Tyr Tyr Trp Gly Trp Ile Arg Gln Xaa Pro Gly Lys Gly Leu Glu
            35                  40                  45

Trp Ile Gly Asp Ile Xaa Tyr Xaa Gly Xaa Thr Tyr Tyr Asn Pro Ser
50                  55                  60

Leu Lys Xaa Arg Val Thr Ile Ser Val Asp Thr Ser Lys Asn Gln Phe
65                  70                  75                  80

Ser Leu Lys Leu Ser Ser Val Thr Ala Xaa Asp Thr Ala Val Tyr Tyr
            85                  90                  95

Cys Ala Arg Xaa Xaa Xaa Xaa Xaa Gly Xaa Xaa Asp Xaa Trp Gly
            100                 105                 110

Gln Gly Thr Leu Val Thr Val Ser Ser
        115                 120

<210> SEQ ID NO 115
<211> LENGTH: 106
<212> TYPE: PRT
<213> ORGANISM: Artificial Sequence
<220> FEATURE:
<223> OTHER INFORMATION: mutations of antibody E9 VL sequence
<220> FEATURE:
<221> NAME/KEY: MISC_FEATURE
<222> LOCATION: (25)..(25)
<223> OTHER INFORMATION: X is Q, E or D
<220> FEATURE:
<221> NAME/KEY: MISC_FEATURE
<222> LOCATION: (26)..(26)
<223> OTHER INFORMATION: X is R, S, G, M, K, L or T
<220> FEATURE:
<221> NAME/KEY: MISC_FEATURE
<222> LOCATION: (29)..(29)
<223> OTHER INFORMATION: X is D or E
<220> FEATURE:
<221> NAME/KEY: MISC_FEATURE
<222> LOCATION: (32)..(32)
<223> OTHER INFORMATION: X is A or V
<220> FEATURE:
<221> NAME/KEY: MISC_FEATURE
<222> LOCATION: (49)..(49)
<223> OTHER INFORMATION: X is E or Q
```

```
<220> FEATURE:
<221> NAME/KEY: MISC_FEATURE
<222> LOCATION: (51)..(51)
<223> OTHER INFORMATION: X is S, L, T, A, E or F
<220> FEATURE:
<221> NAME/KEY: MISC_FEATURE
<222> LOCATION: (52)..(52)
<223> OTHER INFORMATION: X is K, T, E, N, Q, S or M
<220> FEATURE:
<221> NAME/KEY: MISC_FEATURE
<222> LOCATION: (79)..(79)
<223> OTHER INFORMATION: X is P or A
<220> FEATURE:
<221> NAME/KEY: MISC_FEATURE
<222> LOCATION: (92)..(92)
<223> OTHER INFORMATION: X is R, S, M, E, N or K
<220> FEATURE:
<221> NAME/KEY: MISC_FEATURE
<222> LOCATION: (93)..(93)
<223> OTHER INFORMATION: X is D or E
<220> FEATURE:
<221> NAME/KEY: MISC_FEATURE
<222> LOCATION: (94)..(94)
<223> OTHER INFORMATION: X is T, V, A, S or M
<220> FEATURE:
<221> NAME/KEY: MISC_FEATURE
<222> LOCATION: (95)..(95)
<223> OTHER INFORMATION: X is G, A or C
<220> FEATURE:
<221> NAME/KEY: MISC_FEATURE
<222> LOCATION: (99)..(99)
<223> OTHER INFORMATION: X is Y or S
<220> FEATURE:
<221> NAME/KEY: MISC_FEATURE
<222> LOCATION: (102)..(102)
<223> OTHER INFORMATION: X is R or K

<400> SEQUENCE: 115

Ser Tyr Glu Leu Thr Gln Pro Pro Ser Val Ser Val Ser Pro Gly Gln
1               5                   10                  15

Thr Ala Ser Ile Thr Cys Ser Gly Xaa Xaa Leu Gly Xaa Lys Tyr Xaa
                20                  25                  30

Ser Trp Tyr Gln Gln Lys Pro Gly Gln Ser Pro Val Leu Val Ile Tyr
            35                  40                  45

Xaa Asp Xaa Xaa Arg Pro Ser Gly Ile Pro Glu Arg Phe Ser Gly Ser
50                  55                  60

Asn Ser Gly Asp Thr Ala Thr Leu Thr Ile Ser Gly Thr Gln Xaa Met
65                  70                  75                  80

Asp Glu Ala Asp Tyr Tyr Cys Gln Ala Trp Asp Xaa Xaa Xaa Xaa Val
                85                  90                  95

Phe Gly Xaa Gly Thr Xaa Val Thr Val Leu
            100                 105

<210> SEQ ID NO 116
<211> LENGTH: 121
<212> TYPE: PRT
<213> ORGANISM: Artificial Sequence
<220> FEATURE:
<223> OTHER INFORMATION: affinity matured DLL4 antibody E9.4 VH region

<400> SEQUENCE: 116

Glu Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
                20                  25                  30

Ser Tyr Tyr Trp Gly Trp Ile Arg Gln Pro Pro Gly Lys Gly Leu Glu
            35                  40                  45
```

```
Trp Ile Gly Asp Ile Tyr Tyr Thr Gly Ser Thr Tyr Tyr Asn Pro Ser
        50                  55                  60

Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                 85                  90                  95

Cys Ala Arg Tyr Asp Val Ser Leu Gly Gly Ser Ser Asp His Trp Gly
            100                 105                 110

Gln Gly Thr Leu Val Thr Val Ser Ser
            115                 120

<210> SEQ ID NO 117
<211> LENGTH: 7
<212> TYPE: PRT
<213> ORGANISM: Artificial Sequence
<220> FEATURE:
<223> OTHER INFORMATION: DLL4 antibody E9.4 CDR-H1

<400> SEQUENCE: 117

Ser Ser Ser Tyr Tyr Trp Gly
 1               5

<210> SEQ ID NO 118
<211> LENGTH: 16
<212> TYPE: PRT
<213> ORGANISM: Artificial Sequence
<220> FEATURE:
<223> OTHER INFORMATION: DLL4 antibody E9.4 CDR-H2

<400> SEQUENCE: 118

Asp Ile Tyr Tyr Thr Gly Ser Thr Tyr Tyr Asn Pro Ser Leu Lys Ser
 1               5                  10                  15

<210> SEQ ID NO 119
<211> LENGTH: 11
<212> TYPE: PRT
<213> ORGANISM: Artificial Sequence
<220> FEATURE:
<223> OTHER INFORMATION: DLL4 antibody E9.4 CDR-H3

<400> SEQUENCE: 119

Tyr Asp Val Ser Leu Gly Gly Ser Ser Asp His
 1               5                  10

<210> SEQ ID NO 120
<211> LENGTH: 121
<212> TYPE: PRT
<213> ORGANISM: Artificial Sequence
<220> FEATURE:
<223> OTHER INFORMATION: DLL4 antibody E9.11 VH region

<400> SEQUENCE: 120

Glu Val Gln Leu Gln Glu Ser Gly Pro Gly Leu Val Lys Pro Ser Glu
 1               5                  10                  15

Thr Leu Ser Leu Thr Cys Thr Val Ser Gly Gly Ser Ile Ser Ser Ser
                 20                  25                  30

Ser Tyr Tyr Trp Gly Trp Ile Arg Gln Pro Pro Gly Lys Gly Leu Glu
             35                  40                  45

Trp Ile Gly Asp Ile Tyr Tyr Thr Gly Ser Thr Tyr Tyr Asn Pro Ser
        50                  55                  60

Leu Lys Ser Arg Val Thr Ile Ser Val Asp Thr Ser Lys Asn Gln Phe
 65                  70                  75                  80
```

```
Ser Leu Lys Leu Ser Ser Val Thr Ala Ala Asp Thr Ala Val Tyr Tyr
                85                  90                  95

Cys Ala Arg Glu Ala Val Pro Leu Gly Gly Gly Ser Asp Tyr Trp Gly
            100                 105                 110

Gln Gly Thr Leu Val Thr Val Ser Ser
        115                 120
```

<210> SEQ ID NO 121
<211> LENGTH: 7
<212> TYPE: PRT
<213> ORGANISM: Artificial Sequence
<220> FEATURE:
<223> OTHER INFORMATION: DLL4 antibody E9.11 CDR-H1

<400> SEQUENCE: 121

```
Ser Ser Ser Tyr Tyr Trp Gly
1               5
```

<210> SEQ ID NO 122
<211> LENGTH: 16
<212> TYPE: PRT
<213> ORGANISM: Artificial Sequence
<220> FEATURE:
<223> OTHER INFORMATION: DLL4 antibody E9.11 CDR-H2

<400> SEQUENCE: 122

```
Asp Ile Tyr Tyr Thr Gly Ser Thr Tyr Tyr Asn Pro Ser Leu Lys Ser
1               5                   10                  15
```

<210> SEQ ID NO 123
<211> LENGTH: 11
<212> TYPE: PRT
<213> ORGANISM: Artificial Sequence
<220> FEATURE:
<223> OTHER INFORMATION: DLL4 antibody E9.11 CDR-H3

<400> SEQUENCE: 123

```
Glu Ala Val Pro Leu Gly Gly Gly Ser Asp Tyr
1               5                   10
```

<210> SEQ ID NO 124
<211> LENGTH: 121
<212> TYPE: PRT
<213> ORGANISM: Artificial Sequence
<220> FEATURE:
<223> OTHER INFORMATION: DLL4 antibody E9.14 VH region

<400> SEQUENCE: 124

```
Glu Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Asn Ser
            20                  25                  30

Arg Tyr His Trp Gly Trp Ile Arg Gln Ser Pro Gly Lys Gly Leu Glu
        35                  40                  45

Trp Ile Gly Asp Ile Tyr Tyr Thr Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Glu Asp Thr Ala Val Tyr Tyr
                85                  90                  95

Cys Ala Arg Glu Asp Val Ile Leu Arg Gly Ser Asp Tyr Trp Gly
            100                 105                 110
```

```
Gln Gly Thr Leu Val Thr Val Ser Ser
        115                 120

<210> SEQ ID NO 125
<211> LENGTH: 7
<212> TYPE: PRT
<213> ORGANISM: Artificial Sequence
<220> FEATURE:
<223> OTHER INFORMATION: DLL4 antibody E9.14 CDR-H1

<400> SEQUENCE: 125

Asn Ser Arg Tyr His Trp Gly
1               5

<210> SEQ ID NO 126
<211> LENGTH: 16
<212> TYPE: PRT
<213> ORGANISM: Artificial Sequence
<220> FEATURE:
<223> OTHER INFORMATION: DLL4 antibody E9.14 CDR-H2

<400> SEQUENCE: 126

Asp Ile Tyr Tyr Thr Gly Ser Thr Tyr Tyr Asn Pro Ser Leu Lys Ser
1               5                   10                  15

<210> SEQ ID NO 127
<211> LENGTH: 11
<212> TYPE: PRT
<213> ORGANISM: Artificial Sequence
<220> FEATURE:
<223> OTHER INFORMATION: DLL4 antibody E9.14 CDR-H3

<400> SEQUENCE: 127

Glu Asp Val Ile Leu Arg Gly Gly Ser Asp Tyr
1               5                   10

<210> SEQ ID NO 128
<211> LENGTH: 121
<212> TYPE: PRT
<213> ORGANISM: Artificial Sequence
<220> FEATURE:
<223> OTHER INFORMATION: DLL4 antibody E9.17 VH region

<400> SEQUENCE: 128

Glu Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Asp Ile Tyr Tyr Thr Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Glu Glu Ala Ile Leu Gly Gly Gly Ser Asp Tyr Trp Gly
            100                 105                 110

Gln Gly Thr Leu Val Thr Val Ser Ser
        115                 120

<210> SEQ ID NO 129
<211> LENGTH: 7
```

```
<212> TYPE: PRT
<213> ORGANISM: Artificial Sequence
<220> FEATURE:
<223> OTHER INFORMATION: DLL4 antibody E9.17 CDR-H1

<400> SEQUENCE: 129

Ser Ser Ser Tyr Tyr Trp Gly
1               5

<210> SEQ ID NO 130
<211> LENGTH: 16
<212> TYPE: PRT
<213> ORGANISM: Artificial Sequence
<220> FEATURE:
<223> OTHER INFORMATION: DLL4 antibody E9.17 CDR-H2

<400> SEQUENCE: 130

Asp Ile Tyr Tyr Thr Gly Ser Thr Tyr Tyr Asn Pro Ser Leu Lys Ser
1               5                   10                  15

<210> SEQ ID NO 131
<211> LENGTH: 11
<212> TYPE: PRT
<213> ORGANISM: Artificial Sequence
<220> FEATURE:
<223> OTHER INFORMATION: DLL4 antibody E9.17 CDR-H3

<400> SEQUENCE: 131

Glu Glu Ala Ile Leu Gly Gly Gly Ser Asp Tyr
1               5                   10

<210> SEQ ID NO 132
<211> LENGTH: 121
<212> TYPE: PRT
<213> ORGANISM: Artificial Sequence
<220> FEATURE:
<223> OTHER INFORMATION: DLL4 antibody E9.18 VH region

<400> SEQUENCE: 132

Glu Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Gly Tyr Tyr Trp Gly Trp Ile Arg Gln Pro Pro Gly Lys Gly Leu Glu
        35                  40                  45

Trp Ile Gly Asp Ile Asn Tyr Ala Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Glu Asp Val Ile Leu Arg Gly Gly Ser Asp Tyr Trp Gly
            100                 105                 110

Gln Gly Thr Leu Val Thr Val Ser Ser
        115                 120

<210> SEQ ID NO 133
<211> LENGTH: 7
<212> TYPE: PRT
<213> ORGANISM: Artificial Sequence
<220> FEATURE:
<223> OTHER INFORMATION: DLL4 antibody E9.18 CDR-H1

<400> SEQUENCE: 133
```

```
Ser Ser Gly Tyr Tyr Trp Gly
1               5
```

<210> SEQ ID NO 134
<211> LENGTH: 16
<212> TYPE: PRT
<213> ORGANISM: Artificial Sequence
<220> FEATURE:
<223> OTHER INFORMATION: DLL4 antibody E9.18 CDR-H2

<400> SEQUENCE: 134

```
Asp Ile Asn Tyr Ala Gly Ser Thr Tyr Tyr Asn Pro Ser Leu Lys Ser
1               5                   10                  15
```

<210> SEQ ID NO 135
<211> LENGTH: 11
<212> TYPE: PRT
<213> ORGANISM: Artificial Sequence
<220> FEATURE:
<223> OTHER INFORMATION: DLL4 antibody E9.18 CDR-H3

<400> SEQUENCE: 135

```
Glu Asp Val Ile Leu Arg Gly Gly Ser Asp Tyr
1               5                   10
```

<210> SEQ ID NO 136
<211> LENGTH: 121
<212> TYPE: PRT
<213> ORGANISM: Artificial Sequence
<220> FEATURE:
<223> OTHER INFORMATION: DLL4 antibody E9.19 VH region

<400> SEQUENCE: 136

```
Glu Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Asp Ile Tyr Tyr Thr Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Phe Asp Val Ser Leu Gly Gly Ser Asp Thr Trp Gly
            100                 105                 110

Gln Gly Thr Leu Val Thr Val Ser Ser
        115                 120
```

<210> SEQ ID NO 137
<211> LENGTH: 7
<212> TYPE: PRT
<213> ORGANISM: Artificial Sequence
<220> FEATURE:
<223> OTHER INFORMATION: DLL4 antibody E9.19 CDR-H1

<400> SEQUENCE: 137

```
Ser Ser Ser Tyr Tyr Trp Gly
1               5
```

<210> SEQ ID NO 138

```
<211> LENGTH: 16
<212> TYPE: PRT
<213> ORGANISM: Artificial Sequence
<220> FEATURE:
<223> OTHER INFORMATION: DLL4 antibody E9.19 CDR-H2

<400> SEQUENCE: 138

Asp Ile Tyr Tyr Thr Gly Ser Thr Tyr Tyr Asn Pro Ser Leu Lys Ser
1               5                   10                  15

<210> SEQ ID NO 139
<211> LENGTH: 11
<212> TYPE: PRT
<213> ORGANISM: Artificial Sequence
<220> FEATURE:
<223> OTHER INFORMATION: DLL4 antibody E9.19 CDR-H3

<400> SEQUENCE: 139

Phe Asp Val Ser Leu Gly Gly Ser Asp Thr
1               5                   10

<210> SEQ ID NO 140
<211> LENGTH: 121
<212> TYPE: PRT
<213> ORGANISM: Artificial Sequence
<220> FEATURE:
<223> OTHER INFORMATION: DLL4 antibody E9.22 VH region

<400> SEQUENCE: 140

Glu Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Asn Ser
            20                  25                  30

Arg Tyr His Trp Gly Trp Ile Arg Gln Pro Pro Gly Lys Gly Leu Glu
        35                  40                  45

Trp Ile Gly Asp Ile Tyr Tyr Thr Gly Ser Thr Tyr Tyr Asn Pro Ser
    50                  55                  60

Leu Lys Gly Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Glu Asp Val Ile Leu Arg Gly Gly Ser Asp Tyr Trp Gly
            100                 105                 110

Gln Gly Thr Leu Val Thr Val Ser Ser
        115                 120

<210> SEQ ID NO 141
<211> LENGTH: 7
<212> TYPE: PRT
<213> ORGANISM: Artificial Sequence
<220> FEATURE:
<223> OTHER INFORMATION: DLL4 antibody E9.22 CDR-H1

<400> SEQUENCE: 141

Asn Ser Arg Tyr His Trp Gly
1               5

<210> SEQ ID NO 142
<211> LENGTH: 16
<212> TYPE: PRT
<213> ORGANISM: Artificial Sequence
<220> FEATURE:
<223> OTHER INFORMATION: DLL4 antibody E9.22 CDR-H2
```

```
<400> SEQUENCE: 142

Asp Ile Tyr Tyr Thr Gly Ser Thr Tyr Tyr Asn Pro Ser Leu Lys Gly
1               5                   10                  15

<210> SEQ ID NO 143
<211> LENGTH: 11
<212> TYPE: PRT
<213> ORGANISM: Artificial Sequence
<220> FEATURE:
<223> OTHER INFORMATION: DLL4 antibody E9.22 CDR-H3

<400> SEQUENCE: 143

Glu Asp Val Ile Leu Arg Gly Gly Ser Asp Tyr
1               5                   10

<210> SEQ ID NO 144
<211> LENGTH: 121
<212> TYPE: PRT
<213> ORGANISM: Artificial Sequence
<220> FEATURE:
<223> OTHER INFORMATION: DLL4 antibody E9.48 VH region

<400> SEQUENCE: 144

Glu Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Gly Tyr Tyr Trp Gly Trp Ile Arg Gln Pro Pro Gly Lys Gly Leu Glu
        35                  40                  45

Trp Ile Gly Asp Ile Asn Tyr Arg Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Glu Asp Val Ile Leu Arg Gly Gly Ser Asp Tyr Trp Gly
            100                 105                 110

Gln Gly Thr Leu Val Thr Val Ser Ser
        115                 120

<210> SEQ ID NO 145
<211> LENGTH: 7
<212> TYPE: PRT
<213> ORGANISM: Artificial Sequence
<220> FEATURE:
<223> OTHER INFORMATION: DLL4 antibody E9.48 CDR-H1

<400> SEQUENCE: 145

Ser Ser Gly Tyr Tyr Trp Gly
1               5

<210> SEQ ID NO 146
<211> LENGTH: 16
<212> TYPE: PRT
<213> ORGANISM: Artificial Sequence
<220> FEATURE:
<223> OTHER INFORMATION: DLL4 antibody E9.48 CDR-H2

<400> SEQUENCE: 146

Asp Ile Asn Tyr Arg Gly Ser Thr Tyr Tyr Asn Pro Ser Leu Lys Ser
1               5                   10                  15
```

```
<210> SEQ ID NO 147
<211> LENGTH: 11
<212> TYPE: PRT
<213> ORGANISM: Artificial Sequence
<220> FEATURE:
<223> OTHER INFORMATION: DLL4 antibody E9.48 CDR-H3

<400> SEQUENCE: 147

Glu Asp Val Ile Leu Arg Gly Gly Ser Asp Tyr
1               5                   10

<210> SEQ ID NO 148
<211> LENGTH: 121
<212> TYPE: PRT
<213> ORGANISM: Artificial Sequence
<220> FEATURE:
<223> OTHER INFORMATION: DLL4 antibody E9.65 VH region

<400> SEQUENCE: 148

Glu Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Arg Asn Ser
            20                  25                  30

Arg Tyr His Trp Gly Trp Ile Arg Gln Pro Pro Gly Lys Gly Leu Glu
        35                  40                  45

Trp Ile Gly Asp Ile Tyr Tyr Thr Gly Ser Thr Tyr Tyr Asn Pro Ser
    50                  55                  60

Leu Lys Gly Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Glu Asp Val Ile Leu Arg Gly Gly Ser Asp Tyr Trp Gly
            100                 105                 110

Gln Gly Thr Leu Val Thr Val Ser Ser
        115                 120

<210> SEQ ID NO 149
<211> LENGTH: 7
<212> TYPE: PRT
<213> ORGANISM: Artificial Sequence
<220> FEATURE:
<223> OTHER INFORMATION: DLL4 antibody E9.65 CDR-H1

<400> SEQUENCE: 149

Asn Ser Arg Tyr His Trp Gly
1               5

<210> SEQ ID NO 150
<211> LENGTH: 16
<212> TYPE: PRT
<213> ORGANISM: Artificial Sequence
<220> FEATURE:
<223> OTHER INFORMATION: DLL4 antibody E9.65 CDR-H2

<400> SEQUENCE: 150

Asp Ile Tyr Tyr Thr Gly Ser Thr Tyr Tyr Asn Pro Ser Leu Lys Gly
1               5                   10                  15

<210> SEQ ID NO 151
<211> LENGTH: 11
<212> TYPE: PRT
<213> ORGANISM: Artificial Sequence
<220> FEATURE:
<223> OTHER INFORMATION: DLL4 antibody E9.65 CDR-H3
```

<400> SEQUENCE: 151

Glu Asp Val Ile Leu Arg Gly Gly Ser Asp Tyr
1               5                   10

<210> SEQ ID NO 152
<211> LENGTH: 121
<212> TYPE: PRT
<213> ORGANISM: Artificial Sequence
<220> FEATURE:
<223> OTHER INFORMATION: DLL4 antibody E9.66 VH region

<400> SEQUENCE: 152

Glu Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Asp Ile Tyr Tyr Thr Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Glu Gly Val Pro Leu Gly Gly Gly Ala Asp Lys Trp Gly
            100                 105                 110

Gln Gly Thr Leu Val Thr Val Ser Ser
        115                 120

<210> SEQ ID NO 153
<211> LENGTH: 7
<212> TYPE: PRT
<213> ORGANISM: Artificial Sequence
<220> FEATURE:
<223> OTHER INFORMATION: DLL4 antibody E9.66 CDR-H1

<400> SEQUENCE: 153

Ser Ser Ser Tyr Tyr Trp Gly
1               5

<210> SEQ ID NO 154
<211> LENGTH: 16
<212> TYPE: PRT
<213> ORGANISM: Artificial Sequence
<220> FEATURE:
<223> OTHER INFORMATION: DLL4 antibody E9.66 CDR-H2

<400> SEQUENCE: 154

Asp Ile Tyr Tyr Thr Gly Ser Thr Tyr Tyr Asn Pro Ser Leu Lys Ser
1               5                   10                  15

<210> SEQ ID NO 155
<211> LENGTH: 11
<212> TYPE: PRT
<213> ORGANISM: Artificial Sequence
<220> FEATURE:
<223> OTHER INFORMATION: DLL4 antibody E9.66 CDR-H3

<400> SEQUENCE: 155

Glu Gly Val Pro Leu Gly Gly Gly Ala Asp Lys
1               5                   10

<210> SEQ ID NO 156
<211> LENGTH: 121
<212> TYPE: PRT
<213> ORGANISM: Artificial Sequence
<220> FEATURE:
<223> OTHER INFORMATION: DLL4 antibody E9.71 VH region

<400> SEQUENCE: 156

```
Glu Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Asp Ile Tyr Tyr Thr Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Gln Ala Leu Ala Met Gly Gly Gly Ser Asp Lys Trp Gly
            100                 105                 110

Gln Gly Thr Leu Val Thr Val Ser Ser
        115                 120
```

<210> SEQ ID NO 157
<211> LENGTH: 7
<212> TYPE: PRT
<213> ORGANISM: Artificial Sequence
<220> FEATURE:
<223> OTHER INFORMATION: DLL4 antibody E9.71 CDR-H1

<400> SEQUENCE: 157

```
Ser Ser Ser Tyr Tyr Trp Gly
1               5
```

<210> SEQ ID NO 158
<211> LENGTH: 16
<212> TYPE: PRT
<213> ORGANISM: Artificial Sequence
<220> FEATURE:
<223> OTHER INFORMATION: DLL4 antibody E9.71 CDR-H2

<400> SEQUENCE: 158

```
Asp Ile Tyr Tyr Thr Gly Ser Thr Tyr Tyr Asn Pro Ser Leu Lys Ser
1               5                   10                  15
```

<210> SEQ ID NO 159
<211> LENGTH: 11
<212> TYPE: PRT
<213> ORGANISM: Artificial Sequence
<220> FEATURE:
<223> OTHER INFORMATION: DLL4 antibody E9.71 CDR-H3

<400> SEQUENCE: 159

```
Gln Ala Leu Ala Met Gly Gly Gly Ser Asp Lys
1               5                   10
```

<210> SEQ ID NO 160
<211> LENGTH: 121
<212> TYPE: PRT
<213> ORGANISM: Artificial Sequence
<220> FEATURE:

<223> OTHER INFORMATION: DLL4 antibody E9.13 VH region

<400> SEQUENCE: 160

Glu Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Asp Ile Tyr Tyr Thr Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Glu Asp Val Ile Leu Arg Gly Gly Ser Asp Tyr Trp Gly
            100                 105                 110

Gln Gly Thr Leu Val Thr Val Ser Ser
        115                 120

<210> SEQ ID NO 161
<211> LENGTH: 7
<212> TYPE: PRT
<213> ORGANISM: Artificial Sequence
<220> FEATURE:
<223> OTHER INFORMATION: DLL4 antibody E9.13 CDR-H1

<400> SEQUENCE: 161

Ser Ser Ser Tyr Tyr Trp Gly
1               5

<210> SEQ ID NO 162
<211> LENGTH: 16
<212> TYPE: PRT
<213> ORGANISM: Artificial Sequence
<220> FEATURE:
<223> OTHER INFORMATION: DLL4 antibody E9.13 CDR-H2

<400> SEQUENCE: 162

Asp Ile Tyr Tyr Thr Gly Ser Thr Tyr Tyr Asn Pro Ser Leu Lys Ser
1               5                   10                  15

<210> SEQ ID NO 163
<211> LENGTH: 11
<212> TYPE: PRT
<213> ORGANISM: Artificial Sequence
<220> FEATURE:
<223> OTHER INFORMATION: DLL4 antibody E9.13 CDR-H3

<400> SEQUENCE: 163

Glu Asp Val Ile Leu Arg Gly Gly Ser Asp Tyr
1               5                   10

<210> SEQ ID NO 164
<211> LENGTH: 121
<212> TYPE: PRT
<213> ORGANISM: Artificial Sequence
<220> FEATURE:
<223> OTHER INFORMATION: DLL4 antibody E9.16 VH region

<400> SEQUENCE: 164

Glu Val Gln Leu Gln Glu Ser Gly Pro Gly Leu Val Lys Pro Ser Glu
1               5                   10                  15

```
Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
            35                  40                  45

Trp Ile Gly Asp Ile Tyr Tyr Thr Gly Ser Thr Tyr Tyr Asn Pro Ser
 50                  55                  60

Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
             85                  90                  95

Cys Ala Arg Glu Asp Val Ile Leu Arg Gly Gly Ser Asp Tyr Trp Gly
            100                 105                 110

Gln Gly Thr Leu Val Thr Val Ser Ser
        115                 120
```

<210> SEQ ID NO 165
<211> LENGTH: 7
<212> TYPE: PRT
<213> ORGANISM: Artificial Sequence
<220> FEATURE:
<223> OTHER INFORMATION: DLL4 antibody E9.16 CDR-H1

<400> SEQUENCE: 165

```
Ser Ser Ser Tyr Tyr Trp Gly
 1               5
```

<210> SEQ ID NO 166
<211> LENGTH: 16
<212> TYPE: PRT
<213> ORGANISM: Artificial Sequence
<220> FEATURE:
<223> OTHER INFORMATION: DLL4 antibody E9.16 CDR-H2

<400> SEQUENCE: 166

```
Asp Ile Tyr Tyr Thr Gly Ser Thr Tyr Tyr Asn Pro Ser Leu Lys Ser
 1               5                  10                  15
```

<210> SEQ ID NO 167
<211> LENGTH: 11
<212> TYPE: PRT
<213> ORGANISM: Artificial Sequence
<220> FEATURE:
<223> OTHER INFORMATION: DLL4 antibody E9.16 CDR-H3

<400> SEQUENCE: 167

```
Glu Asp Val Ile Leu Arg Gly Gly Ser Asp Tyr
 1               5                  10
```

<210> SEQ ID NO 168
<211> LENGTH: 121
<212> TYPE: PRT
<213> ORGANISM: Artificial Sequence
<220> FEATURE:
<223> OTHER INFORMATION: DLL4 antibody E9.38 VH region

<400> SEQUENCE: 168

```
Glu Val Gln Leu Gln Glu Ser Gly Pro Gly Leu Val Lys Pro Ser Glu
 1               5                  10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
            35                  40                  45
```

```
Trp Ile Gly Asp Ile Tyr Tyr Thr Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Glu Asp Val Ile Leu Arg Gly Gly Ser Asp Tyr Trp Gly
            100                 105                 110

Gln Gly Thr Leu Val Thr Val Ser Ser
        115                 120
```

<210> SEQ ID NO 169
<211> LENGTH: 7
<212> TYPE: PRT
<213> ORGANISM: Artificial Sequence
<220> FEATURE:
<223> OTHER INFORMATION: DLL4 antibody E9.38 CDR-H1

<400> SEQUENCE: 169

```
Ser Ser Ser Tyr Tyr Trp Gly
1               5
```

<210> SEQ ID NO 170
<211> LENGTH: 16
<212> TYPE: PRT
<213> ORGANISM: Artificial Sequence
<220> FEATURE:
<223> OTHER INFORMATION: DLL4 antibody E9.38 CDR-H2

<400> SEQUENCE: 170

```
Asp Ile Tyr Tyr Thr Gly Ser Thr Tyr Tyr Asn Pro Ser Leu Lys Ser
1               5                   10                  15
```

<210> SEQ ID NO 171
<211> LENGTH: 11
<212> TYPE: PRT
<213> ORGANISM: Artificial Sequence
<220> FEATURE:
<223> OTHER INFORMATION: DLL4 antibody E9.38 CDR-H3

<400> SEQUENCE: 171

```
Glu Asp Val Ile Leu Arg Gly Gly Ser Asp Tyr
1               5                   10
```

<210> SEQ ID NO 172
<211> LENGTH: 121
<212> TYPE: PRT
<213> ORGANISM: Artificial Sequence
<220> FEATURE:
<223> OTHER INFORMATION: DLL4 antibody E9.2B VH region

<400> SEQUENCE: 172

```
Glu Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
                20                  25                  30

Asn Tyr Tyr Trp Gly Trp Ile Arg Gln Pro Pro Gly Lys Gly Leu Glu
            35                  40                  45

Trp Ile Gly Asp Ile Asn Tyr Asn Gly Asn Thr Tyr Tyr Asn Pro Ser
    50                  55                  60

Leu Lys Ser Arg Val Thr Ile Ser Val Asp Thr Ser Lys Asn Gln Phe
65                  70                  75                  80
```

```
Ser Leu Lys Leu Ser Ser Val Thr Ala Ala Asp Thr Ala Val Tyr Tyr
                85                  90                  95

Cys Ala Arg Glu Ala Val Ala Leu Gly Gly Ala Asp Asp Trp Gly
            100                 105                 110

Gln Gly Thr Leu Val Thr Val Ser Ser
        115                 120

<210> SEQ ID NO 173
<211> LENGTH: 7
<212> TYPE: PRT
<213> ORGANISM: Artificial Sequence
<220> FEATURE:
<223> OTHER INFORMATION: DLL4 antibody E9.2B CDR-H1

<400> SEQUENCE: 173

Ser Ser Asn Tyr Tyr Trp Gly
1               5

<210> SEQ ID NO 174
<211> LENGTH: 16
<212> TYPE: PRT
<213> ORGANISM: Artificial Sequence
<220> FEATURE:
<223> OTHER INFORMATION: DLL4 antibody E9.2B CDR-H2

<400> SEQUENCE: 174

Asp Ile Asn Tyr Asn Gly Asn Thr Tyr Tyr Asn Pro Ser Leu Lys Ser
1               5                   10                  15

<210> SEQ ID NO 175
<211> LENGTH: 11
<212> TYPE: PRT
<213> ORGANISM: Artificial Sequence
<220> FEATURE:
<223> OTHER INFORMATION: DLL4 antibody E9.2B CDR-H3

<400> SEQUENCE: 175

Glu Ala Val Ala Leu Gly Gly Gly Ala Asp Asp
1               5                   10

<210> SEQ ID NO 176
<211> LENGTH: 121
<212> TYPE: PRT
<213> ORGANISM: Artificial Sequence
<220> FEATURE:
<223> OTHER INFORMATION: DLL4 antibody E9.1F VH region

<400> SEQUENCE: 176

Glu Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Gly
            20                  25                  30

Ser Tyr Tyr Trp Gly Trp Ile Arg Gln Pro Pro Gly Lys Gly Leu Glu
        35                  40                  45

Trp Ile Gly Asp Ile Asn Tyr Ile Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Glu Ala Val Ser Phe Gly Gly Gly Ala Asp Ser Trp Gly
            100                 105                 110
```

```
Gln Gly Thr Leu Val Thr Val Ser Ser
        115                 120
```

<210> SEQ ID NO 177
<211> LENGTH: 7
<212> TYPE: PRT
<213> ORGANISM: Artificial Sequence
<220> FEATURE:
<223> OTHER INFORMATION: DLL4 antibody E9.1F CDR-H1

<400> SEQUENCE: 177

```
Ser Gly Ser Tyr Tyr Trp Gly
1               5
```

<210> SEQ ID NO 178
<211> LENGTH: 16
<212> TYPE: PRT
<213> ORGANISM: Artificial Sequence
<220> FEATURE:
<223> OTHER INFORMATION: DLL4 antibody E9.1F CDR-H2

<400> SEQUENCE: 178

```
Asp Ile Asn Tyr Ile Gly Ser Thr Tyr Tyr Asn Pro Ser Leu Lys Ser
1               5                   10                  15
```

<210> SEQ ID NO 179
<211> LENGTH: 11
<212> TYPE: PRT
<213> ORGANISM: Artificial Sequence
<220> FEATURE:
<223> OTHER INFORMATION: DLL4 antibody E9.1F CDR-H3

<400> SEQUENCE: 179

```
Glu Ala Val Ser Phe Gly Gly Gly Ala Asp Ser
1               5                   10
```

<210> SEQ ID NO 180
<211> LENGTH: 121
<212> TYPE: PRT
<213> ORGANISM: Artificial Sequence
<220> FEATURE:
<223> OTHER INFORMATION: DLL4 antibody E9.10H VH region

<400> SEQUENCE: 180

```
Glu Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Gly Tyr Tyr Trp Gly Trp Ile Arg Gln Pro Pro Gly Lys Gly Leu Glu
        35                  40                  45

Trp Ile Gly Asp Ile Tyr Tyr Thr Gly Asn Thr Tyr Tyr Asn Pro Ser
    50                  55                  60

Leu Lys Asn Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Glu Glu Val Ile Leu Gly Gly Ala Asp Gln Trp Gly
            100                 105                 110

Gln Gly Thr Leu Val Thr Val Ser Ser
        115                 120
```

<210> SEQ ID NO 181

```
<211> LENGTH: 7
<212> TYPE: PRT
<213> ORGANISM: Artificial Sequence
<220> FEATURE:
<223> OTHER INFORMATION: DLL4 antibody E9.10H CDR-H1

<400> SEQUENCE: 181

Ser Ser Gly Tyr Tyr Trp Gly
1               5

<210> SEQ ID NO 182
<211> LENGTH: 16
<212> TYPE: PRT
<213> ORGANISM: Artificial Sequence
<220> FEATURE:
<223> OTHER INFORMATION: DLL4 antibody E9.10H CDR-H2

<400> SEQUENCE: 182

Asp Ile Tyr Tyr Thr Gly Asn Thr Tyr Tyr Asn Pro Ser Leu Lys Asn
1               5                   10                  15

<210> SEQ ID NO 183
<211> LENGTH: 11
<212> TYPE: PRT
<213> ORGANISM: Artificial Sequence
<220> FEATURE:
<223> OTHER INFORMATION: DLL4 antibody E9.10H CDR-H3

<400> SEQUENCE: 183

Glu Glu Val Ile Leu Gly Gly Gly Ala Asp Gln
1               5                   10

<210> SEQ ID NO 184
<211> LENGTH: 121
<212> TYPE: PRT
<213> ORGANISM: Artificial Sequence
<220> FEATURE:
<223> OTHER INFORMATION: DLL4 antibody E9.5E VH region

<400> SEQUENCE: 184

Glu Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Asp Ile Asn Tyr Ile Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Glu Ser Val Pro Leu Gly Gly Gly Ala Asp Glu Trp Gly
            100                 105                 110

Gln Gly Thr Leu Val Thr Val Ser Ser
        115                 120

<210> SEQ ID NO 185
<211> LENGTH: 7
<212> TYPE: PRT
<213> ORGANISM: Artificial Sequence
<220> FEATURE:
<223> OTHER INFORMATION: DLL4 antibody E9.5E CDR-H1
```

```
<400> SEQUENCE: 185

Ser Ser Ser Tyr Tyr Trp Gly
1               5

<210> SEQ ID NO 186
<211> LENGTH: 16
<212> TYPE: PRT
<213> ORGANISM: Artificial Sequence
<220> FEATURE:
<223> OTHER INFORMATION: DLL4 antibody E9.5E CDR-H2

<400> SEQUENCE: 186

Asp Ile Asn Tyr Ile Gly Ser Thr Tyr Tyr Asn Pro Ser Leu Lys Ser
1               5                   10                  15

<210> SEQ ID NO 187
<211> LENGTH: 11
<212> TYPE: PRT
<213> ORGANISM: Artificial Sequence
<220> FEATURE:
<223> OTHER INFORMATION: DLL4 antibody E9.5E CDR-H3

<400> SEQUENCE: 187

Glu Ser Val Pro Leu Gly Gly Gly Ala Asp Glu
1               5                   10

<210> SEQ ID NO 188
<211> LENGTH: 121
<212> TYPE: PRT
<213> ORGANISM: Artificial Sequence
<220> FEATURE:
<223> OTHER INFORMATION: DLL4 antibody E9.10C VH region

<400> SEQUENCE: 188

Glu Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Gly
            20                  25                  30

Ser Tyr Tyr Trp Gly Trp Ile Arg Gln Pro Pro Gly Lys Gly Leu Glu
        35                  40                  45

Trp Ile Gly Asp Ile Tyr Tyr Thr Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Gln Ala Val Met Tyr Gly Gly Gly Ser Asp Asn Trp Gly
            100                 105                 110

Gln Gly Thr Leu Val Thr Val Ser Ser
        115                 120

<210> SEQ ID NO 189
<211> LENGTH: 7
<212> TYPE: PRT
<213> ORGANISM: Artificial Sequence
<220> FEATURE:
<223> OTHER INFORMATION: DLL4 antibody E9.10C CDR-H1

<400> SEQUENCE: 189

Ser Gly Ser Tyr Tyr Trp Gly
1               5
```

```
<210> SEQ ID NO 190
<211> LENGTH: 16
<212> TYPE: PRT
<213> ORGANISM: Artificial Sequence
<220> FEATURE:
<223> OTHER INFORMATION: DLL4 antibody E9.10C CDR-H2

<400> SEQUENCE: 190

Asp Ile Tyr Tyr Thr Gly Ser Thr Tyr Tyr Asn Pro Ser Leu Lys Ser
1               5                   10                  15

<210> SEQ ID NO 191
<211> LENGTH: 11
<212> TYPE: PRT
<213> ORGANISM: Artificial Sequence
<220> FEATURE:
<223> OTHER INFORMATION: DLL4 antibody E9.10C CDR-H3

<400> SEQUENCE: 191

Gln Ala Val Met Tyr Gly Gly Gly Ser Asp Asn
1               5                   10

<210> SEQ ID NO 192
<211> LENGTH: 121
<212> TYPE: PRT
<213> ORGANISM: Artificial Sequence
<220> FEATURE:
<223> OTHER INFORMATION: DLL4 antibody E9.7E VH region

<400> SEQUENCE: 192

Glu Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Asp Ile Tyr Tyr Ala Gly Ser Thr Tyr Tyr Asn Pro Ser
    50                  55                  60

Leu Lys Asp Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Glu Asp Met Ile Leu Gly Gly Gly Ala Asp Asn Trp Gly
            100                 105                 110

Gln Gly Thr Leu Val Thr Val Ser Ser
        115                 120

<210> SEQ ID NO 193
<211> LENGTH: 7
<212> TYPE: PRT
<213> ORGANISM: Artificial Sequence
<220> FEATURE:
<223> OTHER INFORMATION: DLL4 antibody E9.7E CDR-H1

<400> SEQUENCE: 193

Ser Ser Ser Tyr Tyr Trp Gly
1               5

<210> SEQ ID NO 194
<211> LENGTH: 16
<212> TYPE: PRT
<213> ORGANISM: Artificial Sequence
<220> FEATURE:
<223> OTHER INFORMATION: DLL4 antibody E9.7E CDR-H2
```

```
<400> SEQUENCE: 194

Asp Ile Tyr Tyr Ala Gly Ser Thr Tyr Tyr Asn Pro Ser Leu Lys Asp
1               5                   10                  15

<210> SEQ ID NO 195
<211> LENGTH: 11
<212> TYPE: PRT
<213> ORGANISM: Artificial Sequence
<220> FEATURE:
<223> OTHER INFORMATION: DLL4 antibody E9.7E CDR-H3

<400> SEQUENCE: 195

Glu Asp Met Ile Leu Gly Gly Gly Ala Asp Asn
1               5                   10

<210> SEQ ID NO 196
<211> LENGTH: 121
<212> TYPE: PRT
<213> ORGANISM: Artificial Sequence
<220> FEATURE:
<223> OTHER INFORMATION: DLL4 antibody E9.12B VH region

<400> SEQUENCE: 196

Glu Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Asn Tyr Tyr Trp Gly Trp Ile Arg Gln Pro Pro Gly Lys Gly Leu Glu
        35                  40                  45

Trp Ile Gly Asp Ile Tyr Tyr Thr Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Glu Ala Val Ser Phe Gly Gly Gly Ala Asp Ser Trp Gly
            100                 105                 110

Gln Gly Thr Leu Val Thr Val Ser Ser
        115                 120

<210> SEQ ID NO 197
<211> LENGTH: 7
<212> TYPE: PRT
<213> ORGANISM: Artificial Sequence
<220> FEATURE:
<223> OTHER INFORMATION: DLL4 antibody E9.12B CDR-H1

<400> SEQUENCE: 197

Ser Ser Asn Tyr Tyr Trp Gly
1               5

<210> SEQ ID NO 198
<211> LENGTH: 16
<212> TYPE: PRT
<213> ORGANISM: Artificial Sequence
<220> FEATURE:
<223> OTHER INFORMATION: DLL4 antibody E9.12B CDR-H2

<400> SEQUENCE: 198

Asp Ile Tyr Tyr Thr Gly Ser Thr Tyr Tyr Asn Pro Ser Leu Lys Ser
1               5                   10                  15
```

```
<210> SEQ ID NO 199
<211> LENGTH: 11
<212> TYPE: PRT
<213> ORGANISM: Artificial Sequence
<220> FEATURE:
<223> OTHER INFORMATION: DLL4 antibody E9.12B CDR-H3

<400> SEQUENCE: 199

Glu Ala Val Ser Phe Gly Gly Gly Ala Asp Ser
1               5                   10

<210> SEQ ID NO 200
<211> LENGTH: 121
<212> TYPE: PRT
<213> ORGANISM: Artificial Sequence
<220> FEATURE:
<223> OTHER INFORMATION: DLL4 antibody E9.10E VH region

<400> SEQUENCE: 200

Glu Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Asn Ser Gly
            20                  25                  30

Asn Tyr Tyr Trp Gly Trp Ile Arg Gln Pro Pro Gly Lys Gly Leu Glu
        35                  40                  45

Trp Ile Gly Asp Ile Ser Tyr Thr Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Glu Asp Val Met Tyr Gly Gly Gly Asp Ser Trp Gly
            100                 105                 110

Gln Gly Thr Leu Val Thr Val Ser Ser
        115                 120

<210> SEQ ID NO 201
<211> LENGTH: 7
<212> TYPE: PRT
<213> ORGANISM: Artificial Sequence
<220> FEATURE:
<223> OTHER INFORMATION: DLL4 antibody E9.10E CDR-H1

<400> SEQUENCE: 201

Ser Gly Asn Tyr Tyr Trp Gly
1               5

<210> SEQ ID NO 202
<211> LENGTH: 16
<212> TYPE: PRT
<213> ORGANISM: Artificial Sequence
<220> FEATURE:
<223> OTHER INFORMATION: DLL4 antibody E9.10E CDR-H2

<400> SEQUENCE: 202

Asp Ile Ser Tyr Thr Gly Ser Thr Tyr Tyr Asn Pro Ser Leu Lys Ser
1               5                   10                  15

<210> SEQ ID NO 203
<211> LENGTH: 11
<212> TYPE: PRT
<213> ORGANISM: Artificial Sequence
<220> FEATURE:
```

<223> OTHER INFORMATION: DLL4 antibody E9.10E CDR-H3

<400> SEQUENCE: 203

Glu Asp Val Met Tyr Gly Gly Gly Gly Asp Ser
1               5                   10

<210> SEQ ID NO 204
<211> LENGTH: 121
<212> TYPE: PRT
<213> ORGANISM: Artificial Sequence
<220> FEATURE:
<223> OTHER INFORMATION: DLL4 antibody E9.6A VH region

<400> SEQUENCE: 204

Glu Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Asp Ile Asn Tyr Ala Gly Ser Thr Tyr Tyr Asn Pro Ser
    50                  55                  60

Leu Lys Asn Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Glu Ala Val Ala Leu Gly Gly Gly Ala Asp Ser Trp Gly
            100                 105                 110

Gln Gly Thr Leu Val Thr Val Ser Ser
        115                 120

<210> SEQ ID NO 205
<211> LENGTH: 7
<212> TYPE: PRT
<213> ORGANISM: Artificial Sequence
<220> FEATURE:
<223> OTHER INFORMATION: DLL4 antibody E9.6A CDR-H1

<400> SEQUENCE: 205

Ser Ser Ser Tyr Tyr Trp Gly
1               5

<210> SEQ ID NO 206
<211> LENGTH: 16
<212> TYPE: PRT
<213> ORGANISM: Artificial Sequence
<220> FEATURE:
<223> OTHER INFORMATION: DLL4 antibody E9.6A CDR-H2

<400> SEQUENCE: 206

Asp Ile Asn Tyr Ala Gly Ser Thr Tyr Tyr Asn Pro Ser Leu Lys Asn
1               5                   10                  15

<210> SEQ ID NO 207
<211> LENGTH: 11
<212> TYPE: PRT
<213> ORGANISM: Artificial Sequence
<220> FEATURE:
<223> OTHER INFORMATION: DLL4 antibody E9.6A CDR-H3

<400> SEQUENCE: 207

Glu Ala Val Ala Leu Gly Gly Gly Ala Asp Ser
1               5                   10

```
<210> SEQ ID NO 208
<211> LENGTH: 121
<212> TYPE: PRT
<213> ORGANISM: Artificial Sequence
<220> FEATURE:
<223> OTHER INFORMATION: DLL4 antibody E9.7A VH region

<400> SEQUENCE: 208

Glu Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Asp Ile Asn Tyr Ala Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Glu Asp Val Lys Phe Gly Gly Gly Ala Asp Leu Trp Gly
            100                 105                 110

Gln Gly Thr Leu Val Thr Val Ser Ser
        115                 120

<210> SEQ ID NO 209
<211> LENGTH: 7
<212> TYPE: PRT
<213> ORGANISM: Artificial Sequence
<220> FEATURE:
<223> OTHER INFORMATION: DLL4 antibody E9.7A CDR-H1

<400> SEQUENCE: 209

Ser Ser Ser Tyr Tyr Trp Gly
1               5

<210> SEQ ID NO 210
<211> LENGTH: 16
<212> TYPE: PRT
<213> ORGANISM: Artificial Sequence
<220> FEATURE:
<223> OTHER INFORMATION: DLL4 antibody E9.7A CDR-H2

<400> SEQUENCE: 210

Asp Ile Asn Tyr Ala Gly Ser Thr Tyr Tyr Asn Pro Ser Leu Lys Ser
1               5                   10                  15

<210> SEQ ID NO 211
<211> LENGTH: 11
<212> TYPE: PRT
<213> ORGANISM: Artificial Sequence
<220> FEATURE:
<223> OTHER INFORMATION: DLL4 antibody E9.7A CDR-H3

<400> SEQUENCE: 211

Glu Asp Val Lys Phe Gly Gly Gly Ala Asp Leu
1               5                   10

<210> SEQ ID NO 212
<211> LENGTH: 121
<212> TYPE: PRT
<213> ORGANISM: Artificial Sequence
```

<220> FEATURE:
<223> OTHER INFORMATION: DLL4 antibody E9.8H VH region

<400> SEQUENCE: 212

Glu Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Gly
            20                  25                  30

Ser Tyr Tyr Trp Gly Trp Ile Arg Gln Pro Pro Gly Lys Gly Leu Glu
        35                  40                  45

Trp Ile Gly Asp Ile Tyr Tyr Thr Gly Ser Thr Tyr Tyr Asn Pro Ser
    50                  55                  60

Leu Lys Asn Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Glu Ser Val Pro Leu Gly Gly Gly Ala Asp Asn Trp Gly
            100                 105                 110

Gln Gly Thr Leu Val Thr Val Ser Ser
        115                 120

<210> SEQ ID NO 213
<211> LENGTH: 7
<212> TYPE: PRT
<213> ORGANISM: Artificial Sequence
<220> FEATURE:
<223> OTHER INFORMATION: DLL4 antibody E9.8H CDR-H1

<400> SEQUENCE: 213

Ser Gly Ser Tyr Tyr Trp Gly
1               5

<210> SEQ ID NO 214
<211> LENGTH: 16
<212> TYPE: PRT
<213> ORGANISM: Artificial Sequence
<220> FEATURE:
<223> OTHER INFORMATION: DLL4 antibody E9.8H CDR-H2

<400> SEQUENCE: 214

Asp Ile Tyr Tyr Thr Gly Ser Thr Tyr Tyr Asn Pro Ser Leu Lys Asn
1               5                   10                  15

<210> SEQ ID NO 215
<211> LENGTH: 11
<212> TYPE: PRT
<213> ORGANISM: Artificial Sequence
<220> FEATURE:
<223> OTHER INFORMATION: DLL4 antibody E9.8H CDR-H3

<400> SEQUENCE: 215

Glu Ser Val Pro Leu Gly Gly Gly Ala Asp Asn
1               5                   10

<210> SEQ ID NO 216
<211> LENGTH: 106
<212> TYPE: PRT
<213> ORGANISM: Artificial Sequence
<220> FEATURE:
<223> OTHER INFORMATION: DLL4 antibody E9.13 VL region

<400> SEQUENCE: 216

Ser Tyr Glu Leu Thr Gln Pro Pro Ser Val Ser Val Ser Pro Gly Gln

```
                1               5                  10                  15
Thr Ala Ser Ile Thr Cys Ser Gly Asp Thr Leu Gly Asp Lys Tyr Val
                20                  25                  30

Ser Trp Tyr Gln Gln Lys Pro Gly Gln Ser Pro Val Leu Val Ile Tyr
            35                  40                  45

Glu Asp Ser Glu Arg Pro Ser Gly Ile Pro Glu Arg Phe Ser Gly Ser
    50                  55                  60

Asn Ser Gly Asp Thr Ala Thr Leu Thr Ile Ser Gly Thr Gln Pro Met
65                  70                  75                  80

Asp Glu Ala Asp Tyr Tyr Cys Gln Ala Trp Asp Ser Glu Thr Gly Val
                85                  90                  95

Phe Gly Ser Gly Thr Lys Val Thr Val Leu
            100                 105

<210> SEQ ID NO 217
<211> LENGTH: 11
<212> TYPE: PRT
<213> ORGANISM: Artificial Sequence
<220> FEATURE:
<223> OTHER INFORMATION: DLL4 antibody E9.13 CDR-L1

<400> SEQUENCE: 217

Ser Gly Asp Thr Leu Gly Asp Lys Tyr Val Ser
1               5                   10

<210> SEQ ID NO 218
<211> LENGTH: 7
<212> TYPE: PRT
<213> ORGANISM: Artificial Sequence
<220> FEATURE:
<223> OTHER INFORMATION: DLL4 antibody E9.13 CDR-L2

<400> SEQUENCE: 218

Glu Asp Ser Glu Arg Pro Ser
1               5

<210> SEQ ID NO 219
<211> LENGTH: 9
<212> TYPE: PRT
<213> ORGANISM: Artificial Sequence
<220> FEATURE:
<223> OTHER INFORMATION: DLL4 antibody E9.13 CDR-L3

<400> SEQUENCE: 219

Gln Ala Trp Asp Ser Glu Thr Gly Val
1               5

<210> SEQ ID NO 220
<211> LENGTH: 106
<212> TYPE: PRT
<213> ORGANISM: Artificial Sequence
<220> FEATURE:
<223> OTHER INFORMATION: DLL4 antibody E9.16 VL region

<400> SEQUENCE: 220

Ser Tyr Glu Leu Thr Gln Pro Pro Ser Val Ser Val Ser Pro Gly Gln
1               5                   10                  15

Thr Ala Ser Ile Thr Cys Ser Gly Glu Arg Leu Gly Asp Lys Tyr Val
                20                  25                  30

Ser Trp Tyr Gln Gln Lys Pro Gly Gln Ser Pro Val Leu Val Ile Tyr
            35                  40                  45

Glu Asp Phe Lys Arg Pro Ser Gly Ile Pro Glu Arg Phe Ser Gly Ser
```

```
                50                  55                  60
Asn Ser Gly Asp Thr Ala Thr Leu Thr Ile Ser Gly Thr Gln Pro Met
 65                  70                  75                  80

Asp Glu Ala Asp Tyr Tyr Cys Gln Ala Trp Asp Arg Asp Thr Gly Val
                 85                  90                  95

Phe Gly Tyr Gly Thr Lys Val Thr Val Leu
            100                 105

<210> SEQ ID NO 221
<211> LENGTH: 11
<212> TYPE: PRT
<213> ORGANISM: Artificial Sequence
<220> FEATURE:
<223> OTHER INFORMATION: DLL4 antibody E9.16 CDR-L1

<400> SEQUENCE: 221

Ser Gly Glu Arg Leu Gly Asp Lys Tyr Val Ser
 1               5                  10

<210> SEQ ID NO 222
<211> LENGTH: 7
<212> TYPE: PRT
<213> ORGANISM: Artificial Sequence
<220> FEATURE:
<223> OTHER INFORMATION: DLL4 antibody E9.16 CDR-L2

<400> SEQUENCE: 222

Glu Asp Phe Lys Arg Pro Ser
 1               5

<210> SEQ ID NO 223
<211> LENGTH: 9
<212> TYPE: PRT
<213> ORGANISM: Artificial Sequence
<220> FEATURE:
<223> OTHER INFORMATION: DLL4 antibody E9.16 CDR-L3

<400> SEQUENCE: 223

Gln Ala Trp Asp Arg Asp Thr Gly Val
 1               5

<210> SEQ ID NO 224
<211> LENGTH: 106
<212> TYPE: PRT
<213> ORGANISM: Artificial Sequence
<220> FEATURE:
<223> OTHER INFORMATION: DLL4 antibody E9.38 VL region

<400> SEQUENCE: 224

Ser Tyr Glu Leu Thr Gln Pro Pro Ser Val Ser Val Ser Pro Gly Gln
 1               5                  10                  15

Thr Ala Ser Ile Thr Cys Ser Gly Gln Arg Leu Gly Asp Lys Tyr Val
                20                  25                  30

Ser Trp Tyr Gln Gln Lys Pro Gly Gln Ser Pro Val Leu Val Ile Tyr
             35                  40                  45

Glu Asp Ser Lys Arg Pro Ser Gly Ile Pro Glu Arg Phe Ser Gly Ser
         50                  55                  60

Asn Ser Gly Asp Thr Ala Thr Leu Thr Ile Ser Gly Thr Gln Pro Met
 65                  70                  75                  80

Asp Glu Ala Asp Tyr Tyr Cys Gln Ala Trp Asp Arg Asp Val Gly Val
                 85                  90                  95

Phe Gly Ser Gly Thr Lys Val Thr Val Leu
            100                 105
```

<210> SEQ ID NO 225
<211> LENGTH: 11
<212> TYPE: PRT
<213> ORGANISM: Artificial Sequence
<220> FEATURE:
<223> OTHER INFORMATION: DLL4 antibody E9.38 CDR-L1

<400> SEQUENCE: 225

Ser Gly Gln Arg Leu Gly Asp Lys Tyr Val Ser
1               5                   10

<210> SEQ ID NO 226
<211> LENGTH: 7
<212> TYPE: PRT
<213> ORGANISM: Artificial Sequence
<220> FEATURE:
<223> OTHER INFORMATION: DLL4 antibody E9.38 CDR-L2

<400> SEQUENCE: 226

Glu Asp Ser Lys Arg Pro Ser
1               5

<210> SEQ ID NO 227
<211> LENGTH: 9
<212> TYPE: PRT
<213> ORGANISM: Artificial Sequence
<220> FEATURE:
<223> OTHER INFORMATION: DLL4 antibody E9.38 CDR-L3

<400> SEQUENCE: 227

Gln Ala Trp Asp Arg Asp Val Gly Val
1               5

<210> SEQ ID NO 228
<211> LENGTH: 106
<212> TYPE: PRT
<213> ORGANISM: Artificial Sequence
<220> FEATURE:
<223> OTHER INFORMATION: DLL4 antibody E9.4 VL region

<400> SEQUENCE: 228

Ser Tyr Glu Leu Thr Gln Pro Pro Ser Val Ser Val Ser Pro Gly Gln
1               5                   10                  15

Thr Ala Ser Ile Thr Cys Ser Gly Gln Arg Leu Gly Asp Lys Tyr Ala
                20                  25                  30

Ser Trp Tyr Gln Gln Lys Pro Gly Gln Ser Pro Val Leu Val Ile Tyr
            35                  40                  45

Glu Asp Ser Lys Arg Pro Ser Gly Ile Pro Glu Arg Phe Ser Gly Ser
    50                  55                  60

Asn Ser Gly Asp Thr Ala Thr Leu Thr Ile Ser Gly Thr Gln Pro Met
65                  70                  75                  80

Asp Glu Ala Asp Tyr Tyr Cys Gln Ala Trp Asp Arg Asp Thr Gly Val
                85                  90                  95

Phe Gly Tyr Gly Thr Lys Val Thr Val Leu
            100                 105

<210> SEQ ID NO 229
<211> LENGTH: 11
<212> TYPE: PRT
<213> ORGANISM: Artificial Sequence
<220> FEATURE:
<223> OTHER INFORMATION: DLL4 antibody E9.4 CDR-L1

<400> SEQUENCE: 229

Ser Gly Gln Arg Leu Gly Asp Lys Tyr Ala Ser
1               5                   10

<210> SEQ ID NO 230
<211> LENGTH: 7
<212> TYPE: PRT
<213> ORGANISM: Artificial Sequence
<220> FEATURE:
<223> OTHER INFORMATION: DLL4 antibody E9.4 CDR-L2

<400> SEQUENCE: 230

Glu Asp Ser Lys Arg Pro Ser
1               5

<210> SEQ ID NO 231
<211> LENGTH: 9
<212> TYPE: PRT
<213> ORGANISM: Artificial Sequence
<220> FEATURE:
<223> OTHER INFORMATION: DLL4 antibody E9.4 CDR-L3

<400> SEQUENCE: 231

Gln Ala Trp Asp Arg Asp Thr Gly Val
1               5

<210> SEQ ID NO 232
<211> LENGTH: 106
<212> TYPE: PRT
<213> ORGANISM: Artificial Sequence
<220> FEATURE:
<223> OTHER INFORMATION: DLL4 antibody E9.11 VL region

<400> SEQUENCE: 232

Ser Tyr Glu Leu Thr Gln Pro Pro Ser Val Ser Val Ser Pro Gly Gln
1               5                   10                  15

Thr Ala Ser Ile Thr Cys Ser Gly Gln Arg Leu Gly Asp Lys Tyr Ala
                20                  25                  30

Ser Trp Tyr Gln Gln Lys Pro Gly Gln Ser Pro Val Leu Val Ile Tyr
            35                  40                  45

Glu Asp Ser Lys Arg Pro Ser Gly Ile Pro Glu Arg Phe Ser Gly Ser
        50                  55                  60

Asn Ser Gly Asp Thr Ala Thr Leu Thr Ile Ser Gly Thr Gln Pro Met
65                  70                  75                  80

Asp Glu Ala Asp Tyr Tyr Cys Gln Ala Trp Asp Arg Asp Thr Gly Val
                85                  90                  95

Phe Gly Tyr Gly Thr Lys Val Thr Val Leu
            100                 105

<210> SEQ ID NO 233
<211> LENGTH: 11
<212> TYPE: PRT
<213> ORGANISM: Artificial Sequence
<220> FEATURE:
<223> OTHER INFORMATION: DLL4 antibody E9.11 CDR-L1

<400> SEQUENCE: 233

Ser Gly Gln Arg Leu Gly Asp Lys Tyr Ala Ser
1               5                   10

<210> SEQ ID NO 234
<211> LENGTH: 7

```
<212> TYPE: PRT
<213> ORGANISM: Artificial Sequence
<220> FEATURE:
<223> OTHER INFORMATION: DLL4 antibody E9.11 CDR-L2

<400> SEQUENCE: 234

Glu Asp Ser Lys Arg Pro Ser
1               5

<210> SEQ ID NO 235
<211> LENGTH: 9
<212> TYPE: PRT
<213> ORGANISM: Artificial Sequence
<220> FEATURE:
<223> OTHER INFORMATION: DLL4 antibody E9.11 CDR-L3

<400> SEQUENCE: 235

Gln Ala Trp Asp Arg Asp Thr Gly Val
1               5

<210> SEQ ID NO 236
<211> LENGTH: 106
<212> TYPE: PRT
<213> ORGANISM: Artificial Sequence
<220> FEATURE:
<223> OTHER INFORMATION: DLL4 antibody E9.14 VL region

<400> SEQUENCE: 236

Ser Tyr Glu Leu Thr Gln Pro Pro Ser Val Ser Val Ser Pro Gly Gln
1               5                   10                  15

Thr Ala Ser Ile Thr Cys Ser Gly Gln Arg Leu Gly Asp Lys Tyr Ala
            20                  25                  30

Ser Trp Tyr Gln Gln Lys Pro Gly Gln Ser Pro Val Leu Val Ile Tyr
        35                  40                  45

Glu Asp Ser Lys Arg Pro Ser Gly Ile Pro Glu Arg Phe Ser Gly Ser
    50                  55                  60

Asn Ser Gly Asp Thr Ala Thr Leu Thr Ile Ser Gly Thr Gln Pro Met
65                  70                  75                  80

Asp Glu Ala Asp Tyr Tyr Cys Gln Ala Trp Asp Arg Asp Thr Gly Val
                85                  90                  95

Phe Gly Tyr Gly Thr Lys Val Thr Val Leu
            100                 105

<210> SEQ ID NO 237
<211> LENGTH: 11
<212> TYPE: PRT
<213> ORGANISM: Artificial Sequence
<220> FEATURE:
<223> OTHER INFORMATION: DLL4 antibody E9.14 CDR-L1

<400> SEQUENCE: 237

Ser Gly Gln Arg Leu Gly Asp Lys Tyr Ala Ser
1               5                   10

<210> SEQ ID NO 238
<211> LENGTH: 7
<212> TYPE: PRT
<213> ORGANISM: Artificial Sequence
<220> FEATURE:
<223> OTHER INFORMATION: DLL4 antibody E9.14 CDR-L2

<400> SEQUENCE: 238

Glu Asp Ser Lys Arg Pro Ser
1               5
```

<210> SEQ ID NO 239
<211> LENGTH: 9
<212> TYPE: PRT
<213> ORGANISM: Artificial Sequence
<220> FEATURE:
<223> OTHER INFORMATION: DLL4 antibody E9.14 CDR-L3

<400> SEQUENCE: 239

Gln Ala Trp Asp Arg Asp Thr Gly Val
1               5

<210> SEQ ID NO 240
<211> LENGTH: 106
<212> TYPE: PRT
<213> ORGANISM: Artificial Sequence
<220> FEATURE:
<223> OTHER INFORMATION: DLL4 antibody E9.17 VL region

<400> SEQUENCE: 240

Ser Tyr Glu Leu Thr Gln Pro Pro Ser Val Ser Val Ser Pro Gly Gln
1               5                   10                  15

Thr Ala Ser Ile Thr Cys Ser Gly Gln Arg Leu Gly Asp Lys Tyr Ala
            20                  25                  30

Ser Trp Tyr Gln Gln Lys Pro Gly Gln Ser Pro Val Leu Val Ile Tyr
        35                  40                  45

Glu Asp Ser Lys Arg Pro Ser Gly Ile Pro Glu Arg Phe Ser Gly Ser
    50                  55                  60

Asn Ser Gly Asp Thr Ala Thr Leu Thr Ile Ser Gly Thr Gln Pro Met
65                  70                  75                  80

Asp Glu Ala Asp Tyr Tyr Cys Gln Ala Trp Asp Arg Asp Thr Gly Val
                85                  90                  95

Phe Gly Tyr Gly Thr Lys Val Thr Val Leu
            100                 105

<210> SEQ ID NO 241
<211> LENGTH: 11
<212> TYPE: PRT
<213> ORGANISM: Artificial Sequence
<220> FEATURE:
<223> OTHER INFORMATION: DLL4 antibody E9.17 CDR-L1

<400> SEQUENCE: 241

Ser Gly Gln Arg Leu Gly Asp Lys Tyr Ala Ser
1               5                   10

<210> SEQ ID NO 242
<211> LENGTH: 7
<212> TYPE: PRT
<213> ORGANISM: Artificial Sequence
<220> FEATURE:
<223> OTHER INFORMATION: DLL4 antibody E9.17 CDR-L2

<400> SEQUENCE: 242

Glu Asp Ser Lys Arg Pro Ser
1               5

<210> SEQ ID NO 243
<211> LENGTH: 9
<212> TYPE: PRT
<213> ORGANISM: Artificial Sequence
<220> FEATURE:
<223> OTHER INFORMATION: DLL4 antibody E9.17 CDR-L3

```
<400> SEQUENCE: 243

Gln Ala Trp Asp Arg Asp Thr Gly Val
1               5

<210> SEQ ID NO 244
<211> LENGTH: 106
<212> TYPE: PRT
<213> ORGANISM: Artificial Sequence
<220> FEATURE:
<223> OTHER INFORMATION: DLL4 antibody E9.18 VL region

<400> SEQUENCE: 244

Ser Tyr Glu Leu Thr Gln Pro Pro Ser Val Ser Val Ser Pro Gly Gln
1               5                   10                  15

Thr Ala Ser Ile Thr Cys Ser Gly Gln Arg Leu Gly Asp Lys Tyr Ala
            20                  25                  30

Ser Trp Tyr Gln Gln Lys Pro Gly Gln Ser Pro Val Leu Val Ile Tyr
        35                  40                  45

Glu Asp Ser Lys Arg Pro Ser Gly Ile Pro Glu Arg Phe Ser Gly Ser
    50                  55                  60

Asn Ser Gly Asp Thr Ala Thr Leu Thr Ile Ser Gly Thr Gln Pro Met
65                  70                  75                  80

Asp Glu Ala Asp Tyr Tyr Cys Gln Ala Trp Asp Arg Asp Thr Gly Val
                85                  90                  95

Phe Gly Tyr Gly Thr Lys Val Thr Val Leu
            100                 105

<210> SEQ ID NO 245
<211> LENGTH: 11
<212> TYPE: PRT
<213> ORGANISM: Artificial Sequence
<220> FEATURE:
<223> OTHER INFORMATION: DLL4 antibody E9.18 CDR-L1

<400> SEQUENCE: 245

Ser Gly Gln Arg Leu Gly Asp Lys Tyr Ala Ser
1               5                   10

<210> SEQ ID NO 246
<211> LENGTH: 7
<212> TYPE: PRT
<213> ORGANISM: Artificial Sequence
<220> FEATURE:
<223> OTHER INFORMATION: DLL4 antibody E9.18 CDR-L2

<400> SEQUENCE: 246

Glu Asp Ser Lys Arg Pro Ser
1               5

<210> SEQ ID NO 247
<211> LENGTH: 9
<212> TYPE: PRT
<213> ORGANISM: Artificial Sequence
<220> FEATURE:
<223> OTHER INFORMATION: DLL4 antibody E9.18 CDR-L3

<400> SEQUENCE: 247

Gln Ala Trp Asp Arg Asp Thr Gly Val
1               5

<210> SEQ ID NO 248
<211> LENGTH: 106
<212> TYPE: PRT
```

```
<213> ORGANISM: Artificial Sequence
<220> FEATURE:
<223> OTHER INFORMATION: DLL4 antibody E9.19 VL region

<400> SEQUENCE: 248

Ser Tyr Glu Leu Thr Gln Pro Pro Ser Val Ser Val Ser Pro Gly Gln
1               5                   10                  15

Thr Ala Ser Ile Thr Cys Ser Gly Gln Arg Leu Gly Asp Lys Tyr Ala
            20                  25                  30

Ser Trp Tyr Gln Gln Lys Pro Gly Gln Ser Pro Val Leu Val Ile Tyr
        35                  40                  45

Glu Asp Ser Lys Arg Pro Ser Gly Ile Pro Glu Arg Phe Ser Gly Ser
50                  55                  60

Asn Ser Gly Asp Thr Ala Thr Leu Thr Ile Ser Gly Thr Gln Pro Met
65                  70                  75                  80

Asp Glu Ala Asp Tyr Tyr Cys Gln Ala Trp Asp Arg Asp Thr Gly Val
                85                  90                  95

Phe Gly Tyr Gly Thr Lys Val Thr Val Leu
            100                 105

<210> SEQ ID NO 249
<211> LENGTH: 11
<212> TYPE: PRT
<213> ORGANISM: Artificial Sequence
<220> FEATURE:
<223> OTHER INFORMATION: DLL4 antibody E9.19 CDR-L1

<400> SEQUENCE: 249

Ser Gly Gln Arg Leu Gly Asp Lys Tyr Ala Ser
1               5                   10

<210> SEQ ID NO 250
<211> LENGTH: 7
<212> TYPE: PRT
<213> ORGANISM: Artificial Sequence
<220> FEATURE:
<223> OTHER INFORMATION: DLL4 antibody E9.19 CDR-L2

<400> SEQUENCE: 250

Glu Asp Ser Lys Arg Pro Ser
1               5

<210> SEQ ID NO 251
<211> LENGTH: 9
<212> TYPE: PRT
<213> ORGANISM: Artificial Sequence
<220> FEATURE:
<223> OTHER INFORMATION: DLL4 antibody E9.19 CDR-L3

<400> SEQUENCE: 251

Gln Ala Trp Asp Arg Asp Thr Gly Val
1               5

<210> SEQ ID NO 252
<211> LENGTH: 106
<212> TYPE: PRT
<213> ORGANISM: Artificial Sequence
<220> FEATURE:
<223> OTHER INFORMATION: DLL4 antibody E9.22 VL region

<400> SEQUENCE: 252

Ser Tyr Glu Leu Thr Gln Pro Pro Ser Val Ser Val Ser Pro Gly Gln
1               5                   10                  15
```

```
Thr Ala Ser Ile Thr Cys Ser Gly Gln Arg Leu Gly Asp Lys Tyr Ala
            20                  25                  30

Ser Trp Tyr Gln Gln Lys Pro Gly Gln Ser Pro Val Leu Val Ile Tyr
        35                  40                  45

Glu Asp Ser Lys Arg Pro Ser Gly Ile Pro Glu Arg Phe Ser Gly Ser
 50                  55                  60

Asn Ser Gly Asp Thr Ala Thr Leu Thr Ile Ser Gly Thr Gln Pro Met
 65                  70                  75                  80

Asp Glu Ala Asp Tyr Tyr Cys Gln Ala Trp Asp Arg Asp Thr Gly Val
                85                  90                  95

Phe Gly Tyr Gly Thr Lys Val Thr Val Leu
            100                 105

<210> SEQ ID NO 253
<211> LENGTH: 11
<212> TYPE: PRT
<213> ORGANISM: Artificial Sequence
<220> FEATURE:
<223> OTHER INFORMATION: DLL4 antibody E9.22 CDR-L1

<400> SEQUENCE: 253

Ser Gly Gln Arg Leu Gly Asp Lys Tyr Ala Ser
 1               5                  10

<210> SEQ ID NO 254
<211> LENGTH: 7
<212> TYPE: PRT
<213> ORGANISM: Artificial Sequence
<220> FEATURE:
<223> OTHER INFORMATION: DLL4 antibody E9.22 CDR-L2

<400> SEQUENCE: 254

Glu Asp Ser Lys Arg Pro Ser
 1               5

<210> SEQ ID NO 255
<211> LENGTH: 9
<212> TYPE: PRT
<213> ORGANISM: Artificial Sequence
<220> FEATURE:
<223> OTHER INFORMATION: DLL4 antibody E9.22 CDR-L3

<400> SEQUENCE: 255

Gln Ala Trp Asp Arg Asp Thr Gly Val
 1               5

<210> SEQ ID NO 256
<211> LENGTH: 106
<212> TYPE: PRT
<213> ORGANISM: Artificial Sequence
<220> FEATURE:
<223> OTHER INFORMATION: DLL4 antibody E9.48 VL region

<400> SEQUENCE: 256

Ser Tyr Glu Leu Thr Gln Pro Pro Ser Val Ser Val Ser Pro Gly Gln
 1               5                  10                  15

Thr Ala Ser Ile Thr Cys Ser Gly Gln Arg Leu Gly Asp Lys Tyr Ala
            20                  25                  30

Ser Trp Tyr Gln Gln Lys Pro Gly Gln Ser Pro Val Leu Val Ile Tyr
        35                  40                  45

Glu Asp Ser Lys Arg Pro Ser Gly Ile Pro Glu Arg Phe Ser Gly Ser
 50                  55                  60
```

```
Asn Ser Gly Asp Thr Ala Thr Leu Thr Ile Ser Gly Thr Gln Pro Met
 65                  70                  75                  80

Asp Glu Ala Asp Tyr Tyr Cys Gln Ala Trp Asp Arg Asp Thr Gly Val
                 85                  90                  95

Phe Gly Tyr Gly Thr Lys Val Thr Val Leu
            100                 105

<210> SEQ ID NO 257
<211> LENGTH: 11
<212> TYPE: PRT
<213> ORGANISM: Artificial Sequence
<220> FEATURE:
<223> OTHER INFORMATION: DLL4 antibody E9.48 CDR-L1

<400> SEQUENCE: 257

Ser Gly Gln Arg Leu Gly Asp Lys Tyr Ala Ser
1               5                   10

<210> SEQ ID NO 258
<211> LENGTH: 7
<212> TYPE: PRT
<213> ORGANISM: Artificial Sequence
<220> FEATURE:
<223> OTHER INFORMATION: DLL4 antibody E9.48 CDR-L2

<400> SEQUENCE: 258

Glu Asp Ser Lys Arg Pro Ser
1               5

<210> SEQ ID NO 259
<211> LENGTH: 9
<212> TYPE: PRT
<213> ORGANISM: Artificial Sequence
<220> FEATURE:
<223> OTHER INFORMATION: DLL4 antibody E9.48 CDR-L3

<400> SEQUENCE: 259

Gln Ala Trp Asp Arg Asp Thr Gly Val
1               5

<210> SEQ ID NO 260
<211> LENGTH: 106
<212> TYPE: PRT
<213> ORGANISM: Artificial Sequence
<220> FEATURE:
<223> OTHER INFORMATION: DLL4 antibody E9.65 VL region

<400> SEQUENCE: 260

Ser Tyr Glu Leu Thr Gln Pro Pro Ser Val Ser Val Ser Pro Gly Gln
1               5                   10                  15

Thr Ala Ser Ile Thr Cys Ser Gly Gln Arg Leu Gly Asp Lys Tyr Ala
            20                  25                  30

Ser Trp Tyr Gln Gln Lys Pro Gly Gln Ser Pro Val Leu Val Ile Tyr
        35                  40                  45

Glu Asp Ser Lys Arg Pro Ser Gly Ile Pro Glu Arg Phe Ser Gly Ser
    50                  55                  60

Asn Ser Gly Asp Thr Ala Thr Leu Thr Ile Ser Gly Thr Gln Pro Met
 65                 70                  75                  80

Asp Glu Ala Asp Tyr Tyr Cys Gln Ala Trp Asp Arg Asp Thr Gly Val
                85                  90                  95

Phe Gly Tyr Gly Thr Lys Val Thr Val Leu
            100                 105
```

<210> SEQ ID NO 261
<211> LENGTH: 11
<212> TYPE: PRT
<213> ORGANISM: Artificial Sequence
<220> FEATURE:
<223> OTHER INFORMATION: DLL4 antibody E9.65 CDR-L1

<400> SEQUENCE: 261

Ser Gly Gln Arg Leu Gly Asp Lys Tyr Ala Ser
1               5                   10

<210> SEQ ID NO 262
<211> LENGTH: 7
<212> TYPE: PRT
<213> ORGANISM: Artificial Sequence
<220> FEATURE:
<223> OTHER INFORMATION: DLL4 antibody E9.65 CDR-L2

<400> SEQUENCE: 262

Glu Asp Ser Lys Arg Pro Ser
1               5

<210> SEQ ID NO 263
<211> LENGTH: 9
<212> TYPE: PRT
<213> ORGANISM: Artificial Sequence
<220> FEATURE:
<223> OTHER INFORMATION: DLL4 antibody E9.65 CDR-L3

<400> SEQUENCE: 263

Gln Ala Trp Asp Arg Asp Thr Gly Val
1               5

<210> SEQ ID NO 264
<211> LENGTH: 106
<212> TYPE: PRT
<213> ORGANISM: Artificial Sequence
<220> FEATURE:
<223> OTHER INFORMATION: DLL4 antibody E9.66 VL region

<400> SEQUENCE: 264

Ser Tyr Glu Leu Thr Gln Pro Pro Ser Val Ser Val Ser Pro Gly Gln
1               5                   10                  15

Thr Ala Ser Ile Thr Cys Ser Gly Gln Arg Leu Gly Asp Lys Tyr Ala
            20                  25                  30

Ser Trp Tyr Gln Gln Lys Pro Gly Gln Ser Pro Val Leu Val Ile Tyr
        35                  40                  45

Glu Asp Ser Lys Arg Pro Ser Gly Ile Pro Glu Arg Phe Ser Gly Ser
    50                  55                  60

Asn Ser Gly Asp Thr Ala Thr Leu Thr Ile Ser Gly Thr Gln Pro Met
65                  70                  75                  80

Asp Glu Ala Asp Tyr Tyr Cys Gln Ala Trp Asp Arg Asp Thr Gly Val
                85                  90                  95

Phe Gly Tyr Gly Thr Lys Val Thr Val Leu
            100                 105

<210> SEQ ID NO 265
<211> LENGTH: 11
<212> TYPE: PRT
<213> ORGANISM: Artificial Sequence
<220> FEATURE:
<223> OTHER INFORMATION: DLL4 antibody E9.66 CDR-L1

<400> SEQUENCE: 265

Ser Gly Gln Arg Leu Gly Asp Lys Tyr Ala Ser
1               5                   10

<210> SEQ ID NO 266
<211> LENGTH: 7
<212> TYPE: PRT
<213> ORGANISM: Artificial Sequence
<220> FEATURE:
<223> OTHER INFORMATION: DLL4 antibody E9.66 CDR-L2

<400> SEQUENCE: 266

Glu Asp Ser Lys Arg Pro Ser
1               5

<210> SEQ ID NO 267
<211> LENGTH: 9
<212> TYPE: PRT
<213> ORGANISM: Artificial Sequence
<220> FEATURE:
<223> OTHER INFORMATION: DLL4 antibody E9.66 CDR-L3

<400> SEQUENCE: 267

Gln Ala Trp Asp Arg Asp Thr Gly Val
1               5

<210> SEQ ID NO 268
<211> LENGTH: 106
<212> TYPE: PRT
<213> ORGANISM: Artificial Sequence
<220> FEATURE:
<223> OTHER INFORMATION: DLL4 antibody E9.71 VL region

<400> SEQUENCE: 268

Ser Tyr Glu Leu Thr Gln Pro Pro Ser Val Ser Val Ser Pro Gly Gln
1               5                   10                  15

Thr Ala Ser Ile Thr Cys Ser Gly Gln Arg Leu Gly Asp Lys Tyr Ala
                20                  25                  30

Ser Trp Tyr Gln Gln Lys Pro Gly Gln Ser Pro Val Leu Val Ile Tyr
            35                  40                  45

Glu Asp Ser Lys Arg Pro Ser Gly Ile Pro Glu Arg Phe Ser Gly Ser
        50                  55                  60

Asn Ser Gly Asp Thr Ala Thr Leu Thr Ile Ser Gly Thr Gln Pro Met
65                  70                  75                  80

Asp Glu Ala Asp Tyr Tyr Cys Gln Ala Trp Asp Arg Asp Thr Gly Val
                85                  90                  95

Phe Gly Tyr Gly Thr Lys Val Thr Val Leu
            100                 105

<210> SEQ ID NO 269
<211> LENGTH: 11
<212> TYPE: PRT
<213> ORGANISM: Artificial Sequence
<220> FEATURE:
<223> OTHER INFORMATION: DLL4 antibody E9.71 CDR-L1

<400> SEQUENCE: 269

Ser Gly Gln Arg Leu Gly Asp Lys Tyr Ala Ser
1               5                   10

<210> SEQ ID NO 270
<211> LENGTH: 7
<212> TYPE: PRT
<213> ORGANISM: Artificial Sequence
<220> FEATURE:
<223> OTHER INFORMATION: DLL4 antibody E9.71 CDR-L2

<400> SEQUENCE: 270

Glu Asp Ser Lys Arg Pro Ser
1               5

<210> SEQ ID NO 271
<211> LENGTH: 9
<212> TYPE: PRT
<213> ORGANISM: Artificial Sequence
<220> FEATURE:
<223> OTHER INFORMATION: DLL4 antibody E9.71 CDR-L3

<400> SEQUENCE: 271

Gln Ala Trp Asp Arg Asp Thr Gly Val
1               5

<210> SEQ ID NO 272
<211> LENGTH: 106
<212> TYPE: PRT
<213> ORGANISM: Artificial Sequence
<220> FEATURE:
<223> OTHER INFORMATION: DLL4 antibody E9.2B VL region

<400> SEQUENCE: 272

Ser Tyr Glu Leu Thr Gln Pro Pro Ser Val Ser Val Ser Pro Gly Gln
1               5                   10                  15

Thr Ala Ser Ile Thr Cys Ser Gly Glu Gly Leu Gly Asp Lys Tyr Val
            20                  25                  30

Ser Trp Tyr Gln Gln Lys Pro Gly Gln Ser Pro Val Leu Val Ile Tyr
        35                  40                  45

Glu Asp Ser Thr Arg Pro Ser Gly Ile Pro Glu Arg Phe Ser Gly Ser
    50                  55                  60

Asn Ser Gly Asp Thr Ala Thr Leu Thr Ile Ser Gly Thr Gln Pro Met
65                  70                  75                  80

Asp Glu Ala Asp Tyr Tyr Cys Gln Ala Trp Asp Ser Glu Thr Gly Val
                85                  90                  95

Phe Gly Ser Gly Thr Lys Val Thr Val Leu
            100                 105

<210> SEQ ID NO 273
<211> LENGTH: 11
<212> TYPE: PRT
<213> ORGANISM: Artificial Sequence
<220> FEATURE:
<223> OTHER INFORMATION: DLL4 antibody E9.2B CDR-L1

<400> SEQUENCE: 273

Ser Gly Glu Gly Leu Gly Asp Lys Tyr Val Ser
1               5                   10

<210> SEQ ID NO 274
<211> LENGTH: 7
<212> TYPE: PRT
<213> ORGANISM: Artificial Sequence
<220> FEATURE:
<223> OTHER INFORMATION: DLL4 antibody E9.2B CDR-L2

<400> SEQUENCE: 274

Glu Asp Ser Thr Arg Pro Ser
1               5

```
<210> SEQ ID NO 275
<211> LENGTH: 9
<212> TYPE: PRT
<213> ORGANISM: Artificial Sequence
<220> FEATURE:
<223> OTHER INFORMATION: DLL4 antibody E9.2B CDR-L3

<400> SEQUENCE: 275

Gln Ala Trp Asp Ser Glu Thr Gly Val
1               5

<210> SEQ ID NO 276
<211> LENGTH: 106
<212> TYPE: PRT
<213> ORGANISM: Artificial Sequence
<220> FEATURE:
<223> OTHER INFORMATION: DLL4 antibody E9.1F VL region

<400> SEQUENCE: 276

Ser Tyr Glu Leu Thr Gln Pro Pro Ser Val Ser Val Ser Pro Gly Gln
1               5                   10                  15

Thr Ala Ser Ile Thr Cys Ser Gly Asp Arg Leu Gly Asp Lys Tyr Val
            20                  25                  30

Ser Trp Tyr Gln Gln Lys Pro Gly Gln Ser Pro Val Leu Val Ile Tyr
        35                  40                  45

Glu Asp Ser Gln Arg Pro Ser Gly Ile Pro Glu Arg Phe Ser Gly Ser
    50                  55                  60

Asn Ser Gly Asp Thr Ala Thr Leu Thr Ile Ser Gly Thr Gln Ala Met
65                  70                  75                  80

Asp Glu Ala Asp Tyr Tyr Cys Gln Ala Trp Asp Met Glu Ala Gly Val
                85                  90                  95

Phe Gly Ser Gly Thr Lys Val Thr Val Leu
            100                 105

<210> SEQ ID NO 277
<211> LENGTH: 11
<212> TYPE: PRT
<213> ORGANISM: Artificial Sequence
<220> FEATURE:
<223> OTHER INFORMATION: DLL4 antibody E9.1F CDR-L1

<400> SEQUENCE: 277

Ser Gly Asp Arg Leu Gly Asp Lys Tyr Val Ser
1               5                   10

<210> SEQ ID NO 278
<211> LENGTH: 7
<212> TYPE: PRT
<213> ORGANISM: Artificial Sequence
<220> FEATURE:
<223> OTHER INFORMATION: DLL4 antibody E9.1F CDR-L2

<400> SEQUENCE: 278

Glu Asp Ser Gln Arg Pro Ser
1               5

<210> SEQ ID NO 279
<211> LENGTH: 9
<212> TYPE: PRT
<213> ORGANISM: Artificial Sequence
<220> FEATURE:
<223> OTHER INFORMATION: DLL4 antibody E9.1F CDR-L3

<400> SEQUENCE: 279
```

```
Gln Ala Trp Asp Met Glu Ala Gly Val
1               5
```

<210> SEQ ID NO 280
<211> LENGTH: 104
<212> TYPE: PRT
<213> ORGANISM: Artificial Sequence
<220> FEATURE:
<223> OTHER INFORMATION: DLL4 antibody E9.10C VL region

<400> SEQUENCE: 280

```
Ser Tyr Glu Leu Thr Gln Pro Pro Ser Val Ser Val Ser Pro Gly Gln
1               5                   10                  15

Thr Ala Ser Ile Thr Cys Ser Gly Asp Ser Leu Gly Asp Lys Tyr Val
            20                  25                  30

Ser Trp Tyr Gln Gln Lys Pro Gly Gln Ser Pro Val Leu Val Ile Tyr
        35                  40                  45

Glu Asp Ser Glu Arg Pro Ser Gly Ile Pro Glu Arg Phe Ser Gly Ser
    50                  55                  60

Asn Ser Gly Asp Thr Ala Thr Leu Thr Ile Ser Gly Thr Gln Ala Met
65                  70                  75                  80

Asp Glu Ala Asp Tyr Tyr Cys Gln Ala Trp Asp Ser Glu Thr Gly Val
                85                  90                  95

Phe Gly Ser Gly Thr Lys Val Thr
            100
```

<210> SEQ ID NO 281
<211> LENGTH: 11
<212> TYPE: PRT
<213> ORGANISM: Artificial Sequence
<220> FEATURE:
<223> OTHER INFORMATION: DLL4 antibody E9.10C CDR-L1

<400> SEQUENCE: 281

```
Ser Gly Asp Ser Leu Gly Asp Lys Tyr Val Ser
1               5                   10
```

<210> SEQ ID NO 282
<211> LENGTH: 7
<212> TYPE: PRT
<213> ORGANISM: Artificial Sequence
<220> FEATURE:
<223> OTHER INFORMATION: DLL4 antibody E9.10C CDR-L2

<400> SEQUENCE: 282

```
Glu Asp Ser Glu Arg Pro Ser
1               5
```

<210> SEQ ID NO 283
<211> LENGTH: 9
<212> TYPE: PRT
<213> ORGANISM: Artificial Sequence
<220> FEATURE:
<223> OTHER INFORMATION: DLL4 antibody E9.10C CDR-L3

<400> SEQUENCE: 283

```
Gln Ala Trp Asp Ser Glu Thr Gly Val
1               5
```

<210> SEQ ID NO 284
<211> LENGTH: 104
<212> TYPE: PRT
<213> ORGANISM: Artificial Sequence
<220> FEATURE:

<223> OTHER INFORMATION: DLL4 antibody E9.10E VL region

<400> SEQUENCE: 284

Ser Tyr Glu Leu Thr Gln Pro Pro Ser Val Ser Val Ser Pro Gly Gln
1               5                   10                  15

Thr Ala Ser Ile Thr Cys Ser Gly Glu Gly Leu Gly Asp Lys Tyr Val
            20                  25                  30

Ser Trp Tyr Gln Gln Lys Pro Gly Gln Ser Pro Val Leu Val Ile Tyr
        35                  40                  45

Glu Asp Ser Glu Arg Pro Ser Gly Ile Pro Glu Arg Phe Ser Gly Ser
    50                  55                  60

Asn Ser Gly Asp Thr Ala Thr Leu Thr Ile Ser Gly Thr Gln Ala Met
65                  70                  75                  80

Asp Glu Ala Asp Tyr Tyr Cys Gln Ala Trp Asp Ser Glu Ala Gly Val
                85                  90                  95

Phe Gly Ser Gly Thr Lys Val Thr
                100

<210> SEQ ID NO 285
<211> LENGTH: 11
<212> TYPE: PRT
<213> ORGANISM: Artificial Sequence
<220> FEATURE:
<223> OTHER INFORMATION: DLL4 antibody E9.10E CDR-L1

<400> SEQUENCE: 285

Ser Gly Glu Gly Leu Gly Asp Lys Tyr Val Ser
1               5                   10

<210> SEQ ID NO 286
<211> LENGTH: 7
<212> TYPE: PRT
<213> ORGANISM: Artificial Sequence
<220> FEATURE:
<223> OTHER INFORMATION: DLL4 antibody E9.10E CDR-L2

<400> SEQUENCE: 286

Glu Asp Ser Glu Arg Pro Ser
1               5

<210> SEQ ID NO 287
<211> LENGTH: 9
<212> TYPE: PRT
<213> ORGANISM: Artificial Sequence
<220> FEATURE:
<223> OTHER INFORMATION: DLL4 antibody E9.10E CDR-L3

<400> SEQUENCE: 287

Gln Ala Trp Asp Ser Glu Ala Gly Val
1               5

<210> SEQ ID NO 288
<211> LENGTH: 104
<212> TYPE: PRT
<213> ORGANISM: Artificial Sequence
<220> FEATURE:
<223> OTHER INFORMATION: DLL4 antibody E9.7E VL region

<400> SEQUENCE: 288

Ser Tyr Glu Leu Thr Gln Pro Pro Ser Val Ser Val Ser Pro Gly Gln
1               5                   10                  15

Thr Ala Ser Ile Thr Cys Ser Gly Asp Arg Leu Gly Asp Lys Tyr Val
            20                  25                  30

-continued

Ser Trp Tyr Gln Gln Lys Pro Gly Gln Ser Pro Val Leu Val Ile Tyr
        35                  40                  45

Glu Asp Ser Glu Arg Pro Ser Gly Ile Pro Glu Arg Phe Ser Gly Ser
    50                  55                  60

Asn Ser Gly Asp Thr Ala Thr Leu Thr Ile Ser Gly Thr Gln Ala Met
65                  70                  75                  80

Asp Glu Ala Asp Tyr Tyr Cys Gln Ala Trp Asp Ser Glu Ala Gly Val
                85                  90                  95

Phe Gly Ser Gly Thr Lys Val Thr
            100

<210> SEQ ID NO 289
<211> LENGTH: 11
<212> TYPE: PRT
<213> ORGANISM: Artificial Sequence
<220> FEATURE:
<223> OTHER INFORMATION: DLL4 antibody E9.7E CDR-L1

<400> SEQUENCE: 289

Ser Gly Asp Arg Leu Gly Asp Lys Tyr Val Ser
1               5                   10

<210> SEQ ID NO 290
<211> LENGTH: 7
<212> TYPE: PRT
<213> ORGANISM: Artificial Sequence
<220> FEATURE:
<223> OTHER INFORMATION: DLL4 antibody E9.7E CDR-L2

<400> SEQUENCE: 290

Glu Asp Ser Glu Arg Pro Ser
1               5

<210> SEQ ID NO 291
<211> LENGTH: 9
<212> TYPE: PRT
<213> ORGANISM: Artificial Sequence
<220> FEATURE:
<223> OTHER INFORMATION: DLL4 antibody E9.7E CDR-L3

<400> SEQUENCE: 291

Gln Ala Trp Asp Ser Glu Ala Gly Val
1               5

<210> SEQ ID NO 292
<211> LENGTH: 104
<212> TYPE: PRT
<213> ORGANISM: Artificial Sequence
<220> FEATURE:
<223> OTHER INFORMATION: DLL4 antibody E9.5E VL region

<400> SEQUENCE: 292

Ser Tyr Glu Leu Thr Gln Pro Pro Ser Val Ser Val Ser Pro Gly Gln
1               5                   10                  15

Thr Ala Ser Ile Thr Cys Ser Gly Asp Met Leu Gly Asp Lys Tyr Val
            20                  25                  30

Ser Trp Tyr Gln Gln Lys Pro Gly Gln Ser Pro Val Leu Val Ile Tyr
        35                  40                  45

Glu Asp Ser Gln Arg Pro Ser Gly Ile Pro Glu Arg Phe Ser Gly Ser
    50                  55                  60

Asn Ser Gly Asp Thr Ala Thr Leu Thr Ile Ser Gly Thr Gln Pro Met
65                  70                  75                  80

```
Asp Glu Ala Asp Tyr Tyr Cys Gln Ala Trp Asp Ser Glu Thr Gly Val
                85                  90                  95
Phe Gly Ser Gly Thr Lys Val Thr
            100
```

<210> SEQ ID NO 293
<211> LENGTH: 11
<212> TYPE: PRT
<213> ORGANISM: Artificial Sequence
<220> FEATURE:
<223> OTHER INFORMATION: DLL4 antibody E9.5E CDR-L1

<400> SEQUENCE: 293

```
Ser Gly Asp Met Leu Gly Asp Lys Tyr Val Ser
1               5                   10
```

<210> SEQ ID NO 294
<211> LENGTH: 7
<212> TYPE: PRT
<213> ORGANISM: Artificial Sequence
<220> FEATURE:
<223> OTHER INFORMATION: DLL4 antibody E9.5E CDR-L2

<400> SEQUENCE: 294

```
Glu Asp Ser Gln Arg Pro Ser
1               5
```

<210> SEQ ID NO 295
<211> LENGTH: 9
<212> TYPE: PRT
<213> ORGANISM: Artificial Sequence
<220> FEATURE:
<223> OTHER INFORMATION: DLL4 antibody E9.5E CDR-L3

<400> SEQUENCE: 295

```
Gln Ala Trp Asp Ser Glu Thr Gly Val
1               5
```

<210> SEQ ID NO 296
<211> LENGTH: 104
<212> TYPE: PRT
<213> ORGANISM: Artificial Sequence
<220> FEATURE:
<223> OTHER INFORMATION: DLL4 antibody E9.12B VL region

<400> SEQUENCE: 296

```
Ser Tyr Glu Leu Thr Gln Pro Pro Ser Val Ser Val Ser Pro Gly Gln
1               5                   10                  15
Thr Ala Ser Ile Thr Cys Ser Gly Asp Gly Leu Gly Asp Lys Tyr Val
                20                  25                  30
Ser Trp Tyr Gln Gln Lys Pro Gly Gln Ser Pro Val Leu Val Ile Tyr
            35                  40                  45
Glu Asp Ser Thr Arg Pro Ser Gly Ile Pro Glu Arg Phe Ser Gly Ser
        50                  55                  60
Asn Ser Gly Asp Thr Ala Thr Leu Thr Ile Ser Gly Thr Gln Pro Met
65                  70                  75                  80
Asp Glu Ala Asp Tyr Tyr Cys Gln Ala Trp Asp Ser Glu Ser Gly Val
                85                  90                  95
Phe Gly Ser Gly Thr Lys Val Thr
            100
```

<210> SEQ ID NO 297

```
<211> LENGTH: 11
<212> TYPE: PRT
<213> ORGANISM: Artificial Sequence
<220> FEATURE:
<223> OTHER INFORMATION: DLL4 antibody E9.12B CDR-L1

<400> SEQUENCE: 297

Ser Gly Asp Gly Leu Gly Asp Lys Tyr Val Ser
1               5                   10

<210> SEQ ID NO 298
<211> LENGTH: 7
<212> TYPE: PRT
<213> ORGANISM: Artificial Sequence
<220> FEATURE:
<223> OTHER INFORMATION: DLL4 antibody E9.12B CDR-L2

<400> SEQUENCE: 298

Glu Asp Ser Thr Arg Pro Ser
1               5

<210> SEQ ID NO 299
<211> LENGTH: 9
<212> TYPE: PRT
<213> ORGANISM: Artificial Sequence
<220> FEATURE:
<223> OTHER INFORMATION: DLL4 antibody E9.12B CDR-L3

<400> SEQUENCE: 299

Gln Ala Trp Asp Ser Glu Ser Gly Val
1               5

<210> SEQ ID NO 300
<211> LENGTH: 104
<212> TYPE: PRT
<213> ORGANISM: Artificial Sequence
<220> FEATURE:
<223> OTHER INFORMATION: DLL4 antibody E9.10H VL region

<400> SEQUENCE: 300

Ser Tyr Glu Leu Thr Gln Pro Pro Ser Val Ser Val Ser Pro Gly Gln
1               5                   10                  15

Thr Ala Ser Ile Thr Cys Ser Gly Glu Ser Leu Gly Asp Lys Tyr Val
            20                  25                  30

Ser Trp Tyr Gln Gln Lys Pro Gly Gln Ser Pro Val Leu Val Ile Tyr
        35                  40                  45

Glu Asp Ser Lys Arg Pro Ser Gly Ile Pro Glu Arg Phe Ser Gly Ser
    50                  55                  60

Asn Ser Gly Asp Thr Ala Thr Leu Thr Ile Ser Gly Thr Gln Ala Met
65                  70                  75                  80

Asp Glu Ala Asp Tyr Tyr Cys Gln Ala Trp Asp Gly Thr Gly Val
                85                  90                  95

Phe Gly Ser Gly Thr Lys Val Thr
            100

<210> SEQ ID NO 301
<211> LENGTH: 11
<212> TYPE: PRT
<213> ORGANISM: Artificial Sequence
<220> FEATURE:
<223> OTHER INFORMATION: DLL4 antibody E9.10H CDR-L1

<400> SEQUENCE: 301

Ser Gly Glu Ser Leu Gly Asp Lys Tyr Val Ser
```

<210> SEQ ID NO 302
<211> LENGTH: 7
<212> TYPE: PRT
<213> ORGANISM: Artificial Sequence
<220> FEATURE:
<223> OTHER INFORMATION: DLL4 antibody E9.10H CDR-L2

<400> SEQUENCE: 302

Glu Asp Ser Lys Arg Pro Ser
1               5

<210> SEQ ID NO 303
<211> LENGTH: 9
<212> TYPE: PRT
<213> ORGANISM: Artificial Sequence
<220> FEATURE:
<223> OTHER INFORMATION: DLL4 antibody E9.10H CDR-L3

<400> SEQUENCE: 303

Gln Ala Trp Asp Gly Glu Thr Gly Val
1               5

<210> SEQ ID NO 304
<211> LENGTH: 104
<212> TYPE: PRT
<213> ORGANISM: Artificial Sequence
<220> FEATURE:
<223> OTHER INFORMATION: DLL4 antibody E9.6A VL region

<400> SEQUENCE: 304

Ser Tyr Glu Leu Thr Gln Pro Pro Ser Val Ser Val Ser Pro Gly Gln
1               5                   10                  15

Thr Ala Ser Ile Thr Cys Ser Gly Asp Met Leu Gly Asp Lys Tyr Val
            20                  25                  30

Ser Trp Tyr Gln Gln Lys Pro Gly Gln Ser Pro Val Leu Val Ile Tyr
        35                  40                  45

Glu Asp Thr Asn Arg Pro Ser Gly Ile Pro Glu Arg Phe Ser Gly Ser
    50                  55                  60

Asn Ser Gly Asp Thr Ala Thr Leu Thr Ile Ser Gly Thr Gln Ala Met
65                  70                  75                  80

Asp Glu Ala Asp Tyr Tyr Cys Gln Ala Trp Asp Ser Glu Thr Gly Val
                85                  90                  95

Phe Gly Ser Gly Thr Lys Val Thr
            100

<210> SEQ ID NO 305
<211> LENGTH: 11
<212> TYPE: PRT
<213> ORGANISM: Artificial Sequence
<220> FEATURE:
<223> OTHER INFORMATION: DLL4 antibody E9.6A CDR-L1

<400> SEQUENCE: 305

Ser Gly Asp Met Leu Gly Asp Lys Tyr Val Ser
1               5                   10

<210> SEQ ID NO 306
<211> LENGTH: 7
<212> TYPE: PRT
<213> ORGANISM: Artificial Sequence
<220> FEATURE:
<223> OTHER INFORMATION: DLL4 antibody E9.6A CDR-L2

<400> SEQUENCE: 306

Glu Asp Thr Asn Arg Pro Ser
1               5

<210> SEQ ID NO 307
<211> LENGTH: 9
<212> TYPE: PRT
<213> ORGANISM: Artificial Sequence
<220> FEATURE:
<223> OTHER INFORMATION: DLL4 antibody E9.6A CDR-L3

<400> SEQUENCE: 307

Gln Ala Trp Asp Ser Glu Thr Gly Val
1               5

<210> SEQ ID NO 308
<211> LENGTH: 104
<212> TYPE: PRT
<213> ORGANISM: Artificial Sequence
<220> FEATURE:
<223> OTHER INFORMATION: DLL4 antibody E9.7A VL region

<400> SEQUENCE: 308

Ser Tyr Glu Leu Thr Gln Pro Pro Ser Val Ser Val Ser Pro Gly Gln
1               5                   10                  15

Thr Ala Ser Ile Thr Cys Ser Gly Glu Ser Leu Gly Asp Lys Tyr Val
            20                  25                  30

Ser Trp Tyr Gln Gln Lys Pro Gly Gln Ser Pro Val Leu Val Ile Tyr
        35                  40                  45

Gln Asp Ala Met Arg Pro Ser Gly Ile Pro Glu Arg Phe Ser Gly Ser
    50                  55                  60

Asn Ser Gly Asp Thr Ala Thr Leu Thr Ile Ser Gly Thr Gln Ala Met
65                  70                  75                  80

Asp Glu Ala Asp Tyr Tyr Cys Gln Ala Trp Asp Met Glu Thr Gly Val
                85                  90                  95

Phe Gly Ser Gly Thr Lys Val Thr
            100

<210> SEQ ID NO 309
<211> LENGTH: 11
<212> TYPE: PRT
<213> ORGANISM: Artificial Sequence
<220> FEATURE:
<223> OTHER INFORMATION: DLL4 antibody E9.7A CDR-L1

<400> SEQUENCE: 309

Ser Gly Glu Ser Leu Gly Asp Lys Tyr Val Ser
1               5                   10

<210> SEQ ID NO 310
<211> LENGTH: 7
<212> TYPE: PRT
<213> ORGANISM: Artificial Sequence
<220> FEATURE:
<223> OTHER INFORMATION: DLL4 antibody E9.7A CDR-L2

<400> SEQUENCE: 310

Gln Asp Ala Met Arg Pro Ser
1               5

<210> SEQ ID NO 311
<211> LENGTH: 9

```
<212> TYPE: PRT
<213> ORGANISM: Artificial Sequence
<220> FEATURE:
<223> OTHER INFORMATION: DLL4 antibody E9.7A CDR-L3

<400> SEQUENCE: 311

Gln Ala Trp Asp Met Glu Thr Gly Val
1               5

<210> SEQ ID NO 312
<211> LENGTH: 104
<212> TYPE: PRT
<213> ORGANISM: Artificial Sequence
<220> FEATURE:
<223> OTHER INFORMATION: DLL4 antibody E9.8H VL region

<400> SEQUENCE: 312

Ser Tyr Glu Leu Thr Gln Pro Pro Ser Val Ser Val Ser Pro Gly Gln
1               5                   10                  15

Thr Ala Ser Ile Thr Cys Ser Gly Glu Ser Leu Gly Asp Lys Tyr Val
            20                  25                  30

Ser Trp Tyr Gln Gln Lys Pro Gly Gln Ser Pro Val Leu Val Ile Tyr
        35                  40                  45

Glu Asp Ser Met Arg Pro Ser Gly Ile Pro Glu Arg Phe Ser Gly Ser
    50                  55                  60

Asn Ser Gly Asp Thr Ala Thr Leu Thr Ile Ser Gly Thr Gln Pro Met
65                  70                  75                  80

Asp Glu Ala Asp Tyr Tyr Cys Gln Ala Trp Asp Ser Glu Val Gly Val
                85                  90                  95

Phe Gly Ser Gly Thr Lys Val Thr
            100

<210> SEQ ID NO 313
<211> LENGTH: 11
<212> TYPE: PRT
<213> ORGANISM: Artificial Sequence
<220> FEATURE:
<223> OTHER INFORMATION: DLL4 antibody E9.8H CDR-L1

<400> SEQUENCE: 313

Ser Gly Glu Ser Leu Gly Asp Lys Tyr Val Ser
1               5                   10

<210> SEQ ID NO 314
<211> LENGTH: 7
<212> TYPE: PRT
<213> ORGANISM: Artificial Sequence
<220> FEATURE:
<223> OTHER INFORMATION: DLL4 antibody E9.8H CDR-L2

<400> SEQUENCE: 314

Glu Asp Ser Met Arg Pro Ser
1               5

<210> SEQ ID NO 315
<211> LENGTH: 9
<212> TYPE: PRT
<213> ORGANISM: Artificial Sequence
<220> FEATURE:
<223> OTHER INFORMATION: DLL4 antibody E9.8H CDR-L3

<400> SEQUENCE: 315

Gln Ala Trp Asp Ser Glu Val Gly Val
1               5
```

<210> SEQ ID NO 316
<211> LENGTH: 119
<212> TYPE: PRT
<213> ORGANISM: Artificial Sequence
<220> FEATURE:
<223> OTHER INFORMATION: DLL4 antibody A10.3 VH region

<400> SEQUENCE: 316

Glu Val Gln Leu Val Glu Ser Gly Gly Gly Leu Val Lys Ser Gly Gly
1               5                   10                  15

Ser Leu Arg Leu Ser Cys Ala Ala Ser Gly Phe Thr Phe Arg Ser His
            20                  25                  30

Trp Met Ser Trp Val Arg Gln Ala Pro Gly Lys Gly Leu Glu Trp Val
        35                  40                  45

Ala Ile Ile Ser Tyr Asp Gly Ser Asn Lys Tyr Ser Ala Asp Ser Val
    50                  55                  60

Lys Gly Arg Phe Thr Ile Ser Arg Asp Asn Ser Lys Asn Thr Leu Tyr
65                  70                  75                  80

Leu Gln Leu Asn Ser Leu Arg Ala Glu Asp Thr Ala Val Tyr Tyr Cys
                85                  90                  95

Ala Lys Ala Gly Gly Asn Val Gly Phe Asp Ile Trp Gly Gln Gly
            100                 105                 110

Thr Met Val Thr Val Ser Ser
        115

<210> SEQ ID NO 317
<211> LENGTH: 119
<212> TYPE: PRT
<213> ORGANISM: Artificial Sequence
<220> FEATURE:
<223> OTHER INFORMATION: DLL4 antibody A10.K30 VH region

<400> SEQUENCE: 317

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Gly Asn His
            20                  25                  30

Trp Met Ser Trp Val Arg Gln Ala Pro Gly Lys Gly Leu Glu Trp Val
        35                  40                  45

Ala Asp Ile Ser Ser Asp Gly Arg Tyr Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Leu Asn Ser Leu Arg Ala Glu Asp Thr Ala Val Tyr Tyr Cys
                85                  90                  95

Ala Lys Ala Gly Gly Asn Val Gly Phe Asp Ile Trp Gly Gln Gly
            100                 105                 110

Thr Met Val Thr Val Ser Ser
        115

<210> SEQ ID NO 318
<211> LENGTH: 119
<212> TYPE: PRT
<213> ORGANISM: Artificial Sequence
<220> FEATURE:
<223> OTHER INFORMATION: DLL4 antibody A10.K42 VH region

<400> SEQUENCE: 318

-continued

Glu Val Gln Leu Val Glu Ser Gly Gly Gly Leu Val Gln Pro Gly
1               5                   10                  15

Ser Leu Arg Leu Ser Cys Ala Ala Ser Gly Phe Thr Phe Gln Ser His
            20                  25                  30

Trp Met Ser Trp Val Arg Gln Ala Pro Gly Lys Gly Leu Glu Trp Val
            35                  40                  45

Ala Met Ile Ser Tyr Asp Gly Thr Ile Lys Tyr Tyr Ala Asp Ser Val
50                  55                  60

Lys Gly Arg Phe Thr Ile Ser Arg Asp Asn Lys Asn Thr Leu Tyr
65                  70                  75                  80

Leu Gln Leu Asn Ser Leu Arg Ala Glu Asp Thr Ala Val Tyr Tyr Cys
            85                  90                  95

Ala Lys Ala Gly Gly Gly Asn Val Gly Phe Asp Ile Trp Gly Gln Gly
            100                 105                 110

Thr Met Val Thr Val Ser Ser
        115

<210> SEQ ID NO 319
<211> LENGTH: 119
<212> TYPE: PRT
<213> ORGANISM: Artificial Sequence
<220> FEATURE:
<223> OTHER INFORMATION: DLL4 antibody A10.9A VH region

<400> SEQUENCE: 319

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Arg Ser Tyr
            20                  25                  30

Trp Met Ser Trp Val Arg Gln Ala Pro Gly Lys Gly Leu Glu Trp Val
            35                  40                  45

Ala Thr Ile Ser Tyr Asp Gly Arg Asn Lys Asp Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Leu Asn Ser Leu Arg Ala Glu Asp Thr Ala Val Tyr Tyr Cys
            85                  90                  95

Ala Lys Ala Gly Gly Gly Asn Val Gly Phe Asp Ile Trp Gly Gln Gly
            100                 105                 110

Thr Met Val Thr Val Ser Ser
        115

<210> SEQ ID NO 320
<211> LENGTH: 119
<212> TYPE: PRT
<213> ORGANISM: Artificial Sequence
<220> FEATURE:
<223> OTHER INFORMATION: DLL4 antibody A10.8A VH region

<400> SEQUENCE: 320

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Gly Asn His
            20                  25                  30

Trp Met Ser Trp Val Arg Gln Ala Pro Gly Lys Gly Leu Glu Trp Val
            35                  40                  45

Ala Asp Ile Ser Ser Asp Gly Arg Tyr Lys Tyr Tyr Ala Asp Ser Val
50                  55                  60

```
Lys Gly Arg Phe Thr Ile Ser Arg Asp Asn Ser Lys Asn Thr Leu Tyr
 65                  70                  75                  80

Leu Gln Leu Asn Ser Leu Arg Ala Glu Asp Thr Ala Val Tyr Tyr Cys
                 85                  90                  95

Ala Lys Ala Gly Gly Asn Val Gly Phe Asp Ile Trp Gly Gln Gly
            100                 105                 110

Thr Met Val Thr Val Ser Ser
        115

<210> SEQ ID NO 321
<211> LENGTH: 119
<212> TYPE: PRT
<213> ORGANISM: Artificial Sequence
<220> FEATURE:
<223> OTHER INFORMATION: DLL4 antibody A10.1A VH region

<400> SEQUENCE: 321

Glu Val Gln Leu Val Glu Ser Gly Gly Val Val Gln Pro Gly Gly
 1               5                  10                  15

Ser Leu Arg Leu Ser Cys Ala Ala Ser Gly Phe Thr Phe His Ser His
                 20                  25                  30

Trp Met Ser Trp Val Arg Gln Ala Pro Gly Lys Gly Leu Glu Trp Val
             35                  40                  45

Ala Met Ile Ser Asp Asp Gly Arg Asn Lys Asp Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Leu Asn Ser Leu Arg Ala Glu Asp Thr Ala Val Tyr Tyr Cys
                 85                  90                  95

Ala Arg Ala Ala Gly Gly Asn Val Gly Leu Asp Ile Trp Gly Gln Gly
            100                 105                 110

Thr Met Val Thr Val Ser Ser
        115

<210> SEQ ID NO 322
<211> LENGTH: 119
<212> TYPE: PRT
<213> ORGANISM: Artificial Sequence
<220> FEATURE:
<223> OTHER INFORMATION: DLL4 antibody A10.5D VH region

<400> SEQUENCE: 322

Glu Val Gln Leu Val Glu Ser Gly Gly Val Val Gln Ser Gly Gly
 1               5                  10                  15

Ser Leu Arg Leu Ser Cys Ala Ala Ser Gly Phe Thr Phe Gly Ser His
                 20                  25                  30

Trp Met Ser Trp Val Arg Gln Ala Pro Gly Lys Gly Leu Glu Trp Val
             35                  40                  45

Ala Asp Ile Ser Val Asp Gly Ser Asn Lys Tyr Ser Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Ala Ala Gly Gly Asn Val Gly Leu Asp Ser Trp Gly Gln Gly
            100                 105                 110

Thr Met Val Thr Val Ser Ser
```

<210> SEQ ID NO 323
<211> LENGTH: 119
<212> TYPE: PRT
<213> ORGANISM: Artificial Sequence
<220> FEATURE:
<223> OTHER INFORMATION: DLL4 antibody A10.3A VH region

<400> SEQUENCE: 323

```
Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Gly Asn His
            20                  25                  30

Trp Met Ser Trp Val Arg Gln Ala Pro Gly Lys Gly Leu Glu Trp Val
        35                  40                  45

Ala Asp Ile Ser Ser Asp Gly Arg Tyr Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Leu Asn Ser Leu Arg Ala Glu Asp Thr Ala Val Tyr Tyr Cys
                85                  90                  95

Ala Lys Ala Gly Gly Gly Asn Val Gly Phe Asp Ile Trp Gly Gln Gly
            100                 105                 110

Thr Met Val Thr Val Ser Ser
        115
```

<210> SEQ ID NO 324
<211> LENGTH: 119
<212> TYPE: PRT
<213> ORGANISM: Artificial Sequence
<220> FEATURE:
<223> OTHER INFORMATION: DLL4 antibody A10.6B VH region

<400> SEQUENCE: 324

```
Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Gly Asn His
            20                  25                  30

Trp Met Ser Trp Val Arg Gln Ala Pro Gly Lys Gly Leu Glu Trp Val
        35                  40                  45

Ala Asp Ile Ser Ser Asp Gly Arg Tyr Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Leu Asn Ser Leu Arg Ala Glu Asp Thr Ala Val Tyr Tyr Cys
                85                  90                  95

Ala Lys Ala Gly Gly Gly Asn Val Gly Phe Asp Ile Trp Gly Gln Gly
            100                 105                 110

Thr Met Val Thr Val Ser Ser
        115
```

<210> SEQ ID NO 325
<211> LENGTH: 119
<212> TYPE: PRT
<213> ORGANISM: Artificial Sequence
<220> FEATURE:
<223> OTHER INFORMATION: DLL4 antibody A10.3D VH region

<400> SEQUENCE: 325

```
Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Arg Ser His
            20                  25                  30

Trp Met Ser Trp Val Arg Gln Ala Pro Gly Lys Gly Leu Glu Trp Val
        35                  40                  45

Ala Asp Ile Ser Gln Asp Gly Ser Tyr Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Ala Gly Gly Asn Val Gly Phe Asp Ile Trp Gly Gln Gly
            100                 105                 110

Thr Met Val Thr Val Ser Ser
        115

<210> SEQ ID NO 326
<211> LENGTH: 119
<212> TYPE: PRT
<213> ORGANISM: Artificial Sequence
<220> FEATURE:
<223> OTHER INFORMATION: DLL4 antibody A10.4C VH region

<400> SEQUENCE: 326

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Gly Ser His
            20                  25                  30

Trp Met Ser Trp Val Arg Gln Ala Pro Gly Lys Gly Leu Glu Trp Val
        35                  40                  45

Ala Asp Ile Ser Asn Asp Gly Arg Tyr Ala Tyr Ser Ala Asp Ser Val
    50                  55                  60

Lys Gly Arg Phe Thr Ile Ser Arg Asp Asn Ser Lys Asn Thr Leu Tyr
65                  70                  75                  80

Leu Gln Leu Asn Ser Leu Arg Ala Glu Asp Thr Ala Val Tyr Tyr Cys
                85                  90                  95

Ala Lys Ala Gly Gly Gly Asn Val Gly Phe Asp Ile Trp Gly Gln Gly
            100                 105                 110

Thr Met Val Thr Val Ser Ser
        115

<210> SEQ ID NO 327
<211> LENGTH: 106
<212> TYPE: PRT
<213> ORGANISM: Artificial Sequence
<220> FEATURE:
<223> OTHER INFORMATION: DLL4 antibody A10.3 VL region

<400> SEQUENCE: 327

Ser Tyr Glu Leu Thr Gln Pro Pro Ser Val Ser Val Ser Pro Gly Gln
1               5                   10                  15

Thr Ala Ser Ile Thr Cys Ser Ala Asp Lys Leu Gly Thr Lys Tyr Val
            20                  25                  30

Ser Trp Tyr Gln Gln Lys Pro Gly Gln Ser Pro Val Leu Val Ile Tyr
        35                  40                  45

Gln Asp Ala Lys Arg Pro Ser Gly Ile Pro Glu Arg Phe Ser Gly Ser
```

```
                  50                  55                  60

Asn Ser Gly Asn Thr Ala Thr Leu Thr Ile Ser Gly Thr Gln Thr Met
 65                  70                  75                  80

Asp Glu Ala Asp Tyr Leu Cys Gln Ser Trp Asp Arg Ser Asp Val Val
                 85                  90                  95

Phe Gly Gly Gly Thr Lys Leu Thr Val Leu
            100                 105

<210> SEQ ID NO 328
<211> LENGTH: 106
<212> TYPE: PRT
<213> ORGANISM: Artificial Sequence
<220> FEATURE:
<223> OTHER INFORMATION: DLL4 antibody A10.L45 VL region

<400> SEQUENCE: 328

Ser Tyr Glu Leu Thr Gln Pro Pro Ser Val Ser Val Ser Pro Gly Gln
 1               5                  10                  15

Thr Ala Ser Ile Thr Cys Ser Ala Asp Glu Leu Gly Gln Tyr Val
                20                  25                  30

Ser Trp Tyr Gln Gln Lys Pro Gly Gln Ser Pro Val Leu Val Ile Tyr
             35                  40                  45

Gln Asp Ala Thr Arg Pro Ser Gly Ile Pro Glu Arg Phe Ser Gly Ser
         50                  55                  60

Asn Ser Gly Asn Thr Ala Thr Leu Thr Ile Ser Gly Thr Gln Ala Met
 65                  70                  75                  80

Asp Glu Ala Asp Tyr Tyr Cys Gln Ala Trp Asp Arg Ser Gly Val Val
                 85                  90                  95

Phe Gly Gly Gly Thr Lys Leu Thr Val Leu
            100                 105

<210> SEQ ID NO 329
<211> LENGTH: 106
<212> TYPE: PRT
<213> ORGANISM: Artificial Sequence
<220> FEATURE:
<223> OTHER INFORMATION: DLL4 antibody A10.L73 VL region

<400> SEQUENCE: 329

Ser Tyr Glu Leu Thr Gln Pro Pro Ser Val Ser Val Ser Pro Gly Gln
 1               5                  10                  15

Thr Ala Ser Ile Thr Cys Ser Gly Asp Asn Leu Gly Ser Gln Tyr Val
                20                  25                  30

Ser Trp Tyr Gln Gln Lys Pro Gly Gln Ser Pro Val Leu Val Ile Tyr
             35                  40                  45

Gln Asp Ala Gln Arg Pro Ser Gly Ile Pro Glu Arg Phe Ser Gly Ser
         50                  55                  60

Asn Ser Gly Asn Thr Ala Thr Leu Thr Ile Ser Gly Thr Gln Ala Met
 65                  70                  75                  80

Asp Glu Ala Asp Tyr Tyr Cys Gln Ala Trp Asp Arg Ser Gly Val Val
                 85                  90                  95

Phe Gly Gly Gly Thr Lys Leu Thr Val Leu
            100                 105

<210> SEQ ID NO 330
<211> LENGTH: 106
<212> TYPE: PRT
<213> ORGANISM: Artificial Sequence
<220> FEATURE:
```

<223> OTHER INFORMATION: DLL4 antibody A10.3A VL region

<400> SEQUENCE: 330

Ser Tyr Glu Leu Thr Gln Pro Pro Ser Val Ser Val Ser Pro Gly Gln
1               5                   10                  15

Thr Ala Ser Ile Thr Cys Ser Ala Asp Asn Leu Gly Glu Lys Tyr Val
            20                  25                  30

Ser Trp Tyr Gln Gln Lys Pro Gly Gln Ser Pro Val Leu Val Ile Tyr
        35                  40                  45

Gln Asp Ala Thr Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ser Trp Asp Ser Ser Gly Ala Val
                85                  90                  95

Phe Gly Gly Gly Thr Lys Leu Thr Val Leu
            100                 105

<210> SEQ ID NO 331
<211> LENGTH: 106
<212> TYPE: PRT
<213> ORGANISM: Artificial Sequence
<220> FEATURE:
<223> OTHER INFORMATION: DLL4 antibody A10.6B VL region

<400> SEQUENCE: 331

Ser Tyr Glu Leu Thr Gln Pro Pro Ser Val Ser Val Ser Pro Gly Gln
1               5                   10                  15

Thr Ala Ser Ile Thr Cys Ser Ala Asp Asn Leu Gly Asn Gln Tyr Val
            20                  25                  30

Ser Trp Tyr Gln Gln Lys Pro Gly Gln Ser Pro Val Leu Val Ile Tyr
        35                  40                  45

Gln Asp Gly Met Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Asp Trp Ser Gly Glu Val
                85                  90                  95

Phe Gly Gly Gly Thr Lys Leu Thr Val Leu
            100                 105

<210> SEQ ID NO 332
<211> LENGTH: 106
<212> TYPE: PRT
<213> ORGANISM: Artificial Sequence
<220> FEATURE:
<223> OTHER INFORMATION: DLL4 antibody A10.3D VL region

<400> SEQUENCE: 332

Ser Tyr Glu Leu Thr Gln Pro Pro Ser Val Ser Val Ser Pro Gly Gln
1               5                   10                  15

Thr Ala Ser Ile Thr Cys Ser Ala Asp Lys Leu Gly Thr Lys Tyr Val
            20                  25                  30

Ser Trp Tyr Gln Gln Lys Pro Gly Gln Ser Pro Val Leu Val Ile Tyr
        35                  40                  45

Gln Asp Gly Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met

```
                65                  70                  75                  80
Asp Glu Ala Asp Tyr Tyr Cys Gln Ser Trp Asp Gln Ser Gly Ala Val
                    85                  90                  95

Phe Gly Gly Gly Thr Lys Leu Thr Val Leu
                100                 105

<210> SEQ ID NO 333
<211> LENGTH: 106
<212> TYPE: PRT
<213> ORGANISM: Artificial Sequence
<220> FEATURE:
<223> OTHER INFORMATION: DLL4 antibody A10.4C VL region

<400> SEQUENCE: 333

Ser Tyr Glu Leu Thr Gln Pro Pro Ser Val Ser Val Ser Pro Gly Gln
1               5                   10                  15

Thr Ala Ser Ile Thr Cys Ser Ala Asp Asn Leu Gly Asn Gln Tyr Val
                20                  25                  30

Ser Trp Tyr Gln Gln Lys Pro Gly Gln Ser Pro Val Leu Val Ile Tyr
            35                  40                  45

Gln Asp Gly Met Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Asp Ser Ser Gly Ala Val
                85                  90                  95

Phe Gly Gly Gly Thr Lys Leu Thr Val Leu
                100                 105

<210> SEQ ID NO 334
<211> LENGTH: 121
<212> TYPE: PRT
<213> ORGANISM: Artificial Sequence
<220> FEATURE:
<223> OTHER INFORMATION: DLL4 antibody E9.1 VH region

<400> SEQUENCE: 334

Glu Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
                20                  25                  30

Ser Tyr Tyr Trp Gly Trp Ile Arg Gln Pro Pro Gly Lys Gly Leu Glu
            35                  40                  45

Trp Ile Gly Asp Ile Tyr Tyr Thr Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Glu Asp Val Ile Leu Arg Gly Gly Ser Asp Tyr Trp Gly
                100                 105                 110

Gln Gly Thr Leu Val Thr Val Ser Ser
        115                 120

<210> SEQ ID NO 335
<211> LENGTH: 107
<212> TYPE: PRT
<213> ORGANISM: Artificial Sequence
<220> FEATURE:
```

<223> OTHER INFORMATION: DLL4 antibody E9.1 VL region

<400> SEQUENCE: 335

Ser Tyr Glu Leu Thr Gln Pro Pro Ser Val Ser Val Ser Pro Gly Gln
1               5                   10                  15

Thr Ala Ser Ile Thr Cys Ser Gly Gln Arg Leu Gly Asp Lys Tyr Ala
            20                  25                  30

Ser Trp Tyr Gln Gln Lys Pro Gly Gln Ser Pro Val Leu Val Ile Tyr
        35                  40                  45

Glu Asp Ser Lys Arg Pro Ser Gly Ile Pro Glu Arg Phe Ser Gly Ser
    50                  55                  60

Asn Ser Gly Asp Thr Ala Thr Leu Thr Ile Ser Gly Thr Gln Pro Met
65                  70                  75                  80

Asp Glu Ala Asp Tyr Tyr Cys Gln Ala Trp Asp Arg Asp Thr Gly Val
                85                  90                  95

Phe Gly Tyr Gly Thr Arg Val Thr Val Leu Gly
            100                 105

<210> SEQ ID NO 336
<211> LENGTH: 121
<212> TYPE: PRT
<213> ORGANISM: Artificial Sequence
<220> FEATURE:
<223> OTHER INFORMATION: DLL4 antibody E9-SE1 VH region

<400> SEQUENCE: 336

Glu Val Gln Leu Val Glu Ser Gly Gly Gly Leu Val Gln Pro Gly Gly
1               5                   10                  15

Ser Leu Arg Leu Ser Cys Ala Val Ser Gly Gly Ser Ile Ser Ser Ser
            20                  25                  30

Ser Tyr Tyr Trp Gly Trp Ile Arg Gln Ala Pro Gly Lys Gly Leu Glu
        35                  40                  45

Trp Ile Gly Asp Ile Tyr Tyr Thr Gly Ser Thr Tyr Tyr Asn Pro Ser
    50                  55                  60

Leu Lys Ser Arg Val Thr Ile Ser Val Asp Thr Ser Lys Asn Ser Phe
65                  70                  75                  80

Tyr Leu Gln Met Asn Ser Leu Arg Ala Glu Asp Thr Ala Val Tyr Tyr
                85                  90                  95

Cys Ala Arg Glu Asp Val Ile Leu Arg Gly Gly Ser Asp Tyr Trp Gly
            100                 105                 110

Gln Gly Thr Leu Val Thr Val Ser Ser
        115                 120

<210> SEQ ID NO 337
<211> LENGTH: 107
<212> TYPE: PRT
<213> ORGANISM: Artificial Sequence
<220> FEATURE:
<223> OTHER INFORMATION: DLL4 antibody E9-SE1 VL region

<400> SEQUENCE: 337

Leu Tyr Val Leu Thr Gln Pro Pro Ser Val Ser Val Ser Pro Gly Gln
1               5                   10                  15

Thr Ala Ser Ile Thr Cys Ser Gly Gln Arg Leu Gly Asp Lys Tyr Ala
            20                  25                  30

Ser Trp Tyr Gln Gln Lys Pro Gly Gln Ser Pro Val Leu Val Ile Tyr
        35                  40                  45

Glu Asp Ser Lys Arg Pro Ser Gly Ile Pro Glu Arg Phe Ser Gly Ser

```
                    50                  55                  60

Asn Ser Gly Asp Thr Ala Thr Leu Thr Ile Ser Gly Thr Gln Thr Met
 65                  70                  75                  80

Asp Glu Ala Asp Tyr Leu Cys Gln Ala Trp Asp Arg Asp Thr Gly Val
                 85                  90                  95

Phe Gly Gly Gly Thr Lys Val Thr Val Leu Gly
            100                 105

<210> SEQ ID NO 338
<211> LENGTH: 121
<212> TYPE: PRT
<213> ORGANISM: Artificial Sequence
<220> FEATURE:
<223> OTHER INFORMATION: DLL4 antibody E9-SE2 VH region

<400> SEQUENCE: 338

Glu Val Gln Leu Val Glu Ser Gly Gly Gly Leu Val Gln Pro Gly Gly
 1               5                  10                  15

Ser Leu Arg Leu Ser Cys Ala Val Ser Gly Ser Ile Ser Ser Ser
             20                  25                  30

Ser Tyr Tyr Trp Gly Trp Ile Arg Gln Ala Pro Gly Lys Gly Leu Glu
             35                  40                  45

Trp Ile Gly Asp Ile Tyr Tyr Thr Gly Ser Thr Tyr Tyr Asn Pro Ser
 50                  55                  60

Leu Lys Ser Arg Val Thr Ile Ser Val Asp Thr Ser Lys Asn Ser Phe
 65                  70                  75                  80

Tyr Leu Gln Met Asn Ser Leu Arg Ala Glu Asp Thr Ala Val Tyr Tyr
                 85                  90                  95

Cys Ala Arg Glu Asp Val Ile Leu Arg Gly Gly Ser Asp Tyr Trp Gly
            100                 105                 110

Gln Gly Thr Leu Val Thr Val Ser Ser
            115                 120

<210> SEQ ID NO 339
<211> LENGTH: 107
<212> TYPE: PRT
<213> ORGANISM: Artificial Sequence
<220> FEATURE:
<223> OTHER INFORMATION: DLL4 antibody E9-SE2 VL region

<400> SEQUENCE: 339

Ser Tyr Glu Leu Thr Gln Pro Pro Ser Val Ser Val Ser Pro Gly Gln
 1               5                  10                  15

Thr Ala Ser Ile Thr Cys Ser Gly Gln Arg Leu Gly Asp Lys Tyr Ala
             20                  25                  30

Ser Trp Tyr Gln Gln Lys Pro Gly Gln Ser Pro Val Leu Val Ile Tyr
             35                  40                  45

Glu Asp Ser Lys Arg Pro Ser Gly Ile Pro Glu Arg Phe Ser Gly Ser
 50                  55                  60

Asn Ser Gly Asp Thr Ala Thr Leu Thr Ile Ser Gly Thr Gln Pro Met
 65                  70                  75                  80

Asp Glu Ala Asp Tyr Tyr Cys Gln Ala Trp Asp Arg Asp Thr Gly Val
                 85                  90                  95

Phe Gly Tyr Gly Thr Arg Val Thr Val Leu Gly
            100                 105

<210> SEQ ID NO 340
<211> LENGTH: 121
```

<212> TYPE: PRT
<213> ORGANISM: Artificial Sequence
<220> FEATURE:
<223> OTHER INFORMATION: DLL4 antibody E9-SE3 VH region

<400> SEQUENCE: 340

Glu Val Gln Leu Gln Glu Ser Gly Pro Gly Leu Val Lys Pro Gly Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Ala Pro Gly Lys Gly Leu Glu
        35                  40                  45

Trp Ile Gly Asp Ile Tyr Tyr Thr Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Tyr Leu Lys Leu Ser Ser Val Arg Ala Glu Asp Thr Ala Val Tyr Tyr
                85                  90                  95

Cys Ala Arg Glu Asp Val Ile Leu Arg Gly Gly Ser Asp Tyr Trp Gly
            100                 105                 110

Gln Gly Thr Leu Val Thr Val Ser Ser
        115                 120

<210> SEQ ID NO 341
<211> LENGTH: 107
<212> TYPE: PRT
<213> ORGANISM: Artificial Sequence
<220> FEATURE:
<223> OTHER INFORMATION: DLL4 antibody E9-SE3 VL region

<400> SEQUENCE: 341

Ser Tyr Glu Leu Thr Gln Pro Pro Ser Val Ser Val Ser Pro Gly Gln
1               5                   10                  15

Thr Ala Ser Ile Thr Cys Ser Gly Gln Arg Leu Gly Asp Lys Tyr Ala
            20                  25                  30

Ser Trp Tyr Gln Gln Lys Pro Gly Gln Ser Pro Val Leu Val Ile Tyr
        35                  40                  45

Glu Asp Ser Lys Arg Pro Ser Gly Ile Pro Glu Arg Phe Ser Gly Ser
    50                  55                  60

Asn Ser Gly Asp Thr Ala Thr Leu Thr Ile Ser Gly Thr Gln Pro Met
65                  70                  75                  80

Asp Glu Ala Asp Tyr Tyr Cys Gln Ala Trp Asp Arg Asp Thr Gly Val
                85                  90                  95

Phe Gly Tyr Gly Thr Arg Val Thr Val Leu Gly
            100                 105

<210> SEQ ID NO 342
<211> LENGTH: 121
<212> TYPE: PRT
<213> ORGANISM: Artificial Sequence
<220> FEATURE:
<223> OTHER INFORMATION: DLL4 antibody E9-SE4 VH region

<400> SEQUENCE: 342

Glu Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu

```
             35                  40                  45

Trp Ile Gly Asp Ile Tyr Tyr Thr Gly Ser Thr Tyr Tyr Asn Pro Ser
        50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Glu Asp Val Ile Leu Arg Gly Gly Ser Asp Tyr Trp Gly
            100                 105                 110

Gln Gly Thr Leu Val Thr Val Ser Ser
            115                 120

<210> SEQ ID NO 343
<211> LENGTH: 107
<212> TYPE: PRT
<213> ORGANISM: Artificial Sequence
<220> FEATURE:
<223> OTHER INFORMATION: DLL4 antibody E9-SE4 VL region

<400> SEQUENCE: 343

Leu Tyr Val Leu Thr Gln Pro Pro Ser Val Ser Val Ser Pro Gly Gln
1               5                   10                  15

Thr Ala Ser Ile Thr Cys Ser Gly Gln Arg Leu Gly Asp Lys Tyr Ala
            20                  25                  30

Ser Trp Tyr Gln Gln Lys Pro Gly Gln Ser Pro Val Leu Val Ile Tyr
        35                  40                  45

Glu Asp Ser Lys Arg Pro Ser Gly Ile Pro Glu Arg Phe Ser Gly Ser
    50                  55                  60

Asn Ser Gly Asp Thr Ala Thr Leu Thr Ile Ser Gly Thr Gln Thr Met
65                  70                  75                  80

Asp Glu Ala Asp Tyr Leu Cys Gln Ala Trp Asp Arg Asp Thr Gly Val
                85                  90                  95

Phe Gly Gly Gly Thr Lys Val Thr Val Leu Gly
            100                 105

<210> SEQ ID NO 344
<211> LENGTH: 121
<212> TYPE: PRT
<213> ORGANISM: Artificial Sequence
<220> FEATURE:
<223> OTHER INFORMATION: DLL4 antibody E9-SE5 VH region

<400> SEQUENCE: 344

Glu Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Asp Ile Tyr Tyr Thr Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Glu Asp Val Ile Leu Arg Gly Gly Ser Asp Tyr Trp Gly
            100                 105                 110
```

```
Gln Gly Thr Leu Val Thr Val Ser Ser
        115                 120
```

<210> SEQ ID NO 345
<211> LENGTH: 108
<212> TYPE: PRT
<213> ORGANISM: Artificial Sequence
<220> FEATURE:
<223> OTHER INFORMATION: DLL4 antibody E9-SE5 VL region

<400> SEQUENCE: 345

```
Glu Tyr Val Leu Thr Gln Ser Pro Asp Phe Gln Ser Val Thr Pro Lys
1               5                   10                  15

Glu Lys Val Thr Ile Thr Cys Ser Gly Gln Arg Leu Gly Asp Lys Tyr
            20                  25                  30

Ala Ser Trp Tyr Gln Gln Lys Pro Asp Gln Ser Pro Lys Leu Val Ile
        35                  40                  45

Tyr Glu Asp Ser Lys Arg Pro Ser Gly Val Pro Ser Arg Phe Ser Gly
    50                  55                  60

Ser Asn Ser Gly Asp Asp Ala Thr Leu Thr Ile Asn Ser Leu Glu Ala
65                  70                  75                  80

Glu Asp Ala Ala Thr Tyr Tyr Cys Gln Ala Trp Asp Arg Asp Thr Gly
                85                  90                  95

Val Phe Gly Gln Gly Thr Lys Val Glu Ile Lys Arg
            100                 105
```

<210> SEQ ID NO 346
<211> LENGTH: 121
<212> TYPE: PRT
<213> ORGANISM: Artificial Sequence
<220> FEATURE:
<223> OTHER INFORMATION: DLL4 antibody E9-SE6 VH region

<400> SEQUENCE: 346

```
Glu Val Gln Leu Gln Glu Ser Gly Pro Gly Leu Val Lys Pro Gly Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Ala Pro Gly Lys Gly Leu Glu
        35                  40                  45

Trp Ile Gly Asp Ile Tyr Tyr Thr Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Tyr Leu Lys Leu Ser Ser Val Arg Ala Glu Asp Thr Ala Val Tyr Tyr
                85                  90                  95

Cys Ala Arg Glu Asp Val Ile Leu Arg Gly Gly Ser Asp Tyr Trp Gly
            100                 105                 110

Gln Gly Thr Leu Val Thr Val Ser Ser
        115                 120
```

<210> SEQ ID NO 347
<211> LENGTH: 107
<212> TYPE: PRT
<213> ORGANISM: Artificial Sequence
<220> FEATURE:
<223> OTHER INFORMATION: DLL4 antibody E9-SE6 VL region

<400> SEQUENCE: 347

```
Leu Tyr Val Leu Thr Gln Pro Pro Ser Val Ser Val Ser Pro Gly Gln
```

```
                1               5                  10                 15
            Thr Ala Ser Ile Thr Cys Ser Gly Gln Arg Leu Gly Asp Lys Tyr Ala
                            20                  25                  30

Ser Trp Tyr Gln Gln Lys Pro Gly Gln Ser Pro Val Leu Val Ile Tyr
                            35                  40                  45

Glu Asp Ser Lys Arg Pro Ser Gly Ile Pro Glu Arg Phe Ser Gly Ser
                            50                  55                  60

Asn Ser Gly Asp Thr Ala Thr Leu Thr Ile Ser Gly Thr Gln Thr Met
            65                  70                  75                  80

Asp Glu Ala Asp Tyr Leu Cys Gln Ala Trp Asp Arg Asp Thr Gly Val
                            85                  90                  95

Phe Gly Gly Gly Thr Lys Val Thr Val Leu Gly
                            100                 105

<210> SEQ ID NO 348
<211> LENGTH: 121
<212> TYPE: PRT
<213> ORGANISM: Artificial Sequence
<220> FEATURE:
<223> OTHER INFORMATION: DLL4 antibody E9-SE7 VH region

<400> SEQUENCE: 348

Glu Val Gln Leu Val Glu Ser Gly Gly Gly Leu Val Gln Pro Gly Gly
            1               5                  10                  15

Ser Leu Arg Leu Ser Cys Ala Val Ser Gly Gly Ser Ile Ser Ser Ser
                            20                  25                  30

Ser Tyr Tyr Trp Gly Trp Ile Arg Gln Ala Pro Gly Lys Gly Leu Glu
                            35                  40                  45

Trp Ile Gly Asp Ile Tyr Tyr Thr Gly Ser Thr Tyr Tyr Asn Pro Ser
                            50                  55                  60

Leu Lys Ser Arg Val Thr Ile Ser Val Asp Thr Ser Lys Asn Ser Phe
            65                  70                  75                  80

Tyr Leu Gln Met Asn Ser Leu Arg Ala Glu Asp Thr Ala Val Tyr Tyr
                            85                  90                  95

Cys Ala Arg Glu Asp Val Ile Leu Arg Gly Gly Ser Asp Tyr Trp Gly
                            100                 105                 110

Gln Gly Thr Leu Val Thr Val Ser Ser
                    115                 120

<210> SEQ ID NO 349
<211> LENGTH: 108
<212> TYPE: PRT
<213> ORGANISM: Artificial Sequence
<220> FEATURE:
<223> OTHER INFORMATION: DLL4 antibody E9-SE7 VL region

<400> SEQUENCE: 349

Glu Tyr Val Leu Thr Gln Ser Pro Asp Phe Gln Ser Val Thr Pro Lys
            1               5                  10                  15

Glu Lys Val Thr Ile Thr Cys Ser Gly Gln Arg Leu Gly Asp Lys Tyr
                            20                  25                  30

Ala Ser Trp Tyr Gln Gln Lys Pro Asp Gln Ser Pro Lys Leu Val Ile
                            35                  40                  45

Tyr Glu Asp Ser Lys Arg Pro Ser Gly Val Pro Ser Arg Phe Ser Gly
                            50                  55                  60

Ser Asn Ser Gly Asp Asp Ala Thr Leu Thr Ile Asn Ser Leu Glu Ala
            65                  70                  75                  80
```

Glu Asp Ala Ala Thr Tyr Tyr Cys Gln Ala Trp Asp Arg Asp Thr Gly
            85                  90                  95

Val Phe Gly Gln Gly Thr Lys Val Glu Ile Lys Arg
            100                 105

<210> SEQ ID NO 350
<211> LENGTH: 121
<212> TYPE: PRT
<213> ORGANISM: Artificial Sequence
<220> FEATURE:
<223> OTHER INFORMATION: DLL4 antibody E9-SE8 VH region

<400> SEQUENCE: 350

Glu Val Gln Leu Gln Glu Ser Gly Pro Gly Leu Val Lys Pro Gly Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Ala Pro Gly Lys Gly Leu Glu
        35                  40                  45

Trp Ile Gly Asp Ile Tyr Tyr Thr Gly Ser Thr Tyr Tyr Asn Pro Ser
50                  55                  60

Leu Lys Ser Arg Val Thr Ile Ser Val Asp Thr Ser Lys Asn Gln Phe
65                  70                  75                  80

Tyr Leu Lys Leu Ser Ser Val Arg Ala Glu Asp Thr Ala Val Tyr Tyr
                85                  90                  95

Cys Ala Arg Glu Asp Val Ile Leu Arg Gly Gly Ser Asp Tyr Trp Gly
            100                 105                 110

Gln Gly Thr Leu Val Thr Val Ser Ser
        115                 120

<210> SEQ ID NO 351
<211> LENGTH: 108
<212> TYPE: PRT
<213> ORGANISM: Artificial Sequence
<220> FEATURE:
<223> OTHER INFORMATION: DLL4 antibody E9-SE8 VL region

<400> SEQUENCE: 351

Glu Tyr Val Leu Thr Gln Ser Pro Asp Phe Gln Ser Val Thr Pro Lys
1               5                   10                  15

Glu Lys Val Thr Ile Thr Cys Ser Gly Gln Arg Leu Gly Asp Lys Tyr
            20                  25                  30

Ala Ser Trp Tyr Gln Gln Lys Pro Asp Gln Ser Pro Lys Leu Val Ile
        35                  40                  45

Tyr Glu Asp Ser Lys Arg Pro Ser Gly Val Pro Ser Arg Phe Ser Gly
50                  55                  60

Ser Asn Ser Gly Asp Asp Ala Thr Leu Thr Ile Asn Ser Leu Glu Ala
65                  70                  75                  80

Glu Asp Ala Ala Thr Tyr Tyr Cys Gln Ala Trp Asp Arg Asp Thr Gly
                85                  90                  95

Val Phe Gly Gln Gly Thr Lys Val Glu Ile Lys Arg
            100                 105

<210> SEQ ID NO 352
<211> LENGTH: 121
<212> TYPE: PRT
<213> ORGANISM: Artificial Sequence
<220> FEATURE:
<223> OTHER INFORMATION: DLL4 antibody E9-FR1 VH region

```
<400> SEQUENCE: 352

Glu Val Gln Leu Val Gln Ser Gly Thr Glu Val Lys Lys Pro Gly Glu
1               5                   10                  15

Ser Leu Lys Ile Ser Cys Lys Val Ser Gly Gly Ser Ile Ser Ser Ser
                20                  25                  30

Ser Tyr Tyr Trp Gly Trp Ile Arg Gln Met Pro Gly Lys Gly Leu Glu
            35                  40                  45

Trp Ile Gly Asp Ile Tyr Tyr Thr Gly Ser Thr Tyr Tyr Asn Pro Ser
50                  55                  60

Leu Lys Ser Gln Val Thr Ile Ser Val Asp Thr Ser Phe Asn Thr Phe
65                  70                  75                  80

Phe Leu Gln Trp Ser Ser Leu Lys Ala Ser Asp Thr Ala Met Tyr Tyr
                85                  90                  95

Cys Ala Arg Glu Asp Val Ile Leu Arg Gly Gly Ser Asp Tyr Trp Gly
            100                 105                 110

Gln Gly Thr Met Val Thr Val Ser Ser
            115                 120

<210> SEQ ID NO 353
<211> LENGTH: 108
<212> TYPE: PRT
<213> ORGANISM: Artificial Sequence
<220> FEATURE:
<223> OTHER INFORMATION: DLL4 antibody E9-FR1 VL region

<400> SEQUENCE: 353

Glu Tyr Val Leu Thr Gln Ser Pro Ala Thr Leu Ser Val Ser Pro Gly
1               5                   10                  15

Glu Arg Ala Thr Leu Ser Cys Ser Gly Gln Arg Leu Gly Asp Lys Tyr
                20                  25                  30

Ala Ser Trp Tyr Gln Gln Lys Pro Gly Gln Ser Pro Arg Leu Val Ile
            35                  40                  45

Tyr Glu Asp Ser Lys Arg Pro Ser Asp Ile Pro Ala Arg Phe Ser Gly
50                  55                  60

Ser Asn Ser Gly Asp Glu Ala Thr Leu Thr Ile Ser Ser Leu Gln Ser
65                  70                  75                  80

Glu Asp Phe Ala Val Tyr Tyr Cys Gln Ala Trp Asp Arg Asp Thr Gly
                85                  90                  95

Val Phe Gly Gln Gly Thr Arg Leu Glu Ile Lys Arg
            100                 105

<210> SEQ ID NO 354
<211> LENGTH: 121
<212> TYPE: PRT
<213> ORGANISM: Artificial Sequence
<220> FEATURE:
<223> OTHER INFORMATION: DLL4 antibody E9-FR2 VH region

<400> SEQUENCE: 354

Glu Val Thr Leu Arg Glu Ser Gly Pro Ala Leu Val Lys Pro Thr Gln
1               5                   10                  15

Thr Leu Thr Leu Thr Cys Thr Val Ser Gly Gly Ser Ile Ser Ser Ser
                20                  25                  30

Ser Tyr Tyr Trp Gly Trp Ile Arg Gln Pro Pro Gly Lys Gly Leu Glu
            35                  40                  45

Trp Ile Gly Asp Ile Tyr Tyr Thr Gly Ser Thr Tyr Tyr Asn Pro Ser
50                  55                  60
```

```
Leu Lys Ser Arg Val Thr Ile Ser Val Asp Thr Ser Lys Asn Gln Phe
 65                  70                  75                  80

Val Leu Thr Met Thr Asn Met Asp Pro Val Thr Ala Thr Tyr Tyr
                 85                  90                  95

Cys Ala Arg Glu Asp Val Ile Leu Arg Gly Gly Ser Asp Tyr Trp Gly
            100                 105                 110

Gln Gly Thr Thr Val Thr Val Ser Ser
            115                 120

<210> SEQ ID NO 355
<211> LENGTH: 108
<212> TYPE: PRT
<213> ORGANISM: Artificial Sequence
<220> FEATURE:
<223> OTHER INFORMATION: DLL4 antibody E9-FR2 VL region

<400> SEQUENCE: 355

Asp Tyr Val Leu Thr Gln Ser Pro Asp Ser Leu Ala Val Ser Leu Gly
1               5                   10                  15

Glu Arg Ala Thr Ile Asn Cys Ser Gly Gln Arg Leu Gly Asp Lys Tyr
            20                  25                  30

Ala Ser Trp Tyr Gln Gln Lys Pro Gly Gln Ser Pro Lys Leu Val Ile
        35                  40                  45

Tyr Glu Asp Ser Lys Arg Pro Ser Gly Ile Pro Asp Arg Phe Ser Gly
 50                  55                  60

Ser Asn Ser Gly Asp Asp Ala Thr Leu Thr Ile Ser Ser Leu Gln Ala
65                   70                  75                  80

Glu Asp Val Ala Val Tyr Tyr Cys Gln Ala Trp Asp Arg Asp Thr Gly
                85                  90                  95

Val Phe Gly Gly Gly Thr Lys Val Glu Ile Lys Arg
            100                 105

<210> SEQ ID NO 356
<211> LENGTH: 121
<212> TYPE: PRT
<213> ORGANISM: Artificial Sequence
<220> FEATURE:
<223> OTHER INFORMATION: DLL4 antibody E9.71 VH region

<400> SEQUENCE: 356

Glu Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Asp Ile Tyr Tyr Thr Gly Ser Thr Tyr Tyr Asn Pro Ser
 50                  55                  60

Leu Lys Ser Arg Val Thr Ile Ser Val Asp Thr Ser Lys Asn Gln Phe
65                   70                  75                  80

Ser Leu Lys Leu Ser Ser Val Thr Ala Ala Asp Thr Ala Val Tyr Tyr
                85                  90                  95

Cys Ala Arg Gln Ala Leu Ala Met Gly Gly Ser Asp Lys Trp Gly
            100                 105                 110

Gln Gly Thr Leu Val Thr Val Ser Ser
            115                 120

<210> SEQ ID NO 357
```

```
<211> LENGTH: 107
<212> TYPE: PRT
<213> ORGANISM: Artificial Sequence
<220> FEATURE:
<223> OTHER INFORMATION: DLL4 antibody E9.71 VL region

<400> SEQUENCE: 357

Ser Tyr Glu Leu Thr Gln Pro Pro Ser Val Ser Val Ser Pro Gly Gln
1               5                   10                  15

Thr Ala Ser Ile Thr Cys Ser Gly Gln Arg Leu Gly Asp Lys Tyr Ala
            20                  25                  30

Ser Trp Tyr Gln Gln Lys Pro Gly Gln Ser Pro Val Leu Val Ile Tyr
        35                  40                  45

Glu Asp Ser Lys Arg Pro Ser Gly Ile Pro Glu Arg Phe Ser Gly Ser
    50                  55                  60

Asn Ser Gly Asp Thr Ala Thr Leu Thr Ile Ser Gly Thr Gln Pro Met
65                  70                  75                  80

Asp Glu Ala Asp Tyr Tyr Cys Gln Ala Trp Asp Arg Asp Thr Gly Val
                85                  90                  95

Phe Gly Tyr Gly Thr Lys Val Thr Val Leu Gly
            100                 105

<210> SEQ ID NO 358
<211> LENGTH: 121
<212> TYPE: PRT
<213> ORGANISM: Artificial Sequence
<220> FEATURE:
<223> OTHER INFORMATION: DLL4 antibody E9.71(M) VH region

<400> SEQUENCE: 358

Glu Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Asp Ile Tyr Tyr Thr Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Gln Ala Leu Ala Met Gly Gly Gly Ser Asp Lys Trp Gly
            100                 105                 110

Gln Gly Thr Leu Val Thr Val Ser Ser
        115                 120

<210> SEQ ID NO 359
<211> LENGTH: 107
<212> TYPE: PRT
<213> ORGANISM: Artificial Sequence
<220> FEATURE:
<223> OTHER INFORMATION: DLL4 antibody E9.71(M) VL region

<400> SEQUENCE: 359

Ser Tyr Glu Leu Thr Gln Pro Pro Ser Val Ser Val Ser Pro Gly Gln
1               5                   10                  15

Thr Ala Ser Ile Thr Cys Ser Gly Gln Arg Leu Gly Asp Lys Tyr Ala
            20                  25                  30
```

Ser Trp Tyr Gln Gln Lys Pro Gly Gln Ser Pro Val Leu Val Ile Tyr
        35                  40                  45

Glu Asp Ser Lys Arg Pro Ser Gly Ile Pro Arg Phe Ser Gly Ser
 50                  55                  60

Asn Ser Gly Asp Thr Ala Thr Leu Thr Ile Ser Gly Thr Gln Pro Met
65                   70                  75                  80

Asp Glu Ala Asp Tyr Tyr Cys Gln Ala Trp Asp Arg Asp Thr Gly Val
                85                  90                  95

Phe Gly Gly Gly Thr Lys Leu Thr Val Leu Gly
            100                 105

<210> SEQ ID NO 360
<211> LENGTH: 121
<212> TYPE: PRT
<213> ORGANISM: Artificial Sequence
<220> FEATURE:
<223> OTHER INFORMATION: DLL4 antibody E9.71(L) VH region

<400> SEQUENCE: 360

Glu Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Asp Ile Tyr Tyr Thr Gly Ser Thr Tyr Tyr Asn Pro Ser
 50                  55                  60

Leu Lys Ser Arg Val Thr Ile Ser Val Asp Thr Ser Lys Asn Gln Phe
65                   70                  75                  80

Ser Leu Lys Leu Ser Ser Val Thr Ala Ala Asp Thr Ala Val Tyr Tyr
                85                  90                  95

Cys Ala Arg Gln Ala Leu Ala Leu Gly Gly Gly Ser Asp Lys Trp Gly
            100                 105                 110

Gln Gly Thr Leu Val Thr Val Ser Ser
        115                 120

<210> SEQ ID NO 361
<211> LENGTH: 107
<212> TYPE: PRT
<213> ORGANISM: Artificial Sequence
<220> FEATURE:
<223> OTHER INFORMATION: DLL4 antibody E9.71(L) VL region

<400> SEQUENCE: 361

Ser Tyr Glu Leu Thr Gln Pro Pro Ser Val Ser Val Ser Pro Gly Gln
1               5                   10                  15

Thr Ala Ser Ile Thr Cys Ser Gly Gln Arg Leu Gly Asp Lys Tyr Ala
            20                  25                  30

Ser Trp Tyr Gln Gln Lys Pro Gly Gln Ser Pro Val Leu Val Ile Tyr
        35                  40                  45

Glu Asp Ser Lys Arg Pro Ser Gly Ile Pro Glu Arg Phe Ser Gly Ser
 50                  55                  60

Asn Ser Gly Asp Thr Ala Thr Leu Thr Ile Ser Gly Thr Gln Pro Met
65                   70                  75                  80

Asp Glu Ala Asp Tyr Tyr Cys Gln Ala Trp Asp Arg Asp Thr Gly Val
                85                  90                  95

Phe Gly Gly Gly Thr Lys Leu Thr Val Leu Gly
            100                 105

<210> SEQ ID NO 362
<211> LENGTH: 19
<212> TYPE: PRT
<213> ORGANISM: Homo sapiens

<400> SEQUENCE: 362

Met Ala Trp Ser Pro Leu Phe Leu Thr Leu Ile Thr His Cys Ala Gly
1               5                   10                  15

Ser Trp Ala

<210> SEQ ID NO 363
<211> LENGTH: 19
<212> TYPE: PRT
<213> ORGANISM: Homo sapiens

<400> SEQUENCE: 363

Met Ala Trp Ser Pro Leu Phe Leu Thr Leu Ile Thr His Cys Ala Arg
1               5                   10                  15

Val Trp Ala

<210> SEQ ID NO 364
<211> LENGTH: 19
<212> TYPE: PRT
<213> ORGANISM: Homo sapiens

<400> SEQUENCE: 364

Met Ala Trp Thr Pro Leu Leu Leu Pro Leu Leu Thr Phe Cys Thr Val
1               5                   10                  15

Ser Glu Ala

<210> SEQ ID NO 365
<211> LENGTH: 19
<212> TYPE: PRT
<213> ORGANISM: Homo sapiens

<400> SEQUENCE: 365

Met Ala Trp Thr Pro Leu Leu Leu Pro Leu Leu Thr Phe Cys Thr Val
1               5                   10                  15

Ser Glu Ala

<210> SEQ ID NO 366
<211> LENGTH: 22
<212> TYPE: PRT
<213> ORGANISM: Homo sapiens

<400> SEQUENCE: 366

Met Asp Met Arg Val Pro Ala Gln Arg Leu Gly Leu Leu Leu Leu Trp
1               5                   10                  15

Phe Pro Gly Ala Arg Cys
            20

<210> SEQ ID NO 367
<211> LENGTH: 22
<212> TYPE: PRT
<213> ORGANISM: Homo sapiens

<400> SEQUENCE: 367

Met Asp Met Arg Val Pro Ala Gln Arg Leu Gly Leu Leu Leu Leu Trp
1               5                   10                  15

Phe Pro Gly Ala Arg Cys

20

<210> SEQ ID NO 368
<211> LENGTH: 30
<212> TYPE: PRT
<213> ORGANISM: Artificial Sequence
<220> FEATURE:
<223> OTHER INFORMATION: E9.71(M) antibody cleavage site

<400> SEQUENCE: 368

Met Ala Trp Ser Pro Leu Phe Leu Thr Leu Ile Thr His Cys Ala Gly
1               5                   10                  15

Ser Trp Ala Ser Tyr Glu Leu Thr Gln Pro Pro Ser Val Ser
            20                  25                  30

<210> SEQ ID NO 369
<211> LENGTH: 30
<212> TYPE: PRT
<213> ORGANISM: Artificial Sequence
<220> FEATURE:
<223> OTHER INFORMATION: E9.71(M)-1 antibody cleavage site

<400> SEQUENCE: 369

Met Ala Trp Ser Pro Leu Phe Leu Thr Leu Ile Thr His Cys Ala Arg
1               5                   10                  15

Val Trp Ala Ser Tyr Glu Leu Thr Gln Pro Pro Ser Val Ser
            20                  25                  30

<210> SEQ ID NO 370
<211> LENGTH: 30
<212> TYPE: PRT
<213> ORGANISM: Artificial Sequence
<220> FEATURE:
<223> OTHER INFORMATION: E9.71(M)-2 antibody cleavage site

<400> SEQUENCE: 370

Met Ala Trp Thr Pro Leu Leu Leu Pro Leu Leu Thr Phe Cys Thr Val
1               5                   10                  15

Ser Glu Ala Ser Tyr Glu Leu Thr Gln Pro Pro Ser Val Ser
            20                  25                  30

<210> SEQ ID NO 371
<211> LENGTH: 29
<212> TYPE: PRT
<213> ORGANISM: Artificial Sequence
<220> FEATURE:
<223> OTHER INFORMATION: E9.71(M)-3 antibody cleavage site

<400> SEQUENCE: 371

Met Ala Trp Thr Pro Leu Leu Leu Pro Leu Leu Thr Phe Cys Thr Val
1               5                   10                  15

Ser Glu Ala Tyr Glu Leu Thr Gln Pro Pro Ser Val Ser
            20                  25

<210> SEQ ID NO 372
<211> LENGTH: 33
<212> TYPE: PRT
<213> ORGANISM: Artificial Sequence
<220> FEATURE:
<223> OTHER INFORMATION: E9.71(M)-4 antibody cleavage site

<400> SEQUENCE: 372

Met Asp Met Arg Val Pro Ala Gln Arg Leu Gly Leu Leu Leu Leu Trp
1               5                   10                  15

```
Phe Pro Gly Ala Arg Cys Ser Tyr Glu Leu Thr Gln Pro Ser Val
            20                  25                  30

Ser

<210> SEQ ID NO 373
<211> LENGTH: 32
<212> TYPE: PRT
<213> ORGANISM: Artificial Sequence
<220> FEATURE:
<223> OTHER INFORMATION: E9.71(M)-5 antibody cleavage site

<400> SEQUENCE: 373

Met Asp Met Arg Val Pro Ala Gln Arg Leu Gly Leu Leu Leu Leu Trp
1               5                   10                  15

Phe Pro Gly Ala Arg Cys Tyr Glu Leu Thr Gln Pro Pro Ser Val Ser
            20                  25                  30

<210> SEQ ID NO 374
<211> LENGTH: 4
<212> TYPE: PRT
<213> ORGANISM: Artificial Sequence
<220> FEATURE:
<223> OTHER INFORMATION: CDR localization peptide
<220> FEATURE:
<221> NAME/KEY: MISC_FEATURE
<222> LOCATION: (3)..(3)
<223> OTHER INFORMATION: X can be any amino acid

<400> SEQUENCE: 374

Phe Gly Xaa Gly
1

<210> SEQ ID NO 375
<211> LENGTH: 9
<212> TYPE: PRT
<213> ORGANISM: Artificial Sequence
<220> FEATURE:
<223> OTHER INFORMATION: CDR localization peptide
<220> FEATURE:
<221> NAME/KEY: misc_feature
<222> LOCATION: (2)..(9)
<223> OTHER INFORMATION: X can be any amino acid, positions 2-8
<220> FEATURE:
<221> NAME/KEY: misc_feature
<222> LOCATION: (2)..(9)
<223> OTHER INFORMATION: X can be any amino acid

<400> SEQUENCE: 375

Cys Xaa Xaa Xaa Xaa Xaa Xaa Xaa Xaa
1               5

<210> SEQ ID NO 376
<211> LENGTH: 5
<212> TYPE: PRT
<213> ORGANISM: Artificial Sequence
<220> FEATURE:
<223> OTHER INFORMATION: CDR localization peptide

<400> SEQUENCE: 376

Leu Glu Trp Ile Gly
1               5

<210> SEQ ID NO 377
<211> LENGTH: 4
<212> TYPE: PRT
<213> ORGANISM: Artificial Sequence
<220> FEATURE:
<223> OTHER INFORMATION: CDR localization peptide
```

```
<220> FEATURE:
<221> NAME/KEY: MISC_FEATURE
<222> LOCATION: (3)..(3)
<223> OTHER INFORMATION: X can be any amino acid

<400> SEQUENCE: 377

Trp Gly Xaa Gly
1
```